(12) United States Patent
Nakanotani et al.

(10) Patent No.: US 12,120,952 B2
(45) Date of Patent: Oct. 15, 2024

(54) COMPOUND, LIGHT-EMITTING MATERIAL AND LIGHT-EMITTING ELEMENT

(71) Applicants: KYUSHU UNIVERSITY, NATIONAL UNIVERSITY CORPORATION, Fukuoka (JP); KYULUX, INC., Fukuoka (JP)

(72) Inventors: Hajime Nakanotani, Fukuoka (JP); Hiroki Noda, Fukuoka (JP); Chihaya Adachi, Fukuoka (JP); Naoto Notsuka, Fukuoka (JP); Yoshitake Suzuki, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 520 days.

(21) Appl. No.: 16/488,374

(22) PCT Filed: Feb. 23, 2018

(86) PCT No.: PCT/JP2018/006764
§ 371 (c)(1),
(2) Date: Aug. 23, 2019

(87) PCT Pub. No.: WO2018/155642
PCT Pub. Date: Aug. 30, 2018

(65) Prior Publication Data
US 2020/0235313 A1    Jul. 23, 2020

(30) Foreign Application Priority Data

Feb. 24, 2017   (JP) ................. 2017-034159
May 2, 2017    (JP) ................. 2017-091634

(51) Int. Cl.
*H10K 85/60*   (2023.01)
*C07D 209/86*  (2006.01)
(Continued)

(52) U.S. Cl.
CPC ....... *H10K 85/6572* (2023.02); *C07D 209/86* (2013.01); *C09K 11/06* (2013.01);
(Continued)

(58) Field of Classification Search
CPC .......... H10K 85/6572; H10K 2101/10; H10K 50/11; C07D 209/86; C09K 11/06;
(Continued)

(56) References Cited

U.S. PATENT DOCUMENTS 9,502,668 B2 * 11/2016 Adachi ................ C07D 209/18
9,991,453 B2    6/2018 Kita et al.
2015/0105564 A1 * 4/2015 Adachi ............... H01L 51/0072
548/440

FOREIGN PATENT DOCUMENTS

CN    102318101 A    1/2012
CN    104204132 A    12/2014
(Continued)

OTHER PUBLICATIONS

Translation of CN 106316924 A by Duan et al. (Year: 2017).*
(Continued)

*Primary Examiner* — Michael M Dollinger
*Assistant Examiner* — Christina H. W. Rosebach
(74) *Attorney, Agent, or Firm* — BROWDY AND NEIMARK, PLLC

(57) ABSTRACT

Using a compound represented by a general formula (A)m-L-(D)n, a light-emitting device having a high emission efficiency can be provided. L is an (m+n)-valent aromatic linking group; A is a group having a positive Hammett's $\sigma_p$ value; D is a group having a negative Hammett's $\sigma_p$ value; m is an integer of 1 or more; n is an integer of 2 or more. Two of plural D's differ in point of the substituent condition at specific aromatic rings.

9 Claims, 5 Drawing Sheets

(51) Int. Cl.
  *C09K 11/06* (2006.01)
  *H10K 50/11* (2023.01)
  *H10K 101/10* (2023.01)
(52) U.S. Cl.
  CPC .............. *C09K 2211/1007* (2013.01); *C09K 2211/1018* (2013.01); *H10K 50/11* (2023.02); *H10K 2101/10* (2023.02)
(58) Field of Classification Search
  CPC .... C09K 2211/1007; C09K 2211/1018; C09K 211/1007; C09K 211/1018
  See application file for complete search history.

(56) References Cited

FOREIGN PATENT DOCUMENTS

| CN | 106316924 A | * | 1/2017 | .......... C07D 209/82 |
|---|---|---|---|---|
| EP | 0 687 668 A2 | | 12/1995 | |
| JP | 3079293 B | | 8/2000 | |
| JP | 2008-133225 A | | 6/2008 | |
| JP | 2011-176250 A | | 9/2011 | |
| JP | 2014-043541 A | | 3/2014 | |
| JP | 2015-172166 A | | 10/2015 | |
| JP | 2016-526025 A | | 9/2016 | |
| JP | 2017-226838 A | | 12/2017 | |
| JP | 6668152 B | | 3/2020 | |
| KR | 10-2010-0123172 | | 10/2011 | |
| KR | 20170037135 A | | 4/2017 | |
| WO | 2010/113755 A1 | | 10/2010 | |
| WO | 2014/133062 A1 | | 9/2014 | |
| WO | 2014/183080 A1 | | 11/2014 | |
| WO | 2014/189072 A | | 11/2014 | |
| WO | 2015/022987 A1 | | 2/2015 | |
| WO | 2016/124704 A1 | | 8/2016 | |
| WO | 2016/152605 A1 | | 9/2016 | |
| WO | 2016/181846 A1 | | 11/2016 | |
| WO | 2017/082246 A1 | | 5/2017 | |
| WO | 2017/115835 A1 | | 7/2017 | |
| WO | 2017/155102 A1 | | 9/2017 | |
| WO | 2018/047948 A1 | | 3/2018 | |

OTHER PUBLICATIONS

Noda, Nakanotani, Adachi, et al. Excited state engineering for efficient reverse intersystem crossing. Sci. Adv. 2018;4: eaao6910 (Year: 2018).*

Zou, S.J. et al. High-Performance Nondoped Blue Delayed Fluorescence Organic Light-Emitting Diodes Featuring Low Driving Voltage and High Brightness. Adv. Sci. 2020, 7, 1902508. DOI: 10.1002/advs.201902508 (Year: 2020).*

Japanese and English version of International Preliminary Report on Patentability of Chapter I with English Translation dated Feb. 24, 2017.

International Search Report and Search Opinion dated Oct. 4, 2018.

H. Uoyama, et al., "Highly efficient organic light-emitting diodes from delayed fluorescence", Nature 492, 234 (2012).

H. Nakanotani, et al., "Highly efficient organic light-emitting diodes from delayed fluorescence", Scientific Reports, 3, 2127 (2013).

Hansch et al., A Survey of Hammett Substituent Constants and Resonance and Field Parameters, Chem. Rev., 91, 165-195 (1991).

Shuho Tanimoto et al., "Thermally Activated Delayed Fluorescence from Pentacarbazorylbenzonitrile", Chem. Lett., 45, 770 (2016).

Extended European Search Report dated Feb. 10, 2021 issued in the corresponding European patent application No. 18757582.4.

Office Action dated May 31, 2021 issued in the corresponding Taiwan patent application No. 107106181 with its English Translation.

Luo, et al., Donor-Acceptor Fluorophores for Visible-Light-Promoted Organic Synthesis: Photoredox/Ni Dual Catalytic C(sp3)-C(sp2) Cross-Coupling, ACS Catalysis, Jan. 12, 2016, pp. 873-877, vol. 6, No. 2.

Hsieh, et al., Lewis Acid Induced Toggle from Ir(II) to Ir(IV) Pathways in Photocatalytic Reactions: Synthesis of Thiomorpholines and Thiazepanes from Aldehydes and SLAP Reagents, ACS Central Science, Jan. 25, 2017, pp. 66-72, vol. 3, No. 1.

Yamamoto, et al., Regioregular Phthalocyanines Substituted with Bulky Donors at Non-Peripheral Positions, European Jouran, Nov. 2, 2017, pp. 15446-15454, vol. 23, No. 61.

Supplementary Partial European Search Report dated Oct. 26, 2020 for application No. EP 18 75 7582.

Office Action dated Jan. 18, 2022 issued in the corresponding Japanese patent application No. 2019-501841 with its English Machine Translation.

Office Action dated May 17, 2022 issued in the corresponding Chinese patent application No. 201880013706.8 with its English Machine Translation.

Japanese office action dated Aug. 2, 2022, from corresponding Japanese Patent Application No. 2019-501841.

Office Action dated Apr. 5, 2022 issued in the corresponding Japanese patent application No. 2019-501841 with its English Machine Translation.

Office Action dated Oct. 20, 2022, issued in corresponding Chinese patent application No. 201880013706.8 with its English Machine Translation.

Office Action dated Jan. 19, 2023 issued in the corresponding European patent application No. 18757582.4.

Rejection Decision dated May 15, 2023 issued in the corresponding Chinese patent application No. 201880013706.8 with its English Translation.

* cited by examiner

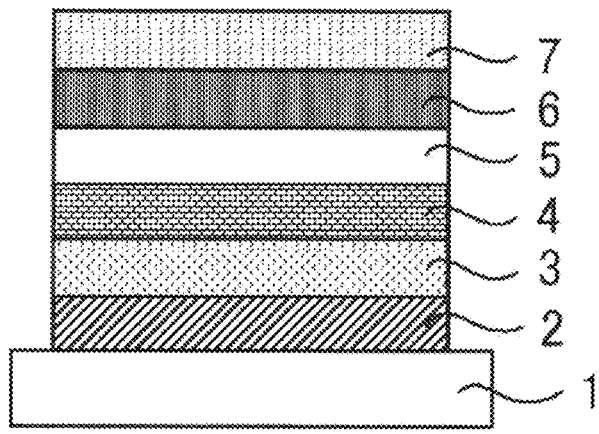
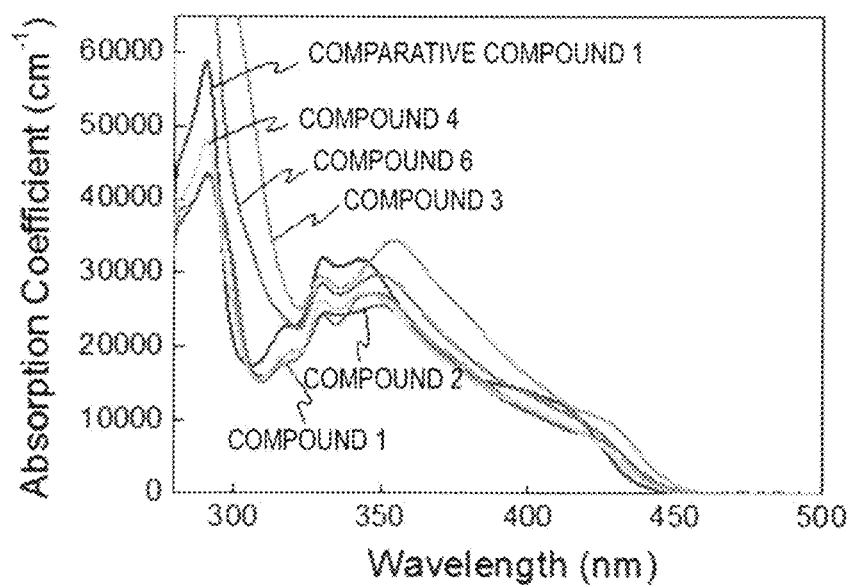

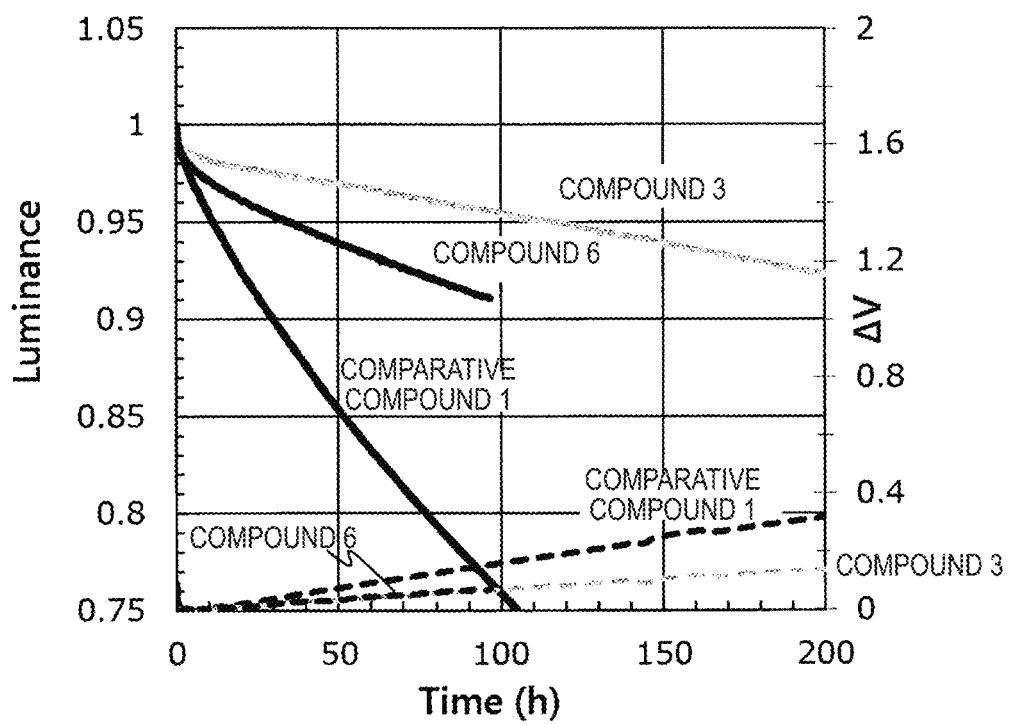

COMPOUND, LIGHT-EMITTING MATERIAL AND LIGHT-EMITTING ELEMENT

TECHNICAL FIELD

The present invention relates to a compound useful as a light-emitting material and to a light-emitting device using the compound.

BACKGROUND ART

Studies for enhancing the light emission efficiency of (organic) light-emitting devices such as organic electroluminescent devices (organic EL devices) are being made actively. In particular, various kinds of efforts have been made for increasing light emission efficiency by newly developing and combining an electron transfer material, a hole transfer material, a light-emitting material and others to constitute an organic electroluminescent device. Among them, there is known a study relating to an organic electroluminescent device that utilizes a delayed fluorescent material.

A delayed fluorescent material is a compound which, in an excited state, after having undergone reverse intersystem crossing from an excited triplet state to an excited singlet state, emits fluorescence when returning back from the excited singlet state to a ground state thereof. Fluorescence through the route is observed later than fluorescence from the excited singlet state directly occurring from the ground state (ordinary fluorescence), and is therefore referred to as delayed fluorescence. Here, for example, in the case where a light-emitting compound is excited through carrier injection thereinto, the occurring probability of the excited singlet state to the excited triplet state is statistically 25%/75%, and therefore improvement of light emission efficiency by the fluorescence alone from the directly occurring excited singlet state is limited. On the other hand, in a delayed fluorescent material, not only the excited singlet state thereof but also the excited triplet state can be utilized for fluorescent emission through the route via the above-mentioned reverse intersystem crossing, and therefore as compared with an ordinary fluorescent material, a delayed fluorescent material can realize a higher emission efficiency.

Regarding such a delayed fluorescent material, PTL 1, proposing a benzene derivative having a heteroaryl group such as a carbazolyl group or a diphenylamino group and at least two cyano groups, confirmed a high emission efficiency of an organic EL device using the benzene derivative in the light-emitting layer therein.

NPL 1 reports that a carbazolyldicyanobenzene derivative represented by the following formula (hereinafter referred to as "4CzIPN") is a thermal activation type delayed fluorescent material and that an organic electroluminescent device using 4CzIPN attained a high internal EL quantum efficiency. Further, NPL 2 reports that an optimized configuration of an organic electroluminescent device using 4CzIPN realized high emission efficiency and high durability.

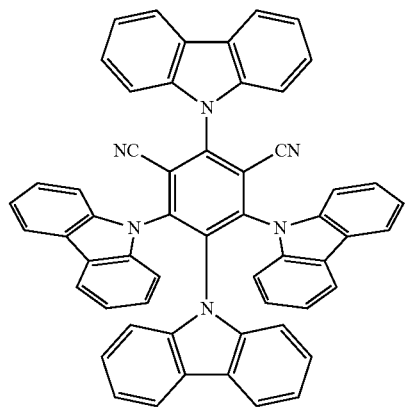 [SMILES: N#Cc1c(-n2c3ccccc3c3ccccc32)c(C#N)c(-n2c3ccccc3c3ccccc32)c(-n2c3ccccc3c3ccccc32)c1-n1c2ccccc2c2ccccc21]

CITATION LIST

Patent Literature

PTL 1: JP 2014-43541A

Non-Patent Literature

NPL 1: H. Uoyama, et al., Nature 492, 234 (2012)
NPL 2: H. Nakanotani, et al., Scientific Reports, 3, 2127 (2013)

SUMMARY OF INVENTION

Technical Problem

As described above, PTL 1 and NPLs 1 and 2 report usefulness of a delayed fluorescent material, 4CzIPN as a material for light-emitting devices. The compound is so configured that cyano groups acting as an acceptor and carbazolyl groups acting as a donor bond to the core benzene ring, and such a configuration of the compound controls the spatial localization between HOMO and LUMO to enhance the emission efficiency thereof. However, as a result of investigations of the emission process of 4CzIPN that the present inventors have made, it has been found that the configuration of the compound could not be said to be a sufficiently optimum one, and there still exists room for significantly improving emission efficiency by further controlling the structure of the donor groups bonding to the core benzene ring.

Given the situation, the present inventors have made further studies for the purpose of finding out a material having a higher emission efficiency and generalizing the material. With that, the present inventors have promoted assiduous studies for the purpose of deriving a general formula of a compound useful as a light-emitting material and generalizing the configuration of a light-emitting device having a higher emission efficiency.

Solution to Problem

As a result of assiduous studies made for the purpose of attaining the above-mentioned object, the present inventors have found that a compound having a configuration such that donor groups and acceptor group(s) bond to a core aromatic ring and two donor groups differ in the substituent condition (the number of substituents, the substitution sites and the configuration of substituents) has excellent emission characteristics superior to those of 4CzIPN. With that, the present inventors have clarified that, using such a compound as a light-emitting material, a light-emitting device having an extremely high emission efficiency can be provided. The present invention has been proposed on the basis of such findings, and specifically has the following constitution.

[1] A compound represented by the following general formula (1): General Formula (1)

(A)$m$-L-(D)$n$ wherein L represents an (m+n)-valent aromatic linking group; A represents a group having a positive Hammett's $\sigma_p$ value or a phenyl group; D represents a group having a negative Hammett's $\sigma_p$ value (but excluding a phenyl group); m represents an integer of 1 or more; n represents an integer of 2 or more; when m is 2 or more, plural A's may be the same as or different from each other; two of plural D's each contain an aromatic ring common to them but have a different structure.

[2] The compound according to [1], wherein two of the plural D's are groups each containing a hetero atom.

[3] The compound according to [2], wherein two of the plural D's are groups each containing a structure having two or more aromatic rings bonding to a hetero atom.

[4] The compound according to [3], wherein two of the plural D's each contain a diarylamine structure (in which, however, two aryl groups constituting the diarylamine structure may bond to each other).

[5] The compound according to [4], wherein the diarylamine structure is a carbazole structure.

[6] The compound according to any one of [1] to [5], wherein m is 1.

[7] The compound according to any one of [1] to [5], wherein m is 2 or more.

[8] The compound according to any one of [1] to [7], wherein two of the plural D's satisfy the following requirement (a) or the following requirement (b):
Requirement (a)
  Two D's each have an aromatic ring that contains an atom bonding to L, and the aromatic ring is common between the two D's, but the two differ from each other in point of at least one condition of the number of the substituents on the aromatic ring, the substitution site of the aromatic ring substituted with the substituent, and the structure of the substituent on the aromatic ring.
Requirement (b)
  Two D's each have a linking group that bonds to L and one aromatic ring bonding to the linking group, and the linking group and the aromatic ring bonding to the linking group are common between the two D's, but the two differ from each other in point of at least one condition of the number of the substituents on the aromatic ring, the substitution site of the aromatic ring substituted with the substituent, and the structure of the substituent on the aromatic ring. Two D's each have a linking group that bonds to L and two or more aromatic rings bonding to the linking group, and the linking group, the number of the aromatic rings bonding to the linking group, and the plural aromatic rings are common between the two D's, but in at least one combination of the aromatic rings common between the two D's, the two differ from each other in point of at least one condition of the number of the substituents on the aromatic ring, the substitution site of the aromatic ring substituted with the substituent, and the structure of the substituent on the aromatic ring.

[9] The compound according to [8], wherein two of the plural D's satisfy the requirement (a).

[10] The compound according to any one of [1] to [9], wherein two of the plural D's each are a group represented by the following general formula (2):

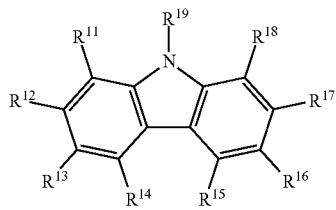

General Formula (2)

wherein $R^{11}$ to $R^{19}$ each independently represent a hydrogen atom, a substituent or a bonding position to L, and one of $R^{11}$ to $R^{19}$ is a bonding position to L.

[11] The compound according to [10], wherein $R^{19}$ in the general formula (2) is a bonding position to L.

[12] The compound according to [10] or [11], wherein one of two of the plural D's is such that at least one of $R^{11}$ to $R^{18}$ in the general formula (2) is a substituent, and the other of two of the plural D's is such that the corresponding substituent of that one of two of the plural D's among $R^{11}$ to $R^{18}$ in the general formula (2) is a hydrogen atom.

[13] The compound according to any one of [10] to [12], wherein one of two of the plural D's is such that at least one of $R^{13}$ and $R^{16}$ in the general formula (2) is a substituent.

[14] The compound according to [12] or [13], wherein the substituent is a substituted or unsubstituted alkyl group or a substituted or unsubstituted aryl group.

[15] The compound according to [1], wherein the compound represented by the general formula (1) is a compound represented by the following general formula (10):

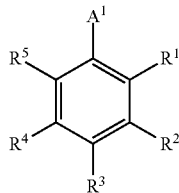

General Formula (10)

wherein $A^1$ represents a group having a positive Hammett's σp value; $R^1$ to $R^5$ each independently represent a hydrogen atom, a group having a positive Hammett's σp value, or a group having a negative Hammett's σp value; at least two of $R^1$ to $R^5$ each are a group having a negative Hammett's σp value (but excluding a phenyl group); when one or more of $R^1$ to $R^5$ each are a group having a positive Hammett's σp value, the group having a positive Hammett's σp value represented by $A^1$ and the group having a positive Hammett's σp value among $R^1$ to $R^5$ may be the same as or different from each other.

[16] The compound according to [15], wherein two groups each having a negative Hammett's σp value among $R^1$ to $R^5$ each satisfy the following requirement (a) or requirement (b):
Requirement (a)
  Two groups having a negative Hammett's σp value each have an aromatic ring that contains an atom bonding to the benzene ring in the general formula (10), and the aromatic ring is common between the two groups having a negative Hammett's σp value, but the two differ from each other in point of at least one condition of the number of the substituents on the aromatic ring, the substitution site of the aromatic ring substituted with the substituent, and the structure of the substituent on the aromatic ring.

Requirement (b)

Two groups having a negative Hammett's σp value each have a linking group that bonds to the benzene ring in the general formula (10) and one aromatic ring bonding to the linking group, and the linking group and the aromatic ring bonding to the linking group are common between the two groups having a negative Hammett's σp value, but the two differ from each other in point of at least one condition of the number of the substituents on the aromatic ring, the substitution site of the aromatic ring substituted with the substituent, and the structure of the substituent on the aromatic ring. Two groups having a negative Hammett's σp value each have a linking group that bonds to the benzene ring in the general formula (10) and two or more aromatic rings bonding to the linking group, and the linking group, the number of the aromatic rings bonding to the linking group, and the plural aromatic rings are common between the two groups having a negative Hammett's σp value, but in at least one combination of the aromatic rings common between the two groups having a negative Hammett's σp value, the two differ from each other in point of at least one condition of the number of the substituents on the aromatic ring, the substitution site of the aromatic ring substituted with the substituent, and the structure of the substituent on the aromatic ring.

[17] The compound according to [16], wherein at least one of the combination of $R^1$ and $R^4$ and the combination of $R^2$ and $R^5$ in the general formula (10) satisfies the requirement (a) or (b).

[18] The compound according to any one of [15] to [17], wherein $R^1$ to $R^5$ in the general formula (10) each are a group having a negative Hammett's σp value (but excluding a phenyl group).

[19] The compound according to [1], wherein the compound represented by the general formula (1) is a compound represented by the following general formula (11):

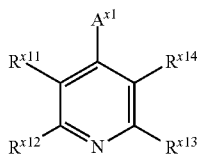

General Formula (11)

wherein $A^{X1}$ represents a group having a positive Hammett's σp value, $R^{X11}$ to $R^{X14}$ each independently represent a hydrogen atom, a group having a positive Hammett's σp value or a group having a negative Hammett's σp value; at least two of $R^{X11}$ to $R^{X14}$ each are a group having a negative Hammett's σp value (but excluding a phenyl group); when one or more of $R^{X11}$ to $R^{X14}$ each are a group having a positive Hammett's σp value, the group having a positive Hammett's σp value represented by $A^{X1}$ and the group having a positive Hammett's σp value among $R^{X11}$ to $R^{X14}$ may be the same as or different from each other.

The compound according to [19], wherein two groups each having a negative Hammett's σp value among $R^{X11}$ to $R^{X14}$ each satisfy the following requirement (a) or requirement (b):

Requirement (a)

Two groups having a negative Hammett's σp value each have an aromatic ring that contains an atom bonding to the benzene ring in the general formula (10), and the aromatic ring is common between the two groups having a negative Hammett's σp value, but the two differ from each other in point of at least one condition of the number of the substituents on the aromatic ring, the substitution site of the aromatic ring substituted with the substituent, and the structure of the substituent on the aromatic ring.

Requirement (b)

Two groups having a negative Hammett's σp value each have a linking group that bonds to the benzene ring in the general formula (10) and one aromatic ring bonding to the linking group, and the linking group and the aromatic ring bonding to the linking group are common between the two groups having a negative Hammett's σp value, but the two differ from each other in point of at least one condition of the number of the substituents on the aromatic ring, the substitution site of the aromatic ring substituted with the substituent, and the structure of the substituent on the aromatic ring. Two groups having a negative Hammett's σp value each have a linking group that bonds to the benzene ring in the general formula (10) and two or more aromatic rings bonding to the linking group, and the linking group, the number of the aromatic rings bonding to the linking group, and the plural aromatic rings are common between the two groups having a negative Hammett's σp value, but in at least one combination of the aromatic rings common between the two groups having a negative Hammett's σp value, the two differ from each other in point of at least one condition of the number of the substituents on the aromatic ring, the substitution site of the aromatic ring substituted with the substituent, and the structure of the substituent on the aromatic ring.

A light-emitting material containing a compound of any one of [1] to [20].

A light-emitting device containing a compound of any one of [1] to [20].

A method for producing a compound represented by the following general formula (1), which includes a step of reacting a compound represented by the following general formula (18) with a compound represented by the following general formula (21) and a compound represented by the following general formula (22): General Formula (18)

(A)m-L-(X)n wherein L represents an (m+n)-valent aromatic linking group; A represents a group having a positive Hammett's σp value or a phenyl group; X represents a halogen atom; m represents an integer of 1 or more; n represents an integer of 2 or more; when m is 2 or more, plural A's may be the same as or different from each other; plural X's may be the same as or different from each other, H-D$^1$             General Formula (21)

wherein $D^1$ represents a group having a negative Hammett's σp value (but excluding a phenyl group), H-D$^2$             General Formula (22)

wherein $D^2$ represents a group having a negative Hammett's σp value (but excluding a phenyl group), and is a group differing from $D^1$ in the structure, (A)m-L-(D)n             General Formula (1)

wherein L represents an (m+n)-valent aromatic linking group; A represents a group having a positive Hammett's $σ_p$ value or a phenyl group; D represents a group having a negative Hammett's $\sigma_p$ value (but excluding a phenyl group); m represents an integer of 1 or more, n represents an integer of 2 or more; when m is 2 or more, plural A's may be the same as or different from each other, two of plural D's each contain an aromatic ring common to them but have a different structure.

A method for producing a compound represented by the following general formula (1), which includes a step of reacting a compound represented by the following general formula (19) with a compound represented by the following general formula (22):

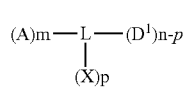

General Formula (19)

wherein L represents an (m+n)-valent aromatic linking group; A represents a group having a positive Hammett's σp value or a phenyl group; D¹ represents a group having a negative Hammett's σp value (but excluding a phenyl group); m represents an integer of 1 or more; n represents an integer of 1 or more; when m is 2 or more, plural A's may be the same as or different from each other; when n is 2 or more, plural D's may be the same as or different from each other; X represents a halogen atom; p represents an integer of 1 or more and less than n, H-D²     General Formula (22)

wherein D² represents a group having a negative Hammett's σp value (but excluding a phenyl group), and is a group differing from D¹ in the structure, (A)m-L-(D)n     General Formula (1)

wherein L represents an (m+n)-valent aromatic linking group; A represents a group having a positive Hammett's $\sigma_p$ value or a phenyl group; D represents a group having a negative Hammett's $\sigma_p$ value (but excluding a phenyl group); m represents an integer of 1 or more, n represents an integer of 2 or more; when m is 2 or more, plural A's may be the same as or different from each other; two of plural D's each contain an aromatic ring common to them but have a different structure.

A compound represented by the following general formula (19):

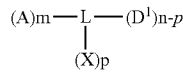

wherein L represents an (m+n)-valent aromatic linking group; A represents a group having a positive Hammett's σp value or a phenyl group; D¹ represents a group having a negative Hammett's σp value (but excluding a phenyl group); m represents an integer of 1 or more; n represents an integer of 1 or more; when m is 2 or more, plural A's may be the same as or different from each other; when n is 2 or more, plural D¹'s may be the same as or different from each other, X represents a halogen atom; p represents an integer of 1 or more and less than n; provided that a compound having the following structure is not included in the general formula (19).

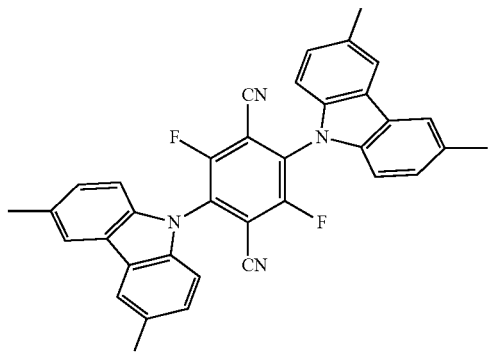

The compound according to [25], wherein the halogen atom is a fluorine atom.

The compound according to [25] or [26], wherein at least one D¹ is a diarylamino group (but in which the two aryl groups constituting the diarylamino group may bond to each other).

The compound according to any one of [25] to [27], wherein at least one A is a cyano group.

Advantageous Effects of Invention

The compound of the present invention has a higher emission efficiency and is useful as a light-emitting material. A light-emitting device using the compound of the present invention as a material can realize an extremely high emission efficiency.

BRIEF DESCRIPTION OF DRAWINGS

FIG. 1 This is a schematic cross-sectional view showing a layer configuration example of an organic electroluminescent device.

FIG. 2 This shows absorption spectra of organic photoluminescent devices using any of compounds 1 to 4 and 6.

FIG. 9 This shows graphs of time-dependent luminance change of organic electroluminescent devices using any of compounds 3 and 6 and a comparative compound 1.

DESCRIPTION OF EMBODIMENTS

Figure 3:
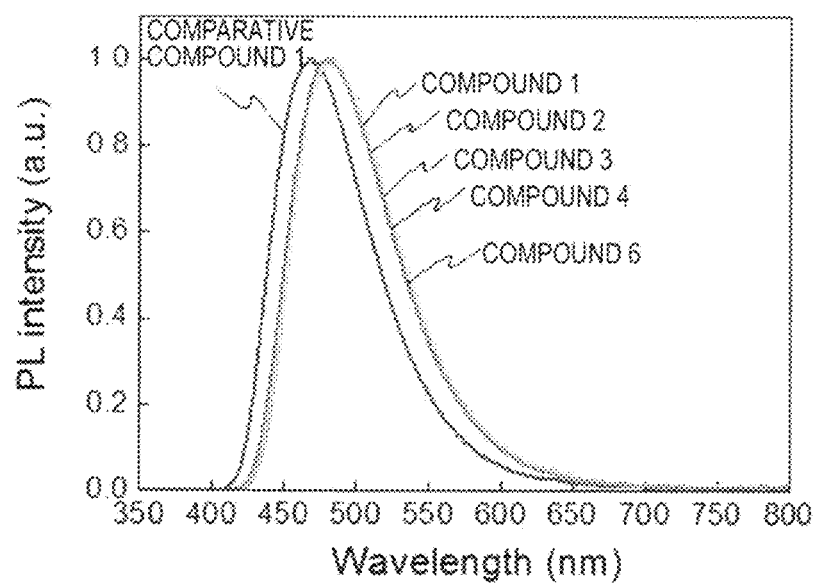
FIG. 3 This shows fluorescence spectra of organic photoluminescent devices using any of compounds 1 to 4 and 6.

The contents of the invention will be described in detail below. The constitutional elements may be described below with reference to representative embodiments and specific examples of the invention, but the invention is not limited to the embodiments and the examples. In the description herein, a numerical range expressed as "to" means a range that includes a numerical range described in the front and the rear of "to" as the upper limit and/or the lower limit. In the invention, the hydrogen atom that is present in the molecules of the compound used in the invention is not particularly limited in isotope species, and for example, all the hydrogen atoms in the molecule may be $^1H$, and all or a part of them may be $^2H$ (deuterium (D)).

[Compound represented by General Formula (1)]

The compound of the present invention is a compound represented by the following general formula (1).

$$(A)m\text{-}L\text{-}(D)n \qquad \text{General Formula (1)}$$

In the general formula (1), L represents an (m+n)-valent aromatic linking group. m and n each correspond to the number of A and the number of D, respectively, bonding to the aromatic linking group. The aromatic linking group represented by L contains an aromatic ring, in which among the substitutable sites of the aromatic ring capable of being substituted with a substituent, A is substituted for a hydrogen atom at a number, m, of sites to bond to a carbon atom, and D is substituted for a hydrogen atom at a number, n, of sites to bond to a carbon atom. Namely, the aromatic linking group represented by L is formed of an aromatic ring from which (m+n) hydrogen atoms are removed. Among the substitutable sites of the aromatic ring capable of being substituted with a substituent, all or a part thereof may be substituted with A or D, but preferably, all the substitutable sites of the aromatic ring are substituted with A or D.

The aromatic ring constituting the aromatic linking group represented by L may be an aromatic ring of hydrocarbon (hereinafter referred to as "aromatic hydrocarbon ring"), or may be an aromatic ring containing a hetero atom (hereinafter referred to as "aromatic hetero ring"). The substitutable group of the aromatic hydrocarbon ring capable of being substituted with a substituent is a methine group (—CH═), and the substitutable group of the aromatic hetero ring capable of being substituted with a substituent includes a methine group (—CH═) and an imino group (—NH—).

The aromatic hydrocarbon ring constituting the aromatic linking group represented by L may be a single ring, or a condensed ring formed through condensation of 2 or more aromatic hydrocarbon rings, or may be a spiro ring formed of 2 or more aromatic hydrocarbon rings that bond in a mode of spiro bonding, or may be a linked ring formed of 2 or more aromatic hydrocarbon rings that link to each other. In the case where 2 or more aromatic hydrocarbon rings link to each other, they may link in a linear or branched manner. The carbon number of the aromatic hydrocarbon ring constituting the aromatic linking group is preferably 6 to 22, more preferably 6 to 18, even more preferably 6 to 14, further more preferably 6 to 10. Specific examples of the aromatic hydrocarbon ring constituting the aromatic linking group include a benzene ring, a naphthalene ring, a biphenyl ring, and a spirofluorene ring.

The aromatic hetero ring constituting the aromatic linking group represented by L may be a single ring, or a condensed ring formed through condensation of 1 or more hetero rings and aromatic hydrocarbon rings or aromatic hetero rings, or may be a spiro ring formed of one hetero ring and one aromatic hydrocarbon ring or aromatic hetero ring that bond in a mode of spiro bonding, or may be a linked ring formed of 1 or more aromatic hetero rings and aromatic hydrocarbon rings or aromatic hetero rings that link to each other. The carbon number of the aromatic hetero ring is preferably 5 to 22, more preferably 5 to 18, even more preferably 5 to 14, further more preferably 5 to 10. The hetero atom constituting the aromatic hetero ring is preferably a nitrogen atom. Specific examples of the aromatic hetero ring include a pyridine ring, a pyridazine ring, a pyrimidine ring, a triazole ring, and a benzotriazole ring.

The aromatic ring constituting the aromatic linking group represented by L is more preferably a benzene ring.

A represents a group having a positive Hammett's $\sigma_p$ value, and D represents a group having a negative Hammett's σp value. However, a phenyl group is included exceptionally in A, but not in D.

Here, "Hammett's $\sigma_p$ value" is one propounded by L. P. Hammett, and is one to quantify the influence of a substituent on the reaction rate or the equilibrium of a para-substituted benzene derivative. Specifically, the value is a constant ($\sigma_p$) peculiar to the substituent in the following equation that is established between a substituent and a reaction rate constant or an equilibrium constant in a para-substituted benzene derivative:

$$\log(k/k_0)=\rho\sigma_p$$

or $$\log(K/K_0)=\rho\sigma_p$$

In the above equations, k represents a rate constant of a benzene derivative not having a substituent; $k_0$ represents a rate constant of a benzene derivative substituted with a substituent; K represents an equilibrium constant of a benzene derivative not having a substituent; $K_0$ represents an equilibrium constant of a benzene derivative substituted with a substituent; ρ represents a reaction constant to be determined by the kind and the condition of reaction. Regarding the description relating to the "Hammett's $\sigma_p$ value" and the numerical value of each substituent, reference may be made to the description relating to $\sigma_p$ value in Hansch, C. et. al., Chem. Rev., 91, 165-195 (1991). A group having a negative Hammett's σp value tends to exhibit electron-donating performance (donor-like performance) and a group having a positive Hammett's σp value tends to exhibit electron-accepting performance (acceptor-like performance).

To the aromatic linking group represented by L, a number, m, of A's bond. m is an integer of 1 or more, and when m is 2 or more, plural A's may be the same as or different from each other. The upper limit of m is, though not specifically limited thereto, preferably smaller than n.

The group having a positive Hammett's σp value represented by A includes, not specifically limited thereto, a cyano group, a group containing a carbonyl group or a sulfonyl group, or a substituted or unsubstituted heteroaryl group. The hetero atom that the heteroaryl group contains include a nitrogen atom, an oxygen atom, a sulfur atom and a boron atom. Preferably, the heteroaryl group contains at least one nitrogen atom as a ring member. Such a heteroaryl group includes a 5-membered or 6-membered ring group containing a nitrogen atom as a ring member, or a group having a condensed ring structure such that a benzene ring is condensed with a 5-membered or 6-membered ring group that contains a nitrogen atom as a ring member, and is preferably a monovalent group formed by removing one hydrogen atom from a pyridine ring, a pyrazine ring, a pyrimidine ring, a pyridazine ring or a triazine ring, or a group having a condensed ring structure such that these aromatic hetero rings have condensed together, or a group having a condensed ring structure such that a benzene ring has condensed with any of these aromatic hetero rings. Also, a monovalent group having a condensed ring structure of a quinone ring or a pyrone ring having condensed with a benzene ring and formed by removing one hydrogen atom from the benzene ring is preferred as a group having a positive Hammett's σp value. Here, the benzene ring having condensed with the quinone ring or the pyrone ring may be substituted with a substituent. In the case where the benzene ring having condensed with a quinone ring or a pyrone ring has a substituent, or where the heteroaryl group has a substituent, examples of the substituent include an alkyl group having 1 to 20 carbon atoms, an aryl group having 6 to 40 carbon atoms, a cyano group, a halogen atom, and a heteroaryl group having 5 to 40 carbon atoms. Among the substituents, those capable of being substituted with a substituent may be substituted. The phenyl group is included in A. When m is 2 or more, the number of the cyano groups among plural A's may be, for example, 0 to 2. A number of 1 is preferred to a number of 2.

In the following, specific examples of the group having a positive Hammett's σp value represented by A are shown. However, in the present invention, the group having a positive Hammett's σp value represented by A is not specifically interpreted by these groups. In those having a ring structure among the groups exemplified hereinunder, a hydrogen atom of any one methine group (—CH═) constituting the ring structure is replaced with L to bond to L. The right and left lines of CO of the carbonyl group (—CO—) and the right and left lines of $SO_2$ of the sulfonyl group (—$SO_2$—) each indicate a single bond (chemical bond). The carbonyl group (—CO—) and the sulfonyl group (—$SO_2$—) each bond directly to L via a single bond, or bond to L via a linking group, and an atomic group bonds to the other single bond. The atomic group includes substituted or unsubstituted alkyl group, aryl group and heteroaryl group, and the carbon umber of the alkyl group is preferably 1 to 20, the carbon number of the aryl group is preferably 6 to 40, and the carbon number of the heteroaryl group is preferably 5 to 40.

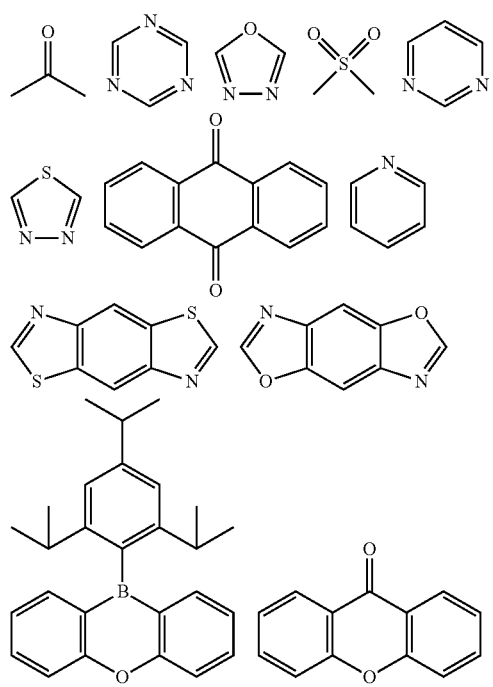

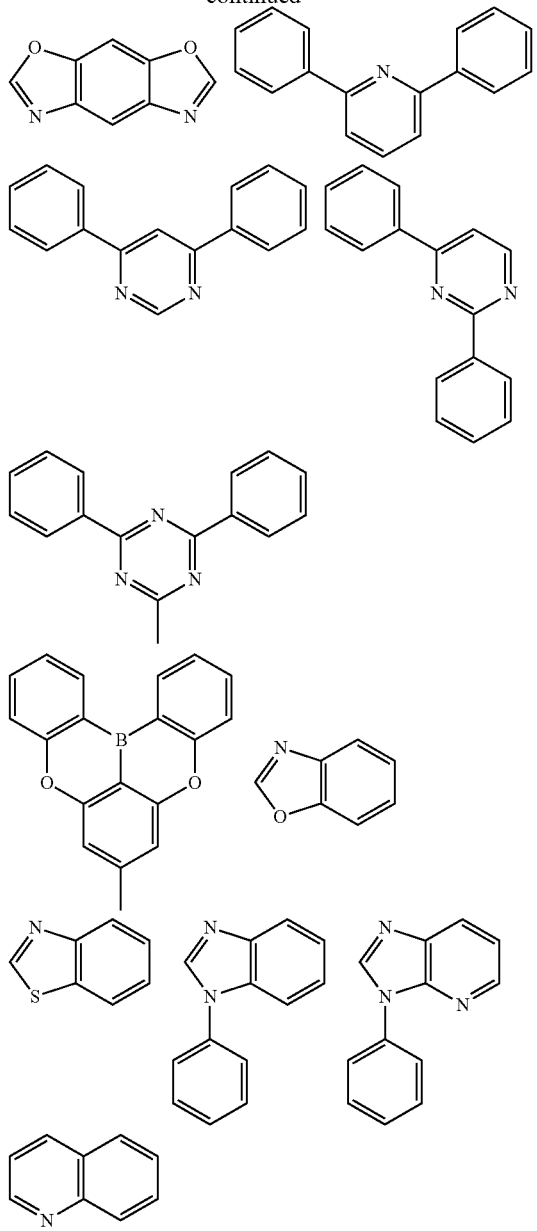

Next described is D.

A number, n, of D's bond to the aromatic linking group represented by L. n is an integer of 2 or more, and two of plural D's each contain an aromatic ring common to them but have a different structure. The type of the common aromatic ring is not specifically limited, and may be an aromatic hydrocarbon ring or an aromatic hetero ring. For the description and the preferred ranges of the aromatic hydrocarbon ring and the aromatic hetero ring, reference may be made to the corresponding site in the following description of the requirements (a) and (b). A preferred aromatic ring is a benzene ring, which, however, is not limitative. Preferred examples of the aromatic ring-containing group include a group containing a diarylamino structure or a carbazolyl structure, which, however, is not also limitative. Preferably, two of plural D's each are a group having a hetero atom, more preferably a group containing a nitrogen atom. Specific structures thereof include groups represented by any of the general formulae (2) to (9) to be mentioned hereinunder.

Preferably, two of plural D's satisfy the following requirement (a) or (b).

Requirement (a)

Two D's each have an aromatic ring that contains an atom bonding to L, and the aromatic ring is common between the two D's, but the two differ from each other in point of at least one condition of the number of the substituents on the aromatic ring, the substitution site of the aromatic ring substituted with the substituent, and the structure of the substituent on the aromatic ring.

Requirement (b)

Two D's each have a linking group that bonds to L and one or more aromatic rings bonding to the linking group, and in the case where the two D's each have one aromatic ring bonding to the linking group, the linking group and the aromatic ring bonding to the linking group are common between the two D's, but the two differ from each other in point of at least one condition of the number of the substituents on the aromatic ring, the substitution site of the aromatic ring substituted with the substituent and the structure of the substituent on the aromatic ring. In the case where the two D's each have two or more aromatic rings each bonding to the linking group, the linking group, the number of the aromatic rings bonding to the linking group, and the plural aromatic rings are common between the two D's, but in at least one combination of the aromatic rings common between the two D's, the two differ from each other in point of at least one condition of the number of the substituents on the aromatic ring, the substitution site of the aromatic ring substituted with the substituent, and the structure of the substituent on the aromatic ring.

In the following description, one of the two D's satisfying the requirement (a) or (b) is referred to as "one D" and the other is referred to as "the other D". The two D's satisfying the requirement (a) or (b) ("one D" and "the other D") may be a pair of plural D's or may also be two or more pairs thereof.

In the requirement (a), the "aromatic ring containing an atom bonding to L" that one D has is referred to as "one aromatic ring", and the "aromatic ring containing an atom bonding to L" that the other D has is referred to as "the other aromatic ring".

In the requirement (b), "in the case where the two D's each have two or more aromatic rings each bonding to the linking group, the linking group, the number of the aromatic rings bonding to the linking group, and the plural aromatic rings are common between the two D's, but in at least one combination of the aromatic rings common between the two D's, the two differ from each other in point of at least one condition of the number of the substituents on the aromatic ring, the substitution site of the aromatic ring substituted with the substituent, and the structure of the substituent on the aromatic ring" is described with reference to one example where, in one D, a benzene ring and a naphthalene ring bond to L via a trivalent linking group. In this case, like in one D, a benzene ring and a naphthalene ring bond to L via a trivalent linking group also in the other D, and in a combination of aromatic rings common to the two, that is, in a combination of the benzene ring in one D and the benzene ring in the other D, or in a combination of the naphthalene ring in one D and the naphthalene ring in the other D, or in both the two combinations, the two differ from each other in point of at least one condition of the number of the substituents on the ring, the substitution site of the ring substituted with the substituent, and the structure of the substituent on the ring. In the requirement (b), in the case where the two D's each have one aromatic ring bonding to the linking group, the "aromatic ring linking to the linking group" that one D has is referred to as "one aromatic ring", and the "aromatic ring bonding to the linking group" that the other D has is referred to as "the other aromatic ring". In the case where the two D's each have two or more aromatic rings bonding to the linking group, one of "the combinations of the aromatic rings common between the two D's" but differ in at least one substituent condition is referred to as "one aromatic ring", and the other is referred to as "the other aromatic ring".

In the following description, "the number of the substituents on the aromatic ring, "the substitution site of the aromatic ring substituted with the substituent", and "the structure of the substituent on the aromatic ring" may be generically referred to as "substituent condition".

The aromatic ring in the requirements (a) and (b) may be an aromatic hydrocarbon ring or an aromatic hetero ring and may be a single ring or a condensed ring. In the case where the aromatic ring constitutes a linked ring structure, the aromatic ring on the side nearest to L in the linked ring structure is the aromatic ring in the requirements (a) and (b). Common aromatic ring means that, between one aromatic ring and the other aromatic ring, the two are all the same in point of the structure except for the number of the hydrogen atoms substituted with a substituent and the substituent condition thereof.

The linking group in the requirement (b) may be a divalent linking group that links L and one aromatic ring, or may be a trivalent or higher linking group that links L and two or more aromatic rings. In the case where two or more aromatic rings bond to the linking group, the aromatic rings bonding to the linking group may be the same as or different from each other.

The difference in the substituent condition between aromatic rings can be determined as follows.

First, one D and another D different from it are compared with each other in point of the number of substituents of the aromatic rings common between the two (the common aromatic ring among the aromatic rings containing an atom bonding to L, or the common aromatic ring among the aromatic rings bonding to L via a linking group). In the case where the two differ in point of the number of substituents, the two are determined to be different from each other in point of the "number of the substituents on the aromatic ring" among the above-mentioned substituent conditions. In the case where the two are the same in point of the number of substituents, the two are compared in point of the position (substitution site) of the aromatic ring substituted with the substituent, and when the two have at least one different substitution site therebetween, they are determined to be different from each other in point of the "substitution site of the aromatic ring substituted with the substituent" among the above-mentioned substituent conditions. In the case where all the substitution sites are the same between the two, the two are compared in point of the structure of the substituent on the aromatic ring. In the case where at least one substituent on the aromatic ring in one D differs from the substituent at the corresponding substitution site of the aromatic ring in the other D in point of the structure, the two are determined to be different from each other in point of the "structure of the substituent on the aromatic ring" among the above-mentioned substituent conditions. Here, the "corresponding substitution site" of the aromatic ring in the other D is the position thereof constitutionally common to the substitution site of the aromatic ring in one D, and specifically, when the structural formulae of the aromatic rings of the two D's are superimposed entirely in point of the substitution sites, the overlapping positions are "the corresponding substitution sites". Alternatively, the positions common between them in point of the position number of the aromatic rings, numbered according to the IUPAC nomenclature system, correspond to "the corresponding substitution sites". However, in the case where the structural formula of the aromatic ring has a line-symmetric structure, this is rotated by 180 degrees around the symmetry axis as a center, and the overlapping positions are also considered to be "corresponding substitution sites", and accordingly, in the case where at least one substituent on the aromatic ring in one D differs from any of the substituents at the corresponding substitution sites of the aromatic ring in the other D, the two are determined to differ in point of "the structure of the substituent on the aromatic ring". For example, a case where a substituent at the 3-position of a carbazole ring differs from both the substituent at the 3-position of another carbazole ring and the substituent at the 6-position thereof corresponds to this case.

"Differ in point of the structure of the substituent" means that the two differ, for example, in point of at least one condition of the kind of the substituent, the kind of the atom constituting the substituent and the number of each atom, presence or absence or the position of a saturated bond, a chain-like structure (a linear structure, a branched structure, the branched position in the case of a branched structure), and a cyclic structure (the number of ring atoms, an aromatic ring or a non-aromatic ring, presence or absence of condensed ring). In the case where two substituents on an aromatic ring bond to each other to form a cyclic structure, the two substituents can be considered as "substituents" in the substituent condition. For example, in the case where an aromatic ring is a naphthalene ring, the naphthalene ring as a whole can be considered as an "aromatic ring", or can also be considered as a benzene ring substituted with a substituent at the neighboring position thereof. In the case where a naphthalene ring is considered as a benzene ring substituted with a substituent at the neighboring position thereof, the relation thereof with an unsubstituted benzene ring is such that the aromatic ring is common between them but the two differ in point of the number of the substituent. In the present invention, a case where the intended aromatic rings are in such a relationship between the two D's is also determined to satisfy the requirement (a) or (b).

Among the substituent conditions, preferably, one aromatic ring differs from the other aromatic ring in point of the "number of the substituents on the aromatic ring", and more preferably, one aromatic ring is substituted with at least one substituent and the other aromatic ring is unsubstituted.

Preferably, two D's satisfying the requirement (a) or (b) each contain a diarylamine structure (provided that the two aryl groups constituting the diarylamine structure may bond to each other). In the present invention, the "diarylamine structure" means a structure such that two aryl groups bond to a nitrogen atom, and the two aryl groups may bond to each other, or each may be substituted with a substituent. For the preferred range and the specific examples of the substituent in the case where the aryl group has a substituent, reference may be made to the preferred range and the specific examples of the substituent that $R^{11}$ to $R^{19}$ in the general formula (2) may have. The aromatic hydrocarbon ring constituting the aryl group of the diarylamine structure may be a single ring, or may also be a condensed ring such that 2 or more aromatic hydrocarbon rings have condensed together. The carbon number of the aromatic hydrocarbon ring constituting the aryl group of the diarylamine structure is preferably 6 to 22, more preferably 6 to 18, even more preferably 6 to 14, further more preferably 6 to 10. Specific examples of the aryl group of the diarylamine structure include a substituted or unsubstituted phenyl group, and a substituted or unsubstituted naphthyl group. In the case where the two aryl groups of the diarylamine structure bond to each other, the two aryl groups may bond via a single bond, or may bond via a linking group. The linking group via which the two aryl groups bond to each other includes an oxygen atom, a sulfur atom, and a substituted or unsubstituted alkylene group. In the case where the alkylene group has a substituent, the substituent includes a substituted or unsubstituted alkyl group, and a substituted or unsubstituted aryl group. Specific examples of the diarylamine structure where the two aryl groups bond to each other include a carbazole structure, a phenoxazine structure, a phenothiazine structure, and an acridine structure, and the two D's satisfying the requirement (a) or (b) preferably contain a carbazole structure.

In a group containing a diarylamine structure, the diarylamine structure may bond to L via a single bond, or may bond to L via a divalent linking group. The divalent linking group is not specifically limited. In the diarylamine structure, any hydrogen atom of the two aryl groups may be replaced with L or a divalent linking group to bond to L or the divalent linking group, or the nitrogen atom in the structure may bond to L or a divalent linking group, but preferably, the nitrogen atom of the diarylamine structure bond to L or a divalent linking group, and more preferably the nitrogen atom of the diarylamine structure directly bond to L (via a single bond). Specifically, the diarylamine structure is preferably a diarylamino group (provided that the two aryl groups constituting the diarylamine structure may bond to each other), more preferably a diarylamino group bonding to L via a single bond.

Here, regarding the relationship between the diarylamine structure and the requirement (a) or (b), first, in the case where the two aryl groups of the diarylamine structure bond to each other and where one aryl group or the nitrogen atom bonds to L via a single bond, the entire diarylamine structure corresponds to the aromatic ring in the requirement (a).

In the case where the two aryl groups of the diarylamine structure bond to each other and where one aryl group or the nitrogen atom bonds to L via a divalent linking group, the divalent linking group corresponds to the linking group in the requirement (b), and the entire diarylamine structure corresponds to the aromatic ring in the requirement (b).

In the case where the two aryl groups of the diarylamine structure do not bond to each other and where one aryl group bonds to L via a single bond, the one aryl group bonding to L via a single bond corresponds to the aromatic ring in the requirement (a).

In the case where the two aryl groups of the diarylamine structure do not bond to each other and where the nitrogen atom of the structure bonds to L via a single bond, the nitrogen atom bonding to L via a single bond corresponds to the linking group in the requirement (b), and the two aryl groups correspond to the aromatic ring in the requirement (b).

In the case where the two aryl groups of the diarylamine structure do not bond to each other and where one aryl group bonds to L via a divalent linking group, the divalent linking group corresponds to the linking group in the requirement (b), and the one aryl group bonding to the divalent linking group corresponds to the aromatic ring in the requirement (b).

In the case where the two aryl groups of the diarylamine structure do not bond to each other and where the nitrogen atom of the structure bonds to L via a divalent linking group, the divalent linking group and the nitrogen atom correspond to the linking group in the requirement (b), and the two aryl groups correspond to the aromatic ring in the requirement (b).

Two D's ("one D" and "the other D") satisfying the requirement (a) are preferably groups represented by the following general formula (2).

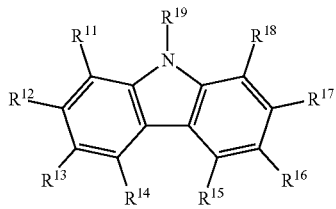

General Formula (2)

In the general formula (2), $R^{11}$ to $R^{19}$ each independently represent a hydrogen atom, a substituent or a bonding position to L, and one of $R^{11}$ to $R^{19}$ is a bonding position to L. One that is a bonding position to L is preferably $R^{19}$. The number of the substituents is not specifically limited. Among $R^{11}$ to $R^{19}$, all except the bonding position to L may be unsubstituted (hydrogen atom). In the case where two or more of $R^{11}$ to $R^{19}$ are substituents, the plural substituents may be the same as or different from each other. However, between the group represented by the general formula (2) that is to be one D and the group represented by the general formula (2) that is to be the other D, at least one condition of the number of the substituents among $R^{11}$ to $R^{19}$, the position of the substituent, and the structure of the substituent differs so as to satisfy the requirement (a).

For example, preferably, in one D, at least one of $R^{11}$ to $R^{18}$ is a substituent and in the other D, one that corresponds to the substituent in one D among $R^{11}$ to $R^{18}$ is a hydrogen atom; and more preferably, in one D, at least one of $R^{13}$ and $R^{16}$ is a substituent and in the other D, one that corresponds to the substituent in one D among $R^{13}$ and $R^{16}$ is a hydrogen atom. Even more preferably, in one D, both $R^{13}$ and $R^{16}$ are substituents, and further more preferably, both $R^{13}$ and $R^{16}$ are substituted or unsubstituted aryl groups. In the other D, even more preferably, all of $R^{11}$ to $R^{18}$ are hydrogen atoms.

Specific examples of the group represented by the general formula (2) are shown below. However, the group represented by the general formula (2) usable in the present invention should not be limitatively interpreted by these specific examples. In the groups exemplified below, a single line extending from the benzene ring and not expressed as a linking group to any other atom indicates a methyl group. The groups exemplified below are such that the hydrogen atom bonding to the 1- to 9-positions of the carbazole ring therein is replaced by L and the group thus bonds to L. The bonding position to L in the carbazole ring is preferably a 9-position thereof. A combination of two D's satisfying the requirement (a) employable herein is, for example, a combination of two groups selected from the following groups.

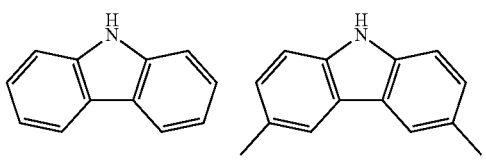

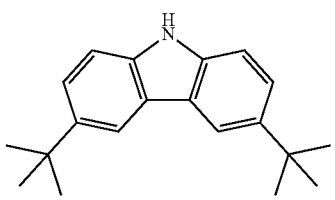

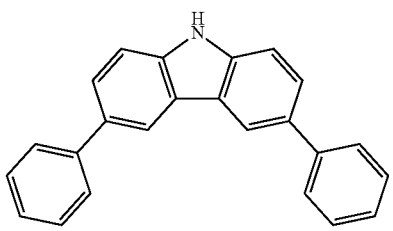

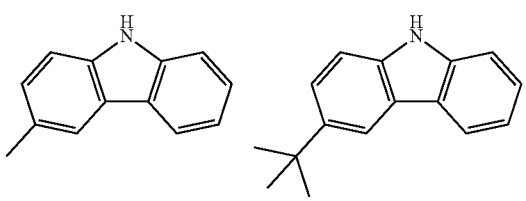

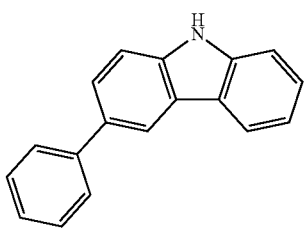

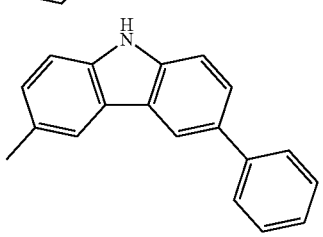

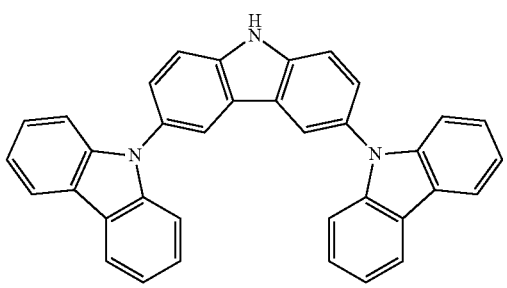

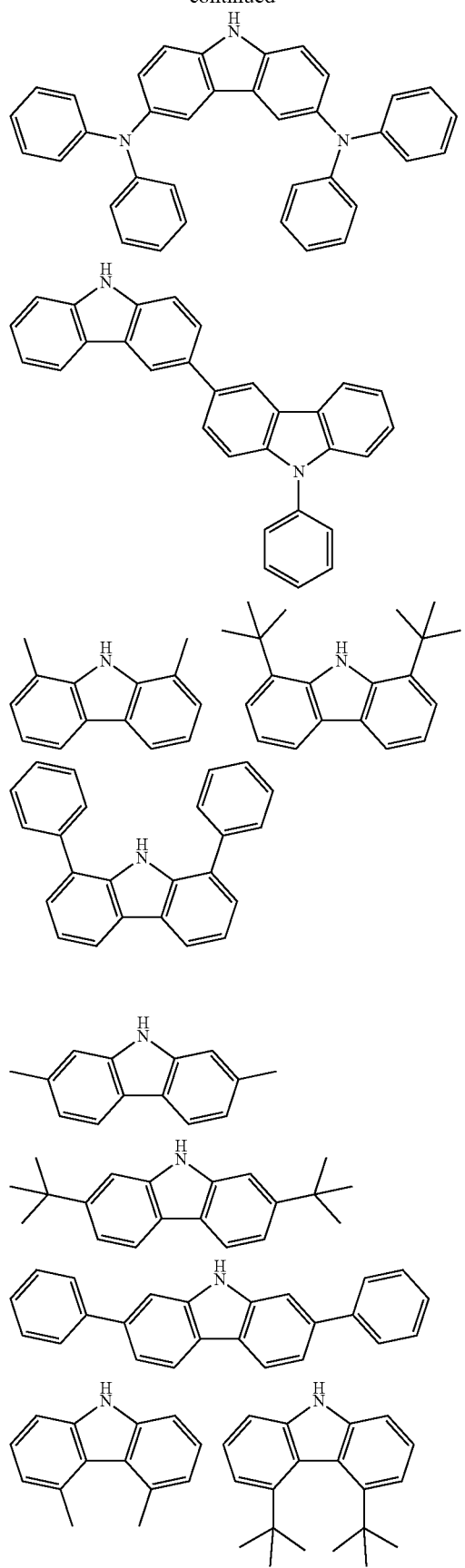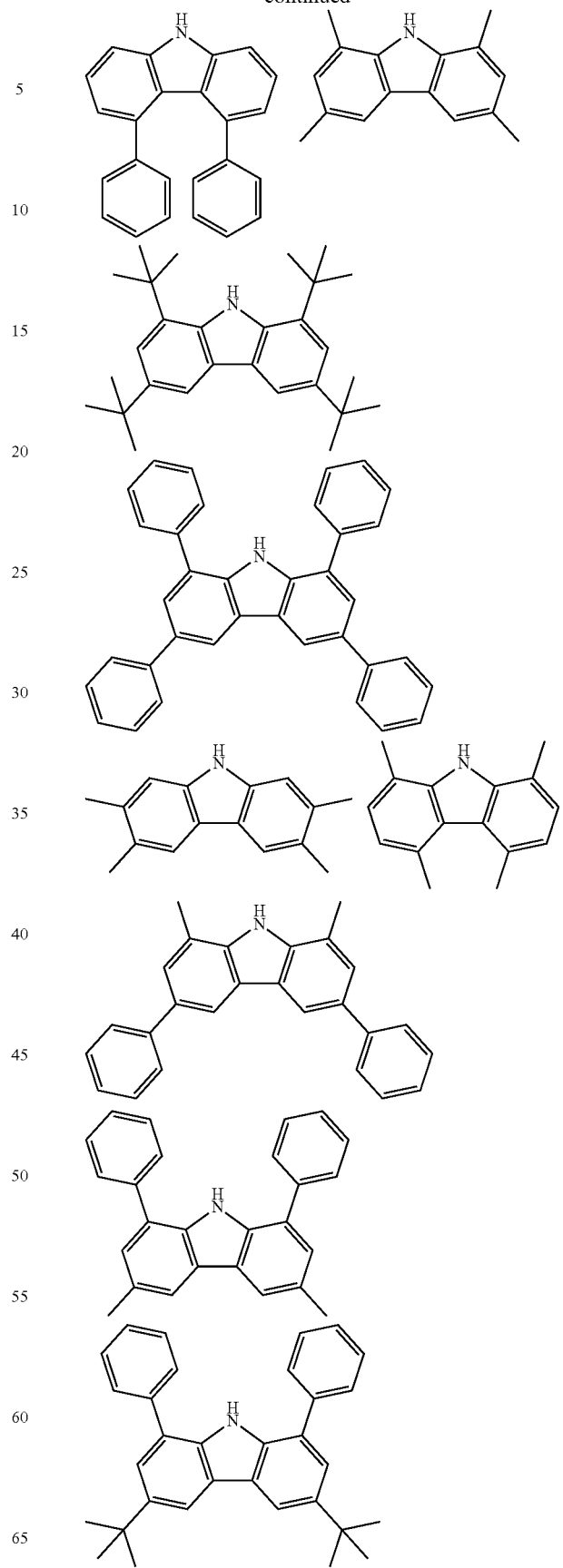

-continued
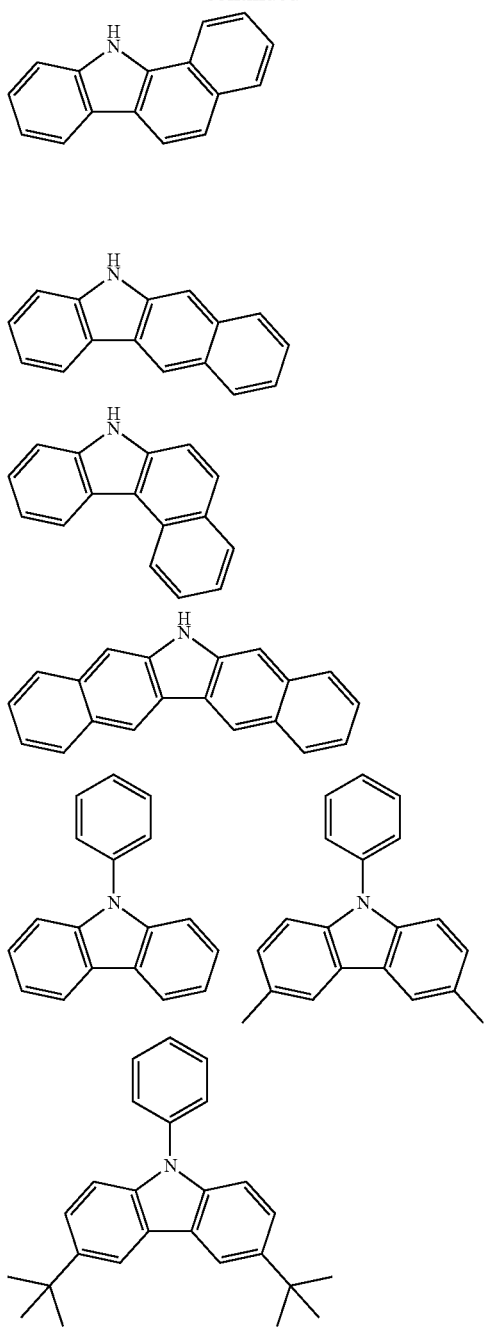
-continued
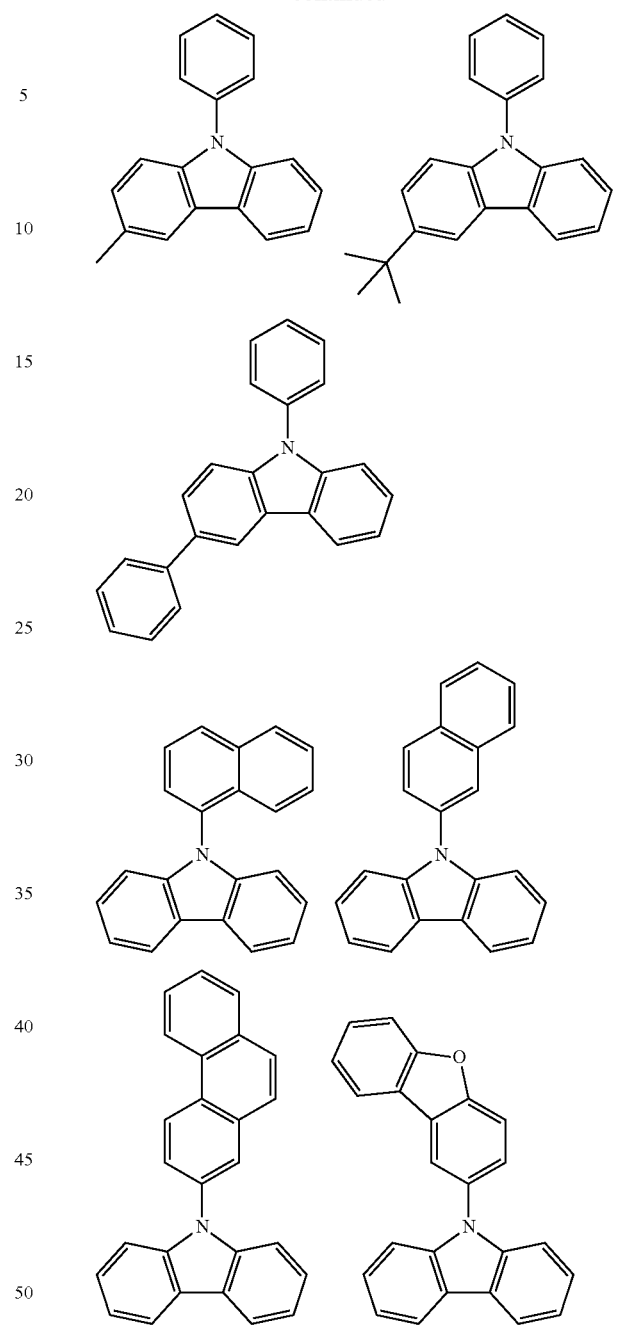
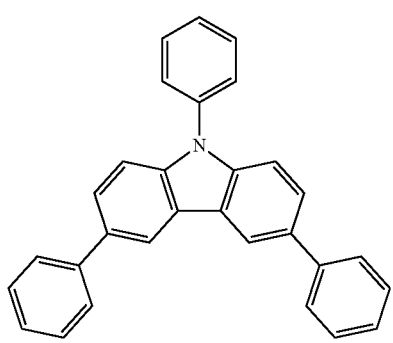
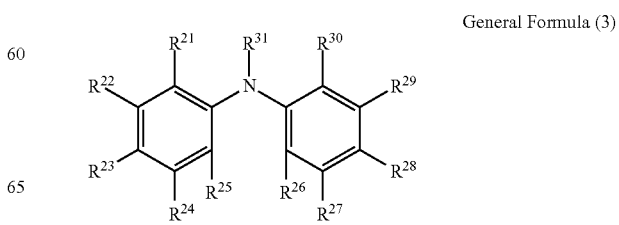
Also preferably, two D's ("one D" and "the other D") satisfying the requirement (a) or (b) are groups represented by any of the following general formulae (3) to (5).
General Formula (3)

General Formula (4)

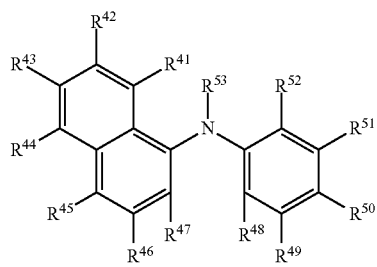

General Formula (5)

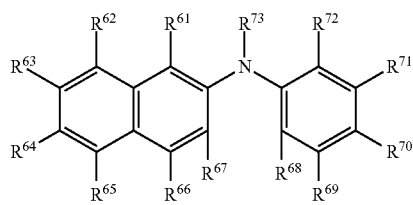

In the general formulae (3) to (5), $R^{21}$ to $R^{31}$, $R^{41}$ to $R^{53}$, and $R^{61}$ to $R^{73}$ each independently represent a hydrogen atom, a substituent or a bonding position to L, one of $R^{21}$ to $R^{31}$, one of $R^{41}$ to $R^{53}$, and one of $R^{61}$ to $R^{73}$ each are a bonding position to L. One that is a bonding position to L is preferably $R^{31}$, $R^{53}$, $R^{73}$. In the case where one of $R^{21}$ to $R^{30}$, one of $R^{41}$ to $R^{52}$, and one of $R^{61}$ to $R^{72}$ each are a bonding position to L, the group represented by any of the general formulae (3) to (5) is one targeted by the requirement (a). In the case where $R^{31}$, $R^{53}$ and $R^{73}$ each are a bonding position to L, the group represented by any of the general formulae (3) to (5) is one targeted by the requirement (b), and in this case, the nitrogen atom corresponds to the linking group in the requirement (b), and the benzene ring and the naphthalene ring bonding to the nitrogen atom correspond to the aromatic ring in the requirement (b). The number of the substituents in the general formulae (3) to (5) is not specifically limited, and among $R^{21}$ to $R^{31}$, $R^{41}$ to $R^{53}$, $R^{61}$ to $R^{67}$, and $R^{68}$ to $R^{72}$, all excepting the bonding position to L may be unsubstituted (hydrogen atom). In the case where the group represented by any of the general formulae (3) to (5) has 2 or more substituents, the substituents may be the same as or different from each other. However, between the group represented by any of the general formulae (3) to (5) to be one D, and the group represented by any of the general formulae (3) to (5) to be the other D, at least any groups of $R^{21}$ to $R^{31}$, $R^{41}$ to $R^{53}$ and $R^{61}$ to $R^{73}$ differ in point of at least one condition of the number of the substituents, the position of the substituent and the structure of the substituent so as to satisfy the requirement (a) or (b).

Specific examples of the groups represented by any of the general formulae (3) to (5) are shown below. However, the groups represented by any of the general formulae (3) to (5) for use in the present invention are not limitatively interpreted by these specific examples. In the groups exemplified below, a single line extending from the benzene ring and not expressed as a linking group to any other atom indicates a methyl group. The groups exemplified below are such that the hydrogen atom of any one methine group (—CH═) constituting the ring structure, or the hydrogen atom bonding to the nitrogen atom is replaced by L and the group thus bonds to L. The bonding position to L in these groups is preferably the nitrogen atom. A combination of two D's satisfying the requirement (a) or (b) employable herein is, for example, a combination of two groups selected from the following groups.

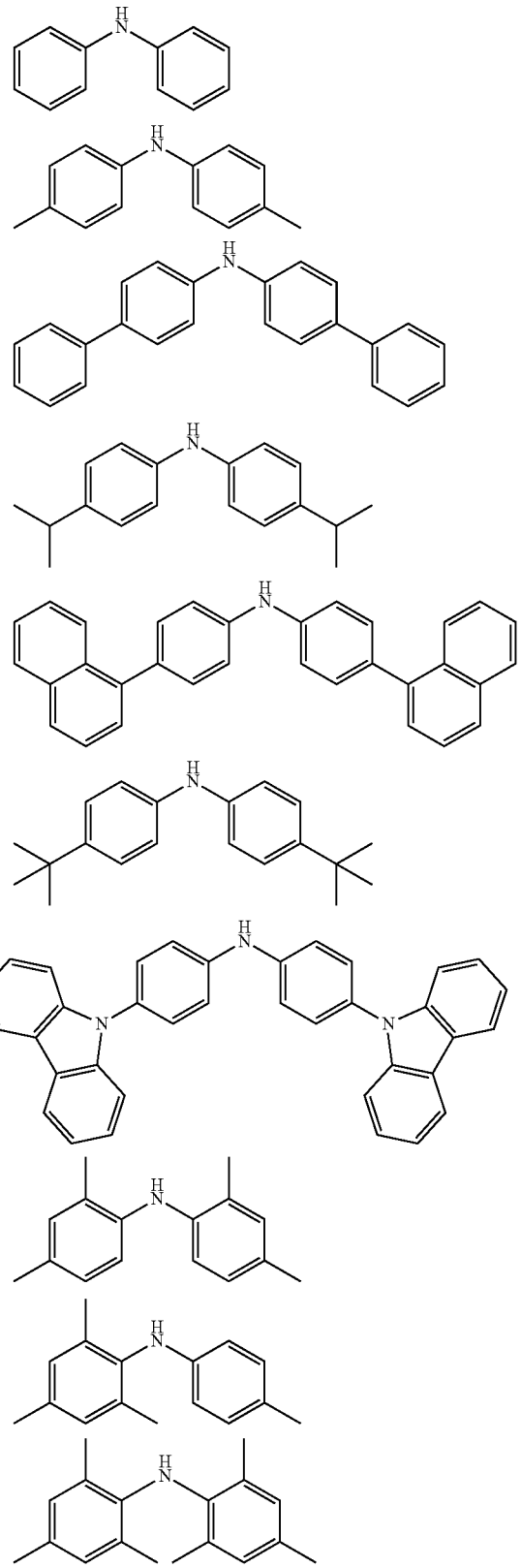

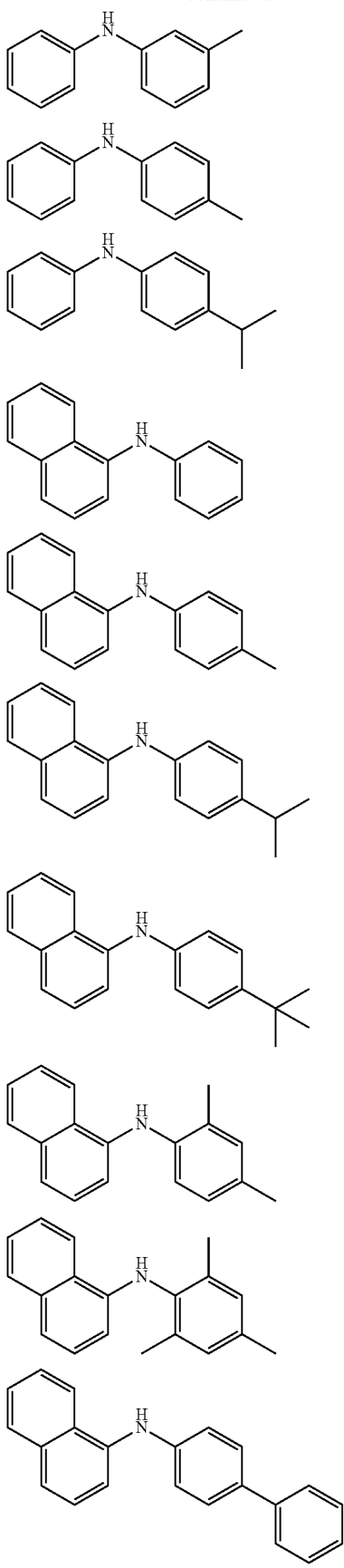
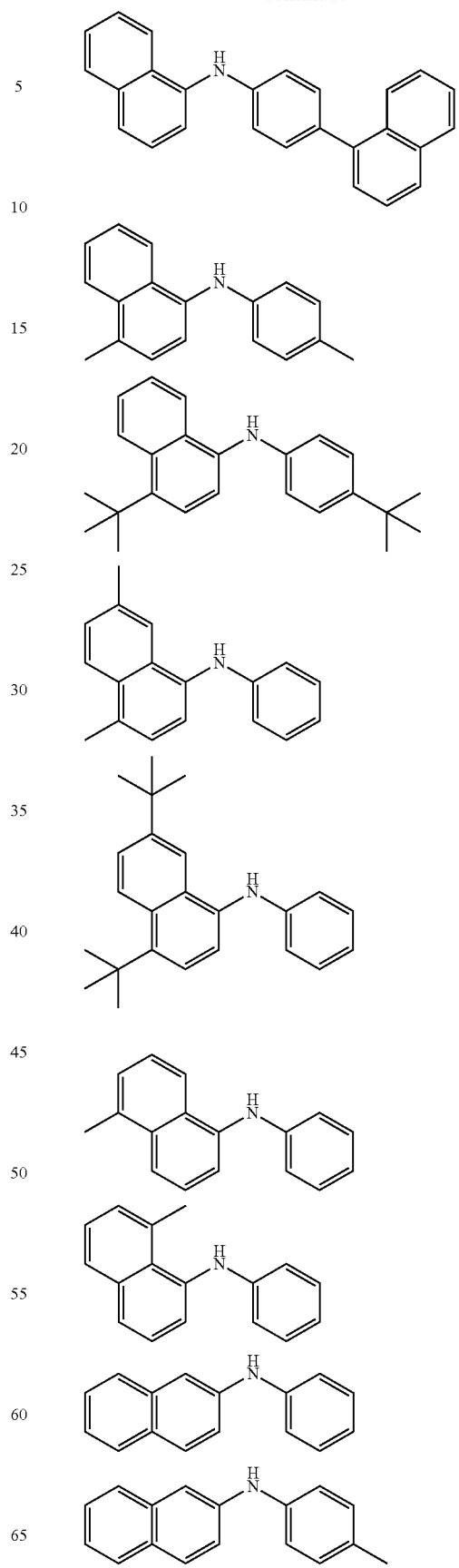

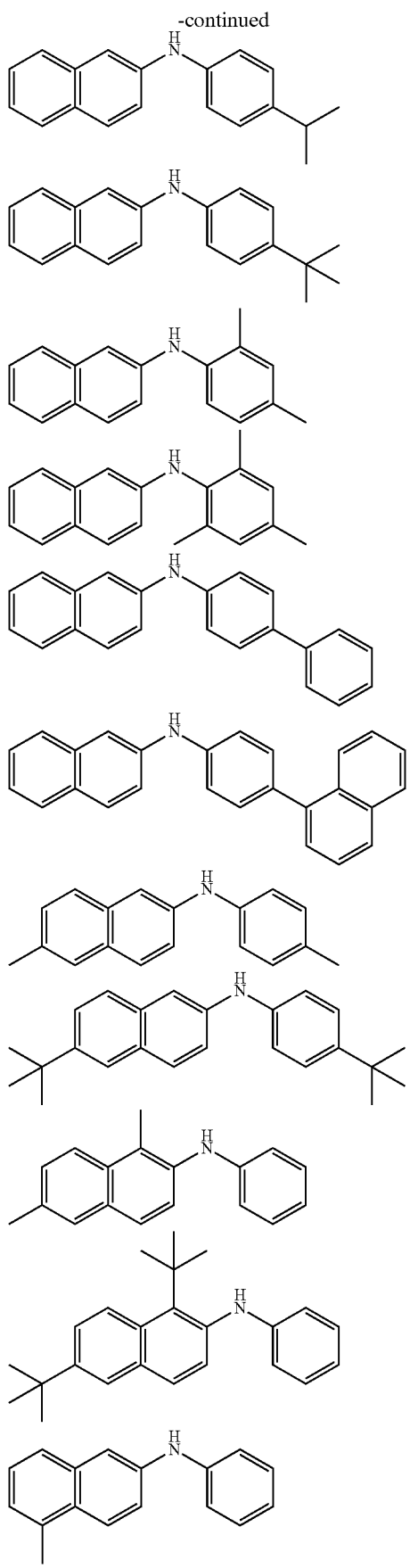
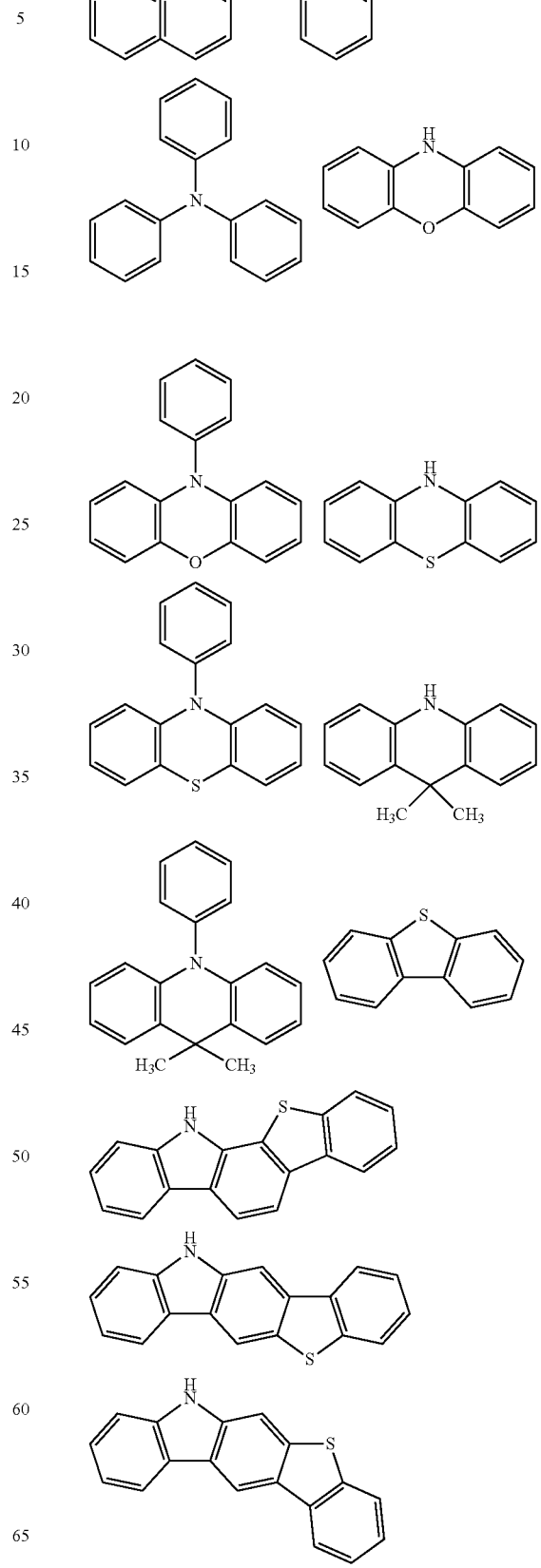

-continued

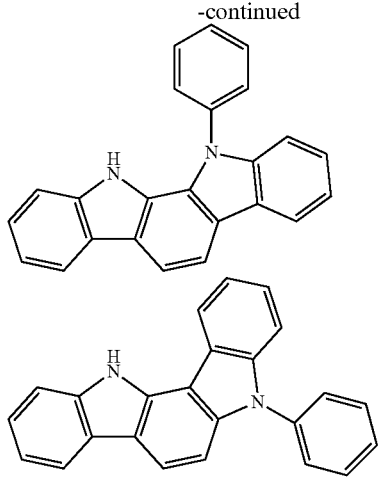

Also preferably, two D's ("one D" and "the other D") satisfying the requirement (a) or (b) are groups represented by the following general formula (6).

General Formula (6)

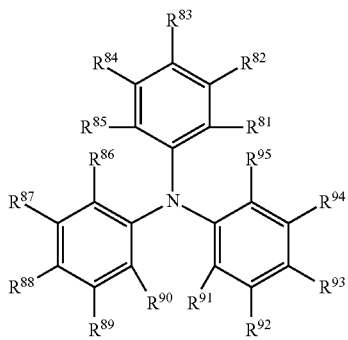

In the general formula (6), $R^{81}$ to $R^{95}$ each independently represent a hydrogen atom, a substituent, or a bonding position to L; one of $R^{81}$ to $R^{95}$ is a bonding position to L. One that is a bonding position to L is preferably $R^{83}$. In the group represented by the general formula (6), the benzene ring having a bonding position to L among the three benzene rings bonding to the nitrogen atom corresponds to the aromatic ring in the requirement (a). Also, the benzene ring having a bonding position to L and the nitrogen atom may be made to correspond to the linking group in the requirement (b), and the remaining two benzene rings can be considered to correspond to the aromatic ring in the requirement (b). The number of the substituents is not specifically limited, and among $R^{81}$ to $R^{95}$, all excepting the bonding position to L may be unsubstituted (hydrogen atom). In the case where 2 or more among $R^{81}$ to $R^{95}$ are substituents, the plural substituents may be the same as or different from each other. However, between the group represented by the general formula (6) to be one D, and the group represented by the general formula (6) to be the other D, at least any groups of $R^{81}$ to $R^{83}$, $R^{86}$ to $R^{90}$ and $R^{91}$ to $R^{95}$ differ in point of at least one condition of the number of the substituents, the position of the substituent and the structure of the substituent so as to satisfy the requirement (a) or (b).

Also preferably, two D's ("one D" and "the other D") satisfying the requirement (a) are groups represented by the following general formula (7).

General Formula (7)

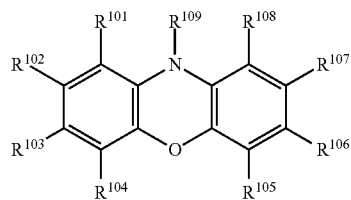

In the general formula (7), $R^{101}$ to $R^{109}$ each independently represent a hydrogen atom, a substituent or a bonding position to L, and one of $R^{101}$ to $R^{109}$ is a bonding position to L. One that is a bonding position to L is preferably $R^{109}$. The number of the substituents is not specifically limited, and among $R^{101}$ to $R^{109}$, all excepting the bonding position to L may be unsubstituted (hydrogen atom). In the case where 2 or more among $R^{101}$ to $R^{109}$ are substituents, the plural substituents may be the same as or different from each other. However, between the group represented by the general formula (7) to be one D, and the group represented by the general formula (7) to be the other D, any groups of $R^{101}$ to $R^{109}$ differ in point of at least one condition of the number of the substituents, the position of the substituent and the structure of the substituent so as to satisfy the requirement (a).

Also preferably, two D's ("one D" and "the other D") satisfying the requirement (a) are groups represented by the following general formula (8).

General Formula (8)

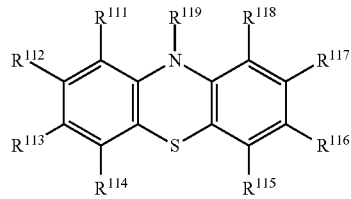

In the general formula (8), $R^{111}$ to $R^{119}$ each independently represent a hydrogen atom, a substituent or a bonding position to L, and one of $R^{111}$ to $R^{119}$ is a bonding position to L. One that is a bonding position to L is preferably $R^{119}$. The number of the substituents is not specifically limited, and among $R^{111}$ to $R^{119}$, all excepting the bonding position to L may be unsubstituted (hydrogen atom). In the case where 2 or more among $R^{111}$ to $R^{119}$ are substituents, the plural substituents may be the same as or different from each other. However, between the group represented by the general formula (8) to be one D, and the group represented by the general formula (8) to be the other D, any groups of $R^{111}$ to $R^{119}$ differ in point of at least one condition of the number of the substituents, the position of the substituent and the structure of the substituent so as to satisfy the requirement (a).

Also preferably, two D's ("one D" and "the other D") satisfying the requirement (a) are groups represented by the following general formula (9).

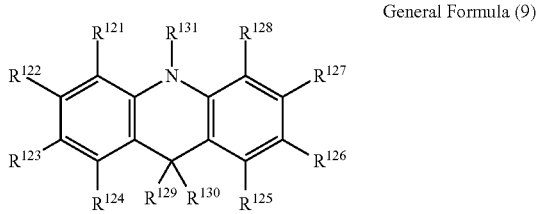

General Formula (9)

In the general formula (9), $R^{121}$ to $R^{131}$ each independently represent a hydrogen atom, a substituent or a bonding position to L, and one of $R^{121}$ to $R^{131}$ is a bonding position to L. One that is a bonding position to L is preferably $R^{131}$. The number of the substituents is not specifically limited, and among $R^{121}$ to $R^{131}$, all excepting the bonding position to L may be unsubstituted (hydrogen atom). In the case where 2 or more among $R^{121}$ to $R^{131}$ are substituents, the plural substituents may be the same as or different from each other. However, between the group represented by the general formula (9) to be one D, and the group represented by the general formula (9) to be the other D, any groups of $R^{121}$ to $R^{131}$ differ in point of at least one condition of the number of the substituents, the position of the substituent and the structure of the substituent so as to satisfy the requirement (a).

Examples of the substituents that $R^{11}$ to $R^{19}$ in the general formula (2), $R^{21}$ to $R^{31}$ in the general formula (3), $R^{41}$ to $R^{53}$ in the general formula (4), $R^{61}$ to $R^{73}$ in the general formula (5), $R^{81}$ to $R^{95}$ in the general formula (6), $R^{101}$ to $R^{109}$ in the general formula (7), $R^{111}$ to $R^{119}$ in the general formula (8) and $R^{121}$ to $R^{131}$ in the general formula (9) may have include a hydroxy group, a halogen atom, a cyano group, an alkyl group having 1 to 20 carbon atoms, an alkoxy group having 1 to 20 carbon atoms, an alkylthio group having 1 to 20 carbon atoms, an alkyl-substituted amino group having 1 to 20 carbon atoms, an acyl group having 2 to 20 carbon atoms, an aryl group having 6 to 40 carbon atoms, a heteroaryl group having 3 to 40 carbon atoms, an alkenyl group having 2 to 10 carbon atoms, an alkynyl group having 2 to 10 carbon atoms, an alkoxycarbonyl group having 2 to 10 carbon atoms, an alkylsulfonyl group having 1 to 10 carbon atoms, a haloalkyl group having 1 to 10 carbon atoms, an amide group, an alkylamide group having 2 to 10 carbon atoms, a trialkylsilyl group having 3 to 20 carbon atoms, a trialkylsilylalkyl group having 4 to 20 carbon atoms, a trialkylsilylalkenyl group having 5 to 20 carbon atoms, a trialkylsilylalkynyl group having 5 to 20 carbon atoms, and a nitro group. Among these substituents, those further substitutable with a substituent may be substituted with, for example, a substituent of these specific examples. More preferred examples of the substituent include a substituted or unsubstituted alkyl group having 1 to 20 carbon atoms, an alkoxy group having 1 to 20 carbon atoms, a substituted or unsubstituted aryl group having 6 to 40 carbon atoms, a substituted or unsubstituted diarylamino group having 1 to 20 carbon atoms, and a substituted or unsubstituted carbazolyl group.

The other groups than those satisfying the requirement (a) or (b) among D may be any groups having a negative Hammett's σp value with no other limitation, but are preferably ones having a diarylamine structure (provided that the two aryl groups constituting the diarylamine structure may bond to each other), more preferably ones including a diarylamino group (provided that the two aryl groups constituting the diarylamino group may bond to each other), and are even more preferably the groups represented by the general formulae (2) to (9). For the description, the preferred ranges and specific examples of these structures and groups, reference may be made to the description, the preferred ranges and the specific examples of the diarylamine structure, the diarylamino group and the groups represented by the general formulae (2) to (9) in the two D's satisfying the requirement (a) or (b), given hereinabove. Regarding the reference, however, the description relating to the requirement (a) or (b) is not included in the contents to be referred to therein.

The compound represented by the general formula (1) is preferably a compound represented by the following general formula (10).

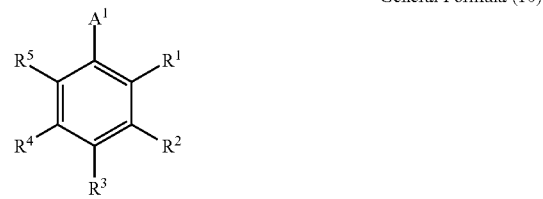

General Formula (10)

In the general formula (10), $A^1$ represents a group having a positive Hammett's σp value; $R^1$ to $R^5$ each independently represent a hydrogen atom, a group having a positive Hammett's σp value, or a group having a negative Hammett's σp value; at least two of $R^1$ to $R^5$ each are a group having a negative Hammett's σp value (but excluding a phenyl group); when one or more of $R^1$ to $R^5$ each are a group having a positive Hammett's σp value, the group having a positive Hammett's σp value represented by $A^1$ and the group having a positive Hammett's σp value among $R^1$ to $R^5$ may be the same as or different from each other.

Two groups having a negative Hammett's σp value among $R^1$ to $R^5$ preferably satisfy the following requirement (a) or requirement (b).

Requirement (a)

Two groups having a negative Hammett's σp value each have an aromatic ring that contains an atom bonding to L, and the aromatic ring is common between the two groups having a negative Hammett's σp value, but the two differ from each other in point of at least one condition of the number of the substituents on the aromatic ring, the substitution site of the aromatic ring substituted with the substituent, and the structure of the substituent on the aromatic ring.

Requirement (b) Two groups having a negative Hammett's σp value each have a linking group that bonds to L and one or more aromatic rings bonding to the linking group, and in the case where the two groups having a negative Hammett's σp value each have one aromatic ring bonding to the linking group, the linking group and the aromatic ring bonding to the linking group are common between the two groups having a negative Hammett's σp value, but the two differ from each other in point of at least one condition of the number of the substituents on the aromatic ring, the substitution site of the aromatic ring substituted with the substituent and the structure of the substituent on the aromatic ring. In the case where the two groups having a negative Hammett's σp value each have two or more aromatic rings each bonding to the linking group, the linking group, the number of the aromatic rings bonding to the linking group, and the plural aromatic rings are common between the two groups having a negative Hammett's σp value, but in at least one combination of the aromatic rings common between the two groups having a negative Hammett's σp value, the two differ from each other in point of at least one condition of the number of the substituents on the aromatic ring, the substitution site of the aromatic ring substituted with the substituent, and the structure of the substituent on the aromatic ring.

For the description, the preferred ranges, the specific examples of the group having a positive Hammett's σp value represented by $A^1$, and $R^1$ to $R^5$, the group having a negative Hammett's σp value represented by $R^1$ to $R^5$, and two groups of $R^1$ to $R^5$ having a negative Hammett's σp value, and for the description of the requirements (a) and (b), reference may be made to the description, the preferred ranges and the specific examples of the group having a positive Hammett's σp value represented by A in the general formula (1), the group having a negative Hammett's σp value represented by D therein and two of plural D's, and also to the description relating to the requirements (a) and (b) given hereinabove.

Preferably, the number of the groups having a positive Hammett's σp value of $R^1$ to $R^5$ is 0 to 3, more preferably 0 to 2, even more preferably 0 or 1, most preferably 0. The number of the groups having a negative Hammett's σp value of $R^1$ to $R^5$ is preferably 2 to 5, more preferably 3 to 5, even more preferably 4 or 5, most preferably 5. Among $R^1$ to $R^5$, one pair or two pairs of two groups may satisfy the requirement (a) or the requirement (b). The combination of two groups satisfying the requirement (a) or the requirement (b) is preferably a combination of groups that are in point symmetry relative to the benzene ring in the general formula (10). Specifically, one or both of a combination of $R^1$ and $R^4$ and a combination of $R^2$ and $R^5$ preferably satisfy the requirement (a) or the requirement (b).

The compound represented by the general formula (1) is also preferably a compound represented by the following general formula (11).

General Formula (11)

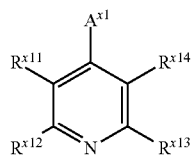

In the general formula (11), $A^{X1}$ represents a group having a positive Hammett's σp value, $R^{X11}$ to $R^{X14}$ each independently represent a hydrogen atom, a group having a positive Hammett's σp value or a group having a negative Hammett's σp value; at least two of $R^{X11}$ to $R^{X14}$ each are a group having a negative Hammett's σp value (but excluding a phenyl group); when one or more of $R^{X11}$ to $R^{X14}$ each are a group having a positive Hammett's σp value, the group having a positive Hammett's σp value represented by $A^{X1}$ and the group having a positive Hammett's σp value among $R^{X11}$ to $R^{X14}$ may be the same as or different from each other.

Preferably, two of $R^{X11}$ to $R^{X14}$ each having a negative Hammett's σp value satisfy the above-mentioned requirement (a) or requirement (b).

For the description, the preferred ranges and the specific examples of the group having a positive Hammett's σp value represented by $A^1$ and $R^{X11}$ to $R^{X14}$, the group having a negative Hammett's σp value represented by $R^{X11}$ to $R^{X14}$, and two groups each having a negative Hammett's σp value among $R^{X11}$ to $R^{X14}$, and for the description of the requirements (a) and (b), reference may be made to the description, the preferred ranges and the specific examples of the group having a positive Hammett's σp value represented by A in the general formula (1), the group having a negative Hammett's σp value represented by D therein, and two groups of plural D's, and to the description of the requirements (a) and (b) given hereinabove.

Preferably, the number of the groups having a positive Hammett's σp value of $R^{X11}$ to $R^{X14}$ is 0 to 2, more preferably 0 or 1, most preferably 0. The number of the groups having a negative Hammett's σp value of $R^{X11}$ to $R^{X14}$ is preferably 2 to 4, more preferably 3 or 4, even more preferably 4. Among $R^{X11}$ to $R^{X14}$, one pair or two pairs of two groups may satisfy the requirement (a) or the requirement (b).

Specific examples of the compound represented by the general formula (1) are shown below. Among the specific examples, compounds 1 to 7 are specifically shown in the following Tables and the structural formulae thereof are also shown below. Compound 8 and others are specifically shown only in the following Tables. However, the compound represented by the general formula (1) for use in the present invention should not be limitatively interpreted by these specific examples.

Compound 1

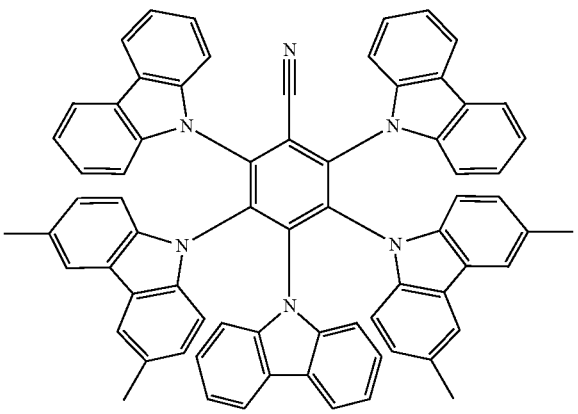

Compound 2

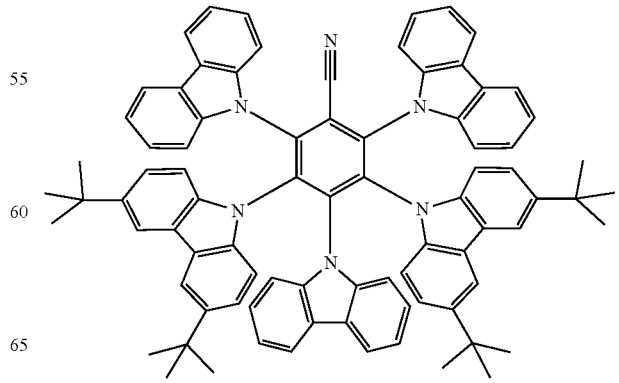

Compound 3
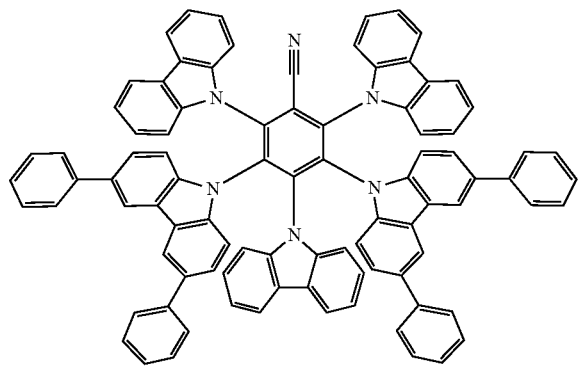
Compound 4
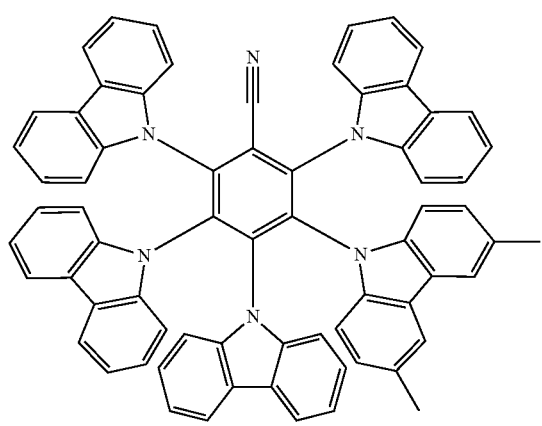
Compound 5
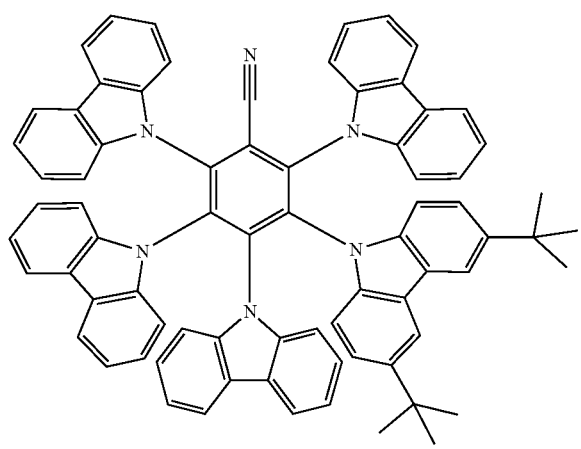
Compound 6
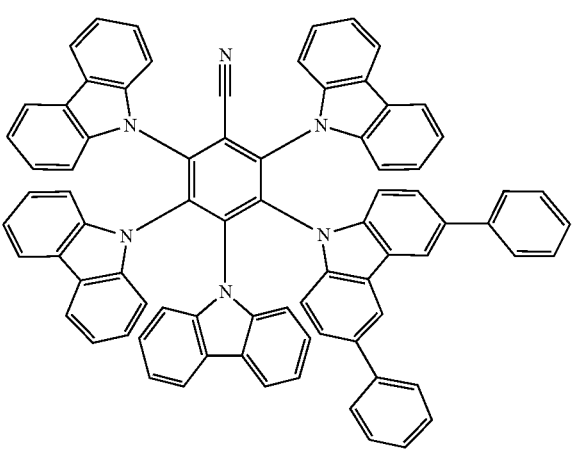
Compound 7
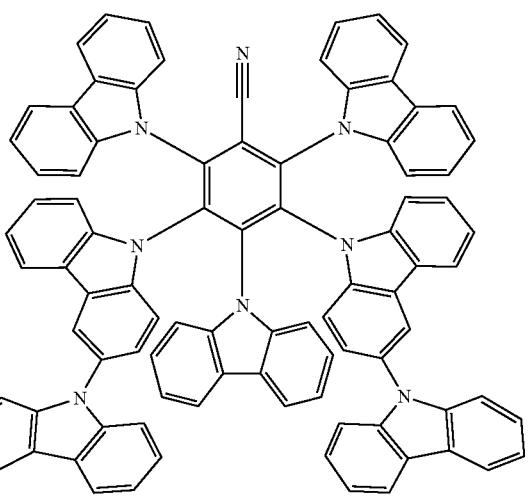
Specific examples of the compounds represented by the general formula (10) and the general formula (11) are shown in the following Table. A general formula (2a) and a general formula (2b) representing the substituents in the general formula (10) and the general formula (11) are shown below.
General Formula (10)
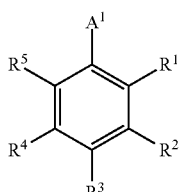
General Formula (11)
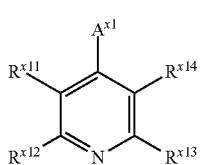

-continued
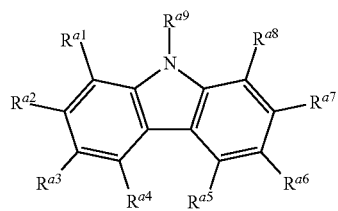
General Formula (2a)
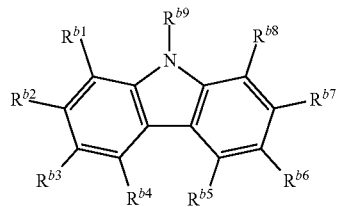
General Formula (2b)

TABLE 1

| Compound No. | A¹ | General Formula (10) R¹ | R² | R³ | R⁴ | R⁵ | General Formula (2a) R^{a1} | R^{a2} | R^{a3} | R^{a4} | R^{a5} | R^{a6} |
|---|---|---|---|---|---|---|---|---|---|---|---|---|
| 1 | CN | General Formula (2a) | General Formula (2b) | General Formula (2b) | General Formula (2a) | General Formula (2a) | H | H | H | H | H | H |
| 2 | CN | General Formula (2a) | General Formula (2b) | General Formula (2b) | General Formula (2a) | General Formula (2a) | H | H | H | H | H | H |
| 3 | CN | General Formula (2a) | General Formula (2b) | General Formula (2b) | General Formula (2a) | General Formula (2a) | H | H | H | H | H | H |
| 4 | CN | General Formula (2a) | General Formula (2b) | General Formula (2b) | General Formula (2a) | General Formula (2a) | H | H | H | H | H | H |
| 5 | CN | General Formula (2a) | General Formula (2b) | General Formula (2b) | General Formula (2a) | General Formula (2a) | H | H | H | H | H | H |
| 6 | CN | General Formula (2a) | General Formula (2b) | General Formula (2b) | General Formula (2a) | General Formula (2a) | H | H | H | H | H | H |
| 7 | CN | General Formula (2a) | General Formula (2b) | General Formula (2b) | General Formula (2a) | General Formula (2a) | H | H | H | H | H | H |
| 8 | CN | General Formula (2a) | General Formula (2b) | General Formula (2b) | General Formula (2a) | General Formula (2a) | H | H | H | H | H | H |
| 9 | CN | General Formula (2a) | General Formula (2b) | General Formula (2b) | General Formula (2a) | General Formula (2a) | H | H | H | H | H | H |
| 10 | CN | General Formula (2a) | General Formula (2b) | General Formula (2b) | General Formula (2a) | General Formula (2a) | H | H | H | H | H | H |
| 11 | CN | General Formula (2a) | General Formula (2b) | General Formula (2b) | General Formula (2a) | General Formula (2a) | H | H | H | H | H | H |
| 12 | CN | General Formula (2a) | General Formula (2b) | General Formula (2b) | General Formula (2a) | General Formula (2a) | H | H | H | H | H | H |
| 13 | CN | General Formula (2a) | General Formula (2b) | General Formula (2b) | General Formula (2a) | General Formula (2a) | H | H | H | H | H | H |
| 14 | CN | General Formula (2a) | General Formula (2b) | General Formula (2b) | General Formula (2a) | General Formula (2a) | H | H | H | H | H | H |
| 15 | CN | General Formula (2a) | General Formula (2b) | General Formula (2b) | General Formula (2a) | General Formula (2a) | H | H | H | H | H | H |
| 16 | CN | General Formula (2a) | General Formula (2b) | General Formula (2b) | General Formula (2a) | General Formula (2a) | H | H | H | H | H | H |
| 17 | CN | General Formula (2a) | General Formula (2b) | General Formula (2b) | General Formula (2a) | General Formula (2a) | H | H | CH₃ | H | H | CH₃ |
| 18 | CN | General Formula (2a) | General Formula (2b) | General Formula (2b) | General Formula (2a) | General Formula (2a) | H | H | CH₃ | H | H | CH₃ |
| 19 | CN | General Formula (2a) | General Formula (2b) | General Formula (2b) | General Formula (2a) | General Formula (2a) | H | H | CH₃ | H | H | CH₃ |
| 20 | CN | General Formula (2a) | General Formula (2b) | General Formula (2b) | General Formula (2a) | General Formula (2a) | H | H | tert-C₄H₉ | H | H | tert-C₄H₉ |
| 21 | CN | General Formula (2a) | General Formula (2b) | General Formula (2b) | General Formula (2a) | General Formula (2a) | H | H | Phenyl | H | H | Phenyl |
| 22 | CN | General Formula (2a) | General Formula (2b) | General Formula (2b) | General Formula (2a) | General Formula (2a) | H | H | H | H | H | H |
| 23 | CN | General Formula (2a) | General Formula (2b) | General Formula (2b) | General Formula (2a) | General Formula (2a) | H | H | Phenyl | H | H | Phenyl |
| 24 | CN | General Formula (2a) | General Formula (2b) | General Formula (2b) | General Formula (2a) | General Formula (2a) | H | H | H | H | H | H |
| 25 | CN | General Formula (2a) | General Formula (2b) | General Formula (2b) | General Formula (2a) | General Formula (2a) | H | H | H | H | H | H |
| 26 | CN | General Formula (2a) | General Formula (2b) | General Formula (2b) | General Formula (2a) | General Formula (2a) | H | H | H | H | H | H |
| 27 | CN | General Formula (2a) | General Formula (2b) | General Formula (2b) | General Formula (2a) | General Formula (2a) | H | H | H | H | H | H |
| 28 | CN | General Formula (2a) | General Formula (2b) | General Formula (2b) | General Formula (2a) | General Formula (2a) | H | H | H | H | H | H |
| 29 | CN | General Formula (2a) | General Formula (2b) | General Formula (2b) | General Formula (2a) | General Formula (2a) | H | H | H | H | H | H |
| 30 | CN | General Formula (2a) | General Formula (2b) | General Formula (2b) | General Formula (2a) | General Formula (2a) | H | H | H | H | H | H |
| 31 | CN | General Formula (2a) | General Formula (2b) | General Formula (2b) | General Formula (2a) | General Formula (2a) | H | H | H | H | H | H |
| 32 | CN | General Formula (2a) | General Formula (2b) | General Formula (2b) | General Formula (2a) | General Formula (2a) | H | H | H | H | H | H |
| 33 | CN | General Formula (2a) | General Formula (2b) | Phenyl | General Formula (2a) | General Formula (2a) | H | H | H | H | H | H |
| 34 | CN | General Formula (2a) | General Formula (2b) | Phenyl | General Formula (2a) | General Formula (2a) | H | H | H | H | H | H |
| 35 | CN | General Formula (2a) | General Formula (2b) | Phenyl | General Formula (2a) | General Formula (2a) | H | H | H | H | H | H |
| 36 | CN | General Formula (2a) | General Formula (2b) | Phenyl | General Formula (2a) | General Formula (2a) | H | H | H | H | H | H |
| 37 | CN | General Formula (2a) | General Formula (2b) | Phenyl | General Formula (2a) | General Formula (2a) | H | H | H | H | H | H |
| 38 | CN | General Formula (2a) | General Formula (2b) | Phenyl | General Formula (2a) | General Formula (2a) | H | H | H | H | H | H |
| 39 | CN | General Formula (2a) | General Formula (2b) | Phenyl | General Formula (2a) | General Formula (2a) | H | H | H | H | H | H |
| 40 | CN | General Formula (2a) | General Formula (2b) | Phenyl | General Formula (2a) | General Formula (2a) | H | H | H | H | H | H |
| 41 | CN | General Formula (2a) | General Formula (2b) | Phenyl | General Formula (2a) | General Formula (2a) | H | H | H | H | H | H |
| 42 | CN | General Formula (2a) | General Formula (2b) | Phenyl | General Formula (2a) | General Formula (2a) | H | H | H | H | H | H |
| 43 | CN | General Formula (2a) | General Formula (2b) | Phenyl | General Formula (2a) | General Formula (2a) | H | H | H | H | H | H |
| 44 | CN | General Formula (2a) | General Formula (2b) | Phenyl | General Formula (2a) | General Formula (2a) | H | H | H | H | H | H |
| 45 | CN | General Formula (2a) | General Formula (2b) | Phenyl | General Formula (2a) | General Formula (2a) | H | H | CH₃ | H | H | CH₃ |
| 46 | CN | General Formula (2a) | General Formula (2b) | Phenyl | General Formula (2a) | General Formula (2a) | H | H | CH₃ | H | H | CH₃ |
| 47 | CN | General Formula (2a) | General Formula (2b) | Phenyl | General Formula (2a) | General Formula (2a) | H | H | CH₃ | H | H | CH₃ |

TABLE 1-continued

| # | | | | | | | | | |
|---|---|---|---|---|---|---|---|---|---|
| 48 | CN | General Formula (2a) | General Formula (2b) | General Formula (2b) | H | H | Phenyl | H | Phenyl |
| 49 | CN | General Formula (2a) | General Formula (2b) | General Formula (2b) | H | H | Phenyl | H | Phenyl |
| 50 | CN | General Formula (2a) | General Formula (2b) | General Formula (2b) | H | H | H | H | H |
| 51 | CN | General Formula (2a) | General Formula (2b) | General Formula (2a) | H | H | H | H | H |
| 52 | CN | General Formula (2a) | General Formula (2b) | General Formula (2a) | H | H | H | H | H |
| 53 | CN | General Formula (2a) | Phenyl | General Formula (2a) | H | H | H | H | H |
| 54 | CN | General Formula (2a) | Phenyl | General Formula (2a) | H | H | H | H | H |
| 55 | CN | General Formula (2a) | H | General Formula (2a) | H | H | H | H | H |
| 56 | CN | General Formula (2a) | H | General Formula (2a) | H | H | H | H | H |
| 57 | CN | General Formula (2a) | H | General Formula (2a) | H | H | H | H | H |
| 58 | CN | General Formula (2a) | H | General Formula (2a) | H | H | H | H | H |
| 59 | CN | General Formula (2a) | General Formula (2a) | General Formula (2a) | H | H | H | H | H |
| 60 | CN | General Formula (2a) | General Formula (2a) | General Formula (2b) | H | H | H | H | H |
| 61 | CN | General Formula (2a) | General Formula (2a) | General Formula (2b) | H | H | H | H | H |
| 62 | CN | General Formula (2a) | General Formula (2a) | General Formula (2b) | H | H | H | H | H |
| 63 | CN | General Formula (2a) | General Formula (2a) | General Formula (2b) | H | H | CH$_3$ | H | CH$_3$ |
| 64 | CN | General Formula (2a) | General Formula (2a) | General Formula (2b) | H | H | H | H | H |
| 65 | CN | General Formula (2a) | General Formula (2a) | General Formula (2b) | H | H | H | H | H |
| 66 | CN | General Formula (2a) | General Formula (2a) | General Formula (2b) | H | H | CH$_3$ | H | CH$_3$ |
| 67 | CN | General Formula (2a) | General Formula (2a) | General Formula (2b) | H | H | H | H | H |
| 68 | CN | General Formula (2a) | General Formula (2a) | General Formula (2b) | H | H | CH$_3$ | H | CH$_3$ |
| 69 | CN | General Formula (2a) | General Formula (2a) | General Formula (2b) | H | H | CH$_3$ | H | CH$_3$ |
| 70 | CN | General Formula (2a) | General Formula (2a) | General Formula (2b) | H | H | CH$_3$ | H | CH$_3$ |
| 71 | CN | General Formula (2a) | General Formula (2a) | General Formula (2b) | H | H | H | H | H |
| 72 | CN | General Formula (2a) | General Formula (2a) | General Formula (2b) | H | H | H | H | H |
| 73 | CN | General Formula (2a) | General Formula (2a) | General Formula (2b) | H | H | tert-C$_4$H$_9$ | H | tert-C$_4$H$_9$ |
| 74 | CN | General Formula (2a) | General Formula (2a) | General Formula (2b) | H | H | tert-C$_4$H$_9$ | H | tert-C$_4$H$_9$ |
| 75 | CN | General Formula (2a) | General Formula (2a) | General Formula (2b) | H | H | Phenyl | H | Phenyl |
| 76 | CN | General Formula (2a) | CN | General Formula (2b) | H | H | H | H | H |
| 77 | CN | General Formula (2a) | CN | General Formula (2b) | H | H | H | H | H |
| 78 | CN | General Formula (2a) | CN | General Formula (2b) | H | H | H | H | H |
| 79 | CN | General Formula (2a) | CN | General Formula (2b) | H | H | CH$_3$ | H | CH$_3$ |
| 80 | CN | General Formula (2a) | CN | General Formula (2b) | H | H | H | H | H |
| 81 | CN | General Formula (2a) | CN | General Formula (2b) | H | H | H | H | H |
| 82 | CN | General Formula (2a) | CN | General Formula (2b) | H | H | CH$_3$ | H | CH$_3$ |
| 83 | CN | General Formula (2a) | CN | General Formula (2b) | H | H | CH$_3$ | H | CH$_3$ |
| 84 | CN | General Formula (2a) | CN | General Formula (2b) | H | H | CH$_3$ | H | CH$_3$ |
| 85 | CN | General Formula (2a) | CN | General Formula (2b) | H | H | H | H | H |
| 86 | CN | General Formula (2a) | CN | General Formula (2b) | H | H | tert-C$_4$H$_9$ | H | tert-C$_4$H$_9$ |
| 87 | CN | General Formula (2a) | CN | General Formula (2b) | H | H | tert-C$_4$H$_9$ | H | tert-C$_4$H$_9$ |
| 88 | CN | General Formula (2a) | CN | General Formula (2b) | H | H | Phenyl | H | Phenyl |
| 89 | CN | General Formula (2a) | CN | General Formula (2b) | H | H | Phenyl | H | Phenyl |
| 90 | CN | General Formula (2a) | CN | General Formula (2b) | H | H | H | H | H |
| 91 | CN | General Formula (2a) | CN | General Formula (2b) | H | H | H | H | H |
| 92 | CN | General Formula (2a) | CN | General Formula (2b) | H | H | CH$_3$ | H | CH$_3$ |
| 93 | CN | General Formula (2a) | CN | H | H | H | H | H | H |
| 94 | CN | General Formula (2a) | CN | H | H | H | H | H | H |
| 95 | CN | General Formula (2a) | CN | H | H | H | CH$_3$ | H | CH$_3$ |
| 96 | CN | General Formula (2a) | CN | H | H | H | tert-C$_4$H$_9$ | H | tert-C$_4$H$_9$ |
| 97 | CN | General Formula (2a) | CN | H | H | H | Phenyl | H | Phenyl |
| 98 | CN | General Formula (2a) | CN | H | H | H | Phenyl | H | Phenyl |
| 99 | CN | General Formula (2a) | CN | General Formula (2b) | H | H | H | H | H |
| 100 | CN | General Formula (2a) | CN | General Formula (2b) | H | H | H | H | H |

TABLE 1-continued

| | | | | | | | | | |
|---|---|---|---|---|---|---|---|---|---|
| 101 | CN | General Formula (2a) | General Formula (2a) | CN | General Formula (2b) | H | H | H | H |
| 102 | CN | General Formula (2a) | General Formula (2a) | CN | General Formula (2b) | H | H | H | H |
| 103 | CN | General Formula (2a) | General Formula (2a) | CN | General Formula (2b) | H | H | CH₃ | CH₃ |
| 104 | CN | General Formula (2a) | General Formula (2a) | CN | General Formula (2a) | H | H | H | H |
| 105 | CN | General Formula (2a) | General Formula (2a) | CN | General Formula (2a) | H | H | H | H |
| 106 | CN | General Formula (2a) | General Formula (2a) | CN | General Formula (2a) | H | H | H | H |
| 107 | CN | General Formula (2a) | General Formula (2a) | CN | General Formula (2a) | H | H | CH₃ | CH₃ |
| 108 | CN | General Formula (2a) | General Formula (2a) | CN | General Formula (2a) | H | H | CH₃ | CH₃ |
| 109 | CN | General Formula (2a) | General Formula (2b) | CN | General Formula (2b) | H | H | H | H |
| 110 | CN | General Formula (2a) | General Formula (2b) | CN | General Formula (2b) | H | H | H | H |
| 111 | CN | General Formula (2a) | General Formula (2b) | CN | General Formula (2b) | H | H | H | H |
| 112 | CN | General Formula (2a) | General Formula (2b) | CN | General Formula (2a) | H | H | CH₃ | CH₃ |
| 113 | CN | General Formula (2a) | General Formula (2b) | CN | General Formula (2a) | H | H | H | H |
| 114 | CN | General Formula (2a) | General Formula (2b) | CN | General Formula (2a) | H | H | H | H |
| 115 | CN | General Formula (2a) | General Formula (2b) | CN | General Formula (2a) | H | H | H | H |
| 116 | CN | General Formula (2a) | General Formula (2b) | CN | General Formula (2a) | H | H | CH₃ | CH₃ |
| 117 | CN | General Formula (2a) | General Formula (2b) | CN | General Formula (2a) | H | H | H | H |
| 118 | CN | General Formula (2a) | General Formula (2b) | CN | General Formula (2a) | H | H | H | H |
| 119 | CN | General Formula (2a) | General Formula (2b) | CN | General Formula (2a) | H | H | H | H |
| 120 | CN | General Formula (2a) | General Formula (2b) | CN | General Formula (2a) | H | H | CH₃ | CH₃ |
| 121 | CN | General Formula (2a) | General Formula (2b) | CN | General Formula (2a) | H | H | H | H |
| 122 | CN | General Formula (2a) | General Formula (2b) | CN | General Formula (2a) | H | H | H | H |
| 123 | CN | General Formula (2a) | General Formula (2b) | CN | General Formula (2a) | H | H | H | H |
| 124 | CN | General Formula (2a) | General Formula (2b) | CN | General Formula (2a) | H | H | CH₃ | CH₃ |
| 125 | CN | Phenyl | General Formula (2b) | CN | General Formula (2b) | H | H | tert-C₄H₉ | tert-C₄H₉ |
| 126 | CN | Phenyl | General Formula (2b) | CN | General Formula (2b) | H | H | tert-C₄H₉ | tert-C₄H₉ |
| 127 | CN | Phenyl | General Formula (2b) | CN | General Formula (2b) | H | H | tert-C₄H₉ | tert-C₄H₉ |
| 128 | CN | Phenyl | General Formula (2b) | CN | General Formula (2b) | H | H | Phenyl | Phenyl |
| 129 | CN | Phenyl | General Formula (2b) | CN | General Formula (2b) | H | H | Phenyl | Phenyl |
| 130 | CN | Phenyl | General Formula (2b) | CN | General Formula (2b) | H | H | H | H |
| 131 | CN | Phenyl | General Formula (2b) | CN | General Formula (2b) | H | H | CH₃ | CH₃ |
| 132 | CN | Phenyl | General Formula (2b) | CN | General Formula (2b) | H | H | CH₃ | CH₃ |
| 133 | CN | General Formula (2a) | Phenyl | CN | General Formula (2a) | H | H | H | H |
| 134 | CN | General Formula (2a) | Phenyl | CN | General Formula (2a) | H | H | tert-C₄H₉ | tert-C₄H₉ |
| 135 | CN | General Formula (2a) | Phenyl | CN | General Formula (2a) | H | H | tert-C₄H₉ | tert-C₄H₉ |
| 136 | CN | General Formula (2a) | Phenyl | CN | General Formula (2a) | H | H | tert-C₄H₉ | tert-C₄H₉ |
| 137 | CN | General Formula (2a) | Phenyl | CN | General Formula (2a) | H | H | Phenyl | Phenyl |
| 138 | CN | General Formula (2a) | Phenyl | CN | General Formula (2a) | H | H | Phenyl | Phenyl |
| 139 | CN | General Formula (2a) | Phenyl | Phenyl | General Formula (2a) | H | H | H | H |
| 140 | CN | General Formula (2a) | Phenyl | Phenyl | General Formula (2a) | H | H | CH₃ | CH₃ |
| 141 | CN | General Formula (2a) | Phenyl | Phenyl | General Formula (2a) | H | H | tert-C₄H₉ | tert-C₄H₉ |
| 142 | CN | General Formula (2a) | Phenyl | Phenyl | General Formula (2a) | H | H | Phenyl | Phenyl |
| 143 | CN | General Formula (2a) | Phenyl | Phenyl | General Formula (2a) | H | H | H | H |
| 144 | CN | General Formula (2a) | Phenyl | Phenyl | General Formula (2a) | H | H | H | H |
| 145 | CN | General Formula (2b) | General Formula (2b) | Phenyl | General Formula (2a) | H | H | CH₃ | CH₃ |
| 146 | CN | General Formula (2b) | General Formula (2b) | Phenyl | General Formula (2a) | H | H | CH₃ | CH₃ |
| 147 | CN | General Formula (2b) | General Formula (2b) | Phenyl | General Formula (2a) | H | H | tert-C₄H₉ | tert-C₄H₉ |
| 148 | CN | General Formula (2b) | General Formula (2b) | Phenyl | General Formula (2a) | H | H | Phenyl | Phenyl |
| 149 | CN | General Formula (2b) | General Formula (2b) | Phenyl | General Formula (2a) | H | H | Phenyl | Phenyl |
| 150 | CN | General Formula (2b) | Phenyl | Phenyl | General Formula (2a) | H | H | H | H |
| 151 | CN | General Formula (2b) | H | m,m-DPP*² | General Formula (2a) | H | H | H | H |
| 152 | CN | General Formula (2b) | Phenyl | Phenyl | General Formula (2a) | H | H | H | H |

TABLE 1-continued

| Compound No. | General Formula (2a) | | | General Formula (2b) | | | | | | | | |
|---|---|---|---|---|---|---|---|---|---|---|---|---|
| | $R^{a7}$ | $R^{a8}$ | $R^{a9}$ | $R^{b1}$ | $R^{b2}$ | $R^{b3}$ | $R^{b4}$ | $R^{b5}$ | $R^{b6}$ | $R^{b7}$ | $R^{b8}$ | $R^{b9}$ |
| 1 | H | H | *1 | H | H | $CH_3$ | H | H | $CH_3$ | H | H | *1 |
| 2 | H | H | *1 | H | H | tert-$C_4H_9$ | H | H | tert-$C_4H_9$ | H | H | *1 |
| 3 | H | H | *1 | H | H | Phenyl | H | H | Phenyl | H | H | *1 |
| 4 | H | H | *1 | H | H | $CH_3$ | H | H | $CH_3$ | H | H | *1 |
| 5 | H | H | *1 | H | H | tert-$C_4H_9$ | H | H | tert-$C_4H_9$ | H | H | *1 |
| 6 | H | H | *1 | H | H | Phenyl | H | H | Phenyl | H | H | *1 |
| 7 | H | H | *1 | H | H | 9-Carbazolyl | H | H | 9-Carbazolyl | H | H | *1 |
| 8 | H | H | *1 | H | H | iso-Butyl | H | H | iso-Butyl | H | H | *1 |
| 9 | H | H | *1 | H | H | 2-Ethylhexyl | H | H | 2-Ethylhexyl | H | H | *1 |
| 10 | H | H | *1 | H | H | Trimethylsilyl | H | H | Trimethylsilyl | H | H | *1 |
| 11 | H | H | *1 | H | H | $CH_3$ | H | H | $CH_3$ | H | H | *1 |
| 12 | H | H | *1 | H | H | Phenyl | H | H | H | H | H | *1 |
| 13 | H | H | *1 | H | H | $CH_3$ | H | H | tert-$C_4H_9$ | H | H | *1 |
| 14 | H | H | *1 | H | H | $CH_3$ | H | H | Phenyl | H | H | *1 |
| 15 | H | H | *1 | H | H | Diphenylamino | H | H | Diphenylamino | H | H | *1 |
| 16 | H | H | *1 | H | H | Diphenylamino | H | H | H | H | H | *1 |
| 17 | H | H | *1 | H | H | H | H | H | H | H | H | *1 |
| 18 | H | H | *1 | H | H | tert-$C_4H_9$ | H | H | tert-$C_4H_9$ | H | H | *1 |
| 19 | H | H | *1 | H | H | Phenyl | H | H | Phenyl | H | H | *1 |
| 20 | H | H | *1 | H | H | $CH_3$ | H | H | $CH_3$ | H | H | *1 |
| 21 | H | H | *1 | H | H | $CH_3$ | H | H | $CH_3$ | H | H | *1 |
| 22 | H | H | *1 | H | H | Phenyl | H | H | H | H | H | *1 |
| 23 | H | H | *1 | H | H | H | H | H | H | H | H | *1 |
| 24 | H | H | *1 | $CH_3$ | $CH_3$ | H | $CH_3$ | $CH_3$ | H | H | H | *1 |
| 25 | H | H | *1 | tert-$C_4H_9$ | tert-$C_4H_9$ | H | Phenyl | Phenyl | H | H | H | *1 |
| 26 | H | H | *1 | H | H | H | H | $CH_3$ | H | H | H | *1 |
| 27 | H | H | *1 | Phenyl | Phenyl | H | $CH_3$ | $CH_3$ | H | H | H | *1 |
| 28 | H | H | *1 | H | H | H | H | H | H | $CH_3$ | $CH_3$ | *1 |
| 29 | H | H | *1 | $CH_3$ | H | H | H | H | H | H | tert-$C_4H_9$ | *1 |
| 30 | H | H | *1 | H | $CH_3$ | H | H | H | H | tert-$C_4H_9$ | H | *1 |
| 31 | H | H | *1 | $CH_3$ | H | $CH_3$ | H | H | $CH_3$ | Phenyl | Phenyl | *1 |
| 32 | H | H | *1 | H | H | $CH_3$ | H | H | $CH_3$ | $CH_3$ | $CH_3$ | *1 |
| 33 | H | H | *1 | $CH_3$ | $CH_3$ | $CH_3$ | H | H | $CH_3$ | H | $CH_3$ | *1 |
| 34 | H | H | *1 | H | H | Phenyl | H | H | H | $CH_3$ | $CH_3$ | *1 |
| 35 | H | H | *1 | H | H | $CH_3$ | H | H | $CH_3$ | H | H | *1 |
| 36 | H | H | *1 | H | H | tert-$C_4H_9$ | H | H | tert-$C_4H_9$ | H | H | *1 |
| 37 | H | H | *1 | H | H | Phenyl | H | H | Phenyl | H | H | *1 |
| 38 | H | H | *1 | H | H | 2-Phenylphenyl | H | H | 2-Phenylphenyl | H | H | *1 |
| 39 | H | H | *1 | H | H | 3-Phenylphenyl | H | H | 3-Phenylphenyl | H | H | *1 |
| 40 | H | H | *1 | H | H | 4-Phenylphenyl | H | H | 4-Phenylphenyl | H | H | *1 |
| 41 | H | H | *1 | H | H | 2-Phenylphenyl | H | H | Phenyl | H | H | *1 |
| 42 | H | H | *1 | H | H | 3-Phenylphenyl | H | H | Phenyl | H | H | *1 |
| 43 | H | H | *1 | H | H | 4-Phenylphenyl | H | H | Phenyl | H | H | *1 |
| 44 | H | H | *1 | H | H | H | H | H | H | H | H | *1 |
| 45 | H | H | *1 | H | H | H | H | H | H | H | H | *1 |
| 46 | H | H | *1 | H | H | tert-$C_4H_9$ | H | H | tert-$C_4H_9$ | H | H | *1 |
| 47 | H | H | *1 | H | H | Phenyl | H | H | Phenyl | H | H | *1 |
| 48 | H | H | *1 | H | H | H | H | H | H | H | H | *1 |
| 49 | H | H | *1 | H | H | $CH_3$ | H | H | $CH_3$ | H | H | *1 |

TABLE 1-continued

| # | | | | | | | | | | | |
|---|---|---|---|---|---|---|---|---|---|---|---|
| 50 | H | H | *1 | H | 2-Phenylphenyl | H | H | Phenyl | H | H | *1 |
| 51 | H | H | *1 | H | 3-Phenylphenyl | H | H | Phenyl | H | H | *1 |
| 52 | H | H | *1 | H | 4-Phenylphenyl | H | H | Phenyl | H | H | *1 |
| 53 | H | H | *1 | H | CH$_3$ | H | H | CH$_3$ | H | H | *1 |
| 54 | H | H | *1 | H | tert-C$_4$H$_9$ | H | H | tert-C$_4$H$_9$ | H | H | *1 |
| 55 | H | H | *1 | H | Phenyl | H | H | Phenyl | H | H | *1 |
| 56 | H | H | *1 | H | 2-Phenylphenyl | H | H | Phenyl | H | H | *1 |
| 57 | H | H | *1 | H | 3-Phenylphenyl | H | H | Phenyl | H | H | *1 |
| 58 | H | H | *1 | H | 4-Phenylphenyl | H | H | Phenyl | H | H | *1 |
| 59 | H | H | *1 | H | CH$_3$ | H | H | CH$_3$ | H | H | *1 |
| 60 | H | H | *1 | H | tert-C$_4$H$_9$ | H | H | tert-C$_4$H$_9$ | H | H | *1 |
| 61 | H | H | *1 | H | Phenyl | H | H | Phenyl | H | H | *1 |
| 62 | H | H | *1 | H | Phenyl | H | H | Phenyl | H | H | *1 |
| 63 | H | H | *1 | H | CH$_3$ | H | H | CH$_3$ | H | H | *1 |
| 64 | H | H | *1 | H | tert-C$_4$H$_9$ | H | H | tert-C$_4$H$_9$ | H | H | *1 |
| 65 | H | H | *1 | H | Phenyl | H | H | Phenyl | H | H | *1 |
| 66 | H | H | *1 | H | Phenyl | H | H | Phenyl | H | H | *1 |
| 67 | H | H | *1 | H | CH$_3$ | H | H | CH$_3$ | H | H | *1 |
| 68 | H | H | *1 | H | tert-C$_4$H$_9$ | H | H | tert-C$_4$H$_9$ | H | H | *1 |
| 69 | H | H | *1 | H | Phenyl | H | H | Phenyl | H | H | *1 |
| 70 | H | H | *1 | H | H | H | H | H | H | H | *1 |
| 71 | H | H | *1 | H | tert-C$_4$H$_9$ | H | H | tert-C$_4$H$_9$ | H | H | *1 |
| 72 | H | H | *1 | H | Phenyl | H | H | Phenyl | H | H | *1 |
| 73 | H | H | *1 | H | H | H | H | H | H | H | *1 |
| 74 | H | H | *1 | H | CH$_3$ | H | H | CH$_3$ | H | H | *1 |
| 75 | H | H | *1 | H | H | H | H | H | H | H | *1 |
| 76 | H | H | *1 | H | CH$_3$ | H | H | CH$_3$ | H | H | *1 |
| 77 | H | H | *1 | H | tert-C$_4$H$_9$ | H | H | tert-C$_4$H$_9$ | H | H | *1 |
| 78 | H | H | *1 | H | Phenyl | H | H | Phenyl | H | H | *1 |
| 79 | H | H | *1 | H | Phenyl | H | H | Phenyl | H | H | *1 |
| 80 | H | H | *1 | H | CH$_3$ | H | H | CH$_3$ | H | H | *1 |
| 81 | H | H | *1 | H | tert-C$_4$H$_9$ | H | H | tert-C$_4$H$_9$ | H | H | *1 |
| 82 | H | H | *1 | H | Phenyl | H | H | Phenyl | H | H | *1 |
| 83 | H | H | *1 | H | H | H | H | H | H | H | *1 |
| 84 | H | H | *1 | H | tert-C$_4$H$_9$ | H | H | tert-C$_4$H$_9$ | H | H | *1 |
| 85 | H | H | *1 | H | Phenyl | H | H | Phenyl | H | H | *1 |
| 86 | H | H | *1 | H | H | H | H | H | H | H | *1 |
| 87 | H | H | *1 | H | CH$_3$ | H | H | CH$_3$ | H | H | *1 |
| 88 | H | H | *1 | H | H | H | H | H | H | H | *1 |
| 89 | H | H | *1 | H | CH$_3$ | H | H | CH$_3$ | H | H | *1 |
| 90 | H | H | *1 | H | CH$_3$ | H | H | CH$_3$ | H | H | *1 |
| 91 | H | H | *1 | H | tert-C$_4$H$_9$ | H | H | tert-C$_4$H$_9$ | H | H | *1 |
| 92 | H | H | *1 | H | Phenyl | H | H | Phenyl | H | H | *1 |
| 93 | H | H | *1 | H | Phenyl | H | H | Phenyl | H | H | *1 |
| 94 | H | H | *1 | H | CH$_3$ | H | H | CH$_3$ | H | H | *1 |
| 95 | H | H | *1 | H | tert-C$_4$H$_9$ | H | H | tert-C$_4$H$_9$ | H | H | *1 |
| 96 | H | H | *1 | H | Phenyl | H | H | Phenyl | H | H | *1 |
| 97 | H | H | *1 | H | H | H | H | H | H | H | *1 |
| 98 | H | H | *1 | H | H | H | H | H | H | H | *1 |
| 99 | H | H | *1 | H | CH$_3$ | H | H | CH$_3$ | H | H | *1 |
| 100 | H | H | *1 | H | tert-C$_4$H$_9$ | H | H | tert-C$_4$H$_9$ | H | H | *1 |
| 101 | H | H | *1 | H | Phenyl | H | H | Phenyl | H | H | *1 |

TABLE 1-continued

| No. | | | | | | | | | | |
|---|---|---|---|---|---|---|---|---|---|---|
| 103 | H | H | *1 | H | H | Phenyl | H | H | H | *1 |
| 104 | H | H | *1 | H | H | CH₃ | H | H | H | *1 |
| 105 | H | H | *1 | H | H | tert-C₄H₉ | H | H | H | *1 |
| 106 | H | H | *1 | H | H | Phenyl | H | H | H | *1 |
| 107 | H | H | *1 | H | H | tert-C₄H₉ | H | H | H | *1 |
| 108 | H | H | *1 | H | H | Phenyl | H | H | H | *1 |
| 109 | H | H | *1 | H | H | CH₃ | H | H | H | *1 |
| 110 | H | H | *1 | H | H | tert-C₄H₉ | H | H | H | *1 |
| 111 | H | H | *1 | H | H | Phenyl | H | H | H | *1 |
| 112 | H | H | *1 | H | H | Phenyl | H | H | H | *1 |
| 113 | H | H | *1 | H | H | CH₃ | H | H | H | *1 |
| 114 | H | H | *1 | H | H | tert-C₄H₉ | H | H | H | *1 |
| 115 | H | H | *1 | H | H | Phenyl | H | H | H | *1 |
| 116 | H | H | *1 | H | H | Phenyl | H | H | H | *1 |
| 117 | H | H | *1 | H | H | CH₃ | H | H | H | *1 |
| 118 | H | H | *1 | H | H | tert-C₄H₉ | H | H | H | *1 |
| 119 | H | H | *1 | H | H | Phenyl | H | H | H | *1 |
| 120 | H | H | *1 | H | H | Phenyl | H | H | H | *1 |
| 121 | H | H | *1 | H | H | CH₃ | H | H | H | *1 |
| 122 | H | H | *1 | H | H | tert-C₄H₉ | H | H | H | *1 |
| 123 | H | H | *1 | H | H | Phenyl | H | H | H | *1 |
| 124 | H | H | *1 | H | H | Phenyl | H | H | H | *1 |
| 125 | H | H | *1 | H | H | Phenyl | H | H | H | *1 |
| 126 | H | H | *1 | H | H | H | H | H | H | *1 |
| 127 | H | H | *1 | H | H | Phenyl | H | H | H | *1 |
| 128 | H | H | *1 | H | H | H | H | H | H | *1 |
| 129 | H | H | *1 | H | H | CH₃ | H | H | H | *1 |
| 130 | H | H | *1 | H | H | Phenyl | H | H | H | *1 |
| 131 | H | H | *1 | H | H | H | H | H | H | *1 |
| 132 | H | H | *1 | H | H | CH₃ | H | H | H | *1 |
| 133 | H | H | *1 | H | H | CH₃ | H | H | H | *1 |
| 134 | H | H | *1 | H | H | tert-C₄H₉ | H | H | H | *1 |
| 135 | H | H | *1 | H | H | Phenyl | H | H | H | *1 |
| 136 | H | H | *1 | H | H | H | H | H | H | *1 |
| 137 | H | H | *1 | H | H | tert-C₄H₉ | H | H | H | *1 |
| 138 | H | H | *1 | H | H | Phenyl | H | H | H | *1 |
| 139 | H | H | *1 | H | H | H | H | H | H | *1 |
| 140 | H | H | *1 | H | H | CH₃ | H | H | H | *1 |
| 141 | H | H | *1 | H | H | Phenyl | H | H | H | *1 |
| 142 | H | H | *1 | H | H | H | H | H | H | *1 |
| 143 | H | H | *1 | H | H | CH₃ | H | H | H | *1 |
| 144 | H | H | *1 | H | H | tert-C₄H₉ | H | H | H | *1 |
| 145 | H | H | *1 | H | H | CH₃ | H | H | H | *1 |
| 146 | H | H | *1 | H | H | H | H | H | H | *1 |

TABLE 1-continued

| 147 | H | H | H | H | H | H | H | H | *1 |
| 148 | H | H | H | H | H | H | H | H | *1 |
| 149 | H | H | H | H | H | H | H | H | *1 |
| 150 | H | H | H | CH₃ | H | H | H | CH₃ | *1 |
| 151 | H | H | H | Phenyl | H | H | H | Phenyl | *1 |
| 152 | H | H | H | Phenyl | H | H | H | Phenyl | *1 |

In the Table, the general formula (2a) and the general formula (2b) are the same meaning as the general formula (2)

*1: This bonds to the benezne corresponding to D in the general formula (1).

*2: "m,m-DPP" is m,m-diphenylphenyl.

TABLE 2

| Compound No. | A¹ | R¹ | R² | R³ | R⁴ | R⁵ | General Formula (2a) R$^{a1}$ | R$^{a2}$ |
|---|---|---|---|---|---|---|---|---|
| 201 | CN | General Formula (2a) | D1 | CN | General Formula (2a) | D1 | H | H |
| 202 | CN | General Formula (2a) | D2 | CN | General Formula (2a) | D2 | H | H |
| 203 | CN | General Formula (2a) | D3 | CN | General Formula (2a) | D3 | H | H |
| 204 | CN | General Formula (2a) | D4 | CN | General Formula (2a) | D4 | H | H |
| 205 | CN | General Formula (2a) | D5 | CN | General Formula (2a) | D5 | H | H |
| 206 | CN | General Formula (2a) | D6 | CN | General Formula (2a) | D6 | H | H |
| 207 | CN | General Formula (2a) | D7 | CN | General Formula (2a) | D7 | H | H |
| 208 | CN | General Formula (2a) | D8 | CN | General Formula (2a) | D8 | H | H |
| 209 | CN | General Formula (2a) | D9 | CN | General Formula (2a) | D9 | H | H |
| 210 | CN | General Formula (2a) | D10 | CN | General Formula (2a) | D10 | H | H |
| 211 | CN | General Formula (2a) | D11 | CN | General Formula (2a) | D11 | H | H |
| 212 | CN | General Formula (2a) | D12 | CN | General Formula (2a) | D12 | H | H |
| 213 | CN | General Formula (2a) | D13 | CN | General Formula (2a) | D13 | H | H |
| 214 | CN | General Formula (2a) | D14 | CN | General Formula (2a) | D14 | H | H |
| 215 | CN | General Formula (2a) | D15 | CN | General Formula (2a) | D15 | H | H |
| 216 | CN | General Formula (2a) | D16 | CN | General Formula (2a) | D16 | H | H |
| 217 | CN | General Formula (2a) | D17 | CN | General Formula (2a) | D17 | H | H |
| 218 | CN | General Formula (2a) | D18 | CN | General Formula (2a) | D18 | H | H |
| 219 | CN | General Formula (2a) | D19 | CN | General Formula (2a) | D19 | H | H |
| 220 | CN | General Formula (2a) | D20 | CN | General Formula (2a) | D20 | H | H |
| 221 | CN | General Formula (2a) | D21 | CN | General Formula (2a) | D21 | H | H |
| 222 | CN | General Formula (2a) | D22 | CN | General Formula (2a) | D22 | H | H |
| 223 | CN | General Formula (2a) | D23 | CN | General Formula (2a) | D23 | H | H |
| 224 | CN | General Formula (2a) | D24 | CN | General Formula (2a) | D24 | H | H |
| 225 | CN | General Formula (2a) | D25 | CN | General Formula (2a) | D25 | H | H |
| 226 | CN | General Formula (2a) | D26 | CN | General Formula (2a) | D26 | H | H |
| 227 | CN | General Formula (2a) | D27 | CN | General Formula (2a) | D27 | H | H |
| 228 | CN | General Formula (2a) | D28 | CN | General Formula (2a) | D28 | H | H |
| 229 | CN | General Formula (2a) | D29 | CN | General Formula (2a) | D29 | H | H |
| 230 | CN | General Formula (2a) | D30 | CN | General Formula (2a) | D30 | H | H |
| 231 | CN | General Formula (2a) | D31 | CN | General Formula (2a) | D31 | H | H |
| 232 | CN | General Formula (2a) | D32 | CN | General Formula (2a) | D32 | H | H |
| 233 | CN | General Formula (2a) | D33 | CN | General Formula (2a) | D33 | H | H |
| 234 | CN | General Formula (2a) | D34 | CN | General Formula (2a) | D34 | H | H |
| 235 | CN | General Formula (2a) | D35 | CN | General Formula (2a) | D35 | H | H |
| 236 | CN | General Formula (2a) | D36 | CN | General Formula (2a) | D36 | H | H |
| 237 | CN | General Formula (2a) | D37 | CN | General Formula (2a) | D37 | H | H |
| 238 | CN | General Formula (2a) | D38 | CN | General Formula (2a) | D38 | H | H |
| 239 | CN | General Formula (2a) | D39 | CN | General Formula (2a) | D39 | H | H |
| 240 | CN | General Formula (2a) | D40 | CN | General Formula (2a) | D40 | H | H |
| 241 | CN | General Formula (2a) | D41 | CN | General Formula (2a) | D41 | H | H |
| 242 | CN | General Formula (2a) | D42 | CN | General Formula (2a) | D42 | H | H |
| 243 | CN | General Formula (2a) | D43 | CN | General Formula (2a) | D43 | H | H |
| 244 | CN | General Formula (2a) | D44 | CN | General Formula (2a) | D44 | H | H |
| 245 | CN | General Formula (2a) | D45 | CN | General Formula (2a) | D45 | H | H |
| 246 | CN | General Formula (2a) | D46 | CN | General Formula (2a) | D46 | H | H |
| 247 | CN | General Formula (2a) | D47 | CN | General Formula (2a) | D47 | H | H |
| 248 | CN | General Formula (2a) | D48 | CN | General Formula (2a) | D48 | H | H |
| 249 | CN | General Formula (2a) | D49 | CN | General Formula (2a) | D49 | H | H |
| 250 | CN | General Formula (2a) | D50 | CN | General Formula (2a) | D50 | H | H |
| 251 | CN | General Formula (2a) | D51 | CN | General Formula (2a) | D51 | H | H |
| 252 | CN | General Formula (2a) | D52 | CN | General Formula (2a) | D52 | H | H |
| 253 | CN | General Formula (2a) | D53 | CN | General Formula (2a) | D53 | H | H |
| 254 | CN | General Formula (2a) | D54 | CN | General Formula (2a) | D54 | H | H |
| 255 | CN | General Formula (2a) | D55 | CN | General Formula (2a) | D55 | H | H |
| 256 | CN | General Formula (2a) | D56 | CN | General Formula (2a) | D56 | H | H |
| 257 | CN | General Formula (2a) | D57 | CN | General Formula (2a) | D57 | H | H |
| 258 | CN | General Formula (2a) | D58 | CN | General Formula (2a) | D58 | H | H |
| 259 | CN | General Formula (2a) | D59 | CN | General Formula (2a) | D59 | H | H |
| 260 | CN | General Formula (2a) | D60 | CN | General Formula (2a) | D60 | H | H |
| 261 | CN | General Formula (2a) | D24 | Phenyl | D24 | General Formula (2a) | H | H |
| 262 | CN | General Formula (2a) | D24 | Phenyl | D24 | General Formula (2a) | H | H |
| 263 | CN | General Formula (2a) | D24 | Phenyl | D24 | General Formula (2a) | H | H |
| 264 | CN | General Formula (2a) | D24 | Phenyl | D24 | General Formula (2a) | H | H |
| 265 | CN | General Formula (2a) | Phenyl | D11 | Phenyl | General Formula (2a) | H | H |
| 266 | CN | General Formula (2a) | Phenyl | D11 | Phenyl | General Formula (2a) | H | H |
| 267 | CN | General Formula (2a) | Phenyl | D11 | Phenyl | General Formula (2a) | H | H |
| 268 | CN | CN | D24 | General Formula (2a) | General Formula (2a) | D24 | H | H |
| 269 | CN | CN | D24 | General Formula (2a) | General Formula (2a) | D24 | H | H |
| 270 | CN | CN | D24 | General Formula (2a) | General Formula (2a) | D24 | H | H |
| 271 | CN | CN | D24 | General Formula (2a) | General Formula (2a) | D24 | H | H |
| 272 | CN | CN | General Formula (2a) | D24 | D24 | General Formula (2a) | H | H |
| 273 | CN | General Formula (2a) | CN | D24 | General Formula (2a) | D24 | H | H |

TABLE 2-continued

| | | | | | | | |
|---|---|---|---|---|---|---|---|
| 274 | CN | D24 | CN | General Formula (2a) | D24 | General Formula (2a) | H H |
| 275 | CN | D24 | General Formula (2a) | CN | D24 | General Formula (2a) | H H |
| 276 | CN | D24 | General Formula (2a) | CN | D24 | General Formula (2a) | H H |
| 277 | CN | D24 | General Formula (2a) | CN | D24 | General Formula (2a) | H H |
| 278 | CN | D24 | General Formula (2a) | CN | D24 | General Formula (2a) | H H |

| Compound No. | General Formula (2a) | | | | | | |
|---|---|---|---|---|---|---|---|
| | $R^{a3}$ | $R^{a4}$ | $R^{a5}$ | $R^{a6}$ | $R^{a7}$ | $R^{a8}$ | $R^{a9}$ |
| 201 | $CH_3$ | H | H | $CH_3$ | H | H | *1 |
| 202 | $CH_3$ | H | H | $CH_3$ | H | H | *1 |
| 203 | $CH_3$ | H | H | $CH_3$ | H | H | *1 |
| 204 | $CH_3$ | H | H | $CH_3$ | H | H | *1 |
| 205 | $CH_3$ | H | H | $CH_3$ | H | H | *1 |
| 206 | $CH_3$ | H | H | $CH_3$ | H | H | *1 |
| 207 | $CH_3$ | H | H | $CH_3$ | H | H | *1 |
| 208 | $CH_3$ | H | H | $CH_3$ | H | H | *1 |
| 209 | $CH_3$ | H | H | $CH_3$ | H | H | *1 |
| 210 | $CH_3$ | H | H | $CH_3$ | H | H | *1 |
| 211 | $CH_3$ | H | H | $CH_3$ | H | H | *1 |
| 212 | $CH_3$ | H | H | $CH_3$ | H | H | *1 |
| 213 | $CH_3$ | H | H | $CH_3$ | H | H | *1 |
| 214 | $CH_3$ | H | H | $CH_3$ | H | H | *1 |
| 215 | $CH_3$ | H | H | $CH_3$ | H | H | *1 |
| 216 | $CH_3$ | H | H | $CH_3$ | H | H | *1 |
| 217 | $CH_3$ | H | H | $CH_3$ | H | H | *1 |
| 218 | $CH_3$ | H | H | $CH_3$ | H | H | *1 |
| 219 | $CH_3$ | H | H | $CH_3$ | H | H | *1 |
| 220 | $CH_3$ | H | H | $CH_3$ | H | H | *1 |
| 221 | $CH_3$ | H | H | $CH_3$ | H | H | *1 |
| 222 | $CH_3$ | H | H | $CH_3$ | H | H | *1 |
| 223 | $CH_3$ | H | H | $CH_3$ | H | H | *1 |
| 224 | $CH_3$ | H | H | $CH_3$ | H | H | *1 |
| 225 | $CH_3$ | H | H | $CH_3$ | H | H | *1 |
| 226 | $CH_3$ | H | H | $CH_3$ | H | H | *1 |
| 227 | $CH_3$ | H | H | $CH_3$ | H | H | *1 |
| 228 | $CH_3$ | H | H | $CH_3$ | H | H | *1 |
| 229 | $CH_3$ | H | H | $CH_3$ | H | H | *1 |
| 230 | $CH_3$ | H | H | $CH_3$ | H | H | *1 |
| 231 | $CH_3$ | H | H | $CH_3$ | H | H | *1 |
| 232 | $CH_3$ | H | H | $CH_3$ | H | H | *1 |
| 233 | $CH_3$ | H | H | $CH_3$ | H | H | *1 |
| 234 | $CH_3$ | H | H | $CH_3$ | H | H | *1 |
| 235 | $CH_3$ | H | H | $CH_3$ | H | H | *1 |
| 236 | $CH_3$ | H | H | $CH_3$ | H | H | *1 |
| 237 | $CH_3$ | H | H | $CH_3$ | H | H | *1 |
| 238 | $CH_3$ | H | H | $CH_3$ | H | H | *1 |
| 239 | $CH_3$ | H | H | $CH_3$ | H | H | *1 |
| 240 | $CH_3$ | H | H | $CH_3$ | H | H | *1 |
| 241 | $CH_3$ | H | H | $CH_3$ | H | H | *1 |
| 242 | $CH_3$ | H | H | $CH_3$ | H | H | *1 |
| 243 | $CH_3$ | H | H | $CH_3$ | H | H | *1 |
| 244 | $CH_3$ | H | H | $CH_3$ | H | H | *1 |
| 245 | $CH_3$ | H | H | $CH_3$ | H | H | *1 |
| 246 | $CH_3$ | H | H | $CH_3$ | H | H | *1 |
| 247 | $CH_3$ | H | H | $CH_3$ | H | H | *1 |
| 248 | $CH_3$ | H | H | $CH_3$ | H | H | *1 |
| 249 | $CH_3$ | H | H | $CH_3$ | H | H | *1 |
| 250 | $CH_3$ | H | H | $CH_3$ | H | H | *1 |
| 251 | $CH_3$ | H | H | $CH_3$ | H | H | *1 |
| 252 | $CH_3$ | H | H | $CH_3$ | H | H | *1 |
| 253 | $CH_3$ | H | H | $CH_3$ | H | H | *1 |
| 254 | $CH_3$ | H | H | $CH_3$ | H | H | *1 |
| 255 | $CH_3$ | H | H | $CH_3$ | H | H | *1 |
| 256 | $CH_3$ | H | H | $CH_3$ | H | H | *1 |
| 257 | $CH_3$ | H | H | $CH_3$ | H | H | *1 |
| 258 | $CH_3$ | H | H | $CH_3$ | H | H | *1 |
| 259 | $CH_3$ | H | H | $CH_3$ | H | H | *1 |
| 260 | $CH_3$ | H | H | $CH_3$ | H | H | *1 |
| 261 | H | H | H | H | H | H | *1 |
| 262 | $CH_3$ | H | H | $CH_3$ | H | H | *1 |
| 263 | tert-$C_4H_9$ | H | H | tert-$C_4H_9$ | H | H | *1 |
| 264 | Phenyl | H | H | Phenyl | H | H | *1 |
| 265 | $CH_3$ | H | H | $CH_3$ | H | H | *1 |
| 266 | tert-$C_4H_9$ | H | H | tert-$C_4H_9$ | H | H | *1 |
| 267 | Phenyl | H | H | Phenyl | H | H | *1 |
| 268 | H | H | H | H | H | H | *1 |
| 269 | $CH_3$ | H | H | $CH_3$ | H | H | *1 |
| 270 | tert-$C_4H_9$ | H | H | tert-$C_4H_9$ | H | H | *1 |

TABLE 2-continued

| | | | | | | | |
|---|---|---|---|---|---|---|---|
| 271 | Phenyl | H | H | Phenyl | H | H | *1 |
| 272 | H | H | H | H | H | H | *1 |
| 273 | tert-$C_4H_9$ | H | H | tert-$C_4H_9$ | H | H | *1 |
| 274 | tert-$C_4H_9$ | H | H | tert-$C_4H_9$ | H | H | *1 |
| 275 | H | H | H | H | H | H | *1 |
| 276 | $CH_3$ | H | H | $CH_3$ | H | H | *1 |
| 277 | tert-$C_4H_9$ | H | H | tert-$C_4H_9$ | H | H | *1 |
| 278 | Phenyl | H | H | Phenyl | H | H | *1 |

TABLE 3

| Compound No. | $A^{x1}$ | General Formula (11) $R^{x11}$ | $R^{x12}$ | $R^{x13}$ | $R^{x14}$ | $R^{a1}$ | $R^{a2}$ | General Formula (2a) $R^{a3}$ | $R^{a4}$ | $R^{a5}$ | $R^{a6}$ | $R^{a7}$ |
|---|---|---|---|---|---|---|---|---|---|---|---|---|
| 301 | CN | General Formula (2a) | General Formula (2a) | General Formula (2a) | General Formula (2b) | H | H | H | H | H | H | H |
| 302 | CN | General Formula (2a) | General Formula (2a) | General Formula (2a) | General Formula (2b) | H | H | H | H | H | H | H |
| 303 | CN | General Formula (2a) | General Formula (2a) | General Formula (2a) | General Formula (2b) | H | H | H | H | H | H | H |
| 304 | CN | General Formula (2a) | General Formula (2a) | General Formula (2a) | General Formula (2b) | H | H | H | H | H | H | H |
| 305 | CN | General Formula (2a) | General Formula (2a) | General Formula (2a) | General Formula (2b) | H | H | H | H | H | H | H |
| 306 | CN | General Formula (2a) | General Formula (2a) | General Formula (2a) | General Formula (2b) | H | H | H | H | H | H | H |
| 307 | CN | General Formula (2a) | General Formula (2a) | General Formula (2a) | General Formula (2b) | H | H | H | H | H | H | H |
| 308 | CN | General Formula (2a) | General Formula (2a) | General Formula (2a) | General Formula (2b) | H | H | H | H | H | H | H |
| 309 | CN | General Formula (2a) | General Formula (2a) | General Formula (2a) | General Formula (2b) | H | H | H | H | H | H | H |
| 310 | CN | General Formula (2a) | General Formula (2a) | General Formula (2a) | General Formula (2b) | H | H | H | H | H | H | H |
| 311 | CN | General Formula (2a) | General Formula (2a) | General Formula (2a) | General Formula (2b) | H | H | H | H | H | H | H |
| 312 | CN | General Formula (2a) | General Formula (2a) | General Formula (2a) | General Formula (2b) | H | H | H | H | H | H | H |
| 313 | CN | General Formula (2a) | General Formula (2a) | General Formula (2a) | General Formula (2b) | H | H | H | H | H | H | H |
| 314 | CN | General Formula (2a) | General Formula (2a) | General Formula (2b) | General Formula (2b) | H | H | H | H | H | H | H |
| 315 | CN | General Formula (2a) | General Formula (2a) | General Formula (2b) | General Formula (2b) | H | H | H | H | H | H | H |
| 316 | CN | General Formula (2a) | General Formula (2a) | General Formula (2b) | General Formula (2b) | H | H | H | H | H | H | H |
| 317 | CN | General Formula (2a) | General Formula (2a) | General Formula (2b) | General Formula (2a) | H | H | H | H | H | H | H |
| 318 | CN | General Formula (2a) | General Formula (2a) | General Formula (2b) | General Formula (2a) | H | H | H | H | H | H | H |
| 319 | CN | General Formula (2a) | General Formula (2a) | General Formula (2b) | General Formula (2a) | H | H | H | H | H | H | H |
| 320 | CN | General Formula (2a) | General Formula (2a) | General Formula (2b) | General Formula (2a) | H | H | H | H | H | H | H |
| 321 | CN | General Formula (2a) | General Formula (2a) | General Formula (2b) | General Formula (2a) | H | H | H | H | H | H | H |
| 322 | CN | General Formula (2a) | General Formula (2a) | General Formula (2b) | General Formula (2a) | H | H | H | H | H | H | H |
| 323 | CN | General Formula (2a) | General Formula (2a) | General Formula (2b) | General Formula (2a) | H | H | H | H | H | H | H |
| 324 | CN | General Formula (2a) | General Formula (2a) | General Formula (2b) | General Formula (2a) | H | H | H | H | H | H | H |
| 325 | CN | General Formula (2a) | General Formula (2a) | General Formula (2b) | General Formula (2a) | H | H | H | H | H | H | H |
| 326 | CN | General Formula (2a) | General Formula (2a) | General Formula (2b) | General Formula (2a) | H | H | H | H | H | H | H |
| 327 | CN | General Formula (2a) | General Formula (2a) | General Formula (2b) | General Formula (2a) | H | H | H | H | H | H | H |
| 328 | CN | General Formula (2a) | General Formula (2a) | General Formula (2b) | General Formula (2a) | H | H | H | H | H | H | H |
| 329 | CN | General Formula (2a) | General Formula (2a) | General Formula (2b) | General Formula (2a) | H | H | H | H | H | H | H |
| 330 | CN | General Formula (2a) | General Formula (2a) | General Formula (2b) | General Formula (2a) | H | H | H | H | H | H | H |
| 331 | CN | General Formula (2a) | General Formula (2a) | General Formula (2b) | General Formula (2a) | H | H | H | H | H | H | H |
| 332 | CN | General Formula (2a) | General Formula (2a) | General Formula (2b) | General Formula (2a) | H | H | H | H | H | H | H |
| 333 | CN | General Formula (2a) | General Formula (2a) | General Formula (2b) | General Formula (2a) | H | H | H | H | H | H | H |
| 334 | CN | General Formula (2a) | General Formula (2a) | General Formula (2b) | General Formula (2a) | H | H | H | H | H | H | H |
| 335 | CN | General Formula (2a) | General Formula (2a) | General Formula (2b) | General Formula (2a) | H | H | H | H | H | H | H |
| 336 | CN | General Formula (2a) | General Formula (2a) | General Formula (2b) | General Formula (2a) | H | H | H | H | H | H | H |
| 337 | CN | General Formula (2a) | General Formula (2a) | General Formula (2b) | General Formula (2a) | H | H | H | H | H | H | H |
| 338 | CN | General Formula (2a) | General Formula (2a) | General Formula (2b) | General Formula (2a) | H | H | H | H | H | H | H |
| 339 | CN | General Formula (2a) | General Formula (2a) | General Formula (2b) | General Formula (2a) | H | H | H | H | H | H | H |
| 340 | CN | General Formula (2a) | General Formula (2a) | General Formula (2b) | General Formula (2a) | H | H | H | H | H | H | H |
| 341 | CN | General Formula (2a) | General Formula (2a) | General Formula (2b) | General Formula (2a) | H | H | H | H | H | H | H |
| 342 | CN | General Formula (2a) | General Formula (2a) | General Formula (2b) | General Formula (2a) | H | H | H | H | H | H | H |
| 343 | CN | General Formula (2a) | General Formula (2a) | General Formula (2b) | General Formula (2a) | H | H | $CH_3$ | H | H | H | H |
| 344 | CN | General Formula (2a) | General Formula (2a) | General Formula (2b) | General Formula (2a) | H | H | tert-$C_4H_9$ | H | H | $CH_3$ | H |
| 345 | CN | General Formula (2a) | General Formula (2a) | General Formula (2b) | General Formula (2a) | H | H | Phenyl | H | H | tert-$C_4H_9$ | H |
| 346 | CN | General Formula (2a) | General Formula (2a) | General Formula (2b) | General Formula (2a) | H | H | $CH_3$ | H | H | Phenyl | H |
| 347 | CN | General Formula (2a) | General Formula (2a) | General Formula (2b) | General Formula (2a) | H | H | tert-$C_4H_9$ | H | H | H | H |

TABLE 3-continued

| Compound No. | General Formula (2a) R^a8 | General Formula (2a) R^a9 | General Formula (2b) R^b1 | General Formula (2b) R^b2 | General Formula (2b) R^b3 | General Formula (2b) R^b4 | General Formula (2b) R^b5 | General Formula (2b) R^b6 | General Formula (2b) R^b7 | General Formula (2b) R^b8 | General Formula (2b) R^b9 |
|---|---|---|---|---|---|---|---|---|---|---|---|
| 348 | H | *1 | H | H | H | H | Phenyl | H | H | H | *1 |
| 301 | H | *1 | H | H | CH$_3$ | H | H | CH$_3$ | H | H | *1 |
| 302 | H | *1 | H | H | tert-C$_4$H$_9$ | H | H | tert-C$_4$H$_9$ | H | H | *1 |
| 303 | H | *1 | H | H | Phenyl | H | H | Phenyl | H | H | *1 |
| 304 | H | *1 | H | H | CH$_3$ | H | H | H | H | H | *1 |
| 305 | H | *1 | H | H | tert-C$_4$H$_9$ | H | H | H | H | H | *1 |
| 306 | H | *1 | H | H | Phenyl | H | H | H | H | H | *1 |
| 307 | H | *1 | H | H | 9-Carbazolyl | H | H | 9-Carbazolyl | H | H | *1 |
| 308 | H | *1 | H | H | iso-Butyl | H | H | iso-Butyl | H | H | *1 |
| 309 | H | *1 | H | H | 2-Ethylhexyl | H | H | 2-Ethylhexyl | H | H | *1 |
| 310 | H | *1 | H | H | Trimethylsilyl | H | H | Trimethylsilyl | H | H | *1 |
| 311 | H | *1 | H | H | Diphenylamino | H | H | Diphenylamino | H | H | *1 |
| 312 | H | *1 | H | H | Diphenylamino | H | H | H | H | H | *1 |
| 313 | H | *1 | H | H | CH$_3$ | H | H | CH$_3$ | H | H | *1 |
| 314 | H | *1 | H | H | tert-C$_4$H$_9$ | H | H | tert-C$_4$H$_9$ | H | H | *1 |
| 315 | H | *1 | H | H | Phenyl | H | H | Phenyl | H | H | *1 |
| 316 | H | *1 | H | H | CH$_3$ | H | H | H | H | H | *1 |
| 317 | H | *1 | H | H | tert-C$_4$H$_9$ | H | H | H | H | H | *1 |
| 318 | H | *1 | H | H | Phenyl | H | H | H | H | H | *1 |
| 319 | H | *1 | H | H | 9-Carbazolyl | H | H | 9-Carbazolyl | H | H | *1 |
| 320 | H | *1 | H | H | iso-Butyl | H | H | iso-Butyl | H | H | *1 |
| 321 | H | *1 | H | H | 2-Ethylhexyl | H | H | 2-Ethylhexyl | H | H | *1 |
| 322 | H | *1 | H | H | Trimethylsilyl | H | H | Trimethylsilyl | H | H | *1 |
| 323 | H | *1 | H | H | Diphenylamino | H | H | Diphenylamino | H | H | *1 |
| 324 | H | *1 | H | H | Diphenylamino | H | H | H | H | H | *1 |
| 325 | H | *1 | H | H | CH$_3$ | H | H | CH$_3$ | H | H | *1 |
| 326 | H | *1 | H | H | tert-C$_4$H$_9$ | H | H | tert-C$_4$H$_9$ | H | H | *1 |
| 327 | H | *1 | H | H | Phenyl | H | H | Phenyl | H | H | *1 |
| 328 | H | *1 | H | H | CH$_3$ | H | H | H | H | H | *1 |
| 329 | H | *1 | H | H | tert-C$_4$H$_9$ | H | H | H | H | H | *1 |
| 330 | H | *1 | H | H | Phenyl | H | H | H | H | H | *1 |
| 331 | H | *1 | H | H | 9-Carbazolyl | H | H | 9-Carbazolyl | H | H | *1 |
| 332 | H | *1 | H | H | iso-Butyl | H | H | iso-Butyl | H | H | *1 |
| 333 | H | *1 | H | H | 2-Ethylhexyl | H | H | 2-Ethylhexyl | H | H | *1 |
| 334 | H | *1 | H | H | Trimethylsilyl | H | H | Trimethylsilyl | H | H | *1 |
| 335 | H | *1 | H | H | Diphenylamino | H | H | Diphenylamino | H | H | *1 |
| 336 | H | *1 | H | H | Diphenylamino | H | H | H | H | H | *1 |
| 337 | H | *1 | H | H | CH$_3$ | H | H | CH$_3$ | H | H | *1 |
| 338 | H | *1 | H | H | tert-C$_4$H$_9$ | H | H | tert-C$_4$H$_9$ | H | H | *1 |
| 339 | H | *1 | H | H | Phenyl | H | H | Phenyl | H | H | *1 |
| 340 | H | *1 | H | H | CH$_3$ | H | H | H | H | H | *1 |
| 341 | H | *1 | H | H | tert-C$_4$H$_9$ | H | H | H | H | H | *1 |
| 342 | H | *1 | H | H | Phenyl | H | H | H | H | H | *1 |
| 343 | H | *1 | H | H | H | H | H | H | H | H | *1 |
| 344 | H | *1 | H | H | H | H | H | H | H | H | *1 |

TABLE 3-continued

| | | | | | | | | | | |
|---|---|---|---|---|---|---|---|---|---|---|
| 345 | H | *1 | H | H | H | H | H | H | H | *1 |
| 346 | H | *1 | H | H | H | H | H | H | H | *1 |
| 347 | H | *1 | H | H | H | H | H | H | H | *1 |
| 348 | H | *1 | H | H | H | H | H | H | H | *1 |

TABLE 4

| Compound No. | A¹ | General Formula (10) | | | | | General Formula (2a) | | | | | |
|---|---|---|---|---|---|---|---|---|---|---|---|---|
| | | R¹ | R² | R³ | R⁴ | R⁵ | Rᵃ¹ | Rᵃ² | Rᵃ³ | Rᵃ⁴ | Rᵃ⁵ | Rᵃ⁶ |
| 401 | A1 | General Formula (2a) | General Formula (2a) | General Formula (2b) | General Formula (2a) | General Formula (2b) | H | H | H | H | H | H |
| 402 | A1 | General Formula (2a) | General Formula (2a) | General Formula (2b) | General Formula (2a) | General Formula (2b) | H | H | H | H | H | H |
| 403 | A1 | General Formula (2a) | General Formula (2a) | General Formula (2b) | General Formula (2a) | General Formula (2b) | H | H | H | H | H | H |
| 404 | A1 | General Formula (2a) | General Formula (2a) | General Formula (2b) | General Formula (2a) | General Formula (2b) | H | H | H | H | H | H |
| 405 | A1 | General Formula (2a) | General Formula (2a) | General Formula (2b) | General Formula (2a) | General Formula (2b) | H | H | H | H | H | H |
| 406 | A1 | General Formula (2a) | General Formula (2a) | General Formula (2b) | General Formula (2a) | General Formula (2b) | H | H | H | H | H | H |
| 407 | A1 | General Formula (2a) | General Formula (2a) | General Formula (2b) | General Formula (2a) | General Formula (2b) | H | H | H | H | H | H |
| 408 | A2 | General Formula (2a) | General Formula (2a) | General Formula (2b) | General Formula (2a) | General Formula (2b) | H | H | H | H | H | H |
| 409 | A2 | General Formula (2a) | General Formula (2a) | General Formula (2b) | General Formula (2a) | General Formula (2b) | H | H | H | H | H | H |
| 410 | A2 | General Formula (2a) | General Formula (2a) | General Formula (2b) | General Formula (2a) | General Formula (2b) | H | H | H | H | H | H |
| 411 | A2 | General Formula (2a) | General Formula (2a) | General Formula (2b) | General Formula (2a) | General Formula (2b) | H | H | H | H | H | H |
| 412 | A2 | General Formula (2a) | General Formula (2a) | General Formula (2b) | General Formula (2a) | General Formula (2b) | H | H | H | H | H | H |
| 413 | A2 | General Formula (2a) | General Formula (2a) | General Formula (2b) | General Formula (2a) | General Formula (2b) | H | H | H | H | H | H |
| 414 | A3 | General Formula (2a) | General Formula (2a) | General Formula (2b) | General Formula (2a) | General Formula (2b) | H | H | H | H | H | H |
| 415 | A3 | General Formula (2a) | General Formula (2a) | General Formula (2b) | General Formula (2a) | General Formula (2b) | H | H | H | H | H | H |
| 416 | A3 | General Formula (2a) | General Formula (2a) | General Formula (2b) | General Formula (2a) | General Formula (2b) | H | H | H | H | H | H |
| 417 | A3 | General Formula (2a) | General Formula (2a) | General Formula (2b) | General Formula (2a) | General Formula (2b) | H | H | H | H | H | H |
| 418 | A3 | General Formula (2a) | General Formula (2a) | General Formula (2b) | General Formula (2a) | General Formula (2b) | H | H | H | H | H | H |
| 419 | A3 | General Formula (2a) | General Formula (2a) | General Formula (2b) | General Formula (2a) | General Formula (2b) | H | H | H | H | H | H |
| 420 | A3 | General Formula (2a) | General Formula (2a) | General Formula (2b) | General Formula (2a) | General Formula (2b) | H | H | H | H | H | H |
| 421 | A4 | General Formula (2a) | General Formula (2a) | General Formula (2b) | General Formula (2a) | General Formula (2b) | H | H | H | H | H | H |
| 422 | A4 | General Formula (2a) | General Formula (2a) | General Formula (2b) | General Formula (2a) | General Formula (2b) | H | H | H | H | H | H |
| 423 | A4 | General Formula (2a) | General Formula (2a) | General Formula (2b) | General Formula (2a) | General Formula (2b) | H | H | H | H | H | H |
| 424 | A4 | General Formula (2a) | General Formula (2a) | General Formula (2b) | General Formula (2a) | General Formula (2b) | H | H | H | H | H | H |
| 425 | A4 | General Formula (2a) | General Formula (2a) | General Formula (2b) | General Formula (2a) | General Formula (2b) | H | H | H | H | H | H |
| 426 | A4 | General Formula (2a) | General Formula (2a) | General Formula (2b) | General Formula (2a) | General Formula (2b) | H | H | H | H | H | H |
| 427 | A4 | General Formula (2a) | General Formula (2a) | General Formula (2b) | General Formula (2a) | General Formula (2b) | H | H | H | H | H | H |
| 428 | A5 | General Formula (2a) | General Formula (2a) | General Formula (2b) | General Formula (2a) | General Formula (2b) | H | H | H | H | H | H |
| 429 | A5 | General Formula (2a) | General Formula (2a) | General Formula (2b) | General Formula (2a) | General Formula (2b) | H | H | H | H | H | H |
| 430 | A5 | General Formula (2a) | General Formula (2a) | General Formula (2b) | General Formula (2a) | General Formula (2b) | H | H | H | H | H | H |
| 431 | A5 | General Formula (2a) | General Formula (2a) | General Formula (2b) | General Formula (2a) | General Formula (2b) | H | H | H | H | H | H |
| 432 | A5 | General Formula (2a) | General Formula (2a) | General Formula (2b) | General Formula (2a) | General Formula (2b) | H | H | H | H | H | H |
| 433 | A5 | General Formula (2a) | General Formula (2a) | General Formula (2b) | General Formula (2a) | General Formula (2b) | H | H | H | H | H | H |
| 434 | A5 | General Formula (2a) | General Formula (2a) | General Formula (2b) | General Formula (2a) | General Formula (2b) | H | H | H | H | H | H |
| 435 | A5 | General Formula (2a) | General Formula (2a) | General Formula (2b) | General Formula (2a) | General Formula (2b) | H | H | H | H | H | H |
| 436 | A6 | General Formula (2a) | General Formula (2a) | General Formula (2b) | General Formula (2a) | General Formula (2b) | H | H | H | H | H | H |
| 437 | A6 | General Formula (2a) | General Formula (2a) | General Formula (2b) | General Formula (2a) | General Formula (2b) | H | H | H | H | H | H |
| 438 | A6 | General Formula (2a) | General Formula (2a) | General Formula (2b) | General Formula (2a) | General Formula (2b) | H | H | H | H | H | H |
| 439 | A6 | General Formula (2a) | General Formula (2a) | General Formula (2b) | General Formula (2a) | General Formula (2b) | H | H | H | H | H | H |
| 440 | A6 | General Formula (2a) | General Formula (2a) | General Formula (2b) | General Formula (2a) | General Formula (2b) | H | H | H | H | H | H |
| 441 | A7 | General Formula (2a) | General Formula (2a) | General Formula (2b) | General Formula (2a) | General Formula (2b) | H | H | H | H | H | H |
| 442 | A7 | General Formula (2a) | General Formula (2a) | General Formula (2b) | General Formula (2a) | General Formula (2b) | H | H | H | H | H | H |
| 443 | A7 | General Formula (2a) | General Formula (2a) | General Formula (2b) | General Formula (2a) | General Formula (2b) | H | H | H | H | H | H |
| 444 | A7 | General Formula (2a) | General Formula (2a) | General Formula (2b) | General Formula (2a) | General Formula (2b) | H | H | H | H | H | H |
| 445 | A7 | General Formula (2a) | General Formula (2a) | General Formula (2b) | General Formula (2a) | General Formula (2b) | H | H | H | H | H | H |
| 446 | A7 | General Formula (2a) | General Formula (2a) | General Formula (2b) | General Formula (2a) | General Formula (2b) | H | H | H | H | H | H |
| 447 | A7 | General Formula (2a) | General Formula (2a) | General Formula (2b) | General Formula (2a) | General Formula (2b) | H | H | H | H | H | H |

TABLE 4-continued

| Compound No. | R^{a7} | R^{a8} | R^{a9} | R^{b1} | R^{b2} | R^{b3} | R^{b4} | R^{b5} | R^{b6} | R^{b7} | R^{b8} | R^{b9} |
|---|---|---|---|---|---|---|---|---|---|---|---|---|
| 448 | A7 | H | General Formula (2a) | General Formula (2b) | H | H | H | H | H | H | H | H |
| 449 | A7 | H | General Formula (2a) | General Formula (2b) | H | H | H | H | H | H | H | H |
| 450 | A7 | H | General Formula (2b) | General Formula (2a) | H | H | H | H | H | H | H | H |
| 451 | A8 | H | General Formula (2a) | General Formula (2b) | H | H | H | H | H | H | H | H |
| 452 | A8 | H | General Formula (2a) | General Formula (2b) | H | H | H | H | H | H | H | H |
| 453 | A8 | H | General Formula (2a) | General Formula (2b) | H | H | H | H | H | H | H | H |
| 454 | A8 | H | General Formula (2a) | General Formula (2b) | H | H | H | H | H | H | H | H |
| 455 | A8 | H | General Formula (2a) | General Formula (2b) | H | H | H | H | H | H | H | H |
| 456 | A8 | H | General Formula (2a) | General Formula (2b) | H | H | H | H | H | H | H | H |
| 457 | A9 | H | General Formula (2a) | General Formula (2b) | H | H | H | H | H | H | H | H |
| 458 | A9 | H | General Formula (2a) | General Formula (2b) | H | H | H | H | H | H | H | H |
| 459 | A9 | H | General Formula (2a) | General Formula (2b) | H | H | H | H | H | H | H | H |
| 460 | A9 | H | General Formula (2a) | General Formula (2b) | H | H | H | H | H | H | H | H |
| 461 | A9 | H | General Formula (2a) | General Formula (2b) | H | H | H | H | H | H | H | H |
| 462 | A9 | H | General Formula (2a) | General Formula (2b) | H | H | H | H | H | H | H | H |
| 463 | A10 | H | General Formula (2a) | General Formula (2b) | H | H | H | H | H | H | H | H |
| 464 | A10 | H | General Formula (2a) | General Formula (2b) | H | H | H | H | H | H | H | H |
| 465 | A10 | H | General Formula (2a) | General Formula (2b) | H | H | H | H | H | H | H | H |
| 466 | A10 | H | General Formula (2a) | General Formula (2b) | H | H | H | H | H | H | H | H |
| 467 | A10 | H | General Formula (2a) | General Formula (2b) | H | H | H | H | H | H | H | H |
| 468 | A10 | H | General Formula (2a) | General Formula (2b) | H | H | H | H | H | H | H | H |
| 469 | A10 | H | General Formula (2a) | General Formula (2b) | H | H | H | H | H | H | H | H |
| 470 | A10 | H | General Formula (2a) | General Formula (2b) | H | H | H | H | H | H | H | H |
| 471 | A10 | H | General Formula (2a) | General Formula (2b) | H | H | H | H | H | H | H | H |
| 472 | A11 | H | General Formula (2a) | General Formula (2b) | H | H | H | H | H | H | H | H |
| 473 | A11 | H | General Formula (2a) | General Formula (2b) | H | H | H | H | H | H | H | H |
| 474 | A11 | H | General Formula (2a) | General Formula (2b) | H | H | H | H | H | H | H | H |
| 475 | A11 | H | General Formula (2a) | General Formula (2b) | H | H | H | H | H | H | H | H |
| 476 | A11 | H | General Formula (2a) | General Formula (2b) | H | H | H | H | H | H | H | H |
| 477 | A11 | H | General Formula (2a) | General Formula (2b) | H | H | H | H | H | H | H | H |
| 478 | A12 | H | General Formula (2a) | General Formula (2b) | H | H | H | H | H | H | H | H |
| 479 | A12 | H | General Formula (2a) | General Formula (2b) | H | H | H | H | H | H | H | H |
| 480 | A12 | H | General Formula (2a) | General Formula (2b) | H | H | H | H | H | H | H | H |
| 481 | A12 | H | General Formula (2a) | General Formula (2b) | H | H | H | H | H | H | H | H |
| 482 | A12 | H | General Formula (2a) | General Formula (2b) | H | H | H | H | H | H | H | H |
| 483 | A12 | H | General Formula (2a) | General Formula (2b) | H | H | H | H | H | H | H | H |
| 484 | A12 | H | General Formula (2a) | General Formula (2b) | H | H | H | H | H | H | H | H |
| 485 | A13 | H | General Formula (2a) | General Formula (2b) | H | H | H | H | H | H | H | H |
| 486 | A13 | H | General Formula (2a) | General Formula (2b) | H | H | H | H | H | H | H | H |
| 487 | A13 | H | General Formula (2a) | General Formula (2b) | H | H | H | H | H | H | H | H |
| 488 | A13 | H | General Formula (2a) | General Formula (2b) | H | H | H | H | H | H | H | H |
| 489 | A13 | H | General Formula (2a) | General Formula (2b) | H | H | H | H | H | H | H | H |
| 490 | A13 | H | General Formula (2a) | General Formula (2b) | H | H | H | H | H | H | H | H |
| 491 | A13 | H | General Formula (2a) | General Formula (2b) | H | H | H | H | H | H | H | H |
| 492 | A13 | H | General Formula (2a) | General Formula (2b) | H | H | H | H | H | H | H | H |

| Compound No. | General Formula (2a) | | | General Formula (2b) | | | | | | | | |
|---|---|---|---|---|---|---|---|---|---|---|---|---|
| | R^{a8} | R^{a9} | | R^{b1} | R^{b2} | R^{b3} | R^{b4} | R^{b5} | R^{b6} | R^{b7} | R^{b8} | R^{b9} |
| 401 | H | *1 | | H | H | CH$_3$ | H | H | CH$_3$ | H | H | *1 |
| 402 | H | *1 | | H | H | tert-C$_4$H$_9$ | H | H | tert-C$_4$H$_9$ | H | H | *1 |
| 403 | H | *1 | | H | H | Phenyl | H | H | Phenyl | H | H | *1 |

TABLE 4-continued

| | | | | | | | | |
|---|---|---|---|---|---|---|---|---|
| 404 | H | H | H | CH₃ | H | CH₃ | H | *1 |
| 405 | H | H | H | tert-C₄H₉ | H | tert-C₄H₉ | H | *1 |
| 406 | H | H | H | Phenyl | H | Phenyl | H | *1 |
| 407 | H | H | H | 9-Carbazolyl | H | 9-Carbazolyl | H | *1 |
| 408 | H | H | H | CH₃ | H | CH₃ | H | *1 |
| 409 | H | H | H | tert-C₄H₉ | H | tert-C₄H₉ | H | *1 |
| 410 | H | H | H | Phenyl | H | Phenyl | H | *1 |
| 411 | H | H | H | 9-Carbazolyl | H | 9-Carbazolyl | H | *1 |
| 412 | H | H | H | CH₃ | H | CH₃ | H | *1 |
| 413 | H | H | H | tert-C₄H₉ | H | tert-C₄H₉ | H | *1 |
| 414 | H | H | H | Phenyl | H | Phenyl | H | *1 |
| 415 | H | H | H | 9-Carbazolyl | H | 9-Carbazolyl | H | *1 |
| 416 | H | H | H | CH₃ | H | CH₃ | H | *1 |
| 417 | H | H | H | tert-C₄H₉ | H | tert-C₄H₉ | H | *1 |
| 418 | H | H | H | Phenyl | H | Phenyl | H | *1 |
| 419 | H | H | H | 9-Carbazolyl | H | 9-Carbazolyl | H | *1 |
| 420 | H | H | H | CH₃ | H | CH₃ | H | *1 |
| 421 | H | H | H | tert-C₄H₉ | H | tert-C₄H₉ | H | *1 |
| 422 | H | H | H | Phenyl | H | Phenyl | H | *1 |
| 423 | H | H | H | 9-Carbazolyl | H | 9-Carbazolyl | H | *1 |
| 424 | H | H | H | CH₃ | H | CH₃ | H | *1 |
| 425 | H | H | H | tert-C₄H₉ | H | tert-C₄H₉ | H | *1 |
| 426 | H | H | H | Phenyl | H | Phenyl | H | *1 |
| 427 | H | H | H | 9-Carbazolyl | H | 9-Carbazolyl | H | *1 |
| 428 | H | H | H | CH₃ | H | CH₃ | H | *1 |
| 429 | H | H | H | tert-C₄H₉ | H | tert-C₄H₉ | H | *1 |
| 430 | H | H | H | Phenyl | H | Phenyl | H | *1 |
| 431 | H | H | H | 9-Carbazolyl | H | 9-Carbazolyl | H | *1 |
| 432 | H | H | H | CH₃ | H | CH₃ | H | *1 |
| 433 | H | H | H | tert-C₄H₉ | H | tert-C₄H₉ | H | *1 |
| 434 | H | H | H | Phenyl | H | Phenyl | H | *1 |
| 435 | H | H | H | 9-Carbazolyl | H | 9-Carbazolyl | H | *1 |
| 436 | H | H | H | CH₃ | H | CH₃ | H | *1 |
| 437 | H | H | H | tert-C₄H₉ | H | tert-C₄H₉ | H | *1 |
| 438 | H | H | H | Phenyl | H | Phenyl | H | *1 |
| 439 | H | H | H | 9-Carbazolyl | H | 9-Carbazolyl | H | *1 |
| 440 | H | H | H | CH₃ | H | CH₃ | H | *1 |
| 441 | H | H | H | tert-C₄H₉ | H | tert-C₄H₉ | H | *1 |
| 442 | H | H | H | Phenyl | H | Phenyl | H | *1 |
| 443 | H | H | H | 9-Carbazolyl | H | 9-Carbazolyl | H | *1 |
| 444 | H | H | H | CH₃ | H | CH₃ | H | *1 |
| 445 | H | H | H | tert-C₄H₉ | H | tert-C₄H₉ | H | *1 |
| 446 | H | H | H | Phenyl | H | Phenyl | H | *1 |
| 447 | H | H | H | 9-Carbazolyl | H | 9-Carbazolyl | H | *1 |
| 448 | H | H | H | CH₃ | H | CH₃ | H | *1 |
| 449 | H | H | H | tert-C₄H₉ | H | tert-C₄H₉ | H | *1 |
| 450 | H | H | H | Phenyl | H | Phenyl | H | *1 |
| 451 | H | H | H | 9-Carbazolyl | H | 9-Carbazolyl | H | *1 |
| 452 | H | H | H | CH₃ | H | CH₃ | H | *1 |
| 453 | H | H | H | tert-C₄H₉ | H | tert-C₄H₉ | H | *1 |
| 454 | H | H | H | Phenyl | H | Phenyl | H | *1 |
| 455 | H | H | H | tert-C₄H₉ | H | tert-C₄H₉ | H | *1 |
| 456 | H | H | H | Phenyl | H | Phenyl | H | *1 |

TABLE 4-continued

| | | | | | | | | |
|---|---|---|---|---|---|---|---|---|
| 457 | H | H | *1 | H | H | 9-Carbazolyl | H | 9-Carbazolyl | H | *1 |
| 458 | H | H | *1 | H | H | CH₃ | H | CH₃ | H | *1 |
| 459 | H | H | *1 | H | H | tert-C₄H₉ | H | tert-C₄H₉ | H | *1 |
| 460 | H | H | *1 | H | H | Phenyl | H | Phenyl | H | *1 |
| 461 | H | H | *1 | H | H | CH₃ | H | CH₃ | H | *1 |
| 462 | H | H | *1 | H | H | tert-C₄H₉ | H | tert-C₄H₉ | H | *1 |
| 463 | H | H | *1 | H | H | Phenyl | H | Phenyl | H | *1 |
| 464 | H | H | *1 | H | H | 9-Carbazolyl | H | 9-Carbazolyl | H | *1 |
| 465 | H | H | *1 | H | H | CH₃ | H | CH₃ | H | *1 |
| 466 | H | H | *1 | H | H | tert-C₄H₉ | H | tert-C₄H₉ | H | *1 |
| 467 | H | H | *1 | H | H | Phenyl | H | Phenyl | H | *1 |
| 468 | H | H | *1 | H | H | CH₃ | H | CH₃ | H | *1 |
| 469 | H | H | *1 | H | H | tert-C₄H₉ | H | tert-C₄H₉ | H | *1 |
| 470 | H | H | *1 | H | H | Phenyl | H | Phenyl | H | *1 |
| 471 | H | H | *1 | H | H | 9-Carbazolyl | H | 9-Carbazolyl | H | *1 |
| 472 | H | H | *1 | H | H | CH₃ | H | CH₃ | H | *1 |
| 473 | H | H | *1 | H | H | tert-C₄H₉ | H | tert-C₄H₉ | H | *1 |
| 474 | H | H | *1 | H | H | Phenyl | H | Phenyl | H | *1 |
| 475 | H | H | *1 | H | H | CH₃ | H | CH₃ | H | *1 |
| 476 | H | H | *1 | H | H | tert-C₄H₉ | H | tert-C₄H₉ | H | *1 |
| 477 | H | H | *1 | H | H | Phenyl | H | Phenyl | H | *1 |
| 478 | H | H | *1 | H | H | 9-Carbazolyl | H | 9-Carbazolyl | H | *1 |
| 479 | H | H | *1 | H | H | CH₃ | H | CH₃ | H | *1 |
| 480 | H | H | *1 | H | H | tert-C₄H₉ | H | tert-C₄H₉ | H | *1 |
| 481 | H | H | *1 | H | H | Phenyl | H | Phenyl | H | *1 |
| 482 | H | H | *1 | H | H | CH₃ | H | CH₃ | H | *1 |
| 483 | H | H | *1 | H | H | tert-C₄H₉ | H | tert-C₄H₉ | H | *1 |
| 484 | H | H | *1 | H | H | Phenyl | H | Phenyl | H | *1 |
| 485 | H | H | *1 | H | H | 9-Carbazolyl | H | 9-Carbazolyl | H | *1 |
| 486 | H | H | *1 | H | H | CH₃ | H | CH₃ | H | *1 |
| 487 | H | H | *1 | H | H | tert-C₄H₉ | H | tert-C₄H₉ | H | *1 |
| 488 | H | H | *1 | H | H | Phenyl | H | Phenyl | H | *1 |
| 489 | H | H | *1 | H | H | CH₃ | H | CH₃ | H | *1 |
| 490 | H | H | *1 | H | H | tert-C₄H₉ | H | tert-C₄H₉ | H | *1 |
| 491 | H | H | *1 | H | H | Phenyl | H | Phenyl | H | *1 |
| 492 | H | H | *1 | H | H | 9-Carbazolyl | H | 9-Carbazolyl | H | *1 |

TABLE 5

| Compound No. | A¹ | R¹ | R² | R³ | R⁴ | R⁵ | R^{a1} | R^{a2} | R^{a3} | R^{a4} | R^{a5} | R^{a6} |
|---|---|---|---|---|---|---|---|---|---|---|---|---|
| 501 | A5 | General Formula (2a) | A5 | General Formula (2a) | General Formula (2b) | General Formula (2b) | H | H | H | H | H | H |
| 502 | A5 | General Formula (2a) | A5 | General Formula (2a) | General Formula (2b) | General Formula (2b) | H | H | H | H | H | H |
| 503 | A5 | General Formula (2a) | A5 | General Formula (2a) | General Formula (2b) | General Formula (2b) | H | H | H | H | H | H |
| 504 | A5 | General Formula (2a) | A5 | General Formula (2a) | General Formula (2b) | General Formula (2b) | H | H | CH₃ | H | H | CH₃ |
| 505 | A5 | General Formula (2a) | A5 | General Formula (2a) | General Formula (2b) | General Formula (2b) | H | H | H | H | H | H |
| 506 | A5 | General Formula (2a) | A5 | General Formula (2a) | General Formula (2b) | General Formula (2b) | H | H | H | H | H | H |
| 507 | A5 | General Formula (2a) | A5 | General Formula (2a) | General Formula (2b) | General Formula (2b) | H | H | H | H | H | H |
| 508 | A5 | General Formula (2a) | A5 | General Formula (2a) | General Formula (2b) | General Formula (2b) | H | H | CH₃ | H | H | CH₃ |
| 509 | A5 | General Formula (2a) | A5 | General Formula (2a) | General Formula (2b) | General Formula (2b) | H | H | CH₃ | H | H | CH₃ |
| 510 | A5 | General Formula (2a) | A5 | General Formula (2a) | General Formula (2b) | General Formula (2b) | H | H | Phenyl | H | H | Phenyl |
| 511 | A5 | General Formula (2a) | A5 | General Formula (2a) | General Formula (2b) | General Formula (2b) | H | H | H | H | H | H |
| 512 | A5 | General Formula (2a) | A5 | General Formula (2a) | General Formula (2b) | General Formula (2b) | H | H | H | H | H | H |
| 513 | A5 | General Formula (2a) | A5 | General Formula (2a) | General Formula (2b) | General Formula (2b) | H | H | CH₃ | H | H | CH₃ |
| 514 | A5 | General Formula (2a) | A5 | General Formula (2a) | General Formula (2b) | General Formula (2b) | H | H | H | H | H | H |
| 515 | A5 | General Formula (2a) | A5 | General Formula (2a) | General Formula (2b) | General Formula (2b) | H | H | H | H | H | H |
| 516 | A5 | General Formula (2a) | A5 | General Formula (2a) | H | General Formula (2b) | H | H | H | H | H | H |
| 517 | A5 | General Formula (2a) | A5 | General Formula (2a) | H | General Formula (2b) | H | H | CH₃ | H | H | CH₃ |
| 518 | A5 | General Formula (2a) | A5 | General Formula (2a) | H | General Formula (2b) | H | H | tert-C₄H₉ | H | H | tert-C₄H₉ |
| 519 | A5 | General Formula (2a) | A5 | General Formula (2a) | H | General Formula (2b) | H | H | Phenyl | H | H | Phenyl |
| 520 | A5 | General Formula (2a) | A6 | General Formula (2a) | General Formula (2b) | General Formula (2b) | H | H | H | H | H | H |
| 521 | A6 | General Formula (2a) | A6 | General Formula (2a) | General Formula (2b) | General Formula (2b) | H | H | H | H | H | H |
| 522 | A6 | General Formula (2a) | A6 | General Formula (2a) | General Formula (2b) | General Formula (2b) | H | H | H | H | H | H |
| 523 | A6 | General Formula (2a) | A6 | General Formula (2a) | General Formula (2b) | General Formula (2b) | H | H | CH₃ | H | H | CH₃ |
| 524 | A6 | General Formula (2a) | A6 | General Formula (2a) | General Formula (2b) | General Formula (2b) | H | H | H | H | H | H |
| 525 | A6 | General Formula (2a) | A6 | General Formula (2a) | General Formula (2b) | General Formula (2b) | H | H | H | H | H | H |
| 526 | A6 | General Formula (2a) | A6 | General Formula (2a) | General Formula (2b) | General Formula (2b) | H | H | H | H | H | H |
| 527 | A6 | General Formula (2a) | A6 | General Formula (2a) | General Formula (2b) | General Formula (2b) | H | H | CH₃ | H | H | CH₃ |
| 528 | A6 | General Formula (2a) | A6 | General Formula (2a) | General Formula (2b) | General Formula (2b) | H | H | CH₃ | H | H | CH₃ |
| 529 | A6 | General Formula (2a) | A6 | General Formula (2a) | General Formula (2b) | General Formula (2b) | H | H | Phenyl | H | H | Phenyl |
| 530 | A6 | General Formula (2a) | A6 | General Formula (2a) | General Formula (2b) | General Formula (2b) | H | H | H | H | H | H |
| 531 | A6 | General Formula (2a) | A6 | General Formula (2a) | General Formula (2b) | General Formula (2b) | H | H | H | H | H | H |
| 532 | A6 | General Formula (2a) | A6 | General Formula (2a) | General Formula (2b) | General Formula (2b) | H | H | CH₃ | H | H | CH₃ |
| 533 | A6 | General Formula (2a) | A6 | General Formula (2a) | General Formula (2b) | General Formula (2b) | H | H | H | H | H | H |
| 534 | A6 | General Formula (2a) | A6 | General Formula (2a) | General Formula (2b) | General Formula (2b) | H | H | H | H | H | H |
| 535 | A6 | General Formula (2a) | A6 | General Formula (2a) | H | General Formula (2b) | H | H | H | H | H | H |
| 536 | A6 | General Formula (2a) | A6 | General Formula (2a) | H | General Formula (2b) | H | H | CH₃ | H | H | CH₃ |
| 537 | A6 | General Formula (2a) | A6 | General Formula (2a) | H | General Formula (2b) | H | H | tert-C₄H₉ | H | H | tert-C₄H₉ |
| 538 | A6 | General Formula (2a) | A6 | General Formula (2a) | H | General Formula (2b) | H | H | Phenyl | H | H | Phenyl |
| 539 | A6 | General Formula (2a) | A7 | General Formula (2a) | General Formula (2b) | General Formula (2b) | H | H | H | H | H | H |
| 540 | A7 | General Formula (2a) | A7 | General Formula (2a) | General Formula (2b) | General Formula (2b) | H | H | H | H | H | H |
| 541 | A7 | General Formula (2a) | A7 | General Formula (2a) | General Formula (2b) | General Formula (2b) | H | H | H | H | H | H |
| 542 | A7 | General Formula (2a) | A7 | General Formula (2a) | General Formula (2b) | General Formula (2b) | H | H | CH₃ | H | H | CH₃ |
| 543 | A7 | General Formula (2a) | A7 | General Formula (2a) | General Formula (2b) | General Formula (2b) | H | H | H | H | H | H |
| 544 | A7 | General Formula (2a) | A7 | General Formula (2a) | General Formula (2b) | General Formula (2b) | H | H | H | H | H | H |
| 545 | A7 | General Formula (2a) | A7 | General Formula (2a) | General Formula (2b) | General Formula (2b) | H | H | H | H | H | H |
| 546 | A7 | General Formula (2a) | A7 | General Formula (2a) | General Formula (2b) | General Formula (2b) | H | H | CH₃ | H | H | CH₃ |
| 547 | A7 | General Formula (2a) | A7 | General Formula (2a) | General Formula (2b) | General Formula (2b) | H | H | CH₃ | H | H | CH₃ |

TABLE 5-continued

| No. | | | | | | | | | |
|---|---|---|---|---|---|---|---|---|---|
| 548 | General Formula (2a) | A7 | General Formula (2a) | General Formula (2b) | H | H | CH₃ | H | CH₃ |
| 549 | General Formula (2a) | A7 | General Formula (2a) | General Formula (2b) | H | H | CH₃ | H | CH₃ |
| 550 | General Formula (2a) | A7 | General Formula (2a) | General Formula (2b) | H | H | Phenyl | H | Phenyl |
| 551 | General Formula (2a) | A7 | General Formula (2a) | General Formula (2b) | H | H | H | H | H |
| 552 | General Formula (2a) | A7 | General Formula (2a) | General Formula (2b) | H | H | H | H | H |
| 553 | General Formula (2a) | A7 | General Formula (2a) | General Formula (2b) | H | H | H | H | H |
| 554 | General Formula (2a) | A7 | General Formula (2a) | General Formula (2b) | H | H | CH₃ | H | CH₃ |
| 555 | General Formula (2a) | A7 | H | General Formula (2b) | H | H | H | H | H |
| 556 | General Formula (2a) | A7 | H | General Formula (2b) | H | H | H | H | H |
| 557 | General Formula (2a) | A7 | H | General Formula (2b) | H | H | H | H | H |
| 558 | General Formula (2a) | A7 | H | General Formula (2b) | H | H | CH₃ | H | CH₃ |
| 559 | General Formula (2a) | A7 | H | General Formula (2b) | H | H | tert-C₄H₉ | H | tert-C₄H₉ |
| 560 | General Formula (2a) | A7 | H | General Formula (2b) | H | H | Phenyl | H | Phenyl |
| 561 | General Formula (2a) | A5 | A5 | General Formula (2b) | H | H | H | H | H |
| 562 | General Formula (2a) | A5 | A5 | General Formula (2b) | H | H | H | H | H |
| 563 | General Formula (2a) | A5 | A5 | General Formula (2b) | H | H | H | H | H |
| 564 | General Formula (2a) | A5 | A5 | General Formula (2b) | H | H | CH₃ | H | CH₃ |
| 565 | General Formula (2a) | A5 | A5 | General Formula (2b) | H | H | H | H | H |
| 566 | General Formula (2a) | A5 | A5 | General Formula (2b) | H | H | H | H | H |
| 567 | General Formula (2a) | A5 | A5 | General Formula (2b) | H | H | H | H | H |
| 568 | General Formula (2a) | A5 | A5 | General Formula (2b) | H | H | CH₃ | H | CH₃ |
| 569 | General Formula (2a) | A5 | A5 | General Formula (2b) | H | H | H | H | H |
| 570 | General Formula (2a) | A5 | A5 | General Formula (2b) | H | H | H | H | H |
| 571 | General Formula (2a) | A5 | A5 | General Formula (2b) | H | H | H | H | H |
| 572 | General Formula (2a) | A5 | A5 | General Formula (2b) | H | H | CH₃ | H | CH₃ |
| 573 | General Formula (2a) | A5 | General Formula (2a) | General Formula (2b) | H | H | H | H | H |
| 574 | General Formula (2a) | A5 | General Formula (2a) | General Formula (2b) | H | H | H | H | H |
| 575 | General Formula (2a) | A5 | General Formula (2a) | General Formula (2b) | H | H | H | H | H |
| 576 | General Formula (2a) | A5 | General Formula (2a) | General Formula (2b) | H | H | CH₃ | H | CH₃ |
| 577 | General Formula (2a) | A5 | A5 | General Formula (2b) | H | H | H | H | H |
| 578 | General Formula (2a) | A5 | A5 | General Formula (2b) | H | H | H | H | H |
| 579 | General Formula (2a) | A5 | A5 | General Formula (2b) | H | H | H | H | H |
| 580 | General Formula (2a) | A5 | A5 | General Formula (2b) | H | H | CH₃ | H | CH₃ |
| 581 | General Formula (2a) | A5 | A5 | General Formula (2b) | H | H | H | H | H |
| 582 | General Formula (2a) | A5 | A5 | General Formula (2b) | H | H | H | H | H |
| 583 | General Formula (2a) | A5 | A5 | General Formula (2b) | H | H | H | H | H |
| 584 | General Formula (2a) | A5 | A5 | General Formula (2b) | H | H | CH₃ | H | CH₃ |
| 585 | General Formula (2a) | A6 | A6 | General Formula (2b) | H | H | H | H | H |
| 586 | General Formula (2a) | A6 | A6 | General Formula (2b) | H | H | H | H | H |
| 587 | General Formula (2a) | A6 | A6 | General Formula (2b) | H | H | H | H | H |
| 588 | General Formula (2a) | A6 | A6 | General Formula (2b) | H | H | CH₃ | H | CH₃ |
| 589 | General Formula (2a) | A6 | A6 | General Formula (2b) | H | H | H | H | H |
| 590 | General Formula (2a) | A6 | A6 | General Formula (2b) | H | H | H | H | H |
| 591 | General Formula (2a) | A6 | A6 | General Formula (2b) | H | H | H | H | H |
| 592 | General Formula (2a) | A6 | A6 | General Formula (2b) | H | H | CH₃ | H | CH₃ |
| 593 | General Formula (2a) | A6 | A6 | General Formula (2b) | H | H | H | H | H |
| 594 | General Formula (2a) | A6 | A6 | General Formula (2b) | H | H | H | H | H |
| 595 | General Formula (2a) | A6 | A6 | General Formula (2b) | H | H | H | H | H |
| 596 | General Formula (2a) | A6 | A6 | General Formula (2b) | H | H | CH₃ | H | CH₃ |
| 597 | General Formula (2a) | A6 | A6 | General Formula (2b) | H | H | H | H | H |
| 598 | General Formula (2a) | A6 | A6 | General Formula (2b) | H | H | H | H | H |
| 599 | General Formula (2a) | A6 | A6 | General Formula (2b) | H | H | H | H | H |
| 600 | General Formula (2a) | A6 | A6 | General Formula (2b) | H | H | CH₃ | H | CH₃ |

TABLE 5-continued

| Compound No. | | R^a7 | R^a8 | General Formula (2a) R^a9 | | | |
|---|---|---|---|---|---|---|---|
| 601 | A6 | H | H | General Formula (2a) | A6 | General Formula (2b) | H |
| 602 | A6 | H | H | General Formula (2a) | A6 | General Formula (2b) | H |
| 603 | A6 | H | H | General Formula (2a) | A6 | General Formula (2b) | H |
| 604 | A6 | H | H | General Formula (2a) | A6 | General Formula (2b) | CH3 |
| 605 | A6 | H | H | General Formula (2a) | A6 | General Formula (2b) | H |
| 606 | A6 | H | H | General Formula (2a) | A6 | General Formula (2b) | H |
| 607 | A6 | H | H | General Formula (2a) | A6 | General Formula (2b) | H |
| 608 | A6 | H | H | General Formula (2a) | A6 | General Formula (2b) | CH3 |
| 609 | A7 | H | *1 | General Formula (2a) | A7 | | H |
| 610 | A7 | H | *1 | General Formula (2a) | A7 | General Formula (2b) | H |
| 611 | A7 | H | *1 | General Formula (2a) | A7 | General Formula (2b) | H |
| 612 | A7 | H | *1 | General Formula (2a) | A7 | General Formula (2b) | CH3 |
| 613 | A7 | H | *1 | General Formula (2a) | A7 | General Formula (2b) | H |
| 614 | A7 | H | *1 | General Formula (2a) | A7 | General Formula (2b) | H |
| 615 | A7 | H | *1 | General Formula (2a) | A7 | General Formula (2b) | H |
| 616 | A7 | H | *1 | General Formula (2a) | A7 | General Formula (2b) | CH3 |
| 617 | A7 | H | *1 | General Formula (2a) | A7 | General Formula (2b) | H |
| 618 | A7 | H | *1 | General Formula (2a) | A7 | General Formula (2b) | H |
| 619 | A7 | H | *1 | General Formula (2a) | A7 | General Formula (2b) | H |
| 620 | A7 | H | *1 | General Formula (2a) | A7 | General Formula (2b) | CH3 |
| 621 | A7 | H | *1 | General Formula (2a) | A7 | General Formula (2b) | H |
| 622 | A7 | H | *1 | General Formula (2a) | A7 | General Formula (2b) | H |
| 623 | A7 | H | *1 | General Formula (2a) | A7 | General Formula (2b) | H |
| 624 | A7 | H | *1 | General Formula (2a) | A7 | General Formula (2b) | CH3 |
| 625 | A7 | H | *1 | General Formula (2a) | A7 | General Formula (2b) | H |
| 626 | A7 | H | *1 | General Formula (2a) | A7 | General Formula (2b) | H |
| 627 | A7 | H | *1 | General Formula (2a) | A7 | General Formula (2b) | H |
| 628 | A7 | H | *1 | General Formula (2a) | A7 | General Formula (2b) | CH3 |
| 629 | A7 | H | *1 | General Formula (2a) | A7 | General Formula (2b) | H |
| 630 | A7 | H | *1 | General Formula (2a) | A7 | General Formula (2b) | H |
| 631 | A7 | H | *1 | General Formula (2a) | A7 | General Formula (2b) | H |
| 632 | A7 | H | *1 | General Formula (2a) | A7 | General Formula (2b) | CH3 |

| Compound No. | R^b1 | R^b2 | R^b3 | General Formula (2b) R^b4 | R^b5 | R^b6 | R^b7 | R^b8 | R^b9 |
|---|---|---|---|---|---|---|---|---|---|
| 501 | H | H | CH3 | H | H | CH3 | H | H | *1 |
| 502 | H | H | tert-C4H9 | H | H | tert-C4H9 | H | H | *1 |
| 503 | H | H | Phenyl | H | H | Phenyl | H | H | *1 |
| 504 | H | H | Phenyl | H | H | Phenyl | H | H | *1 |
| 505 | H | H | CH3 | H | H | CH3 | H | H | *1 |
| 506 | H | H | tert-C4H9 | H | H | tert-C4H9 | H | H | *1 |
| 507 | H | H | Phenyl | H | H | Phenyl | H | H | *1 |
| 508 | H | H | H | H | H | H | H | H | *1 |
| 509 | H | H | H | H | H | Phenyl | H | H | *1 |
| 510 | H | H | CH3 | H | H | H | H | H | *1 |
| 511 | H | H | CH3 | H | H | CH3 | H | H | *1 |
| 512 | H | H | tert-C4H9 | H | H | tert-C4H9 | H | H | *1 |
| 513 | H | H | Phenyl | H | H | Phenyl | H | H | *1 |
| 514 | H | H | Phenyl | H | H | Phenyl | H | H | *1 |
| 515 | H | H | CH3 | H | H | CH3 | H | H | *1 |
| 516 | H | H | tert-C4H9 | H | H | tert-C4H9 | H | H | *1 |

TABLE 5-continued

| No. | | | | | | | | | | |
|---|---|---|---|---|---|---|---|---|---|---|
| 517 | H | H | H | H | Phenyl | H | H | Phenyl | H | *1 |
| 518 | H | H | H | H | H | H | H | H | H | *1 |
| 519 | H | H | H | H | H | H | H | H | H | *1 |
| 520 | H | H | H | H | H | H | H | H | H | *1 |
| 521 | H | H | H | H | CH$_3$ | H | H | CH$_3$ | H | *1 |
| 522 | H | H | H | H | tert-C$_4$H$_9$ | H | H | tert-C$_4$H$_9$ | H | *1 |
| 523 | H | H | H | H | Phenyl | H | H | Phenyl | H | *1 |
| 524 | H | H | H | H | Phenyl | H | H | Phenyl | H | *1 |
| 525 | H | H | H | H | CH$_3$ | H | H | CH$_3$ | H | *1 |
| 526 | H | H | H | H | tert-C$_4$H$_9$ | H | H | tert-C$_4$H$_9$ | H | *1 |
| 527 | H | H | H | H | Phenyl | H | H | Phenyl | H | *1 |
| 528 | H | H | H | H | H | H | H | H | H | *1 |
| 529 | H | H | H | H | Phenyl | H | H | Phenyl | H | *1 |
| 530 | H | H | H | H | H | H | H | H | H | *1 |
| 531 | H | H | H | H | CH$_3$ | H | H | CH$_3$ | H | *1 |
| 532 | H | H | H | H | tert-C$_4$H$_9$ | H | H | tert-C$_4$H$_9$ | H | *1 |
| 533 | H | H | H | H | Phenyl | H | H | Phenyl | H | *1 |
| 534 | H | H | H | H | Phenyl | H | H | Phenyl | H | *1 |
| 535 | H | H | H | H | CH$_3$ | H | H | CH$_3$ | H | *1 |
| 536 | H | H | H | H | tert-C$_4$H$_9$ | H | H | tert-C$_4$H$_9$ | H | *1 |
| 537 | H | H | H | H | Phenyl | H | H | Phenyl | H | *1 |
| 538 | H | H | H | H | H | H | H | H | H | *1 |
| 539 | H | H | H | H | H | H | H | H | H | *1 |
| 540 | H | H | H | H | H | H | H | H | H | *1 |
| 541 | H | H | H | H | CH$_3$ | H | H | CH$_3$ | H | *1 |
| 542 | H | H | H | H | tert-C$_4$H$_9$ | H | H | tert-C$_4$H$_9$ | H | *1 |
| 543 | H | H | H | H | Phenyl | H | H | Phenyl | H | *1 |
| 544 | H | H | H | H | Phenyl | H | H | Phenyl | H | *1 |
| 545 | H | H | H | H | CH$_3$ | H | H | CH$_3$ | H | *1 |
| 546 | H | H | H | H | tert-C$_4$H$_9$ | H | H | tert-C$_4$H$_9$ | H | *1 |
| 547 | H | H | H | H | Phenyl | H | H | Phenyl | H | *1 |
| 548 | H | H | H | H | H | H | H | H | H | *1 |
| 549 | H | H | H | H | Phenyl | H | H | Phenyl | H | *1 |
| 550 | H | H | H | H | H | H | H | H | H | *1 |
| 551 | H | H | H | H | CH$_3$ | H | H | CH$_3$ | H | *1 |
| 552 | H | H | H | H | tert-C$_4$H$_9$ | H | H | tert-C$_4$H$_9$ | H | *1 |
| 553 | H | H | H | H | Phenyl | H | H | Phenyl | H | *1 |
| 554 | H | H | H | H | Phenyl | H | H | Phenyl | H | *1 |
| 555 | H | H | H | H | CH$_3$ | H | H | CH$_3$ | H | *1 |
| 556 | H | H | H | H | tert-C$_4$H$_9$ | H | H | tert-C$_4$H$_9$ | H | *1 |
| 557 | H | H | H | H | Phenyl | H | H | Phenyl | H | *1 |
| 558 | H | H | H | H | H | H | H | H | H | *1 |
| 559 | H | H | H | H | H | H | H | H | H | *1 |
| 560 | H | H | H | H | H | H | H | H | H | *1 |
| 561 | H | H | H | H | CH$_3$ | H | H | CH$_3$ | H | *1 |
| 562 | H | H | H | H | tert-C$_4$H$_9$ | H | H | tert-C$_4$H$_9$ | H | *1 |
| 563 | H | H | H | H | Phenyl | H | H | Phenyl | H | *1 |
| 564 | H | H | H | H | Phenyl | H | H | Phenyl | H | *1 |
| 565 | H | H | H | H | CH$_3$ | H | H | CH$_3$ | H | *1 |
| 566 | H | H | H | H | tert-C$_4$H$_9$ | H | H | tert-C$_4$H$_9$ | H | *1 |
| 567 | H | H | H | H | Phenyl | H | H | Phenyl | H | *1 |
| 568 | H | H | H | H | Phenyl | H | H | Phenyl | H | *1 |
| 569 | H | H | H | H | CH$_3$ | H | H | CH$_3$ | H | *1 |

TABLE 5-continued

| | | | | | | | | | |
|---|---|---|---|---|---|---|---|---|---|
| 570 | H | H | | H | tert-C₄H₉ | H | tert-C₄H₉ | H | *1 |
| 571 | H | H | | H | Phenyl | H | Phenyl | H | *1 |
| 572 | H | H | | H | Phenyl | H | Phenyl | H | *1 |
| 573 | H | H | | H | CH₃ | H | CH₃ | H | *1 |
| 574 | H | H | | H | tert-C₄H₉ | H | tert-C₄H₉ | H | *1 |
| 575 | H | H | | H | Phenyl | H | Phenyl | H | *1 |
| 576 | H | H | | H | Phenyl | H | Phenyl | H | *1 |
| 577 | H | H | | H | CH₃ | H | CH₃ | H | *1 |
| 578 | H | H | | H | tert-C₄H₉ | H | tert-C₄H₉ | H | *1 |
| 579 | H | H | | H | Phenyl | H | Phenyl | H | *1 |
| 580 | H | H | | H | Phenyl | H | Phenyl | H | *1 |
| 581 | H | H | | H | CH₃ | H | CH₃ | H | *1 |
| 582 | H | H | | H | tert-C₄H₉ | H | tert-C₄H₉ | H | *1 |
| 583 | H | H | | H | Phenyl | H | Phenyl | H | *1 |
| 584 | H | H | | H | Phenyl | H | Phenyl | H | *1 |
| 585 | H | H | | H | CH₃ | H | CH₃ | H | *1 |
| 586 | H | H | | H | tert-C₄H₉ | H | tert-C₄H₉ | H | *1 |
| 587 | H | H | | H | Phenyl | H | Phenyl | H | *1 |
| 588 | H | H | | H | Phenyl | H | Phenyl | H | *1 |
| 589 | H | H | | H | CH₃ | H | CH₃ | H | *1 |
| 590 | H | H | | H | tert-C₄H₉ | H | tert-C₄H₉ | H | *1 |
| 591 | H | H | | H | Phenyl | H | Phenyl | H | *1 |
| 592 | H | H | | H | Phenyl | H | Phenyl | H | *1 |
| 593 | H | H | | H | CH₃ | H | CH₃ | H | *1 |
| 594 | H | H | | H | tert-C₄H₉ | H | tert-C₄H₉ | H | *1 |
| 595 | H | H | | H | Phenyl | H | Phenyl | H | *1 |
| 596 | H | H | | H | Phenyl | H | Phenyl | H | *1 |
| 597 | H | H | | H | CH₃ | H | CH₃ | H | *1 |
| 598 | H | H | | H | tert-C₄H₉ | H | tert-C₄H₉ | H | *1 |
| 599 | H | H | | H | Phenyl | H | Phenyl | H | *1 |
| 600 | H | H | | H | Phenyl | H | Phenyl | H | *1 |
| 601 | H | H | | H | CH₃ | H | CH₃ | H | *1 |
| 602 | H | H | | H | tert-C₄H₉ | H | tert-C₄H₉ | H | *1 |
| 603 | H | H | | H | Phenyl | H | Phenyl | H | *1 |
| 604 | H | H | | H | Phenyl | H | Phenyl | H | *1 |
| 605 | H | H | | H | CH₃ | H | CH₃ | H | *1 |
| 606 | H | H | | H | tert-C₄H₉ | H | tert-C₄H₉ | H | *1 |
| 607 | H | H | | H | Phenyl | H | Phenyl | H | *1 |
| 608 | H | H | | H | Phenyl | H | Phenyl | H | *1 |
| 609 | H | H | | H | CH₃ | H | CH₃ | H | *1 |
| 610 | H | H | | H | tert-C₄H₉ | H | tert-C₄H₉ | H | *1 |
| 611 | H | H | | H | Phenyl | H | Phenyl | H | *1 |
| 612 | H | H | | H | Phenyl | H | Phenyl | H | *1 |
| 613 | H | H | | H | CH₃ | H | CH₃ | H | *1 |
| 614 | H | H | | H | tert-C₄H₉ | H | tert-C₄H₉ | H | *1 |
| 615 | H | H | | H | Phenyl | H | Phenyl | H | *1 |
| 616 | H | H | | H | Phenyl | H | Phenyl | H | *1 |
| 617 | H | H | | H | CH₃ | H | CH₃ | H | *1 |
| 618 | H | H | | H | tert-C₄H₉ | H | tert-C₄H₉ | H | *1 |
| 619 | H | H | | H | Phenyl | H | Phenyl | H | *1 |
| 620 | H | H | | H | Phenyl | H | Phenyl | H | *1 |
| 621 | H | H | | H | CH₃ | H | CH₃ | H | *1 |
| 622 | H | H | | H | tert-C₄H₉ | H | tert-C₄H₉ | H | *1 |

TABLE 5-continued

| | | | | | | | | |
|---|---|---|---|---|---|---|---|---|
| 623 | H | H | *1 | H | H | Phenyl | H | H | *1 |
| 624 | H | H | *1 | H | H | Phenyl | H | H | *1 |
| 625 | H | H | *1 | H | H | $CH_3$ | H | H | *1 |
| 626 | H | H | *1 | H | H | tert-$C_4H_9$ | H | H | *1 |
| 627 | H | H | *1 | H | H | Phenyl | H | H | *1 |
| 628 | H | H | *1 | H | H | Phenyl | H | H | *1 |
| 629 | H | H | *1 | H | H | $CH_3$ | H | H | *1 |
| 630 | H | H | *1 | H | H | tert-$C_4H_9$ | H | H | *1 |
| 631 | H | H | *1 | H | H | Phenyl | H | H | *1 |
| 632 | H | H | *1 | H | H | Phenyl | H | H | *1 |

TABLE 6

| Compound No. | A¹ | General Formula (10) R¹ | R² | R³ | R⁴ | R⁵ | R^{a1} | R^{a2} | R^{a3} | R^{a4} | R^{a5} | R^{a6} |
|---|---|---|---|---|---|---|---|---|---|---|---|---|
| 701 | CN | General Formula (2a) | General Formula (2a) | A5 | General Formula (2b) | General Formula (2b) | H | H | H | H | H | H |
| 702 | CN | General Formula (2a) | General Formula (2a) | A5 | General Formula (2b) | General Formula (2a) | H | H | H | H | H | H |
| 703 | CN | General Formula (2a) | General Formula (2a) | A6 | General Formula (2b) | General Formula (2b) | H | H | H | H | H | H |
| 704 | CN | General Formula (2a) | General Formula (2a) | A6 | General Formula (2b) | General Formula (2a) | H | H | H | H | H | H |
| 705 | CN | General Formula (2a) | General Formula (2a) | A7 | General Formula (2b) | General Formula (2b) | H | H | H | H | H | H |
| 706 | CN | General Formula (2a) | General Formula (2a) | A7 | General Formula (2b) | General Formula (2a) | H | H | H | H | H | H |
| 707 | CN | General Formula (2a) | General Formula (2a) | A9 | General Formula (2b) | General Formula (2b) | H | H | H | H | H | H |
| 708 | CN | General Formula (2a) | General Formula (2a) | A9 | General Formula (2b) | General Formula (2a) | H | H | H | H | H | H |
| 709 | CN | General Formula (2a) | General Formula (2a) | A10 | General Formula (2b) | General Formula (2b) | H | H | H | H | H | H |
| 710 | CN | General Formula (2a) | General Formula (2a) | A10 | General Formula (2b) | General Formula (2a) | H | H | H | H | H | H |
| 711 | A5 | General Formula (2a) | General Formula (2a) | A5 | General Formula (2b) | General Formula (2b) | H | H | H | H | H | H |
| 712 | A5 | General Formula (2a) | General Formula (2a) | A7 | General Formula (2b) | General Formula (2a) | H | H | H | H | H | H |
| 713 | A5 | General Formula (2a) | General Formula (2a) | A9 | General Formula (2b) | General Formula (2b) | H | H | CH₃ | H | H | CH₃ |
| 714 | A5 | General Formula (2a) | General Formula (2a) | A10 | General Formula (2b) | General Formula (2a) | H | H | CH₃ | H | H | CH₃ |
| 715 | A5 | General Formula (2a) | General Formula (2a) | A10 | General Formula (2b) | General Formula (2b) | H | H | H | H | H | H |
| 716 | A5 | General Formula (2a) | General Formula (2a) | H | General Formula (2b) | General Formula (2a) | H | H | H | H | H | H |
| 717 | A7 | General Formula (2a) | General Formula (2a) | H | General Formula (2b) | General Formula (2b) | H | H | H | H | H | H |
| 718 | A7 | General Formula (2a) | General Formula (2a) | H | General Formula (2b) | General Formula (2a) | H | H | H | H | H | H |
| 719 | A7 | General Formula (2a) | General Formula (2a) | H | General Formula (2b) | General Formula (2b) | H | H | CH₃ | H | H | CH₃ |
| 720 | A7 | General Formula (2a) | General Formula (2a) | H | General Formula (2b) | General Formula (2a) | H | H | tert-C₄H₉ | H | H | tert-C₄H₉ |
| 721 | A7 | General Formula (2a) | General Formula (2a) | H | General Formula (2b) | General Formula (2b) | H | H | tert-C₄H₉ | H | H | tert-C₄H₉ |
| 722 | A7 | General Formula (2a) | General Formula (2a) | H | General Formula (2b) | General Formula (2a) | H | H | Phenyl | H | H | Phenyl |
| 723 | A7 | General Formula (2a) | General Formula (2a) | H | General Formula (2b) | General Formula (2b) | H | H | H | H | H | H |
| 724 | A7 | General Formula (2a) | General Formula (2a) | A7 | General Formula (2b) | General Formula (2a) | H | H | H | H | H | H |
| 725 | A7 | General Formula (2a) | General Formula (2a) | A9 | General Formula (2b) | General Formula (2b) | H | H | H | H | H | H |
| 726 | A7 | General Formula (2a) | General Formula (2a) | A9 | General Formula (2b) | General Formula (2a) | H | H | CH₃ | H | H | CH₃ |
| 727 | A7 | General Formula (2a) | General Formula (2a) | A10 | General Formula (2b) | General Formula (2b) | H | H | CH₃ | H | H | CH₃ |
| 728 | A7 | General Formula (2a) | General Formula (2a) | A10 | General Formula (2b) | General Formula (2a) | H | H | tert-C₄H₉ | H | H | tert-C₄H₉ |
| 729 | A9 | General Formula (2a) | General Formula (2a) | H | General Formula (2b) | General Formula (2b) | H | H | H | H | H | H |
| 730 | A9 | General Formula (2a) | General Formula (2a) | H | General Formula (2b) | General Formula (2a) | H | H | CH₃ | H | H | CH₃ |
| 731 | A9 | General Formula (2a) | General Formula (2a) | H | General Formula (2b) | General Formula (2b) | H | H | CH₃ | H | H | CH₃ |
| 732 | A9 | General Formula (2a) | General Formula (2a) | H | General Formula (2b) | General Formula (2a) | H | H | tert-C₄H₉ | H | H | tert-C₄H₉ |
| 733 | A9 | General Formula (2a) | General Formula (2a) | H | General Formula (2b) | General Formula (2b) | H | H | tert-C₄H₉ | H | H | tert-C₄H₉ |
| 734 | A9 | General Formula (2a) | General Formula (2a) | H | General Formula (2b) | General Formula (2a) | H | H | Phenyl | H | H | Phenyl |
| 735 | A9 | General Formula (2a) | General Formula (2a) | H | General Formula (2b) | General Formula (2b) | H | H | Phenyl | H | H | Phenyl |
| 736 | A9 | General Formula (2a) | General Formula (2a) | H | General Formula (2b) | General Formula (2a) | H | H | H | H | H | H |
| 737 | A9 | General Formula (2a) | General Formula (2a) | H | General Formula (2b) | General Formula (2b) | H | H | H | H | H | H |
| 738 | A9 | General Formula (2a) | General Formula (2a) | H | General Formula (2b) | General Formula (2a) | H | H | H | H | H | H |
| 739 | A9 | General Formula (2a) | General Formula (2a) | H | General Formula (2b) | General Formula (2b) | H | H | H | H | H | H |
| 740 | A9 | General Formula (2a) | General Formula (2a) | H | General Formula (2b) | General Formula (2a) | H | H | H | H | H | H |
| 741 | A9 | General Formula (2a) | General Formula (2a) | A9 | General Formula (2b) | General Formula (2b) | H | H | CH₃ | H | H | CH₃ |
| 742 | A9 | General Formula (2a) | General Formula (2a) | A9 | General Formula (2b) | General Formula (2a) | H | H | CH₃ | H | H | H |
| 743 | A9 | General Formula (2a) | General Formula (2a) | A9 | General Formula (2b) | General Formula (2b) | H | H | CH₃ | H | H | H |
| 744 | A9 | General Formula (2a) | General Formula (2a) | A9 | General Formula (2b) | General Formula (2a) | H | H | H | H | H | H |
| 745 | A9 | General Formula (2a) | General Formula (2a) | A9 | General Formula (2b) | General Formula (2b) | H | H | H | H | H | CH₃ |
| 746 | A9 | General Formula (2a) | General Formula (2a) | A9 | General Formula (2b) | General Formula (2a) | H | H | H | H | H | H |
| 747 | A9 | General Formula (2a) | General Formula (2a) | A9 | General Formula (2b) | General Formula (2a) | H | H | H | H | H | H |

TABLE 6-continued

| Compound No. | R^a7 | R^a8 | R^a9 | | | R^b1 | R^b2 | R^b3 | R^b4 | R^b5 | R^b6 | R^b7 | R^b8 | R^b9 |
|---|---|---|---|---|---|---|---|---|---|---|---|---|---|---|
| 748 | A9 | H | General Formula (2a) | General Formula (2b) | A9 | H | H | H | H | CH3 | H | H | H | *1 |
| 749 | A9 | H | General Formula (2a) | General Formula (2b) | A9 | H | H | CH3 | H | H | CH3 | H | H | *1 |
| 750 | A9 | H | General Formula (2a) | General Formula (2b) | A9 | H | H | H | H | H | H | H | H | *1 |
| 751 | A9 | H | General Formula (2a) | General Formula (2b) | A10 | H | H | H | H | H | H | H | H | *1 |
| 752 | A9 | H | General Formula (2a) | General Formula (2b) | A10 | H | H | H | H | H | H | H | H | *1 |
| 753 | A9 | H | General Formula (2a) | General Formula (2b) | A10 | H | H | CH3 | H | H | CH3 | H | H | CH3 |
| 754 | A9 | H | General Formula (2a) | General Formula (2b) | A10 | H | H | CH3 | H | H | tert-C4H9 | H | H | tert-C4H9 |
| 755 | A9 | H | General Formula (2a) | General Formula (2b) | A10 | H | H | CH3 | H | H | tert-C4H9 | H | H | tert-C4H9 |
| 756 | A9 | H | General Formula (2a) | General Formula (2b) | A10 | H | H | CH3 | H | H | CH3 | H | H | H |
| 757 | A9 | H | General Formula (2a) | General Formula (2b) | A10 | H | H | CH3 | H | H | CH3 | H | H | H |
| 758 | A9 | H | General Formula (2a) | General Formula (2b) | A10 | H | H | CH3 | H | H | CH3 | H | H | H |
| 759 | A9 | H | General Formula (2a) | General Formula (2b) | A10 | H | H | CH3 | H | H | CH3 | H | H | CH3 |
| 760 | A9 | H | General Formula (2a) | General Formula (2b) | A10 | H | H | CH3 | H | H | CH3 | H | H | H |
| 761 | A9 | H | General Formula (2a) | General Formula (2b) | General Formula (2b) | H | H | CH3 | H | H | CH3 | H | H | CH3 |
| 762 | A10 | H | General Formula (2a) | General Formula (2b) | H | H | H | H | H | H | H | H | H | *1 |
| 763 | A10 | H | General Formula (2a) | General Formula (2b) | A10 | H | H | CH3 | H | H | CH3 | H | H | H |
| 764 | A10 | H | General Formula (2a) | General Formula (2b) | A10 | H | H | CH3 | H | H | CH3 | H | H | CH3 |
| 765 | A10 | H | General Formula (2a) | General Formula (2b) | A10 | H | H | CH3 | H | H | CH3 | H | H | H |
| 766 | A10 | H | General Formula (2a) | General Formula (2b) | A10 | H | H | CH3 | H | H | H | H | H | H |

| Compound No. | General Formula (2a) | | | General Formula (2b) | | | | | | | | |
|---|---|---|---|---|---|---|---|---|---|---|---|---|
| | R^a7 | R^a8 | R^a9 | R^b1 | R^b2 | R^b3 | R^b4 | R^b5 | R^b6 | R^b7 | R^b8 | R^b9 |
| 701 | H | H | *1 | H | H | CH3 | H | H | CH3 | H | H | *1 |
| 702 | H | H | *1 | H | H | CH3 | H | H | CH3 | H | H | *1 |
| 703 | H | H | *1 | H | H | CH3 | H | H | CH3 | H | H | *1 |
| 704 | H | H | *1 | H | H | CH3 | H | H | CH3 | H | H | *1 |
| 705 | H | H | *1 | H | H | CH3 | H | H | CH3 | H | H | *1 |
| 706 | H | H | *1 | H | H | CH3 | H | H | CH3 | H | H | *1 |
| 707 | H | H | *1 | H | H | CH3 | H | H | CH3 | H | H | *1 |
| 708 | H | H | *1 | H | H | CH3 | H | H | CH3 | H | H | *1 |
| 709 | H | H | *1 | H | H | CH3 | H | H | CH3 | H | H | *1 |
| 710 | H | H | *1 | H | H | CH3 | H | H | CH3 | H | H | *1 |
| 711 | H | H | *1 | H | H | CH3 | H | H | CH3 | H | H | *1 |
| 712 | H | H | *1 | H | H | H | H | H | H | H | H | *1 |
| 713 | H | H | *1 | H | H | H | H | H | H | H | H | *1 |
| 714 | H | H | *1 | H | H | CH3 | H | H | CH3 | H | H | *1 |
| 715 | H | H | *1 | H | H | CH3 | H | H | CH3 | H | H | *1 |
| 716 | H | H | *1 | H | H | tert-C4H9 | H | H | tert-C4H9 | H | H | *1 |
| 717 | H | H | *1 | H | H | Phenyl | H | H | Phenyl | H | H | *1 |
| 718 | H | H | *1 | H | H | H | H | H | H | H | H | *1 |
| 719 | H | H | *1 | H | H | tert-C4H9 | H | H | tert-C4H9 | H | H | *1 |
| 720 | H | H | *1 | H | H | H | H | H | H | H | H | *1 |
| 721 | H | H | *1 | H | H | CH3 | H | H | CH3 | H | H | *1 |
| 722 | H | H | *1 | H | H | CH3 | H | H | CH3 | H | H | *1 |
| 723 | H | H | *1 | H | H | tert-C4H9 | H | H | tert-C4H9 | H | H | *1 |
| 724 | H | H | *1 | H | H | CH3 | H | H | CH3 | H | H | *1 |
| 725 | H | H | *1 | H | H | CH3 | H | H | CH3 | H | H | *1 |
| 726 | H | H | *1 | H | H | H | H | H | H | H | H | *1 |
| 727 | H | H | *1 | H | H | CH3 | H | H | CH3 | H | H | *1 |
| 728 | H | H | *1 | H | H | CH3 | H | H | CH3 | H | H | *1 |
| 729 | H | H | *1 | H | H | H | H | H | H | H | H | *1 |

TABLE 6-continued

| | | | | | | | | | | |
|---|---|---|---|---|---|---|---|---|---|---|
| 730 | H | H | *1 | H | CH₃ | H | H | CH₃ | H | *1 |
| 731 | H | H | *1 | H | CH₃ | H | H | CH₃ | H | *1 |
| 732 | H | H | *1 | H | H | H | H | H | H | *1 |
| 733 | H | H | *1 | H | tert-C₄H₉ | H | H | tert-C₄H₉ | H | *1 |
| 734 | H | H | *1 | H | H | H | H | H | H | *1 |
| 735 | H | H | *1 | H | CH₃ | H | H | CH₃ | H | *1 |
| 736 | H | H | *1 | H | H | H | H | H | H | *1 |
| 737 | H | H | *1 | H | CH₃ | H | H | CH₃ | H | *1 |
| 738 | H | H | *1 | H | CH₃ | H | H | CH₃ | H | *1 |
| 739 | H | H | *1 | H | tert-C₄H₉ | H | H | tert-C₄H₉ | H | *1 |
| 740 | H | H | *1 | H | Phenyl | H | H | Phenyl | H | *1 |
| 741 | H | H | *1 | H | CH₃ | H | H | CH₃ | H | *1 |
| 742 | H | H | *1 | H | tert-C₄H₉ | H | H | tert-C₄H₉ | H | *1 |
| 743 | H | H | *1 | H | Phenyl | H | H | Phenyl | H | *1 |
| 744 | H | H | *1 | H | tert-C₄H₉ | H | H | tert-C₄H₉ | H | *1 |
| 745 | H | H | *1 | H | CH₃ | H | H | CH₃ | H | *1 |
| 746 | H | H | *1 | H | tert-C₄H₉ | H | H | tert-C₄H₉ | H | *1 |
| 747 | H | H | *1 | H | Phenyl | H | H | Phenyl | H | *1 |
| 748 | H | H | *1 | H | tert-C₄H₉ | H | H | tert-C₄H₉ | H | *1 |
| 749 | H | H | *1 | H | CH₃ | H | H | CH₃ | H | *1 |
| 750 | H | H | *1 | H | tert-C₄H₉ | H | H | tert-C₄H₉ | H | *1 |
| 751 | H | H | *1 | H | Phenyl | H | H | Phenyl | H | *1 |
| 752 | H | H | *1 | H | tert-C₄H₉ | H | H | tert-C₄H₉ | H | *1 |
| 753 | H | H | *1 | H | H | H | H | H | H | *1 |
| 754 | H | H | *1 | H | CH₃ | H | H | CH₃ | H | *1 |
| 755 | H | H | *1 | H | CH₃ | H | H | CH₃ | H | *1 |
| 756 | H | H | *1 | H | tert-C₄H₉ | H | H | tert-C₄H₉ | H | *1 |
| 757 | H | H | *1 | H | Phenyl | H | H | Phenyl | H | *1 |
| 758 | H | H | *1 | H | H | H | H | H | H | *1 |
| 759 | H | H | *1 | H | CH₃ | H | H | CH₃ | H | *1 |
| 760 | H | H | *1 | H | H | H | H | H | H | *1 |
| 761 | H | H | *1 | H | CH₃ | H | H | CH₃ | H | *1 |
| 762 | H | H | *1 | H | CH₃ | H | H | CH₃ | H | *1 |
| 763 | H | H | *1 | H | tert-C₄H₉ | H | H | tert-C₄H₉ | H | *1 |
| 764 | H | H | *1 | H | CH₃ | H | H | CH₃ | H | *1 |
| 765 | H | H | *1 | H | tert-C₄H₉ | H | H | tert-C₄H₉ | H | *1 |
| 766 | H | H | *1 | H | tert-C₄H₉ | H | H | tert-C₄H₉ | H | *1 |

TABLE 7

| Compound No. | A¹ | General Formula (10) R¹ | R² | R³ | R⁴ | R⁵ | General Formula (2a) R^{a1} | R^{a2} | R^{a3} | R^{a4} | R^{a5} | R^{a6} | R^{a7} | R^{a8} | R^{a9} |
|---|---|---|---|---|---|---|---|---|---|---|---|---|---|---|---|
| 801 | A5 | General Formula (2a) | D11 | H | D11 | General Formula (2a) | H | H | tert-C₄H₉ | H | H | tert-C₄H₉ | H | H | *1 |
| 802 | A5 | D11 | General Formula (2a) | H | General Formula (2a) | D11 | H | H | CH₃ | H | H | CH₃ | H | H | *1 |
| 803 | A5 | D24 | General Formula (2a) | H | General Formula (2a) | D24 | H | H | H | H | H | H | H | H | *1 |
| 804 | A5 | D24 | General Formula (2a) | H | General Formula (2a) | D24 | H | H | CH₃ | H | H | CH₃ | H | H | *1 |
| 805 | A5 | D24 | General Formula (2a) | General Formula (2a) | General Formula (2a) | D11 | H | H | H | H | H | H | H | H | *1 |
| 806 | A5 | D11 | General Formula (2a) | General Formula (2a) | General Formula (2a) | D24 | H | H | H | H | H | H | H | H | *1 |
| 807 | A5 | D11 | General Formula (2a) | A5 | D11 | General Formula (2a) | H | H | CH₃ | H | H | CH₃ | H | H | *1 |
| 808 | A5 | D11 | General Formula (2a) | A5 | D11 | General Formula (2a) | H | H | CH₃ | H | H | CH₃ | H | H | *1 |
| 809 | A5 | D11 | General Formula (2a) | A7 | D11 | General Formula (2a) | H | H | CH₃ | H | H | CH₃ | H | H | *1 |
| 810 | A5 | D11 | General Formula (2a) | A9 | D11 | General Formula (2a) | H | H | CH₃ | H | H | CH₃ | H | H | *1 |
| 811 | A5 | D11 | General Formula (2a) | A9 | D11 | General Formula (2a) | H | H | CH₃ | H | H | CH₃ | H | H | *1 |
| 812 | A5 | D24 | General Formula (2a) | A9 | D24 | General Formula (2a) | H | H | CH₃ | H | H | CH₃ | H | H | *1 |
| 813 | A5 | General Formula (2a) | D11 | A10 | D11 | General Formula (2a) | H | H | H | H | H | H | H | H | *1 |
| 814 | A5 | General Formula (2a) | D24 | A10 | D11 | General Formula (2a) | H | H | CH₃ | H | H | CH₃ | H | H | *1 |
| 815 | A5 | D24 | General Formula (2a) | A10 | D24 | D24 | H | H | H | H | H | H | H | H | *1 |
| 816 | A7 | D11 | General Formula (2a) | H | General Formula (2a) | D11 | H | H | CH₃ | H | H | CH₃ | H | H | *1 |
| 817 | A7 | D11 | General Formula (2a) | H | General Formula (2a) | D11 | H | H | H | H | H | H | H | H | *1 |
| 818 | A7 | D11 | General Formula (2a) | H | General Formula (2a) | D11 | H | H | CH₃ | H | H | CH₃ | H | H | *1 |
| 819 | A7 | D24 | General Formula (2a) | H | General Formula (2a) | D24 | H | H | tert-C₄H₉ | H | H | tert-C₄H₉ | H | H | *1 |
| 820 | A7 | D11 | General Formula (2a) | H | General Formula (2a) | D11 | H | H | H | H | H | H | H | H | *1 |
| 821 | A7 | D11 | General Formula (2a) | General Formula (2a) | General Formula (2a) | D11 | H | H | CH₃ | H | H | CH₃ | H | H | *1 |
| 822 | A7 | D11 | General Formula (2a) | General Formula (2a) | General Formula (2a) | D11 | H | H | CH₃ | H | H | CH₃ | H | H | *1 |
| 823 | A7 | D24 | General Formula (2a) | General Formula (2a) | General Formula (2a) | D24 | H | H | CH₃ | H | H | CH₃ | H | H | *1 |
| 824 | A7 | D11 | General Formula (2a) | A7 | D11 | General Formula (2a) | H | H | H | H | H | H | H | H | *1 |
| 825 | A7 | D11 | General Formula (2a) | A7 | D11 | General Formula (2a) | H | H | CH₃ | H | H | CH₃ | H | H | *1 |
| 826 | A7 | General Formula (2a) | D11 | A9 | D11 | General Formula (2a) | H | H | CH₃ | H | H | CH₃ | H | H | *1 |
| 827 | A7 | General Formula (2a) | D24 | A9 | D24 | General Formula (2a) | H | H | CH₃ | H | H | CH₃ | H | H | *1 |
| 828 | A7 | General Formula (2a) | D24 | A9 | D24 | General Formula (2a) | H | H | CH₃ | H | H | CH₃ | H | H | *1 |
| 829 | A7 | D11 | General Formula (2a) | A9 | D11 | General Formula (2a) | H | H | CH₃ | H | H | CH₃ | H | H | *1 |
| 830 | A7 | D11 | General Formula (2a) | A9 | D11 | General Formula (2a) | H | H | CH₃ | H | H | CH₃ | H | H | *1 |
| 831 | A7 | D24 | General Formula (2a) | A9 | D24 | General Formula (2a) | H | H | CH₃ | H | H | CH₃ | H | H | *1 |
| 832 | A7 | General Formula (2a) | D11 | A10 | D24 | General Formula (2a) | H | H | CH₃ | H | H | CH₃ | H | H | *1 |
| 833 | A7 | General Formula (2a) | D11 | A10 | D11 | General Formula (2a) | H | H | CH₃ | H | H | CH₃ | H | H | *1 |
| 834 | A7 | D11 | General Formula (2a) | A10 | D11 | General Formula (2a) | H | H | CH₃ | H | H | CH₃ | H | H | *1 |
| 835 | A7 | D11 | General Formula (2a) | A10 | D24 | General Formula (2a) | H | H | CH₃ | H | H | CH₃ | H | H | *1 |
| 836 | A7 | D24 | General Formula (2a) | A10 | D11 | General Formula (2a) | H | H | CH₃ | H | H | CH₃ | H | H | *1 |
| 837 | A7 | D24 | General Formula (2a) | H | D24 | General Formula (2a) | H | H | H | H | H | H | H | H | *1 |
| 838 | A7 | General Formula (2a) | D11 | H | D11 | General Formula (2a) | H | H | H | H | H | H | H | H | *1 |
| 839 | A7 | General Formula (2a) | D11 | H | D11 | General Formula (2a) | H | H | CH₃ | H | H | CH₃ | H | H | *1 |
| 840 | A7 | General Formula (2a) | D11 | H | D11 | General Formula (2a) | H | H | Phenyl | H | H | Phenyl | H | H | *1 |
| 841 | A7 | D11 | General Formula (2a) | H | General Formula (2a) | D11 | H | H | tert-C₄H₉ | H | H | tert-C₄H₉ | H | H | *1 |
| 842 | A7 | D11 | General Formula (2a) | H | General Formula (2a) | D11 | H | H | H | H | H | H | H | H | *1 |
| 843 | A9 | General Formula (2a) | D24 | A9 | D24 | General Formula (2a) | H | H | H | H | H | H | H | H | *1 |

TABLE 7-continued

| Compound No. | A¹ | R¹ | R² | R³ | R⁴ | R⁵ | $R^{a1}$ | $R^{a2}$ | $R^{a3}$ | $R^{a4}$ | $R^{a5}$ | $R^{a6}$ | $R^{a7}$ | $R^{a8}$ | $R^{a9}$ |
|---|---|---|---|---|---|---|---|---|---|---|---|---|---|---|---|
| | | | | General Formula (10) | | | | | | General Formula (2a) | | | | | |
| 844 | A9 | General Formula (2a) | D24 | A9 | D24 | General Formula (2a) | H | H | CH₃ | H | H | CH₃ | H | H | *1 |
| 845 | A9 | General Formula (2a) | D24 | A10 | D24 | General Formula (2a) | H | H | H | H | H | H | H | H | *1 |
| 846 | A9 | General Formula (2a) | D24 | A10 | D24 | D11 | H | H | CH₃ | H | H | CH₃ | H | H | *1 |
| 847 | A10 | D11 | General Formula (2a) | A10 | General Formula (2a) | D11 | H | H | CH₃ | H | H | CH₃ | H | H | *1 |

TABLE 8
| Compound No. | General Formula (10) | | | | |
|---|---|---|---|---|---|
| | A¹ | R¹ | R² | R³ | R⁴ | R⁵ |
| 901 | CN | D11 | CN | D24 | D11 | D24 |
| 902 | CN | D11 | D24 | A7 | D11 | D24 |
| 903 | A5 | D11 | D24 | A9 | D11 | D24 |
| 904 | A5 | D24 | D11 | A9 | D11 | D24 |
| 905 | A5 | D11 | D24 | A10 | D11 | D24 |
| 906 | A7 | D11 | D24 | H | D11 | D24 |
| 907 | A7 | D24 | D11 | H | D11 | D24 |
| 908 | A7 | D11 | D24 | A9 | D11 | D24 |
| 909 | A7 | D11 | D24 | A9 | D24 | D11 |
| 910 | A7 | D11 | D24 | A10 | D24 | D11 |
| 911 | A7 | D11 | D24 | A10 | D11 | D24 |
| 912 | A7 | D24 | D11 | D11 | D11 | D24 |
The structures of D1 to D60 and A1 to A13 in Tables 1 to 8 are shown below.
D1
D2
D3
D4
D5
D6
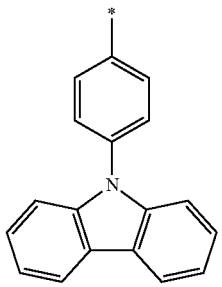
D7
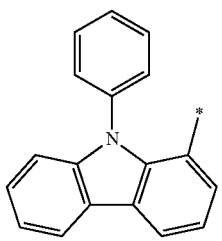
D8
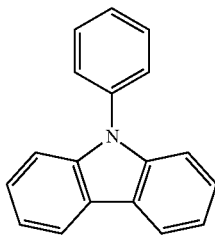
D9
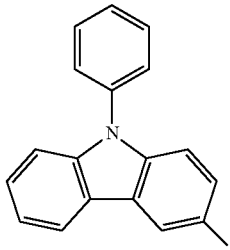
D10
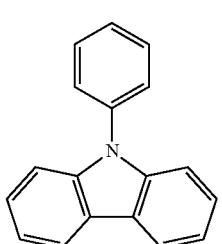
D11
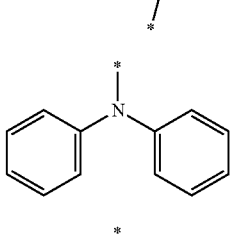
D12
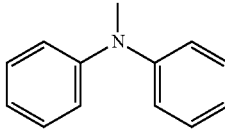

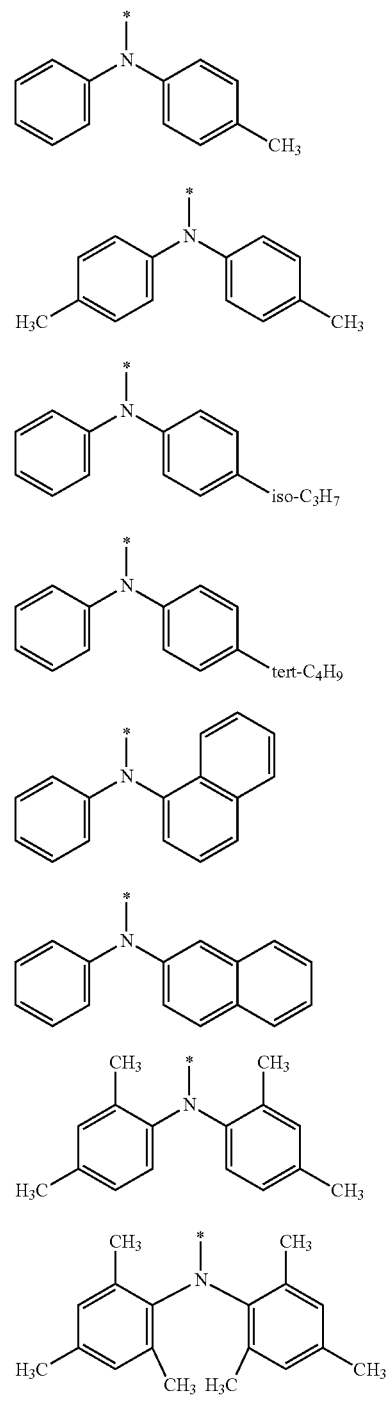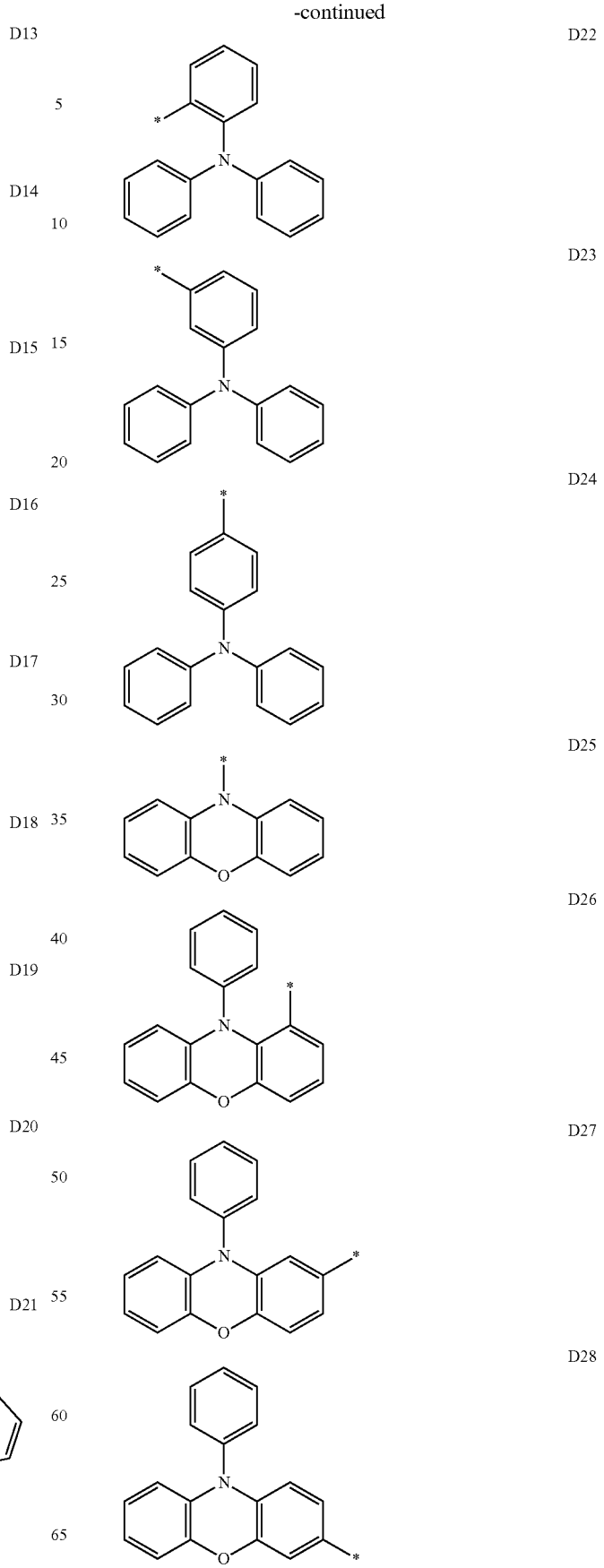

D29 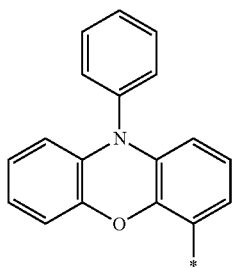
D30 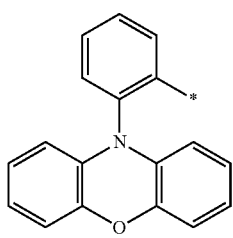
D31 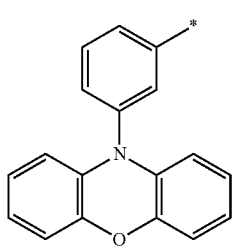
D32 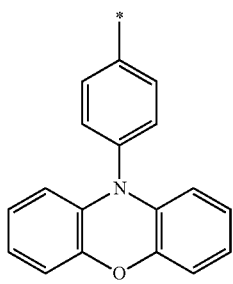
D33 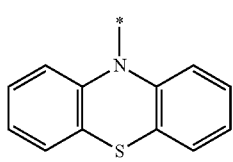
D34 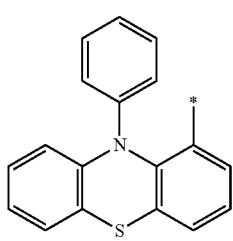
D35 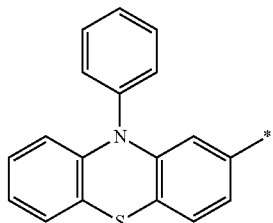
D36 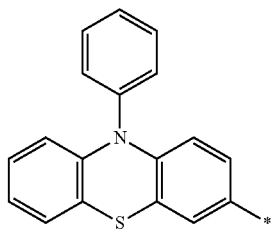
D37 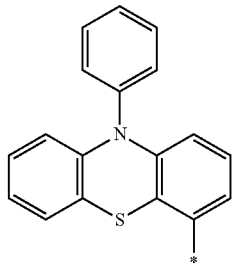
D38 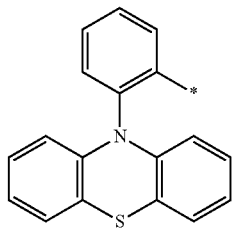
D39 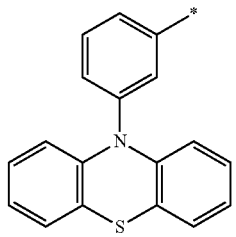
D40 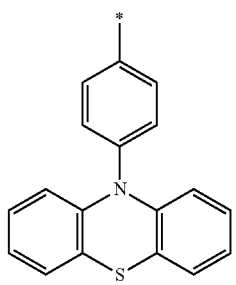

|     |     |
| --- | --- |
| D41 | 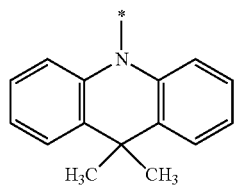 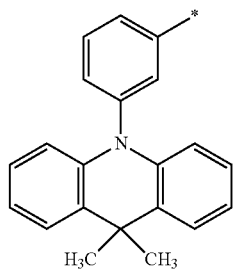 D47 |
| D42 | 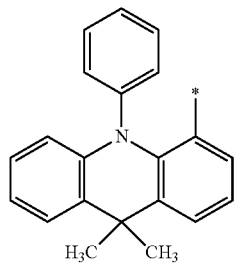 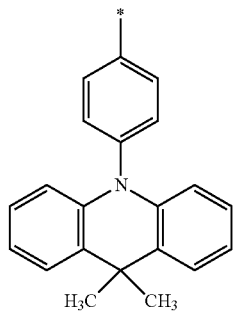 D48 |
| D43 | 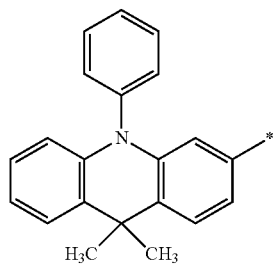 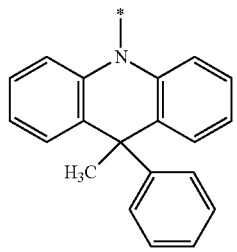 D49 |
| D44 | 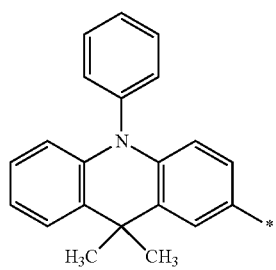 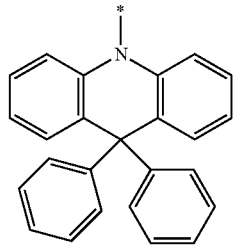 D50 |
| D45 | 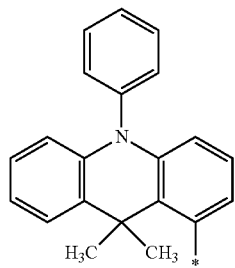 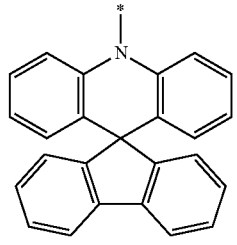 D51 |
| D46 | 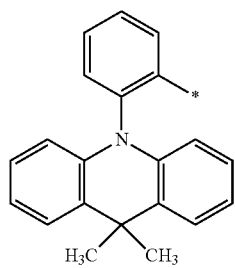 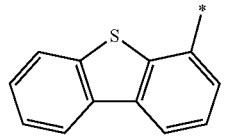 D52 |
|     | 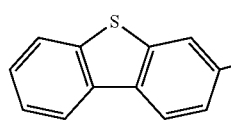 D53 |

103
-continued
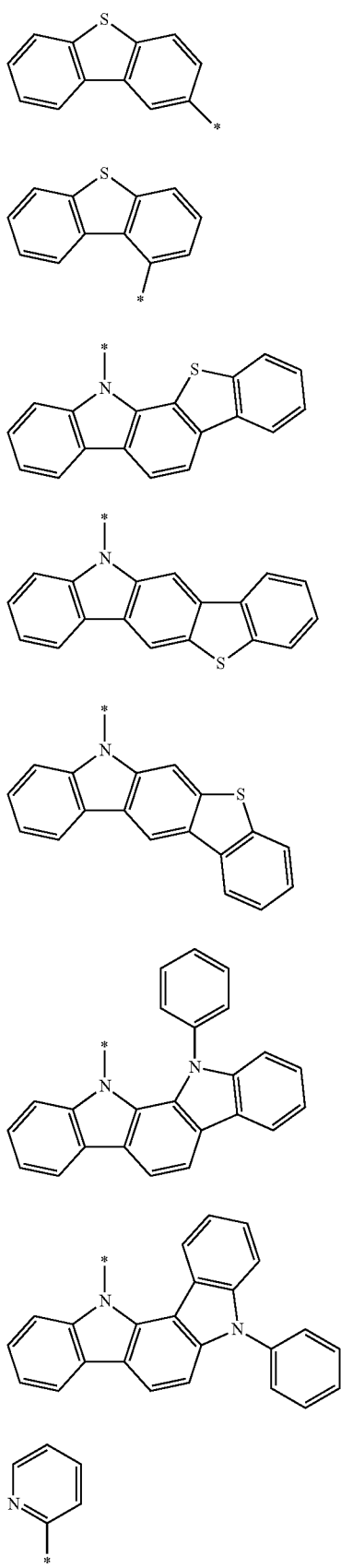
104
-continued
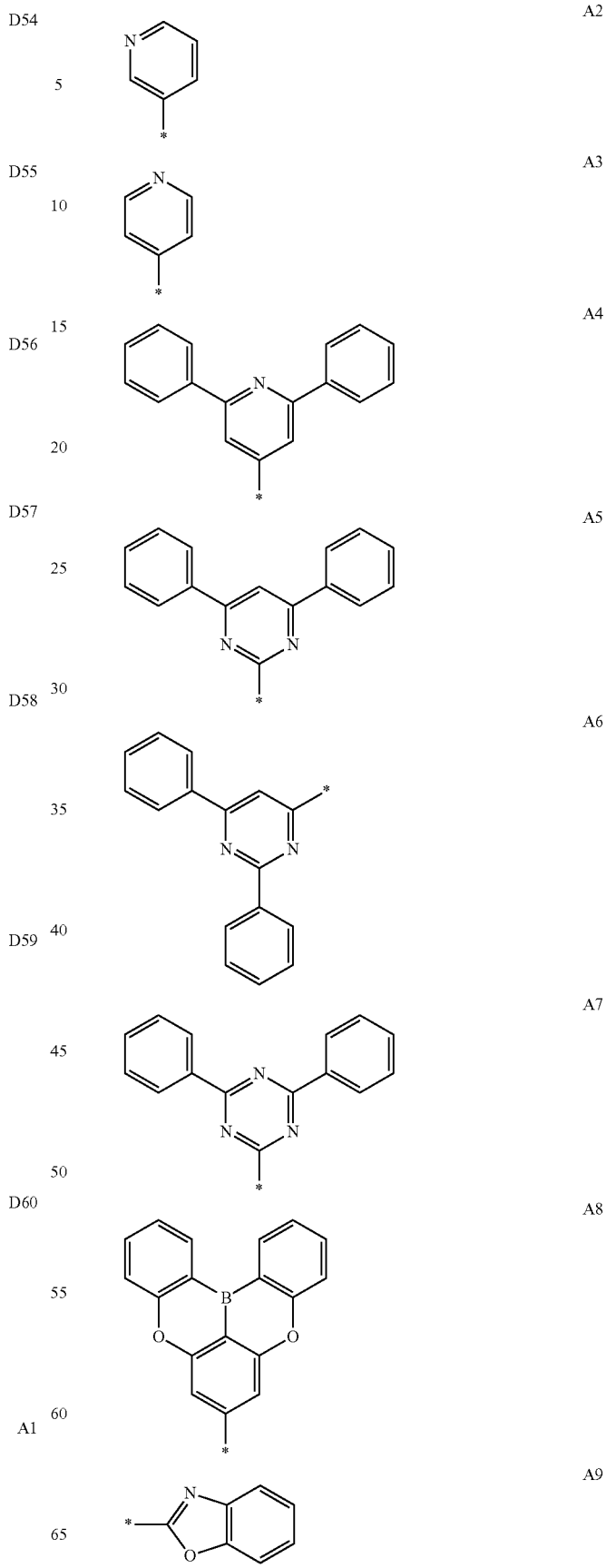

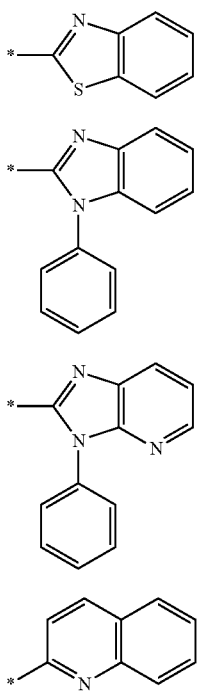

A10

A11

A12

A13

The molecular weight of the compound represented by the general formula (1) is, for example, in the case where an organic layer containing the compound represented by the general formula (1) is intended to be formed according to a vapor deposition method and used in devices, preferably 1500 or less, more preferably 1200 or less, even more preferably 1000 or less, and further more preferably 800 or less. The lower limit of the molecular weight is the smallest molecular weight that the general formula (1) can take.

Irrespective of the molecular weight thereof, the compound represented by the general formula (1) may be formed into a film according to a coating method. When a coating method is employed, even a compound having a relatively large molecular weight can be formed into a film.

Applying the present invention, it is considered to use a compound containing plural structures represented by the general formula (1) in the molecule as a light-emitting material.

For example, it is considered that a polymerizable group is previously introduced into a structure represented by the general formula (1) and the polymerizable group is polymerized to give a polymer, and the polymer is used as a light-emitting material. Specifically, a monomer containing a polymerizable functional group in any of L, A and D in the general formula (1) is prepared, and this is homo-polymerized or copolymerized with any other monomer to give a polymer having a recurring unit, and the polymer can be used as a material for a light-emitting material. Alternatively, compounds each having a structure represented by the general formula (1) are coupled to give a dimer or a trimer, and it can be used as a light-emitting material.

Examples of the polymer having a recurring unit containing a structure represented by the general formula (1) include polymers containing a structure represented by the following general formula (12) or (13).

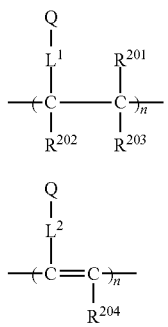

General Formula (12)

General Formula (13)

In the general formula (12) or (13), Q represents a group containing a structure represented by the general formula (1), and $L^1$ and $L^2$ each represent a linking group. The carbon number of the linking group is preferably 0 to 20, more preferably 1 to 15, even more preferably 2 to 10. Preferably, the linking group has a structure represented by $—X^{11}-L^{11}—$. Here, $X^{11}$ represents an oxygen atom or a sulfur atom and is preferably an oxygen atom. $L^{11}$ represents a linking group, and is preferably a substituted or unsubstituted alkylene group, or a substituted or unsubstituted arylene group, more preferably a substituted or unsubstituted alkylene group having 1 to 10 carbon atoms, or a substituted or unsubstituted phenylene group.

In the general formula (12) or (13), $R^{201}$, $R^{202}$, $R^{203}$ and $R^{204}$ each independently represent a substituent. Preferably, the substituent is a substituted or unsubstituted alkyl group having 1 to 6 carbon atoms, a substituted or unsubstituted alkoxy group having 1 to 6 carbon atoms, or a halogen atom, more preferably an unsubstituted alkyl group having 1 to 3 carbon atoms, an unsubstituted alkoxy group having 1 to 3 carbon atoms, a fluorine atom, or a chlorine atom, and even more preferably an unsubstituted alkyl group having 1 to 3 carbon atoms, or an unsubstituted alkoxy group having 1 to 3 carbon atoms.

The linking group represented by $L^1$ and $L^2$ may bond to any of L, A and D in the structure of the general formula (1) constituting Q. Two or more linking groups may bond to one Q to form a crosslinked structure or a network structure.

Specific examples of the structure of the recurring unit include structure represented by the following general formulae (14) to (17).

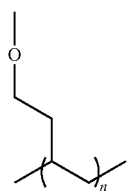

General Formula (14)

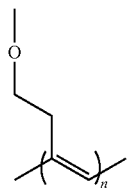

General Formula (15)

General Formula (16)

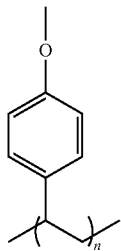

General Formula (17)

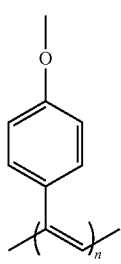

The polymer having the recurring unit containing the structure represented by any of the general formulae (14) to (17) may be synthesized in such a manner that a hydroxyl group is introduced to any of L, A and D in the structure represented by the general formula (1), and the hydroxyl group as a linker is reacted with the following compound to introduce a polymerizable group thereinto, followed by polymerizing the polymerizable group.

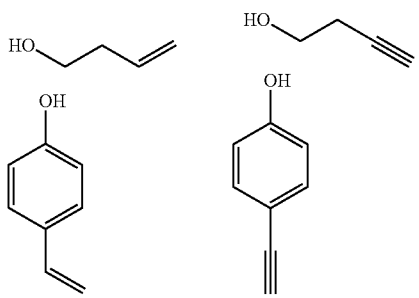

The polymer containing the structure represented by the general formula (1) in the molecule may be a polymer containing only a recurring unit having the structure represented by the general formula (1), or a polymer further containing a recurring unit having another structure. The recurring unit having the structure represented by the general formula (1) contained in the polymer may be only one kind or two or more kinds. Examples of the recurring unit that does not have the structure represented by the general formula (1) include a recurring unit derived from a monomer that is used for ordinary copolymerization. Examples of the recurring unit include a recurring unit derived from a monomer having an ethylenic unsaturated bond, such as ethylene and styrene.

[Synthesis Method for Compound Represented by General Formula (1)]

The compound represented by the general formula (1) can be synthesized by combining known reactions. For example, D is further introduced into an aromatic compound having A already introduced thereinto to synthesize the intended compound. Introduction of D can be attained, for example, through aromatic nucleophilic substitution reaction. Some schemes that generalize the reaction are shown below as examples.

(Scheme 1)

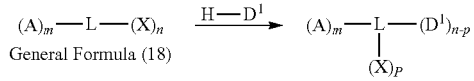

General Formula (18)     General Formula (19)

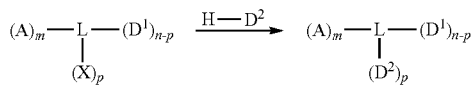

General Formula (19)     General Formula (20)

The definitions of A, L, m and n in the general formulae (18) to (20) are the same as those in the general formula (1). X in the general formulae (18) and (19) represents a halogen atom. The halogen atom includes a fluorine atom, a chlorine atom, a bromine atom and an iodine atom; and a fluorine atom, a chlorine atom and a bromine atom are preferred, a fluorine atom and a chlorine atom are more preferred, and a fluorine atom is even more preferred. $D^1$ in the general formulae (19) and (20) and $H-D^1$, and $D^2$ in the general formula (20) and $H-D^2$ each independently represent a group having a negative Hammett's σp value (but excluding a phenyl group). However, $D^1$ and $D^2$ differ from each other in point of the structure. p is an integer of 1 or more and less than n. Plural A's, if any, in the molecule may be the same as or different from each other. Plural X's, if any, in the molecule may be the same as or different from each other.

In the above-mentioned (scheme 1), a halogen-substituted aromatic compound having A already introduced thereinto is used as a starting material. The starting material is reacted with $H-D^1$ to thereby substitute at least one halogen atom bonding to the aromatic ring with $D^1$. Accordingly, a compound represented by the general formula (19) is thus obtained. In this process, by controlling the reaction condition, or by changing the purification condition, or by differentiating the halogen species at the position X into which $D^1$ is desired to be introduced from that at the position X into which $D^2$ is desired to be introduced, the value p in the resultant general formula (19 and the site for $D^1$ introduction in the aromatic ring can be controlled. Next, the resultant compound of the general formula (19) is reacted with $H-D^2$ to thereby substitute the remaining halogen atom bonding to the aromatic ring with $D^2$. Accordingly, a compound represented by the general formula (20) is thus obtained. The compound represented by the general formula (20) is the compound represented by the general formula (1).

(Scheme 1) is for synthesizing the compound represented by the general formula (1) in two-stage reaction with $H-D^1$ and then with $H-D^2$, but apart from this, the compound represented by the general formula (1) can also be synthesized in three-stage reaction with first $H-D^1$, then with $H-D^2$, and further with $H-D^3$. Here, $D^3$ is a group having a negative Hammett's σp value and having a structure differing from that of $D^1$ and $D^2$. According to the three-stage reaction, a compound represented by the general formula (1) and having three different D's, $D^1$, $D^2$ and $D^3$ can be obtained. Further applying this technical idea to attain multi-stage reaction, a compound having the general formula (1) and having w kinds of D's, $D^1$, $D^2$, $D^3$ ... $D^w$ can be obtained.

(Scheme 1) is a successive reaction to react with $H-D^1$ and then with $H-D^2$, but apart from this, both $H-D^1$ and $H-D^2$ are made to exist in a reaction mixture along with the starting material of the general formula (18) to produce the compound represented by the general formula (20) at a time, as shown in the following (scheme 2). In this case, by controlling the reaction condition, the abundance ratio of H-D¹ and H-D², the halogen atom species and the purification condition, a compound having a desired p can be obtained. Applying the reaction scheme 2 and making H-D¹, H-D² . . . H-D^w exist in a reaction mixture, a compound of the general formula (1) having w kinds of D's, D¹, D², D³ . . . D^w can be obtained.

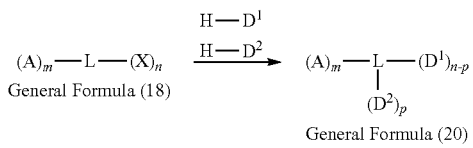

(Scheme 2)

$$\text{(A)}_m\text{—L—(X)}_n \xrightarrow{\text{H—D}^1, \text{H—D}^2} \text{(A)}_m\text{—L—(D}^1)_{n\text{-}p}\text{—(D}^2)_p$$

General Formula (18) → General Formula (20)

The target compound in (scheme 1) and (scheme 2) can be synthesized by applying an aromatic nucleophilic substitution reaction as described below. The compound can also be synthesized according to the method described in S. Tanimoto, et al., Chem. Lett., 45, 770 (2016). For specific reaction conditions and synthesis routes, reference may be made to the corresponding description in the section of Synthesis Examples given hereinunder.

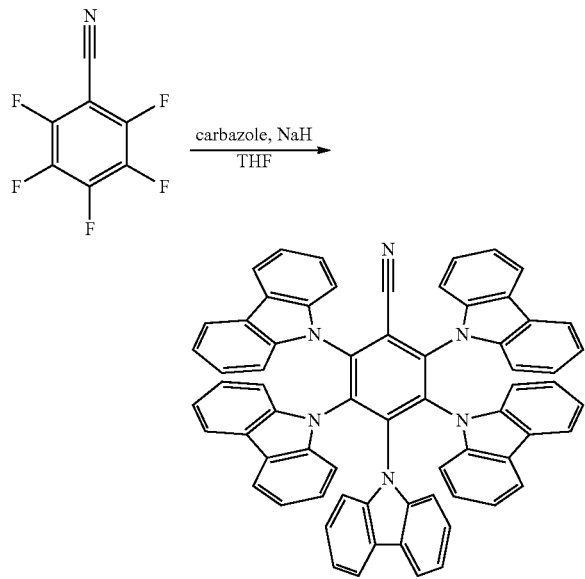

(Synthetic Intermediate)

The compound represented by the general formula (19) is useful as a synthetic intermediate for the compound represented by the general formula (20) [the compound represented by the general formula (1)].

For the description and the preferred ranges of A, L, m and n in the general formula (19), reference may be made to the description and the preferred ranges of A, L, m and n in the general formula (1). In the general formula (19), p is an integer of 1 or more and less than n, but is preferably within a range of 1 to 3, more preferably 1 or 2. For D¹ in the general formula (19), reference may be made to the description and the preferred range of D in the general formula (1), but preferably D¹ is a group containing a hetero atom, more preferably a group where an aromatic ring bonds to a hetero atom. As the hetero atom, a nitrogen atom is preferably employed. Preferred examples of the group include a group containing a diarylamine structure or a carbazolyl structure. A cyano group is preferably employed as A. When p is 2 or more and L is a 6-membered aromatic linking group, preferably, at least two X's bond to the para-position of the 6-membered aromatic ring.

For specific examples of the compound of the general formula (19), reference may be made to specific examples of the compounds of the general formula (1) in the Tables given hereinabove, in which the group represented by the general formula (2b) is substituted with a halogen atom. Specifically, compounds derived from compounds Nos. 1 to 912 listed hereinabove as specific examples of the compound of the general formula (1), by substituting the group represented by the general formula (2b) therein with a fluorine atom, are exemplified here as compounds Nos. 1001 to 1912 for specific examples of the compound of the general formula (19). Also, compounds derived from compounds Nos. 1 to 912 listed hereinabove as specific examples of the compound of the general formula (1), by substituting the group represented by the general formula (2b) therein with a chlorine atom, are exemplified as compounds Nos. 2001 to 2912. Further, compounds derived from compounds Nos. 1 to 912 listed hereinabove as specific examples of the compound of the general formula (1), by substituting the group represented by the general formula (2b) therein with a bromine atom, are exemplified as compounds Nos. 3001 to 3912. Further, compounds derived from compounds Nos. 1 to 912 listed hereinabove as specific examples of the compound of the general formula (1), by substituting the group represented by the general formula (2b) therein with an iodine atom, are exemplified as compounds Nos. 4001 to 4912. Among the compounds Nos. 1001 to 4921, those for which the corresponding compounds Nos. 1 to 912 do not have a group of the general formula (2b) are unassigned numbers.

[Organic Light-Emitting Device]

The compound represented by the general formula (1) of the present invention is useful as a material for light-emitting devices, and is especially favorably used as a light-emitting material for organic light-emitting devices. Accordingly, the compound represented by the general formula (1) of the present invention can be effectively used as a light-emitting material in a light-emitting layer of an organic light-emitting device. The compound represented by the general formula (1) include a delayed fluorescent material (delayed phosphor) that emits delayed fluorescence. Specifically, the present invention includes an invention of a delayed fluorescent material having a structure represented by the general formula (1), an invention of using the compound represented by the general formula (1) as a delayed fluorescent material, and an invention of a method of using the compound represented by the general formula (1) for emitting delayed fluorescence. An organic light-emitting device using such a compound as a light-emitting material is characterized that it emits delayed fluorescence and has a high emission efficiency. The principle will be described below with reference to an organic electroluminescent device taken as an example.

In an organic electroluminescent device, carriers are injected from an anode and a cathode to a light-emitting material to form an excited state for the light-emitting material, with which light is emitted. In the case of a carrier injection type organic electroluminescent device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy utilization. However, the excited triplet state has a long lifetime and thus causes saturation of the excited state and deactivation of energy through mutual action with the excitons in the excited triplet state, and therefore the quantum yield of phosphorescence may generally be often not high. A delayed fluorescent material emits fluorescent light through the mechanism that the energy of excitons transits to the excited triplet state through intersystem crossing or the like, and then transits to the excited singlet state through reverse intersystem crossing due to triplet-triplet annihilation or absorption of thermal energy, thereby emitting fluorescent light. It is considered that among the materials, a thermal activation type delayed fluorescent material emitting light through absorption of thermal energy is particularly useful for an organic electroluminescent device. In the case where a delayed fluorescent material is used in an organic electroluminescent device, the excitons in the excited singlet state normally emit fluorescent light. On the other hand, the excitons in the excited triplet state emit fluorescent light through intersystem crossing to the excited singlet state by absorbing the heat generated by the device. At this time, the light emitted through reverse intersystem crossing from the excited triplet state to the excited singlet state has the same wavelength as fluorescent light since it is light emission from the excited singlet state, but has a longer lifetime (light emission lifetime) than the normal fluorescent light, and thus the light is observed as fluorescent light that is delayed from the normal fluorescent light. The light may be defined as delayed fluorescent light. The use of the thermal activation type exciton transition mechanism may raise the proportion of the compound in the excited singlet state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency.

In particular, the compound represented by the general formula (1) and capable of emitting delayed fluorescence has an extremely large rate constant kusc in reverse intersystem crossing from the triplet excited state to the singlet excited state, and therefore it is presumed that accumulation of triplet excitons in the excitation process can be effectively retarded. Accordingly, in the light-emitting device using the compound represented by the general formula (1), exciton annihilation or device degradation caused by accumulation of triplet excitons can be retarded and therefore a higher emission efficiency and a more excellent high durability can be realized. In addition, since exciton annihilation can be retarded, the present invention can greatly contribute toward realizing organic lasers.

Using the compound represented by the general formula (1) of the present invention as a light-emitting material in a light-emitting layer, excellent organic light-emitting devices such as an organic photoluminescent device (organic PL device) and an organic electroluminescent device (organic EL device) can be provided. In these, the compound represented by the general formula (1) of the present invention can have a function of assisting light emission of any other light-emitting material contained in a light-emitting layer, as a so-called assist adjuvant. Specifically, the compound represented by the general formula (1) of the present invention contained in a light-emitting layer may have a lowest excited singlet energy level between the lowest excited singlet energy level of the host material contained in the light-emitting layer and the lowest excited singlet energy level of the other light-emitting material contained in the light-emitting layer.

An organic photoluminescent device has a structure where at least a light-emitting layer is formed on a substrate. An organic electroluminescent device has a structure including at least an anode, a cathode and an organic layer formed between the anode and the cathode. The organic layer contains at least a light-emitting layer, and may be formed of a light-emitting layer alone, or may has one or more other organic layers in addition to a light-emitting layer. The other organic layers include a hole transport layer, a hole injection layer, an electron blocking layer, a hole blocking layer, an electron injection layer, an electron transport layer, and an exciton blocking layer. The hole transport layer may be a hole injection transport layer having a hole injection function, and the electron transport layer may be an electron injection transport layer having an electron injection function. A configuration example of an organic electroluminescent device is shown in FIG. 1. In FIG. 1, 1 is a substrate, 2 is an anode, 3 is a hole injection layer, 4 is a hole transport layer, 5 is a light-emitting layer, 6 is an electron transport layer, and 7 is a cathode.

In the following, the constituent members and the layers of the organic electroluminescent device are described. The description of the substrate and the light-emitting layer given below may apply to the substrate and the light-emitting layer of an organic photoluminescent device.

(Substrate)

The organic electroluminescent device of the invention is preferably supported by a substrate. The substrate is not particularly limited and may be those that have been commonly used in an organic electroluminescent device, and examples thereof used include those formed of glass, transparent plastics, quartz and silicon.

(Anode)

The anode of the organic electroluminescent device used is preferably formed of, as an electrode material, a metal, an alloy, or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 µm or more), the pattern may be formed with a mask having a desired shape on vapor deposition or sputtering of the electrode material. In alternative, in the case where a material capable of being coated, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred ohm per square or less. The thickness of the anode may be generally selected from a range of from 10 to 1,000 nm, and preferably from 10 to 200 nm, while depending on the material used.

(Cathode)

The cathode is preferably formed of as an electrode material a metal (which is referred to as an electron injection metal), an alloy, or an electroconductive compound, having a small work function (4 eV or less), or a mixture thereof. Specific examples of the electrode material include sodium, a sodium-potassium alloy, magnesium, lithium, a magnesium-copper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, is preferred from the standpoint of the electron injection property and the durability against oxidation and the like. The cathode may be produced by forming the electrode material into a thin film by such a method as vapor deposition or sputtering. The cathode preferably has a sheet resistance of several hundred ohm per square or less, and the thickness thereof may be generally selected from a range of from 10 nm to 5 µm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

(Light-Emitting Layer)

The light-emitting layer is a layer in which holes and electrons injected from an anode and a cathode are recombined to give excitons for light emission. A light-emitting material may be used singly in the light-emitting layer, but preferably, the layer contains a light-emitting layer and a host material. As the light-emitting material, one or more selected from a group of the compounds of the present invention represented by the general formula (1) can be used. In order that the organic electroluminescent device and the organic photoluminescent device of the present invention can express a high light emission efficiency, it is important to confine the singlet exciton and the triplet exciton formed in the light-emitting material to the light-emitting material. Accordingly, preferably, a host material is used in addition to the light-emitting material in the light-emitting layer. As the host material, an organic compound, of which at least any one of the excited singlet energy and the excited triplet energy is higher than that of the light-emitting material of the present invention, may be used. As a result, the singlet exciton and the triplet exciton formed in the light-emitting material of the present invention can be confined to the molecule of the light-emitting material of the present invention to sufficiently derive the light emission efficiency thereof. Needless-to-say, there may be a case where a high light emission efficiency could be attained even though the singlet exciton and the triplet exciton could not be sufficiently confined, and therefore, any host material capable of realizing a high light emission efficiency can be used in the present invention with no specific limitation. In the organic light-emitting device or the organic electroluminescent device of the present invention, light emission occurs from the light-emitting material of the present invention contained in the light-emitting layer. The light emission contains both of fluorescent emission and delayed fluorescent emission. In addition, a part of light emission may be partially from a host material.

In the case where a hots material is used, the content of the compound serving as a light-emitting material of the present invention in the light-emitting layer is preferably 0.1% by weight or more, more preferably 1% by weight or more, and is preferably 50% by weight or less, more preferably 20% by weight or less, even more preferably 10% by weight or less.

The host material in the light-emitting layer is preferably an organic compound having hole transport competence and electron transport competence, capable of preventing prolongation of emission wavelength and having a high glass transition temperature.

(Injection Layer)

The injection layer is a layer that is provided between the electrode and the organic layer, for decreasing the driving voltage and enhancing the light emission luminance, and includes a hole injection layer and an electron injection layer, which may be provided between the anode and the light-emitting layer or the hole transport layer and between the cathode and the light emitting layer or the electron transport layer. The injection layer may be provided depending on necessity.

(Blocking Layer)

The blocking layer is a layer that is capable of inhibiting charges (electrons or holes) and/or excitons present in the light-emitting layer from being diffused outside the light-emitting layer. The electron blocking layer may be disposed between the light-emitting layer and the hole transport layer, and inhibits electrons from passing through the light-emitting layer toward the hole transport layer. Similarly, the hole blocking layer may be disposed between the light-emitting layer and the electron transport layer, and inhibits holes from passing through the light-emitting layer toward the electron transport layer. The blocking layer may also be used for inhibiting excitons from being diffused outside the light-emitting layer. Thus, the electron blocking layer and the hole blocking layer each may also have a function as an exciton blocking layer. The term "the electron blocking layer" or "the exciton blocking layer" referred to herein is intended to include a layer that has both the functions of an electron blocking layer and an exciton blocking layer by one layer.

(Hole Blocking Layer)

The hole blocking layer has the function of an electron transport layer in a broad sense. The hole blocking layer has a function of inhibiting holes from reaching the electron transport layer while transporting electrons, and thereby enhances the recombination probability of electrons and holes in the light-emitting layer. As the material for the hole blocking layer, the material for the electron transport layer to be mentioned below may be used optionally.

(Electron Blocking Layer)

The electron blocking layer has the function of transporting holes in a broad sense. The electron blocking layer has a function of inhibiting electrons from reaching the hole transport layer while transporting holes, and thereby enhances the recombination probability of electrons and holes in the light-emitting layer.

(Exciton Blocking Layer)

The exciton blocking layer is a layer for inhibiting excitons generated through recombination of holes and electrons in the light-emitting layer from being diffused to the charge transporting layer, and the use of the layer inserted enables effective confinement of excitons in the light-emitting layer, and thereby enhances the light emission efficiency of the device. The exciton blocking layer may be inserted adjacent to the light-emitting layer on any of the side of the anode and the side of the cathode, and on both the sides. Specifically, in the case where the exciton blocking layer is present on the side of the anode, the layer may be inserted between the hole transport layer and the light-emitting layer and adjacent to the light-emitting layer, and in the case where the layer is inserted on the side of the cathode, the layer may be inserted between the light-emitting layer and the cathode and adjacent to the light-emitting layer. Between the anode and the exciton blocking layer that is adjacent to the light-emitting layer on the side of the anode, a hole injection layer, an electron blocking layer and the like may be provided, and between the cathode and the exciton blocking layer that is adjacent to the light-emitting layer on the side of the cathode, an electron injection layer, an electron transport layer, a hole blocking layer and the like may be provided. In the case where the blocking layer is provided, preferably, at least one of the excited singlet energy and the excited triplet energy of the material used as the blocking layer is higher than the excited singlet energy and the excited triplet energy of the light-emitting layer, respectively, of the light-emitting material.

(Hole Transport Layer)

The hole transport layer is formed of a hole transport material having a function of transporting holes, and the hole transport layer may be provided as a single layer or plural layers.

The hole transport material has one of injection or transporting property of holes and blocking property of electrons, and may be any of an organic material and an inorganic material. Examples of known hole transport materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. Among these, a porphyrin compound, an aromatic tertiary amine compound and a styrylamine compound are preferably used, and an aromatic tertiary amine compound is more preferably used.

(Electron Transport Layer)

The electron transport layer is formed of a material having a function of transporting electrons, and the electron transport layer may be a single layer or may be formed of plural layers.

The electron transport material (often also acting as a hole blocking material) may have a function of transmitting the electrons injected from a cathode to a light-emitting layer. The electron transport layer usable here includes, for example, nitro-substituted fluorene derivatives, diphenylquinone derivatives, thiopyran dioxide derivatives, carbodiimides, fluorenylidenemethane derivatives, anthraquinodimethane and anthrone derivatives, oxadiazole derivatives, etc. Further, thiadiazole derivatives derived from the above-mentioned oxadiazole derivatives by substituting the oxygen atom in the oxadiazole ring with a sulfur atom, and quinoxaline derivatives having a quinoxaline ring known as an electron-attractive group are also usable as the electron transport material. Further, polymer materials prepared by introducing these materials into the polymer chain, or having these material in the polymer main chain are also usable.

In producing the organic electroluminescent device, the compound represented by the general formula (1) may be used not only in the light-emitting layer but also in any other layer than the light-emitting layer. In so doing, the compound represented by the general formula (1) used in the light-emitting layer and the compound represented by the general formula (1) used in the other layer than the light-emitting layer may be the same as or different from each other. For example, the compound represented by the general formula (1) may be used in the above-mentioned injection layer, the blocking layer, the hole blocking layer, the electron blocking layer, the exciton blocking layer, the hole transport layer, and the electron transport layer. The method for forming these layers is not specifically limited, and the layers may be formed according to any of a dry process or a wet process.

Preferred materials for use for the organic electroluminescent device are concretely exemplified below. However, the materials for use in the present invention are not limitatively interpreted by the following exemplary compounds. Compounds, even though exemplified as materials having a specific function, can also be used as other materials having any other function.

First, preferred compounds for use as a host material in a light-emitting layer are mentioned below.

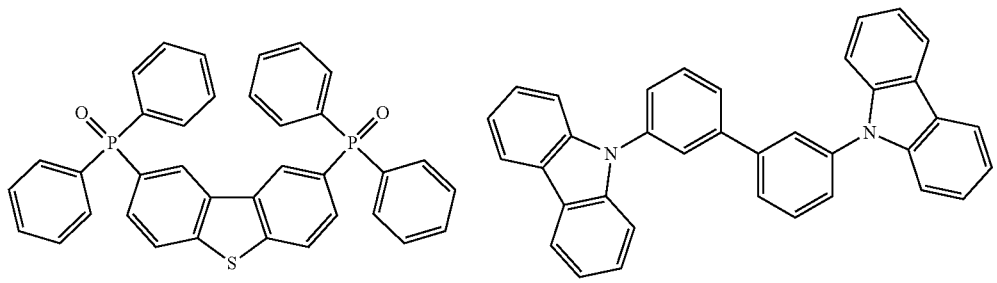

-continued
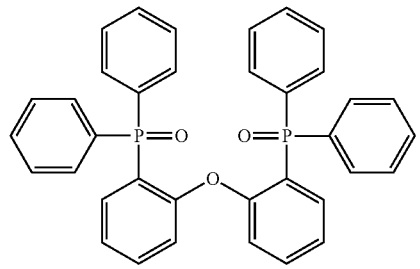
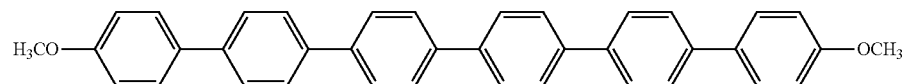
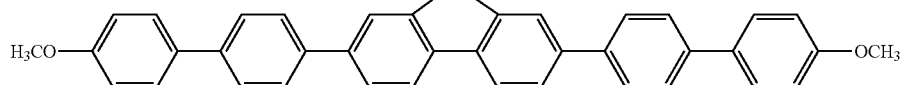
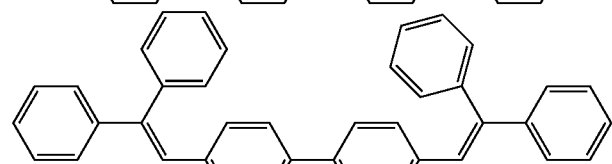
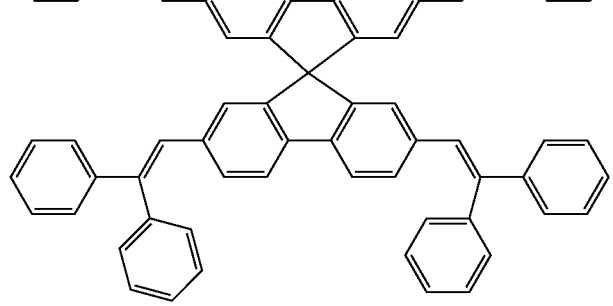
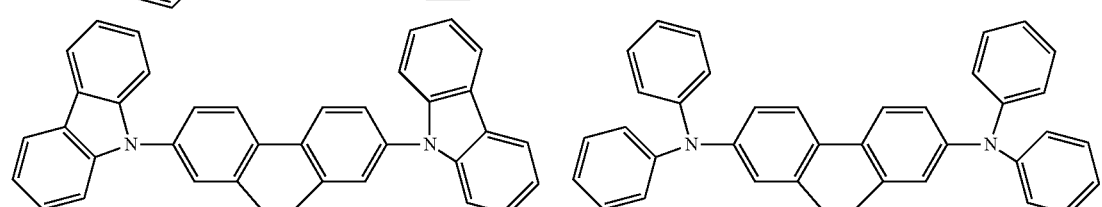
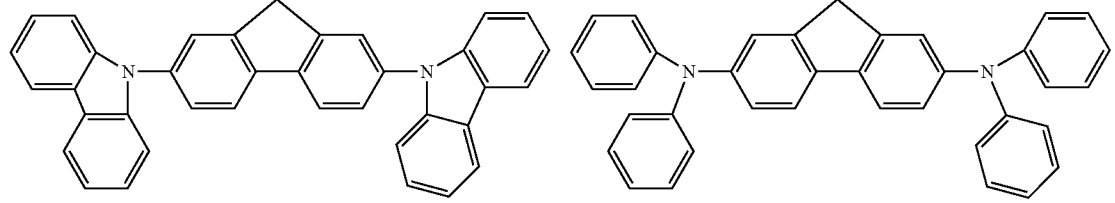
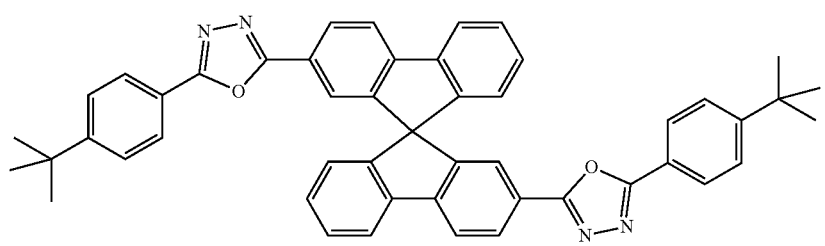

-continued
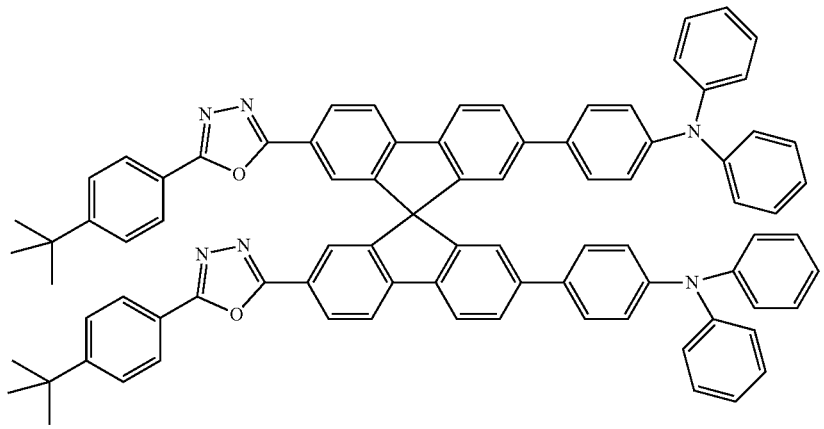
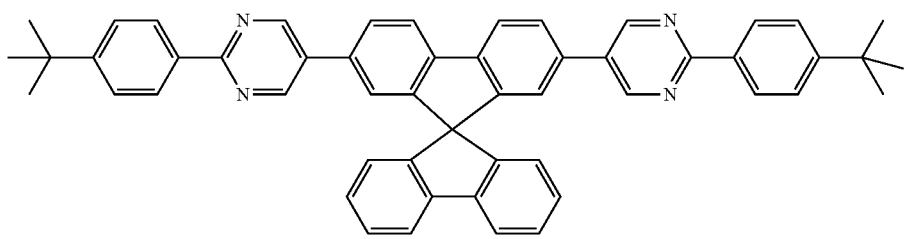
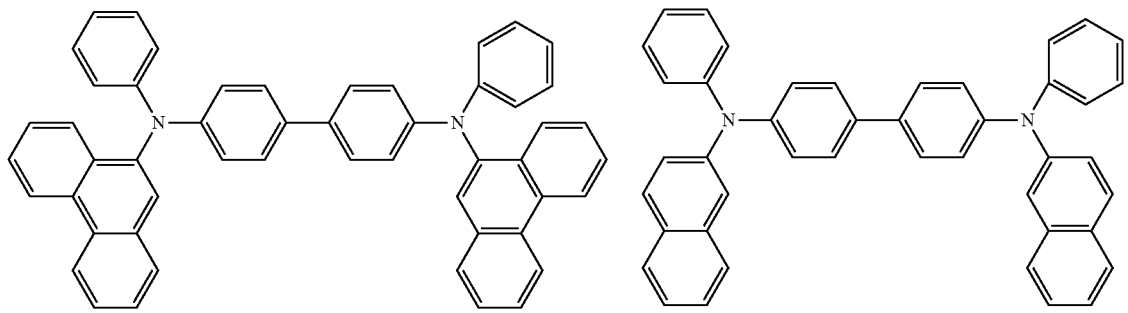
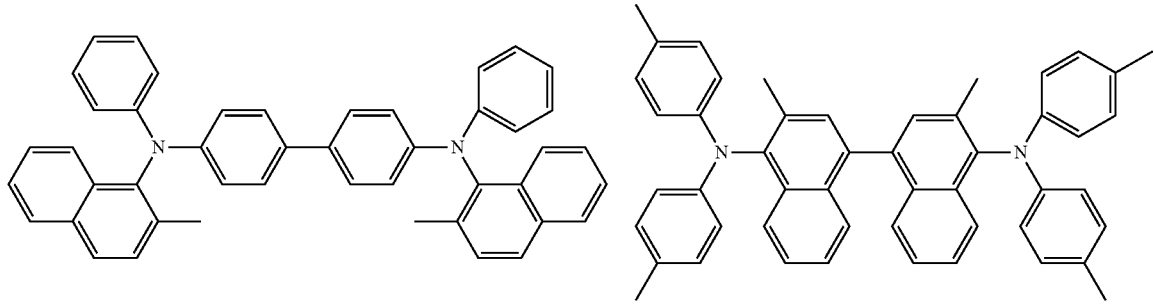
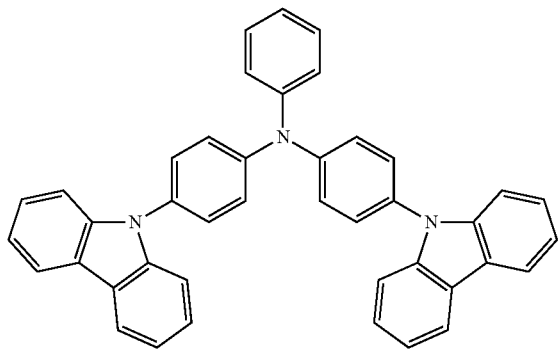

121 122
-continued
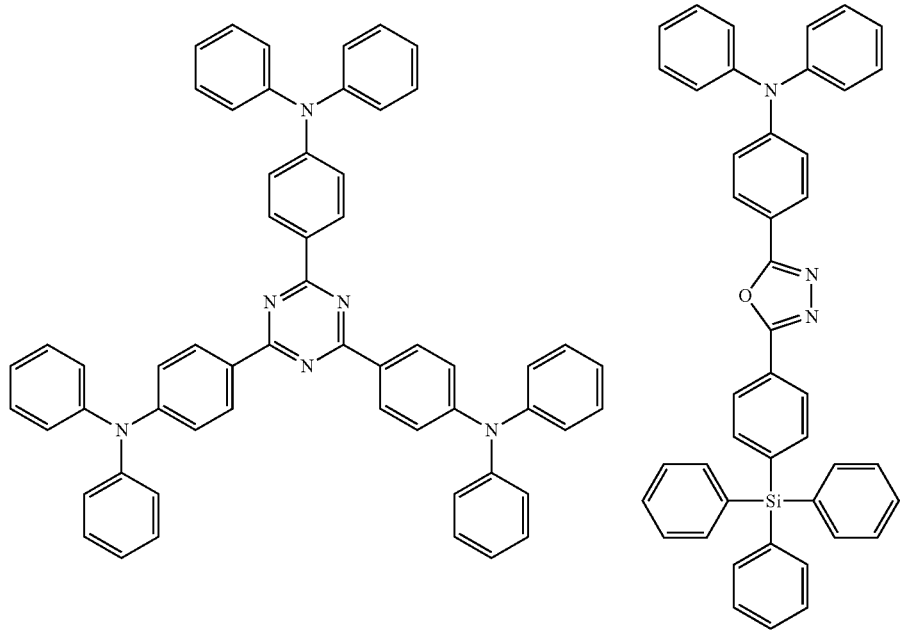
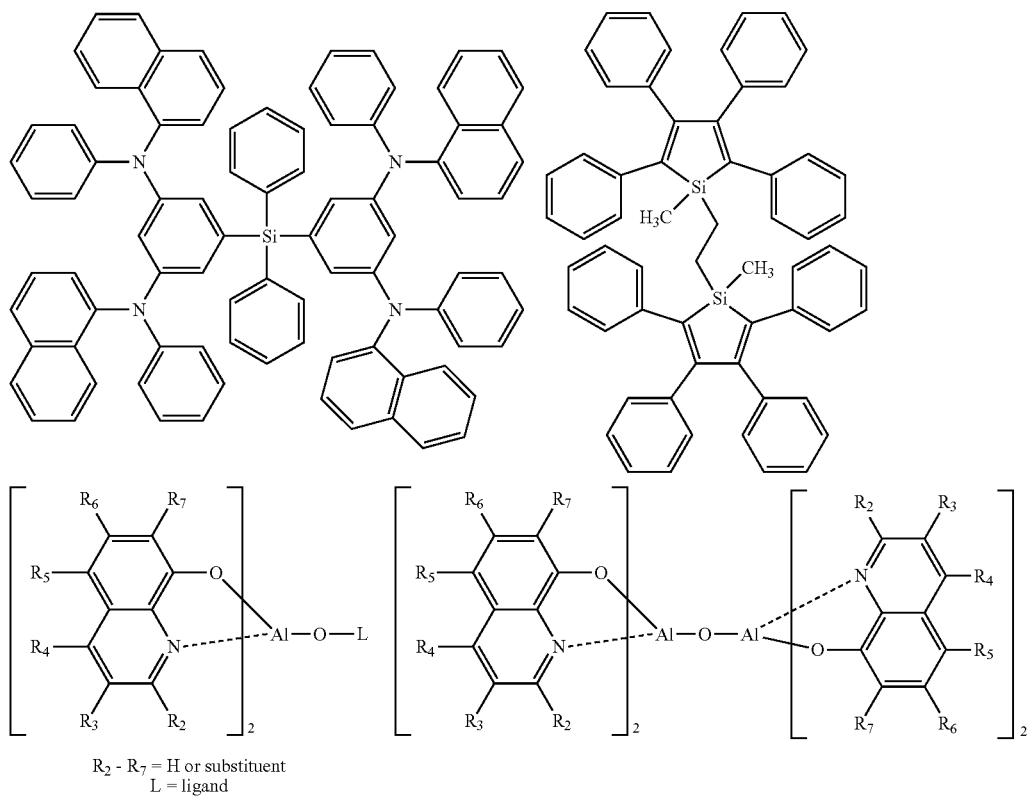
R₂ - R₇ = H or substituent
L = ligand
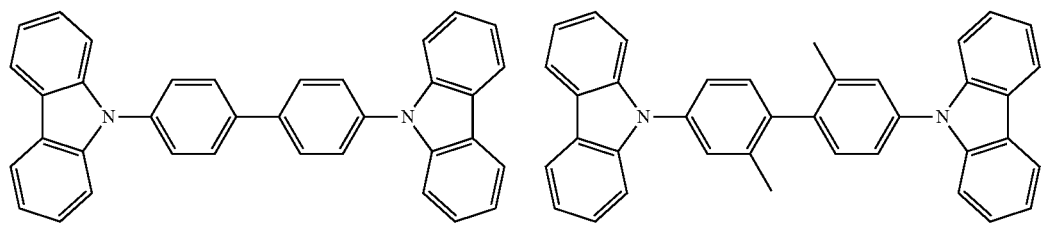

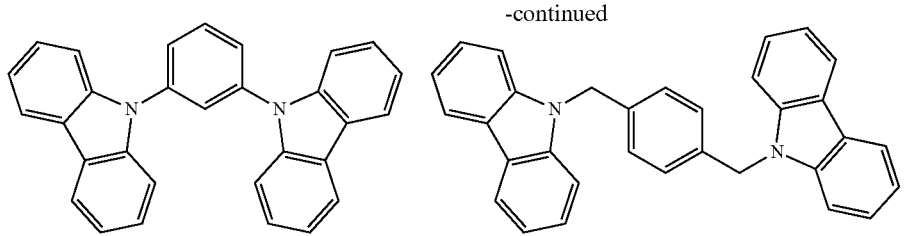
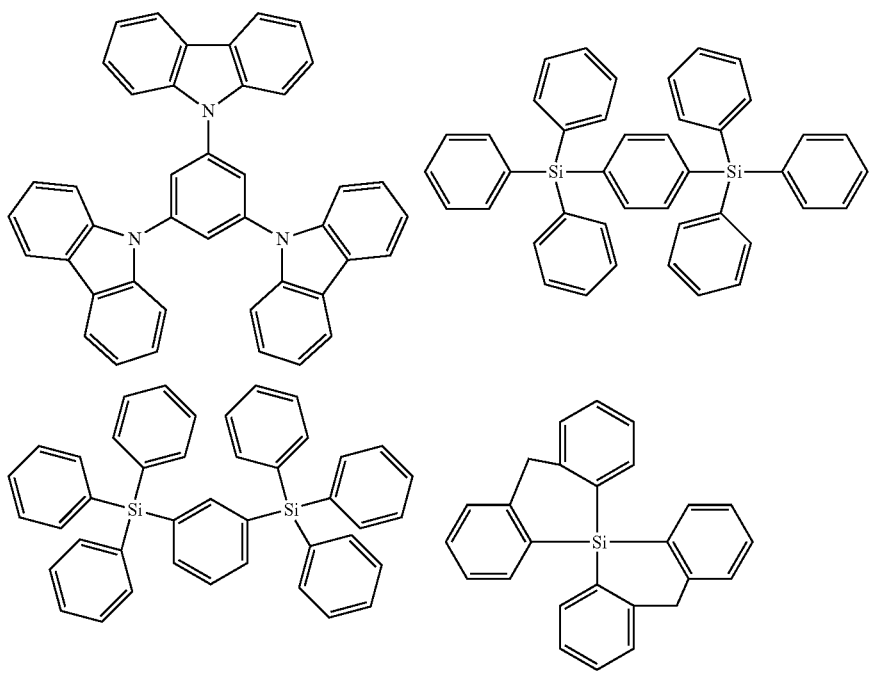
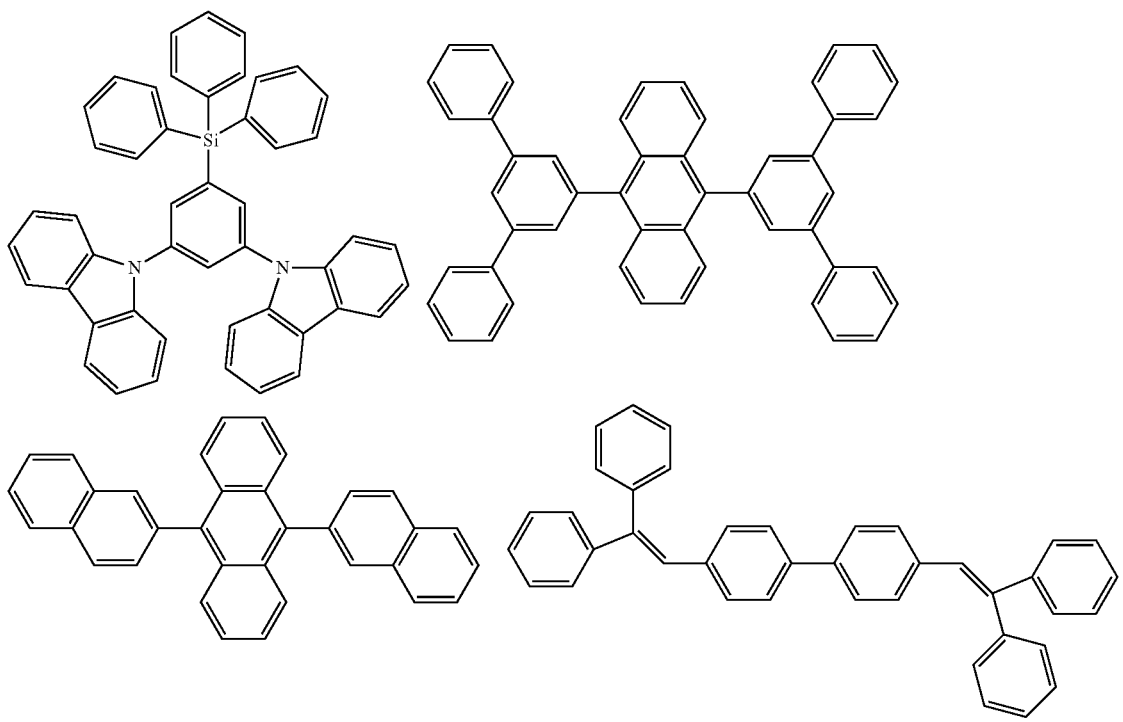

125 126
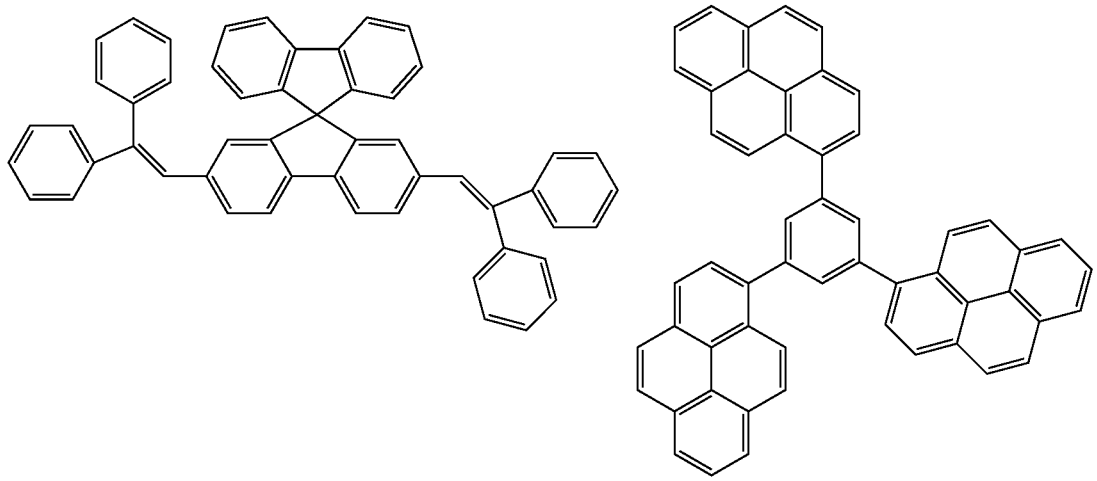
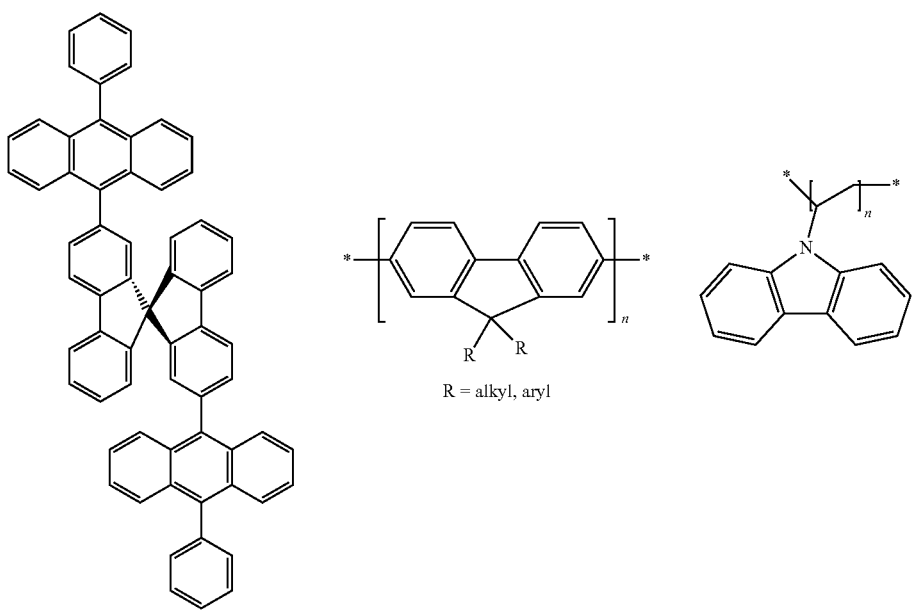
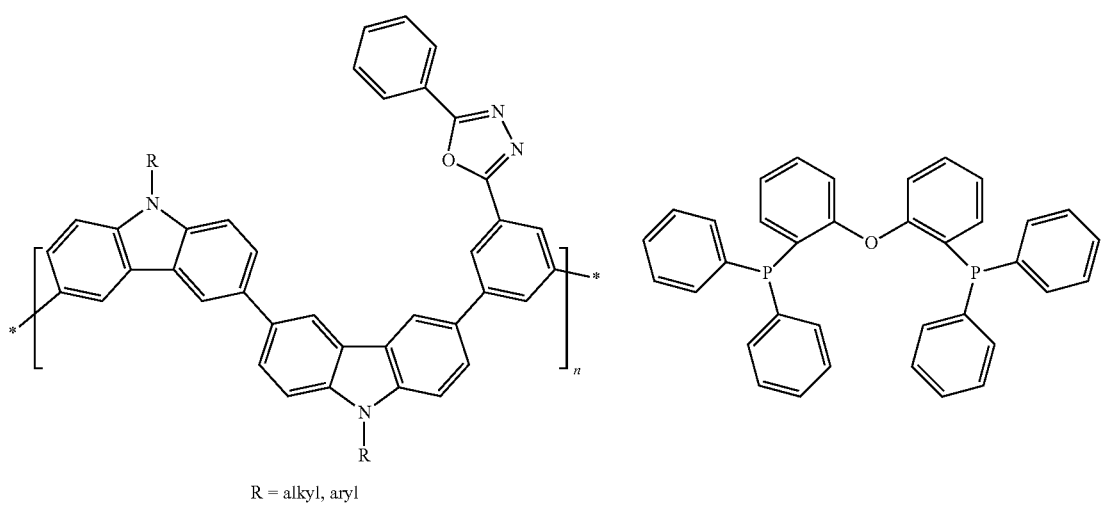

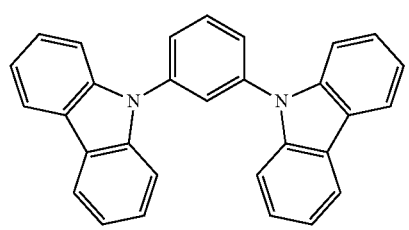
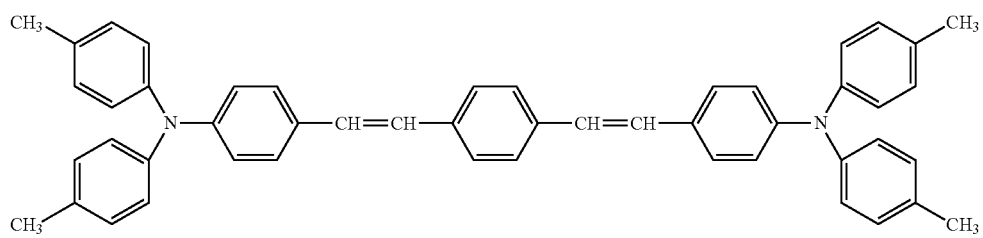
Next, preferred compounds for use as a hole injection material are mentioned below.
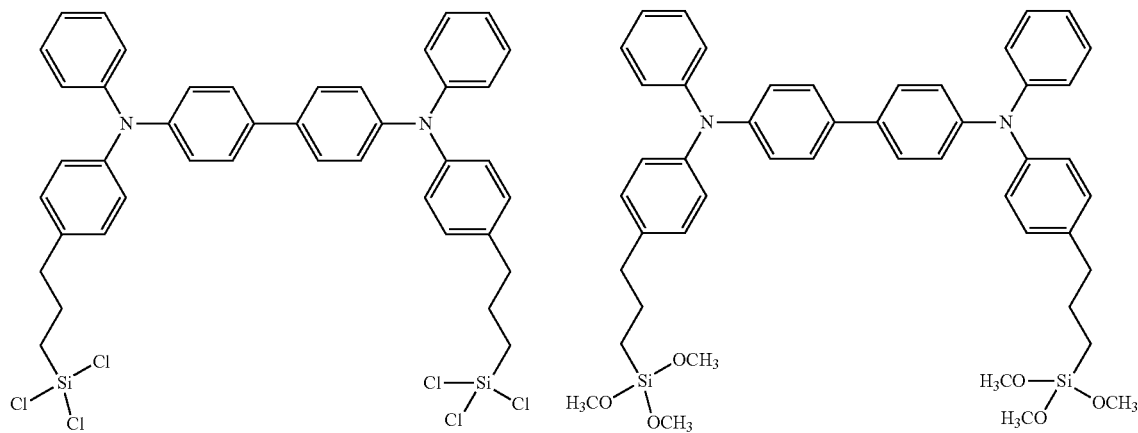
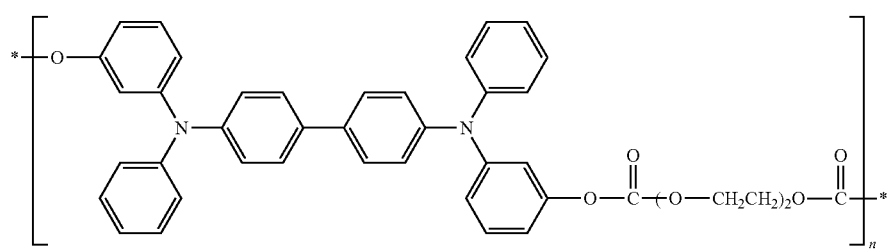

-continued
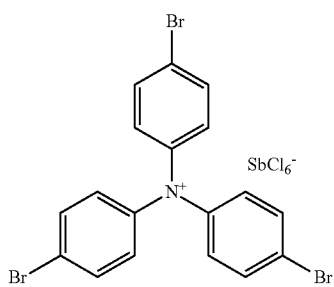
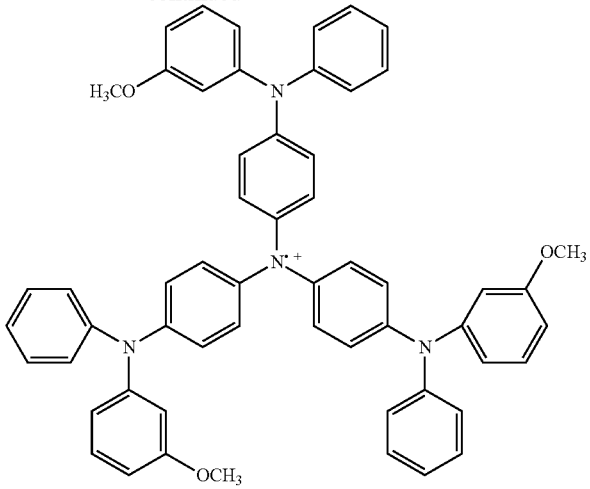
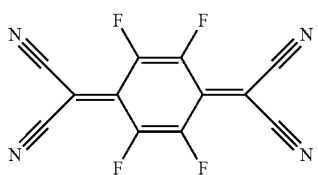
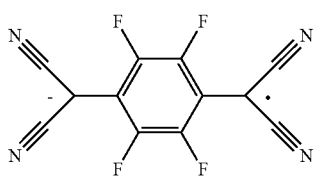
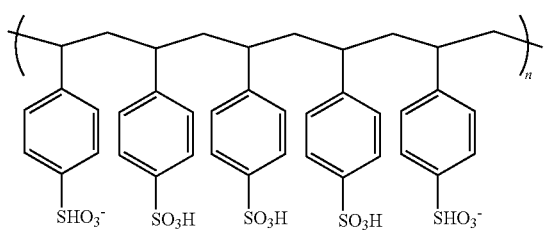
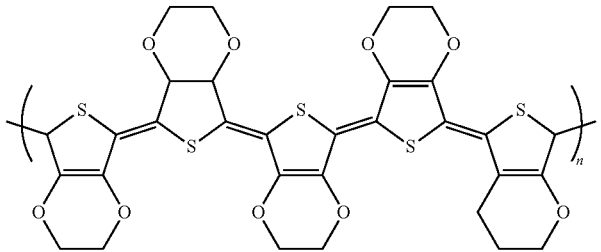
Next, preferred compounds for use as a hole transport material are mentioned below.
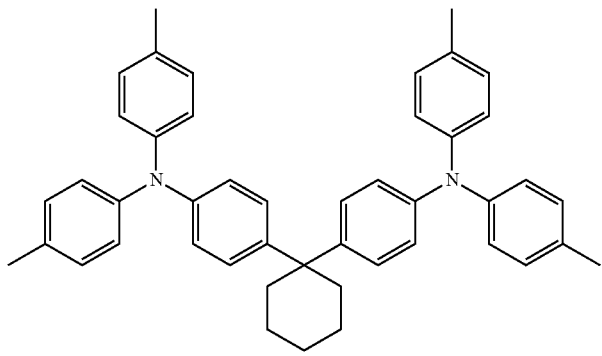
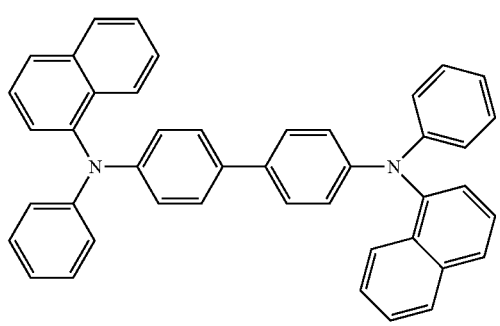

-continued
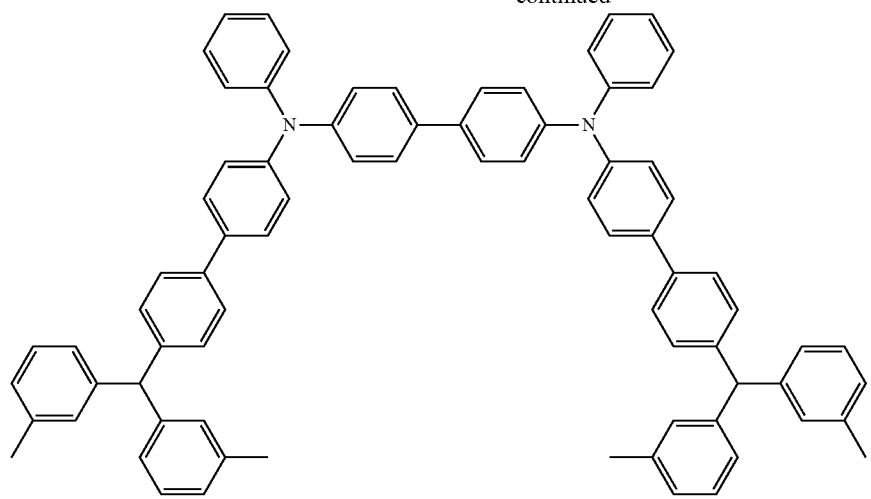
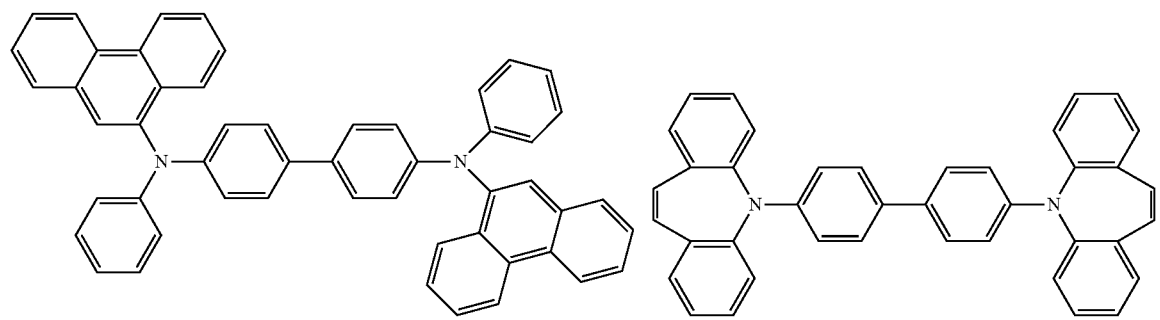
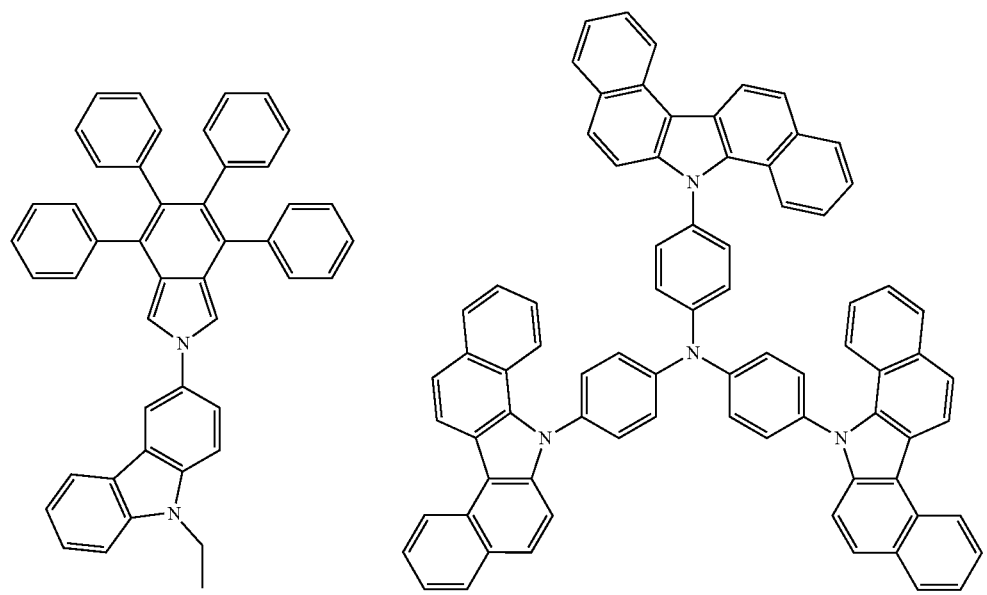

-continued
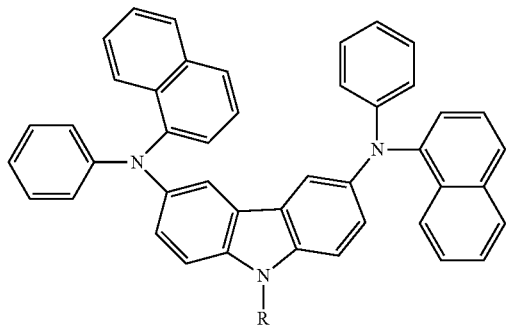
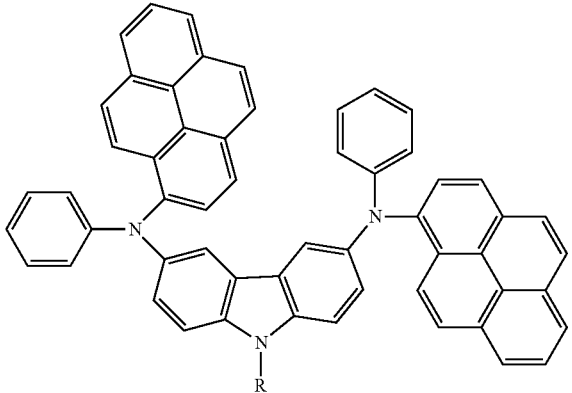
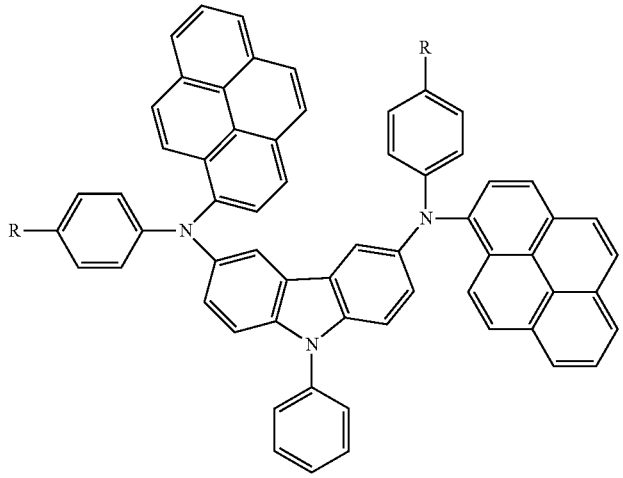
R = alkyl, aryl, alkoxy, aryloxy, 9,9′-dialkylfluorene
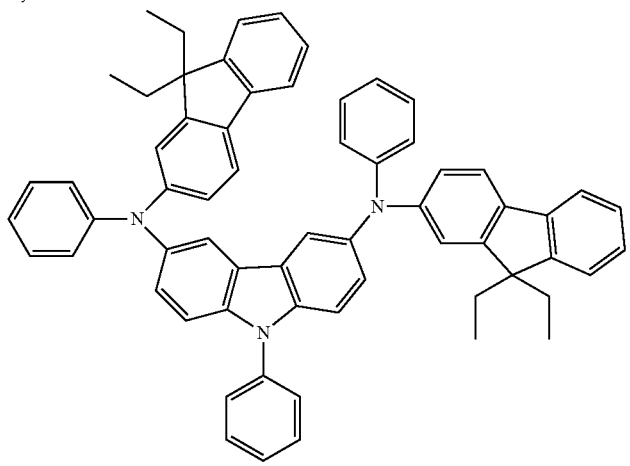
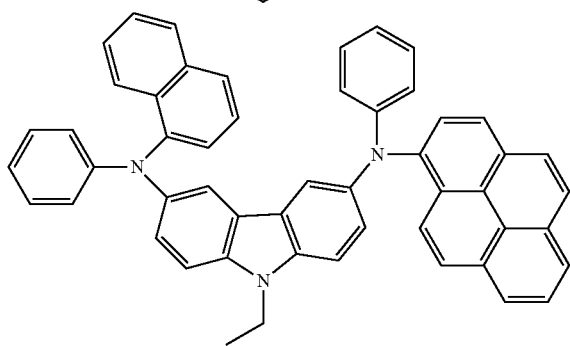

-continued
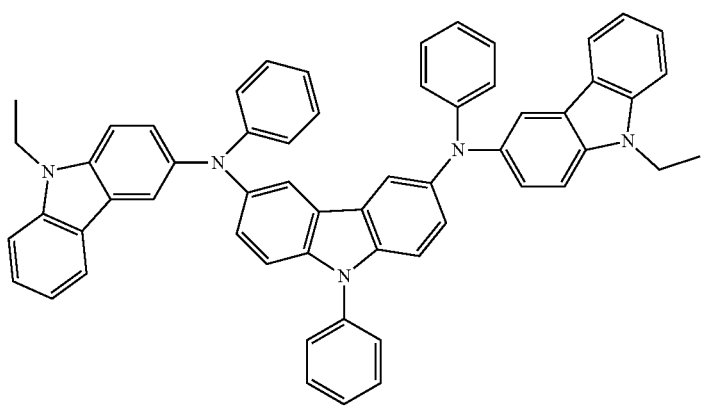
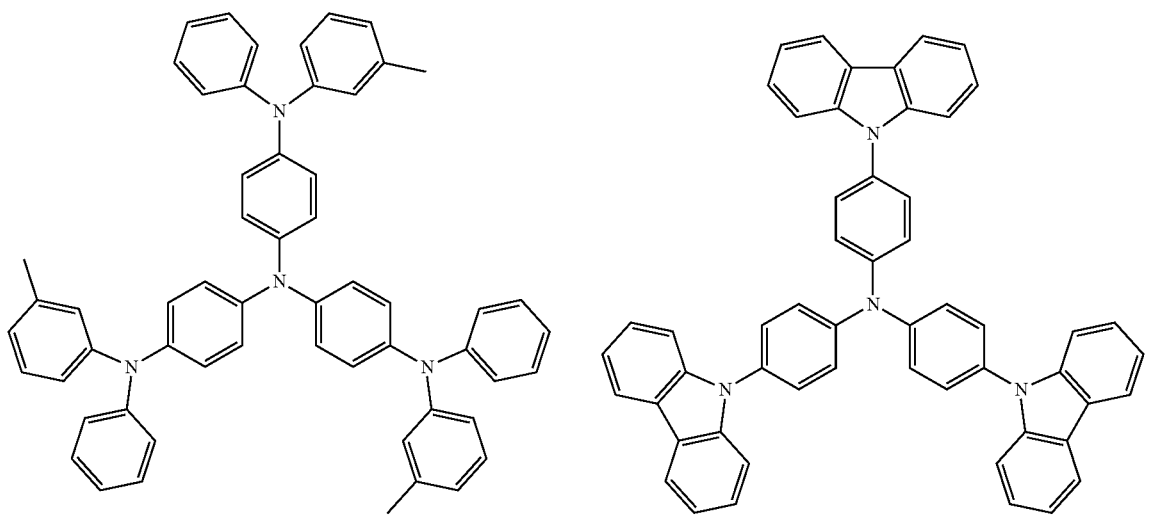
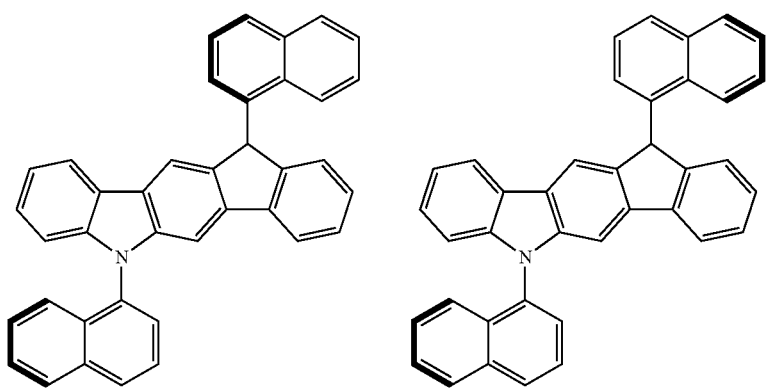

137
-continued
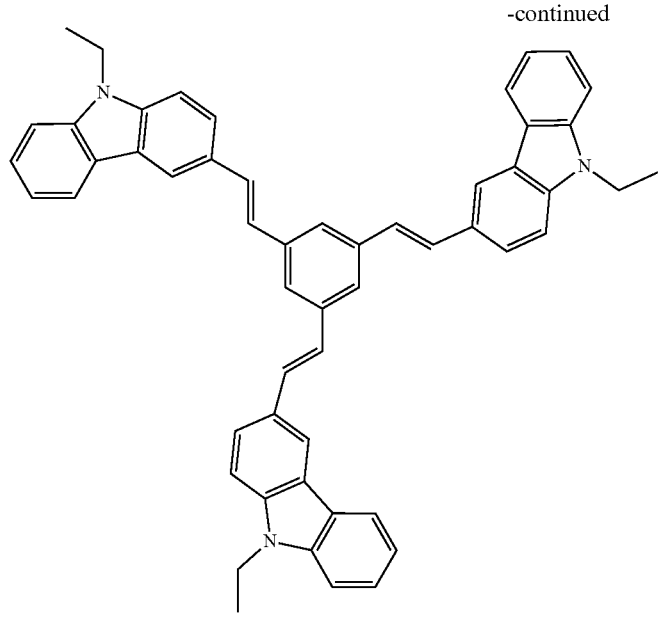
138
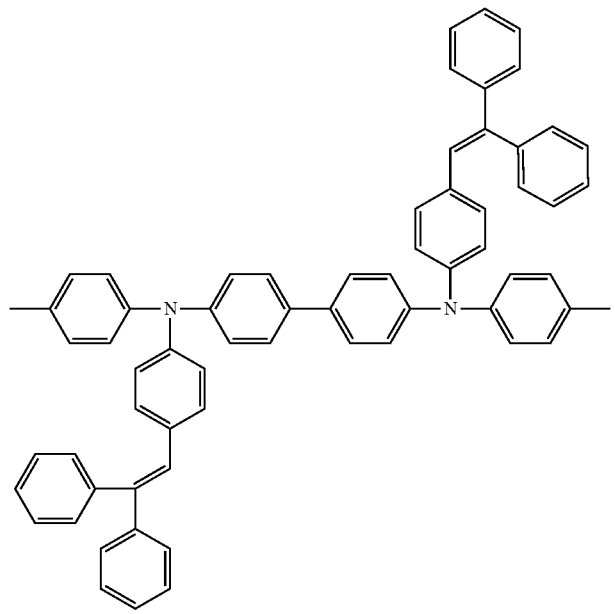
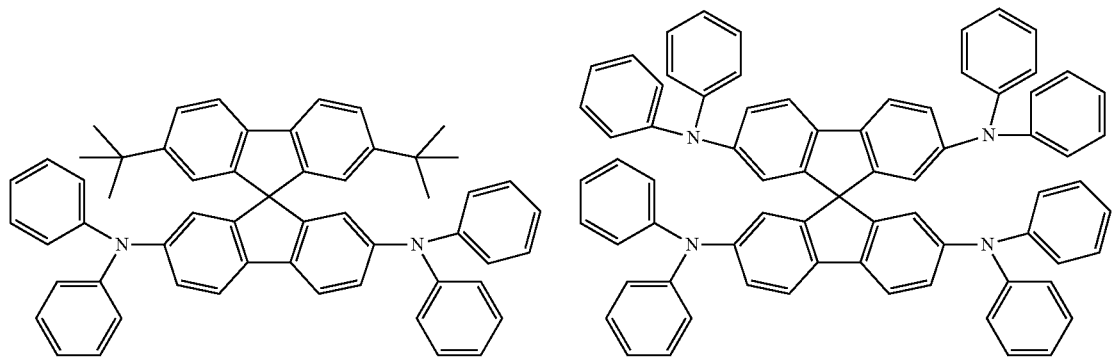

-continued
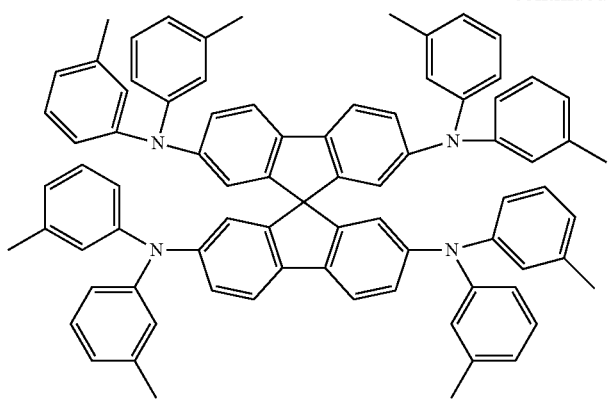
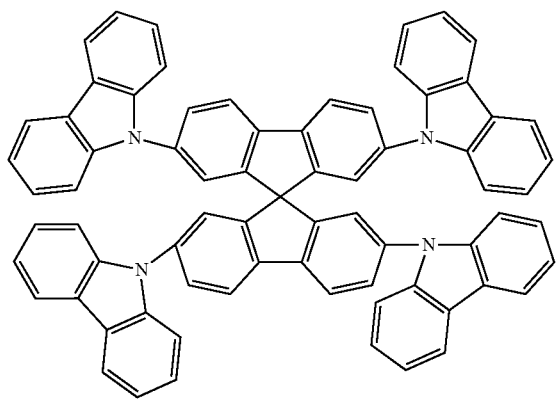
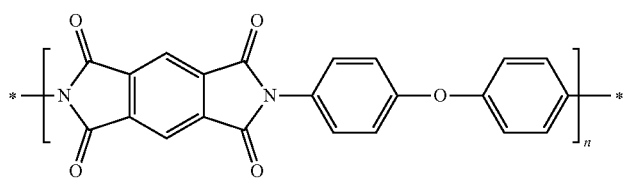
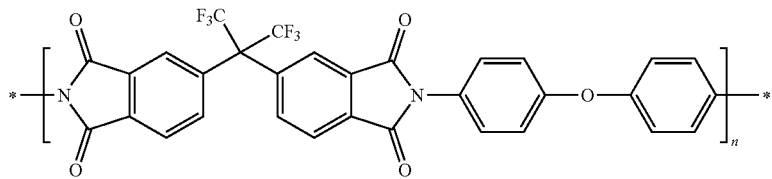
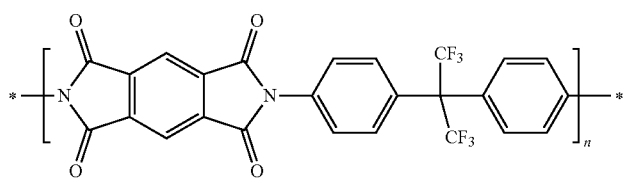
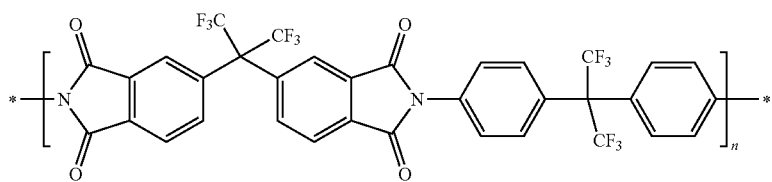

141
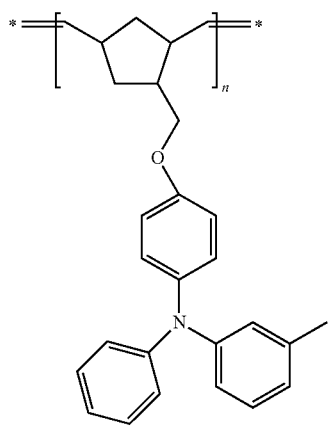
142
-continued
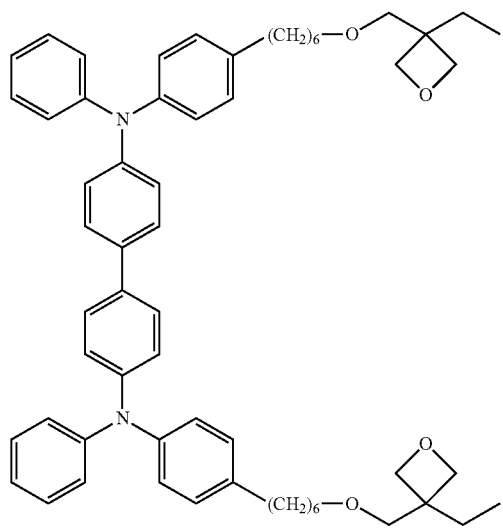
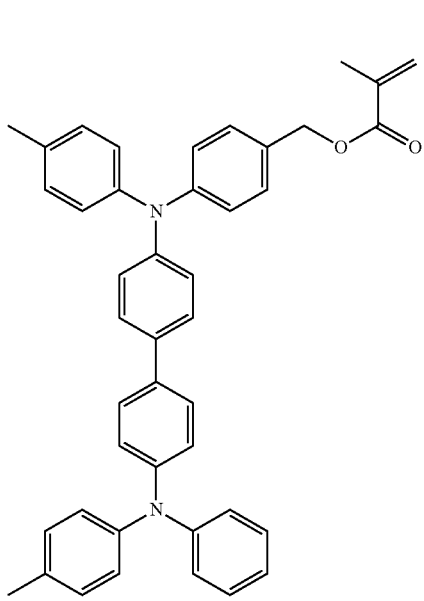
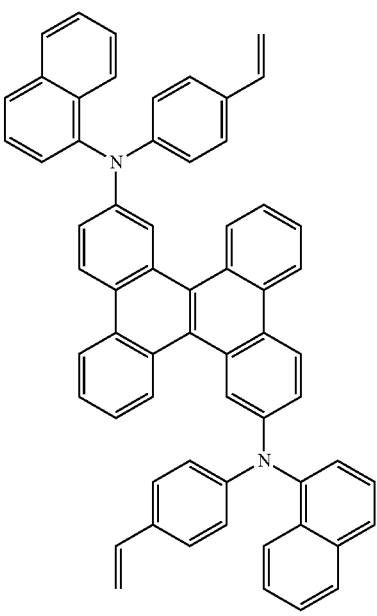
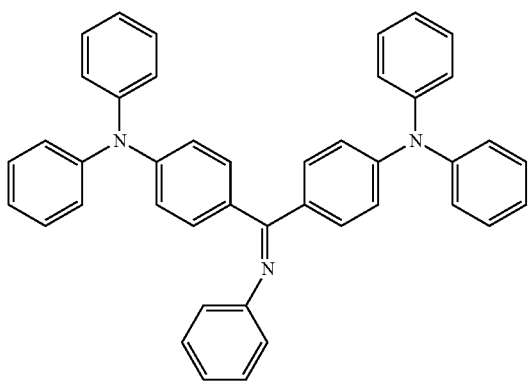

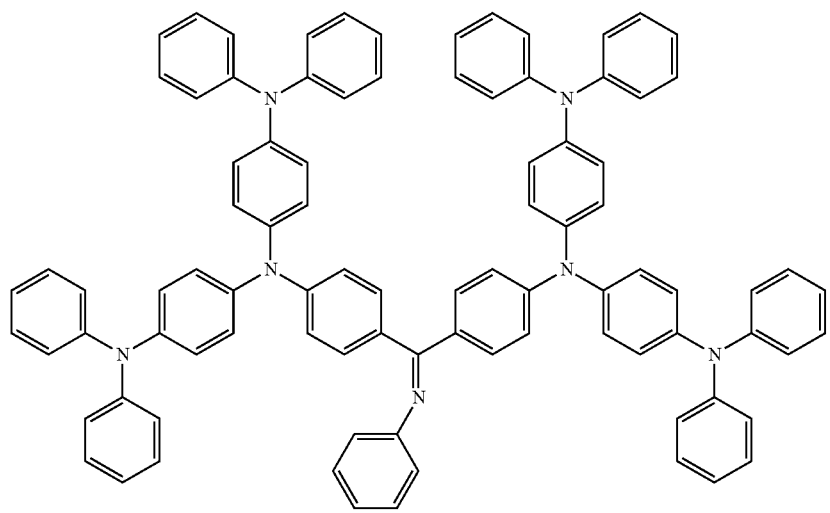
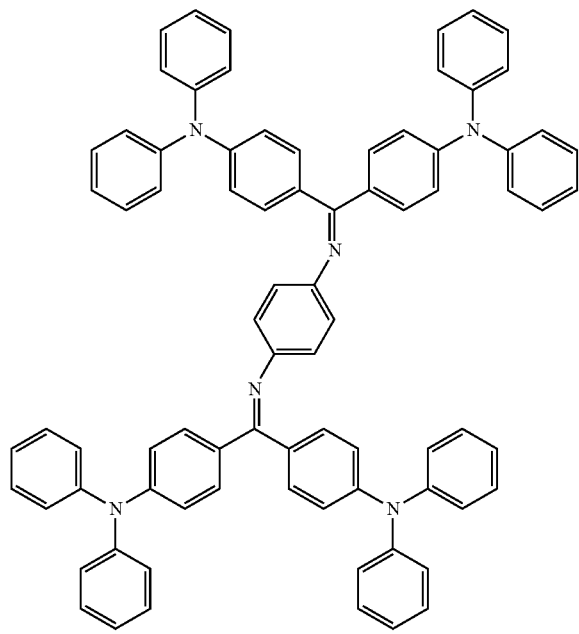

-continued
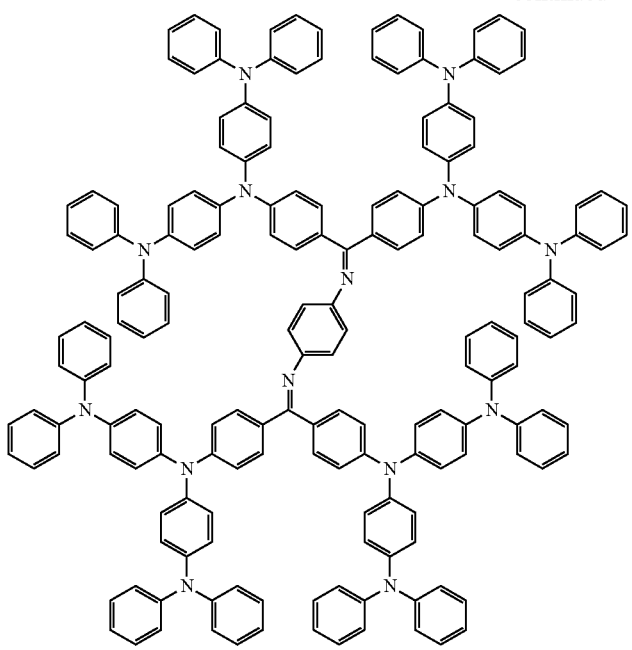
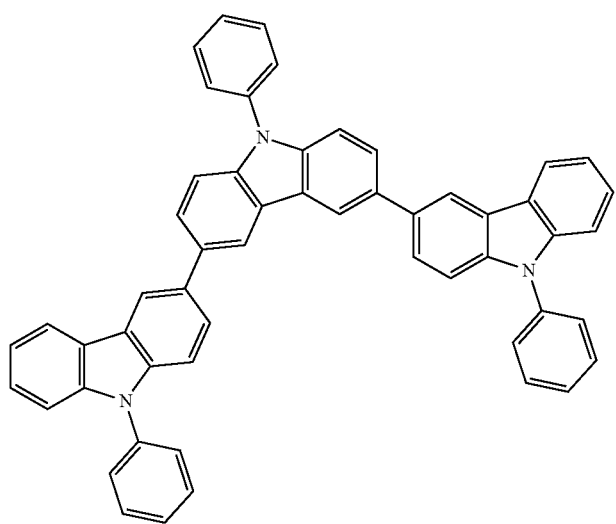

Next, preferred compounds for use as an electron blocking material are mentioned below.
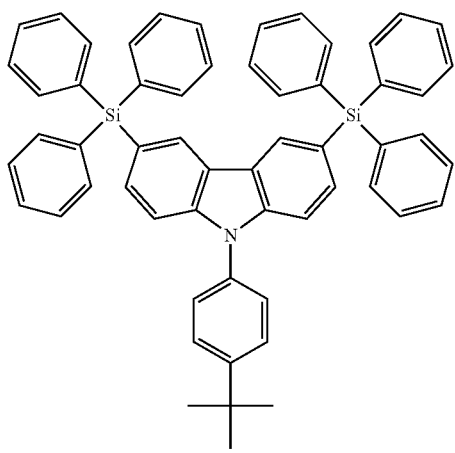
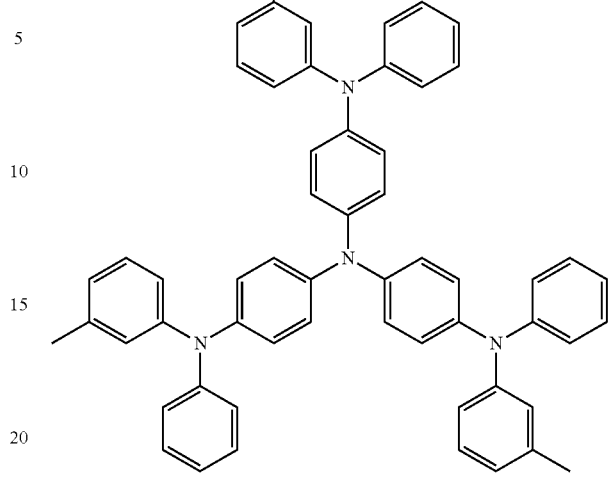
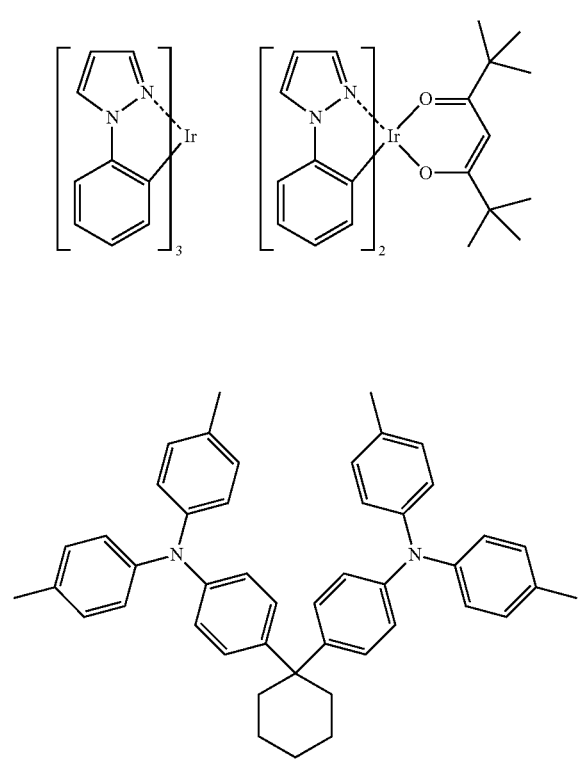
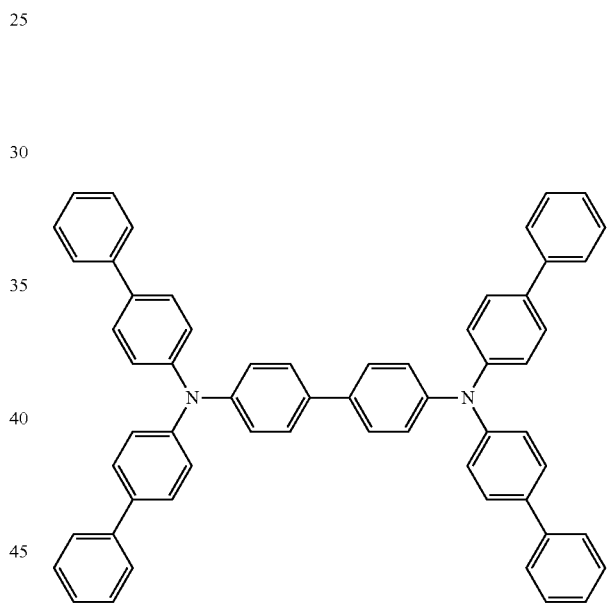
Next, preferred compounds for use as a hole blocking material are mentioned below.
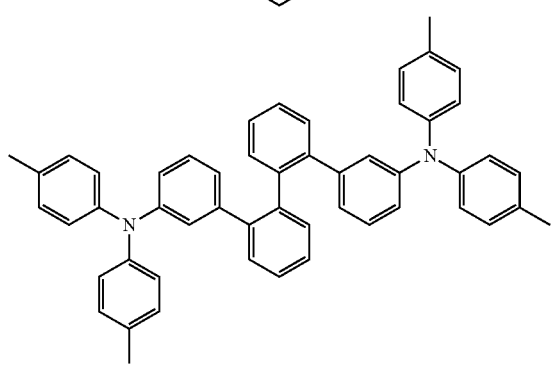
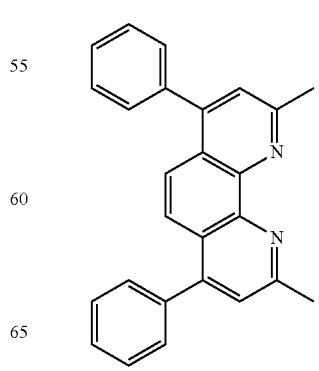

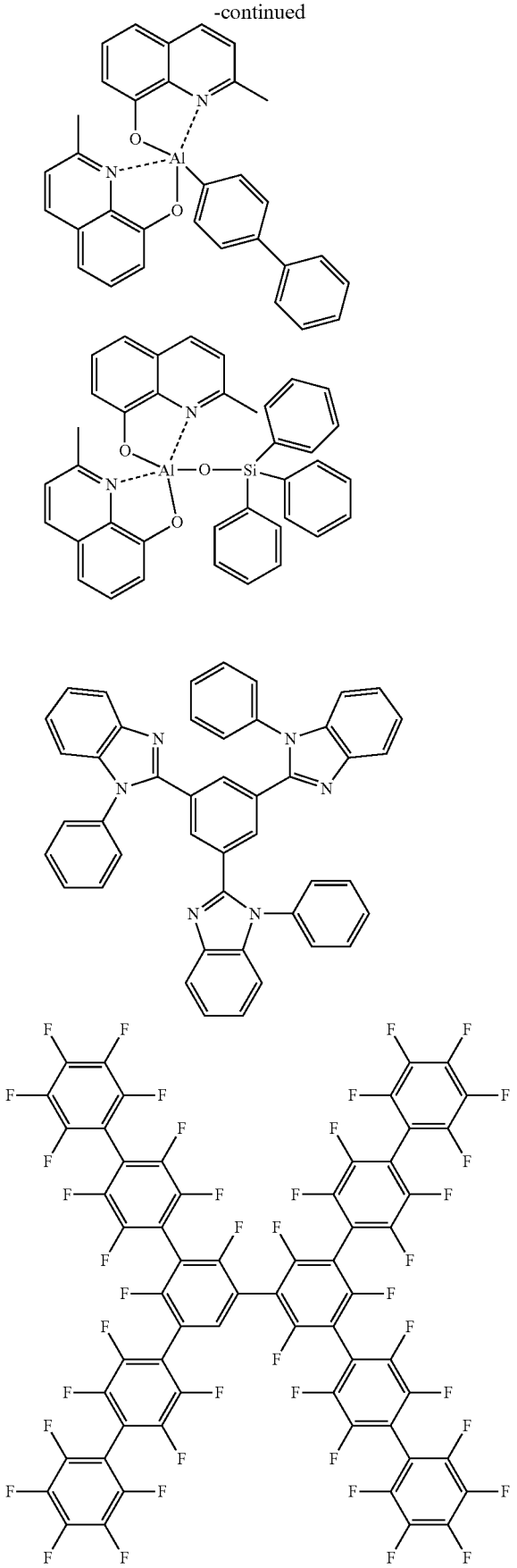
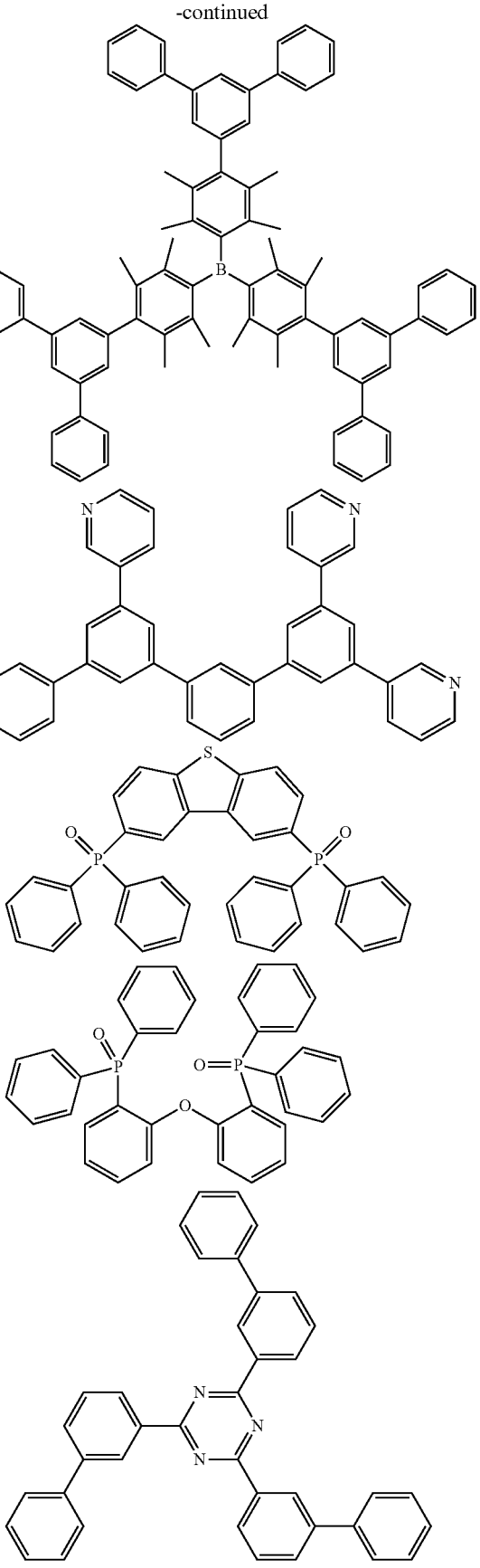

Next, preferred compounds for use as an electron transport material are mentioned below.
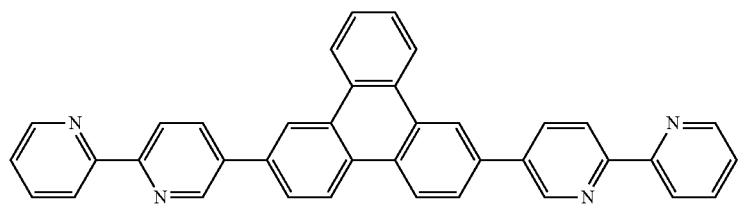
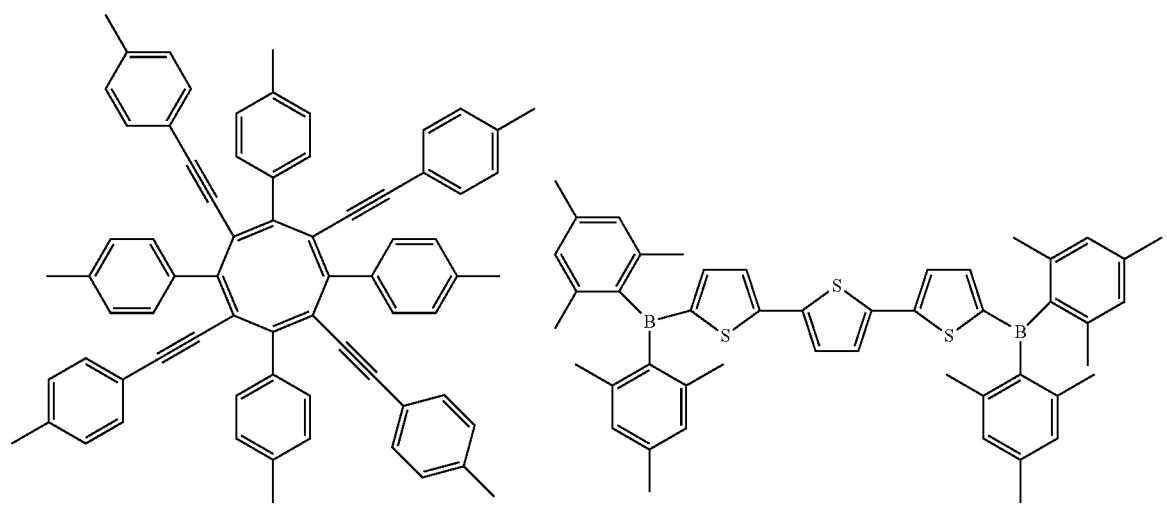
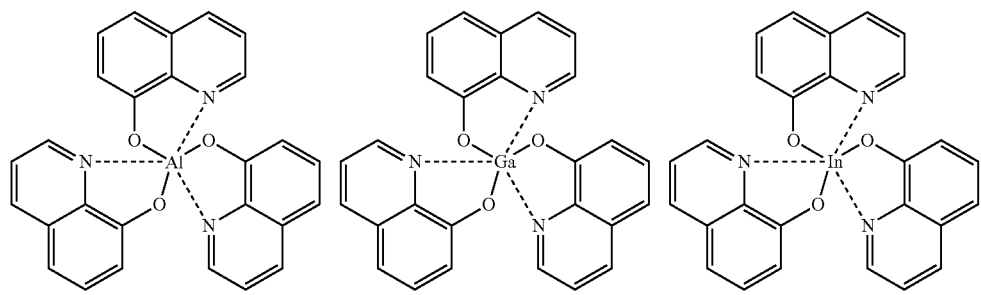
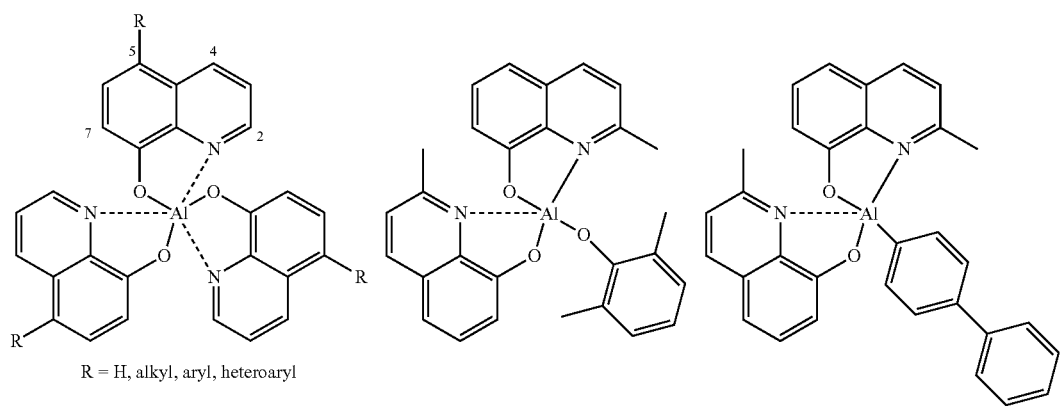
R = H, alkyl, aryl, heteroaryl 153 154
-continued
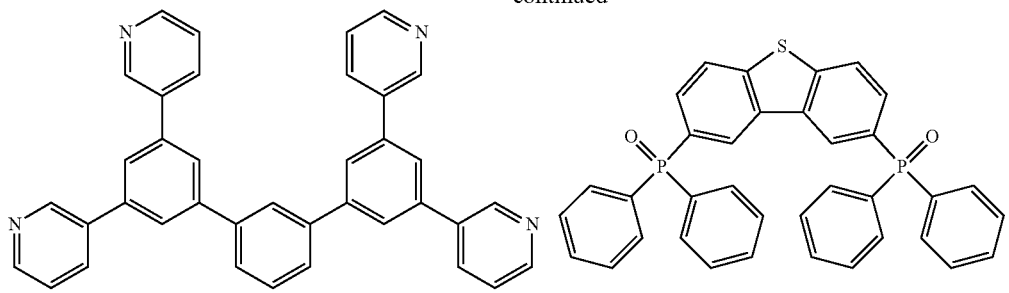
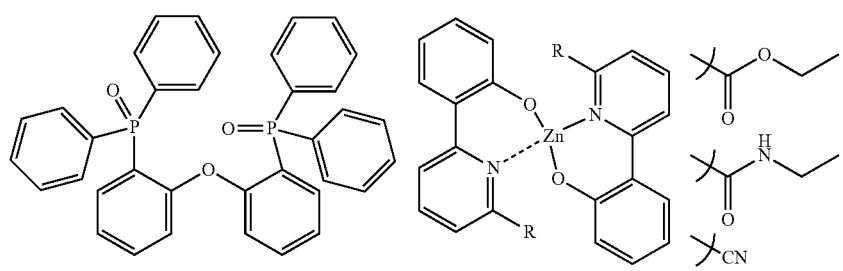
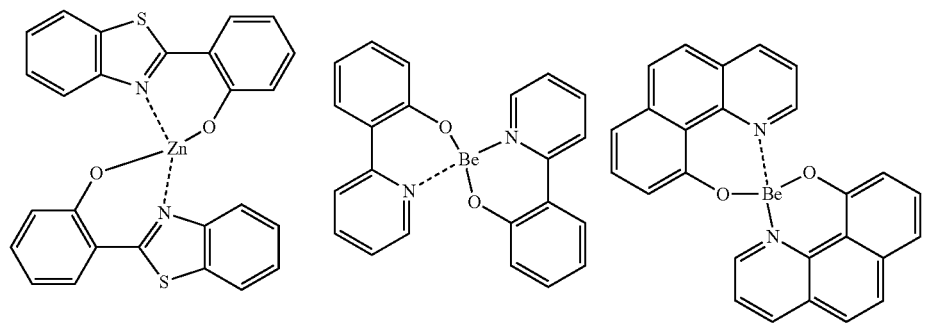
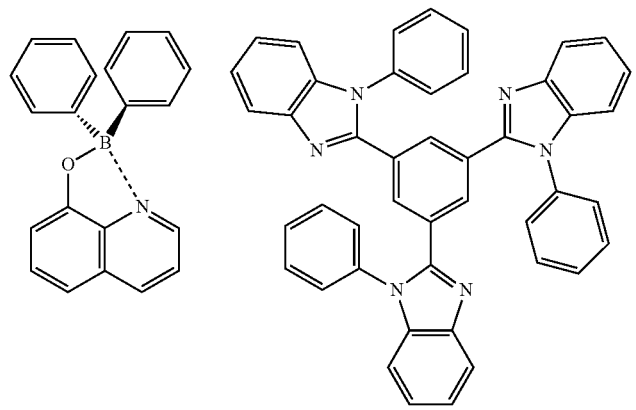

-continued
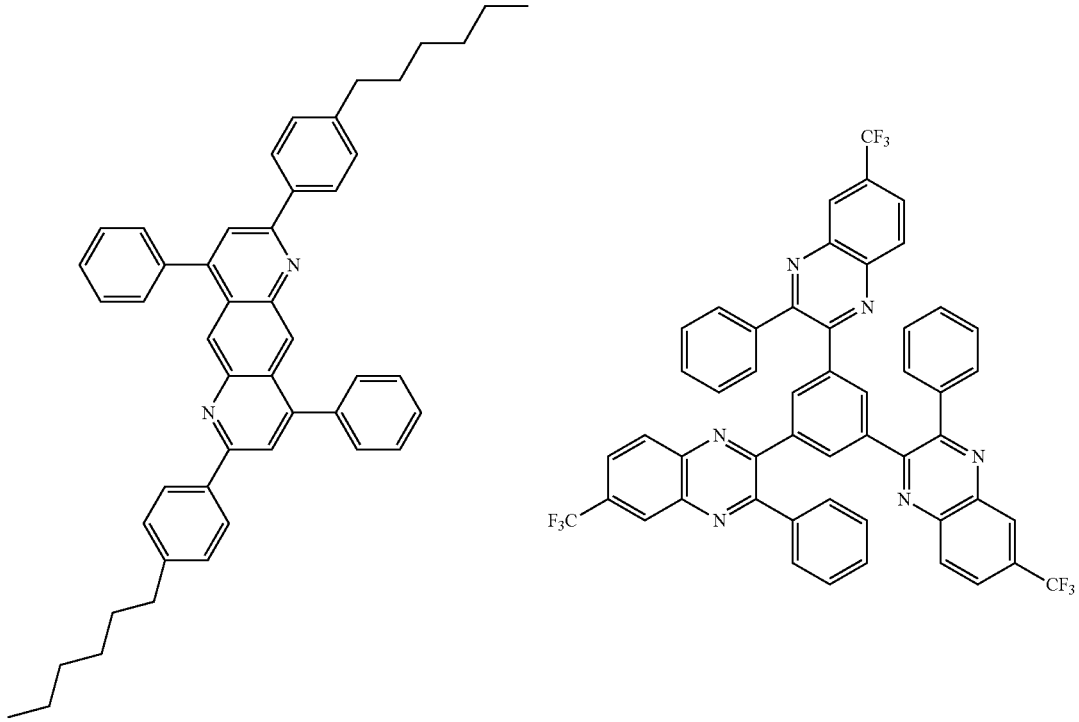
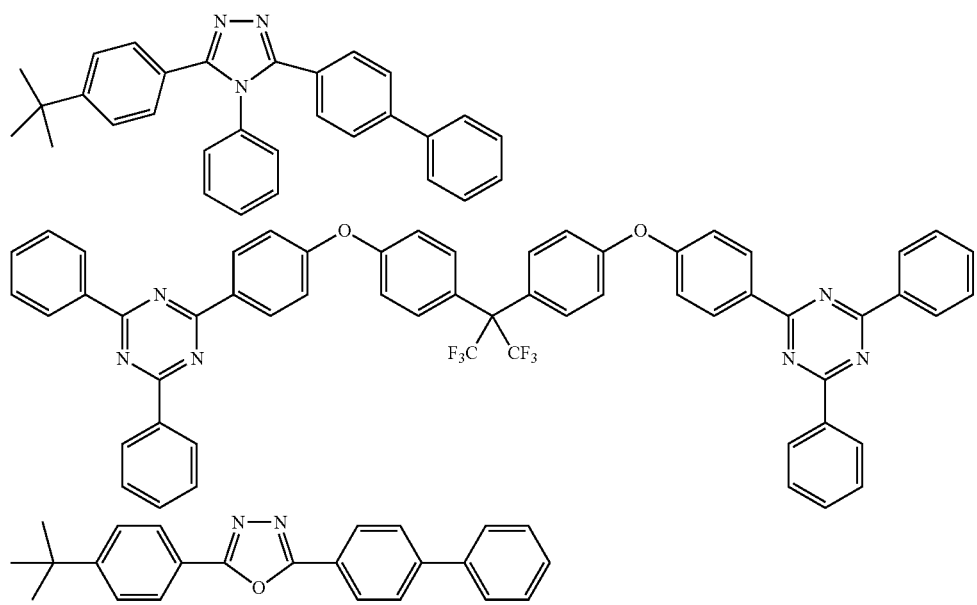
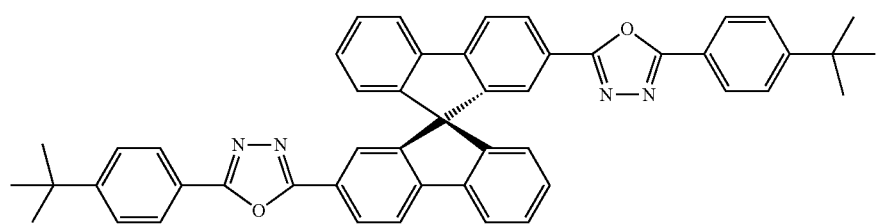

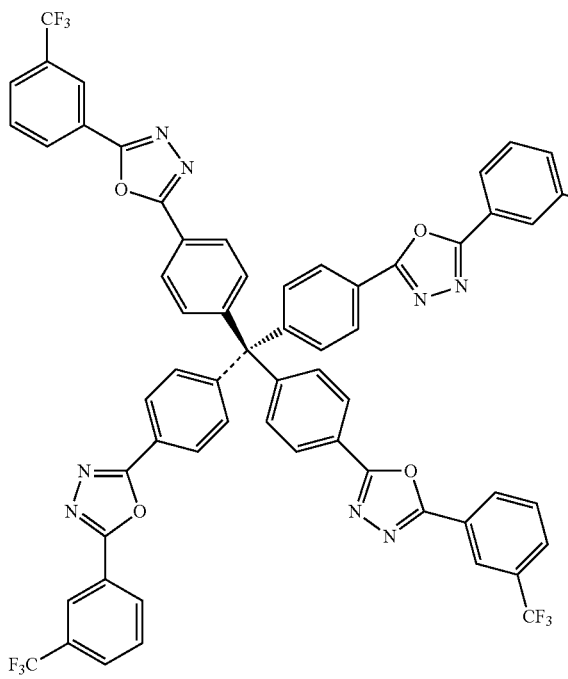
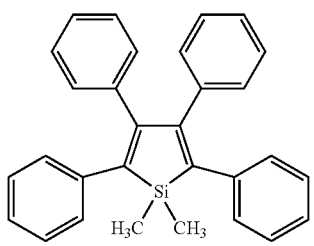
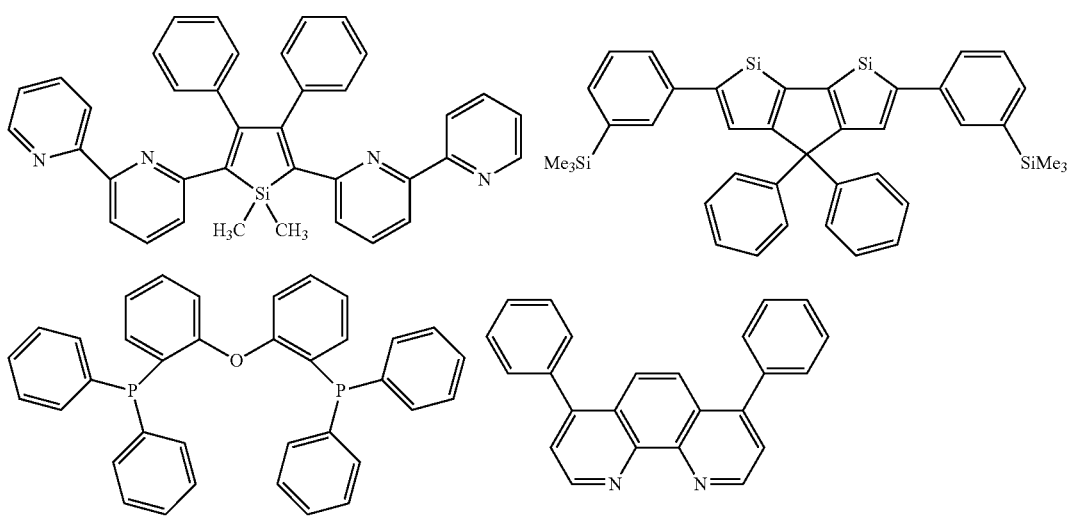
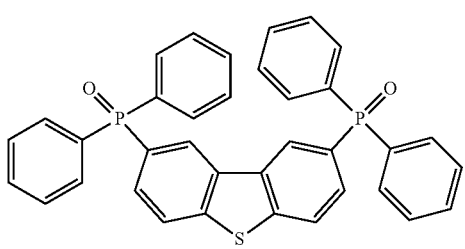

Next, preferred compounds for use as an electron injection material are mentioned below.

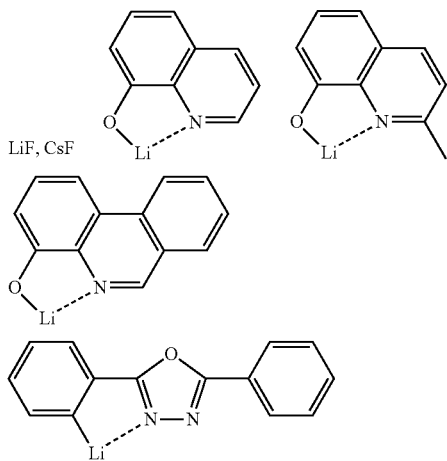

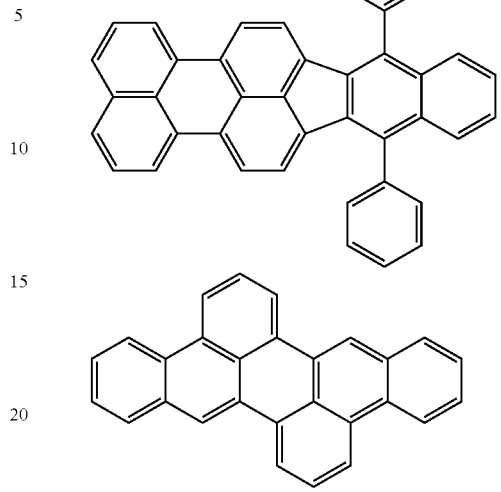

Further, preferred compounds for use as additional materials are mentioned below. For example, these are considered to be added as a stabilization material.

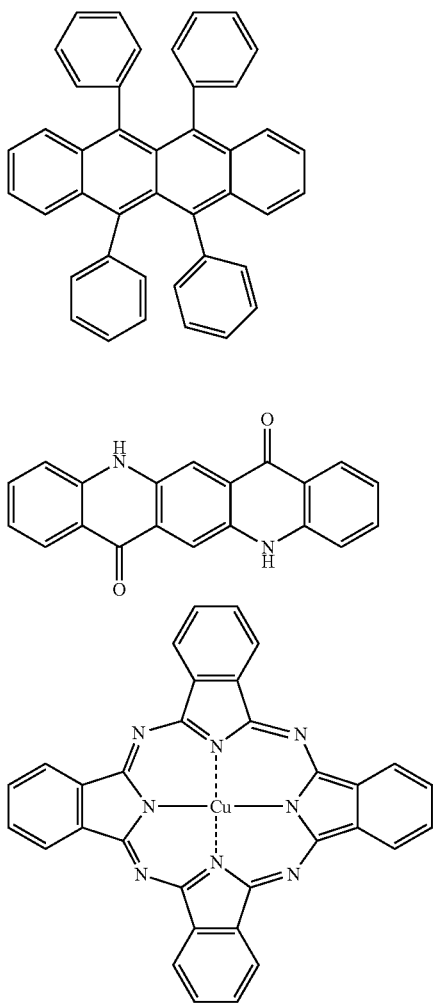

The organic electroluminescent device thus produced by the aforementioned method emits light on application of an electric field between the anode and the cathode of the device. In this case, when the light emission is caused by the excited singlet energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetime may be distinguished between the fluorescent light and the delayed fluorescent light.

On the other hand, the phosphorescent light may substantially not be observed with a normal organic compound such as the compound of the present invention at room temperature since the excited triplet energy is converted to heat or the like due to the instability thereof, and is immediately deactivated with a short lifetime. The excited triplet energy of the normal organic compound may be measured by observing light emission under an extremely low temperature condition.

The organic electroluminescent device of the invention may be applied to any of a single device, a device with plural structures disposed in an array, and a structure having anodes and cathodes disposed in an X-Y matrix. According to the present invention using the compound represented by the general formula (1) in a light-emitting layer, an organic light-emitting device having a markedly improved light emission efficiency can be obtained. The organic light-emitting device such as the organic electroluminescent device of the present invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

The present invention also includes the following matters.

[1] A compound represented by the following general formula (1):

(A)m-L-(D)n　　　　　　　　　　General Formula (1)

wherein L represents an (m+n)-valent aromatic linking group; A represents a group having a positive Hammett's $\sigma_p$ value; D represents a group having a negative Hammett's $\sigma_p$ value; m represents an integer of 1 or more; n represents an integer of 2 or more; when m is 2 or more, plural A's may be the same as or different from each other; two of plural D's each satisfy the following requirement (a) or the following requirement (b):
Requirement (a)
　　Two D's each have an aromatic ring that contains an atom bonding to L, and the aromatic ring is common between the two D's, but the two differ from each other in point of at least one condition of the number of the substituents on the aromatic ring, the substitution site of the aromatic ring substituted with the substituent, and the structure of the substituent on the aromatic ring.
Requirement (b)
　　Two D's each have a linking group that bonds to L and one aromatic ring bonding to the linking group, and the linking group and the aromatic ring bonding to the linking group are common between the two D's, but the two differ from each other in point of at least one condition of the number of the substituents on the aromatic ring, the substitution site of the aromatic ring substituted with the substituent, and the structure of the substituent on the aromatic ring. Two D's each have a linking group that bonds to L and two or more aromatic rings bonding to the linking group, and the linking group, the number of the aromatic rings bonding to the linking group, and the plural aromatic rings are common between the two D's, but in at least one combination of the aromatic rings common between the two D's, the two differ from each other in point of at least one condition of the number of the substituents on the aromatic ring, the substitution site of the aromatic ring substituted with the substituent, and the structure of the substituent on the aromatic ring.
[2] The compound according to [1], wherein two of the plural D's each contain a diarylamine structure (in which, however, two aryl groups constituting the diarylamine structure may bond to each other).
[3] The compound according to [2], wherein the diarylamine structure is a carbazole structure.
[4] The compound according to [1], wherein two of the plural D's each contain a diarylamino group (in which, however, two aryl groups constituting the diarylamino group may bond to each other).
[5] The compound according to [4], wherein the diarylamino group bonds to L via a single bond.
[6] The compound according to any one of [1] to [5], wherein two of the plural D's satisfy the requirement (a).
[7] The compound according to [1], wherein two of the plural D's each are a group represented by the following general formula (2):

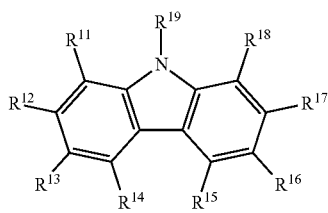

General Formula (2)

wherein $R^{11}$ to $R^{19}$ each independently represent a hydrogen atom, a substituent or a bonding position to L, and one of $R^{11}$ to $R^{19}$ is a bonding position to L.
[8] The compound according to [7], wherein $R^{19}$ in the general formula (2) is a bonding position to L.
[9] The compound according to [7] or [8], wherein one of two of the plural D's is such that at least one of $R^{11}$ to $R^{18}$ in the general formula (2) is a substituent, and the other of two of the plural D's is such that the corresponding substituent of that one of two of the plural D's among $R^{11}$ to $R^{18}$ in the general formula (2) is a hydrogen atom.
[10] The compound according to any one of [7] to [9], wherein one of two of the plural D's is such that at least one of $R^{13}$ and $R^{16}$ in the general formula (2) is a substituent.
[11] The compound according to [9] or [10], wherein the substituent is a substituted or unsubstituted alkyl group or a substituted or unsubstituted aryl group.
[12] The compound according to [1], wherein the compound represented by the general formula (1) is a compound represented by the following general formula (10):

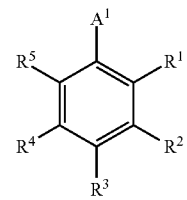

General Formula (10)

wherein $A^1$ represents a group having a positive Hammett's σp value; $R^1$ to $R^5$ each independently represent a hydrogen atom, a group having a positive Hammett's σp value, or a group having a negative Hammett's σp value; at least two of $R^1$ to $R^5$ each are a group having a negative Hammett's σp value; when one or more of $R^1$ to $R^5$ each are a group having a positive Hammett's σp value, the group having a positive Hammett's σp value represented by $A^1$ and the group having a positive Hammett's σp value among $R^1$ to $R^5$ may be the same as or different from each other; two groups each having a negative Hammett's σp value among $R^1$ to $R^5$ each satisfy the following requirement (a) or requirement (b):
Requirement (a)
　　Two groups having a negative Hammett's σp value each have an aromatic ring that contains an atom bonding to the benzene ring in the general formula (10), and the aromatic ring is common between the two groups having a negative Hammett's σp value, but the two differ from each other in point of at least one condition of the number of the substituents on the aromatic ring, the substitution site of the aromatic ring substituted with the substituent, and the structure of the substituent on the aromatic ring.
Requirement (b)
　　Two groups having a negative Hammett's σp value each have a linking group that bonds to the benzene ring in the general formula (10) and one aromatic ring bonding to the linking group, and the linking group and the aromatic ring bonding to the linking group are common between the two groups having a negative Hammett's σp value, but the two differ from each other in point of at least one condition of the number of the substituents on the aromatic ring, the substitution site of the aromatic ring substituted with the substituent, and the structure of the substituent on the aromatic ring. Two groups having a negative Hammett's σp value each have a linking group that bonds to the benzene ring in the general formula (10) and two or more aromatic rings bonding to the linking group, and the linking group, the number of the aromatic rings bonding to the linking group, and the plural aromatic rings are common between the two groups having a negative Hammett's σp value, but in at least one combination of the aromatic rings common between the two groups having a negative Hammett's σp value, the two differ from each other in point of at least one condition of the number of the substituents on the aromatic ring, the substitution site of the aromatic ring substituted with the substituent, and the structure of the substituent on the aromatic ring.

The compound according to [12], wherein $R^1$ to $R^5$ in the general formula (10) each are a group having a negative Hammett's σp value.

The compound according to [13], wherein at least one of the combination of $R^1$ and $R^4$ and the combination of $R^2$ and $R^5$ in the general formula (10) satisfies the requirement (a) or (b).

A light-emitting material containing a compound of any one of [1] to [14].

A light-emitting device containing a compound of any one of [1] to [14].

EXAMPLES

The features of the present invention will be described more specifically with reference to Examples given below. The materials, processes, procedures and the like shown below may be appropriately modified unless they deviate from the substance of the invention. Accordingly, the scope of the invention is not construed as being limited to the specific examples shown below. The light emission characteristics were evaluated using Source Meter (available from Keithley Instruments Corporation: 2400 series), a semiconductor parameter analyzer (available from Agilent Corporation, E5273A), an optical power meter device (available from Newport Corporation, 1930C), an optical spectroscope (available from Ocean Optics Corporation, USB2000), a spectroradiometer (available from Topcon Corporation, SR-3) and a streak camera (available from Hamamatsu Photonics K.K., C4334).

The radiative rate constant $k_r$ from the excited singlet state of the compound used in Examples, the non-radiative rate constant $k_{nr}^T$ from the excited triplet state thereof, the rate constant $k_{ISC}$ in intersystem crossing from the excited singlet state to the excited triplet state thereof, and the rate constant $k_{RISC}$ in reverse intersystem crossing from the excited triplet state to the excited singlet state thereof were determined from the life of the prompt component (ordinary fluorescent component), that of the delayed component and the emission quantum yield before and after argon bubbling.

The difference $\Delta E_{ST}$ between the lowest excited singlet energy level ($E_{SI}$) and the lowest excited triplet energy level ($E_{TI}$) of the compound used in Examples was calculated as $\Delta E_{ST}=E_{SI}-E_{TI}$, in which the lowest excited singlet energy level ($E_{SI}$) and the lowest excited triplet energy level ($E_{TI}$) were determined according to the methods mentioned below.

(1) Lowest Excited Singlet Energy Level ($E_{SI}$)

A toluene solution containing the compound to be analyzed (concentration: $10^{-5}$ mol/L) was prepared as a measurement sample, and the fluorescent spectrum of the sample was measured at room temperature (300 K). For the fluorescent spectrum, the emission intensity was on the vertical axis and the wavelength was on the horizontal axis. A tangent line was drawn to the rising of the emission spectrum on the short wavelength side, and the wavelength value λedge [nm] at the intersection between the tangent line and the horizontal axis was read. The wavelength value was converted into an energy value according to the following conversion expression to calculate $E_{SI}$.

Conversion Expression: $E_{SI}$ [eV]=1239.85/λedge

For the measurement of the emission spectrum, an LED light source (available from Thorlabs Corporation, M340L4) was used as an excitation light source along with a detector (available from Hamamatsu Photonics K.K., PMA-50).

(2) Lowest Excited Triplet Energy Level ($E_{TI}$)

The same sample as that for measurement of the lowest excited singlet energy level (Es) was cooled to 77 [K] with liquid nitrogen, and the sample for phosphorescence measurement was irradiated with excitation light (340 nm), and using a detector, the phosphorescence thereof was measured. The emission after 100 milliseconds from irradiation with the excitation light was drawn as a phosphorescent spectrum. A tangent line was drawn to the rising of the phosphorescent spectrum on the short wavelength side, and the wavelength value ledge [nm] at the intersection between the tangent line and the horizontal axis was read. The wavelength value was converted into an energy value according to the following conversion expression to calculate $E_{TI}$.

Conversion Expression: $E_{TI}$[eV]=1239.85/λedge

The tangent line to the rising of the phosphorescent spectrum on the short wavelength side was drawn as follows. While moving on the spectral curve from the short wavelength side of the phosphorescent spectrum toward the maximum value on the shortest wavelength side among the maximum values of the spectrum, a tangent line at each point on the curve toward the long wavelength side was taken into consideration. With rising thereof (that is, with increase in the vertical axis), the inclination of the tangent line increases. The tangent line drawn at the point at which the inclination value has a maximum value was referred to as the tangent line to the rising on the short wavelength side of the phosphorescent spectrum.

The maximum point having a peak intensity of 10% or less of the maximum peak intensity of the spectrum was not included in the maximum value on the above-mentioned shortest wavelength side, and the tangent line drawn at the point which is closest to the maximum value on the shortest wavelength side and at which the inclination value has a maximum value was referred to as the tangent lint to the rising on the short wavelength side of the phosphorescent spectrum.

Synthesis of Compound (Synthesis Example 1) Synthesis of Compound 1

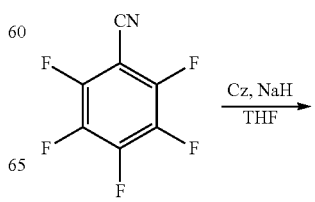

165

-continued

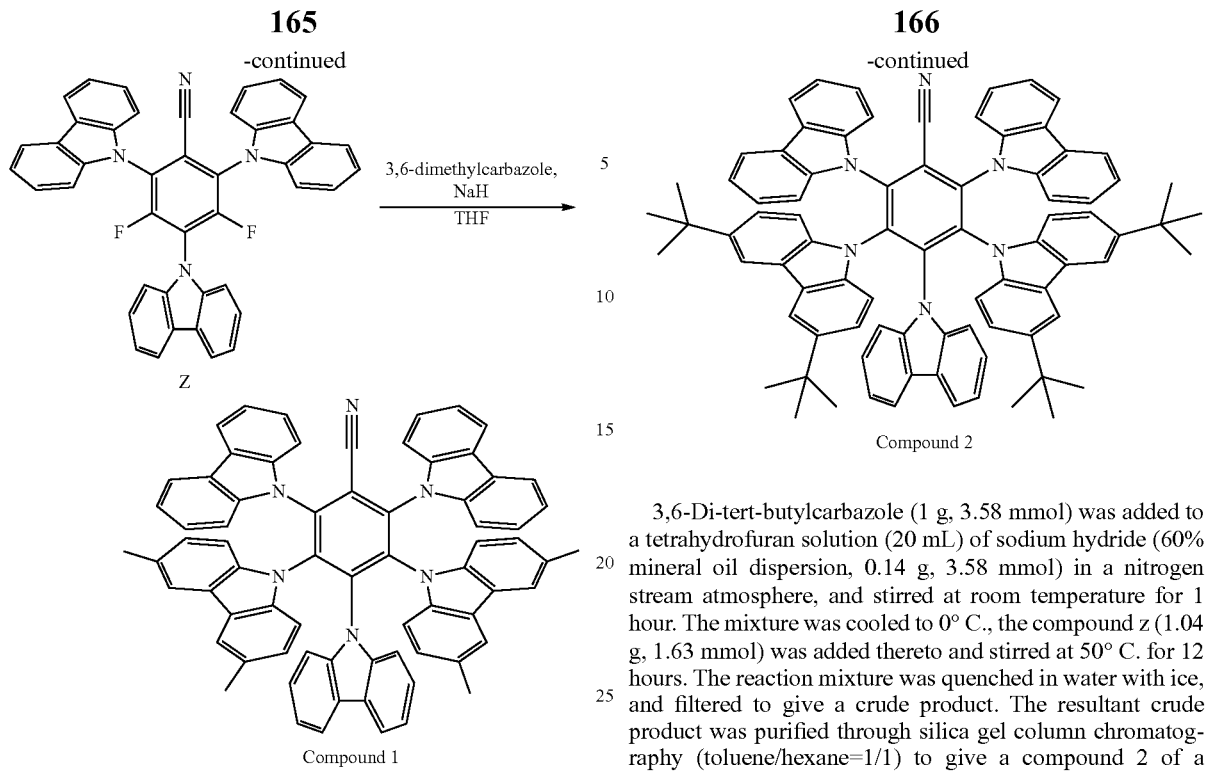

Compound 1

A compound z was synthesized according to a method equivalent to the method described in Adv. Opt. Mater. 4, 688-693 (2016).

Next, 3,6-dimethylcarbazole (0.39 g, 1.98 mmol) was added to a tetrahydrofuran solution (20 mL) of sodium hydride (60% mineral oil dispersion, 0.08 g, 1.98 mmol) in a nitrogen stream atmosphere, and stirred at room temperature for 1 hour. The mixture was cooled to 0° C., the compound z (0.5 g, 0.79 mmol) was added thereto and stirred at 50° C. for 12 hours. The reaction mixture was quenched in water with ice, and filtered to give a crude product. The resultant crude product was purified through silica gel column chromatography (toluene/hexane=3/2) to give a compound 1 of a yellow solid (0.79 g, 0.75 mmol, yield 95%).

$^1$H NMR: (500 MHz, acetone-d6): δ (ppm)=7.83 (d, J=8.2 Hz, 4H), 7.71 (d, J=7.1 Hz, 4H), 7.64 (d, J=8.3 Hz, 2H), 7.45 (d, J=8.4 Hz, 2H), 7.34 (d, J=7.2 Hz, 2H), 7.09 (m, 12H), 6.72 (t, J=7.9 Hz, 2H), 6.62 (d, J=8.4 Hz, 2H), 6.45 (d, J=8.3 Hz, 4H), 2.11 (s, 12H)

(Synthesis Example 2) Synthesis of Compound 2

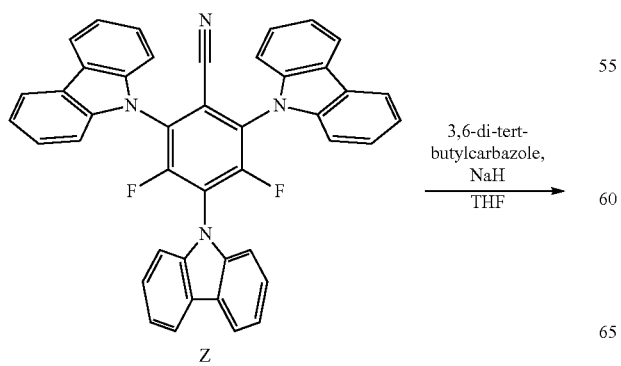

166

-continued

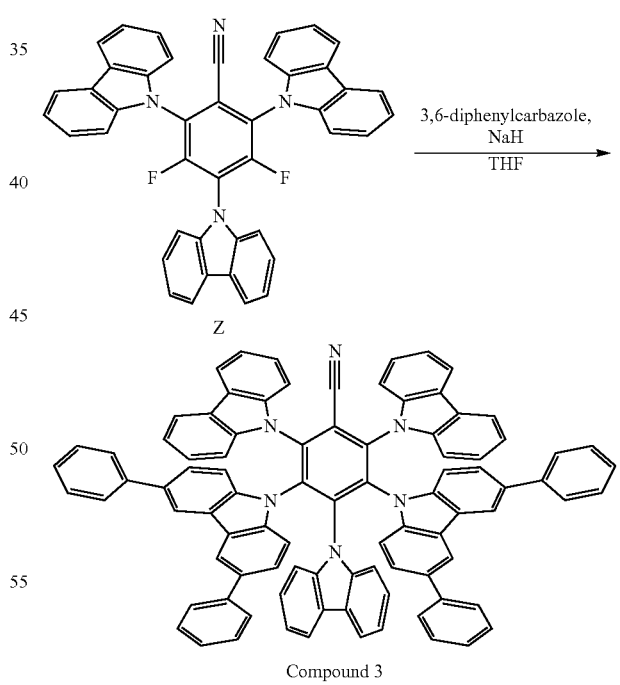

Compound 2

3,6-Di-tert-butylcarbazole (1 g, 3.58 mmol) was added to a tetrahydrofuran solution (20 mL) of sodium hydride (60% mineral oil dispersion, 0.14 g, 3.58 mmol) in a nitrogen stream atmosphere, and stirred at room temperature for 1 hour. The mixture was cooled to 0° C., the compound z (1.04 g, 1.63 mmol) was added thereto and stirred at 50° C. for 12 hours. The reaction mixture was quenched in water with ice, and filtered to give a crude product. The resultant crude product was purified through silica gel column chromatography (toluene/hexane=1/1) to give a compound 2 of a yellow solid (1.8 g, 1.56 mmol, yield 96%).

(Synthesis Example 3) Synthesis of Compound 3

Compound 3

3,6-Di-phenylcarbazole (1 g, 3.15 mmol) was added to a tetrahydrofuran solution (20 mL) of sodium hydride (60% mineral oil dispersion, 0.13 g, 3.15 mmol) in a nitrogen stream atmosphere, and stirred at room temperature for 1 hour. The mixture was cooled to 0° C., the compound z (0.8 g, 1.26 mmol) was added thereto and stirred at 50° C. for 12 hours. The reaction mixture was quenched in water with ice, and filtered to give a crude product. The resultant crude product was purified through silica gel column chromatography (toluene/hexane=3/2) to give a compound 3 of a yellow solid (1.36 g, 1.10 mmol, yield 87%).

$^1$H NMR: (500 MHz, acetone-d6): δ (ppm)=7.82 (m, 14H), 7.72 (d, J=8.7 Hz, 4H), 7.45 (m, 8H), 7.35 (m, 10H), 7.26 (t, J=8.6 Hz, 4H), 7.16 (t, J=8.3 Hz, 4H), 7.10 (t, J=7.9 Hz, 4H), 6.98 (d, J=8.6 Hz, 4H), 6.75 (m, 4H)

(Synthesis Example 4) Synthesis of Compound 4

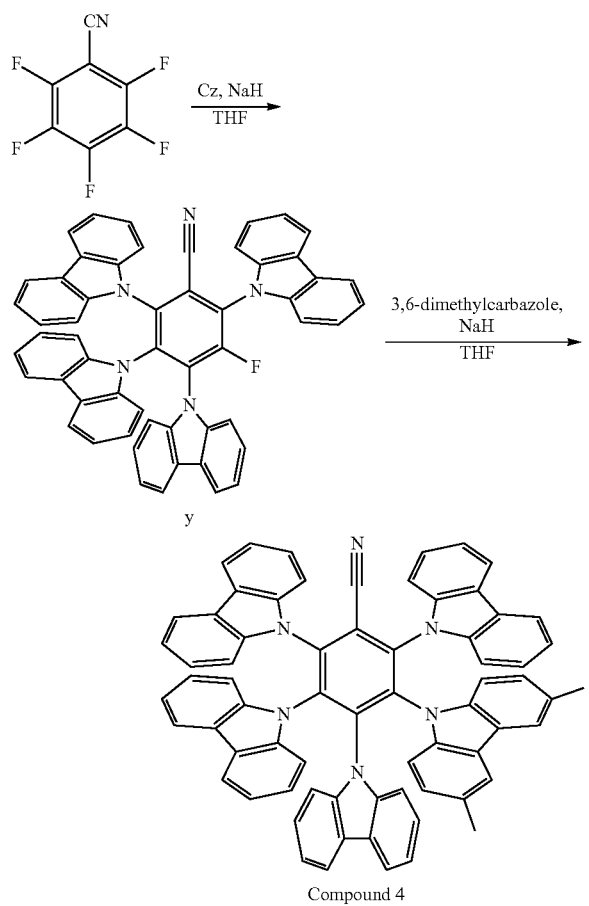

A compound y was synthesized according to a method equivalent to the method described in Adv. Opt. Mater. 4, 688-693 (2016).

Next, 3,6-dimethylcarbazole (0.37 g, 1.92 mmol) was added to a tetrahydrofuran solution (20 mL) of sodium hydride (60% mineral oil dispersion, 0.08 g, 1.92 mmol) in a nitrogen stream atmosphere, and stirred at room temperature for 1 hour. The mixture was cooled to 0° C., the compound y (1.0 g, 1.28 mmol) was added thereto and stirred at 50° C. for 12 hours. The reaction mixture was quenched in water with ice, and filtered to give a crude product. The resultant crude product was purified through silica gel column chromatography (toluene/hexane=3/2) to give a compound 4 of a yellow solid (1.08 g, 1.13 mmol, yield 88%).

(Synthesis Example 5) Synthesis of Compound 5

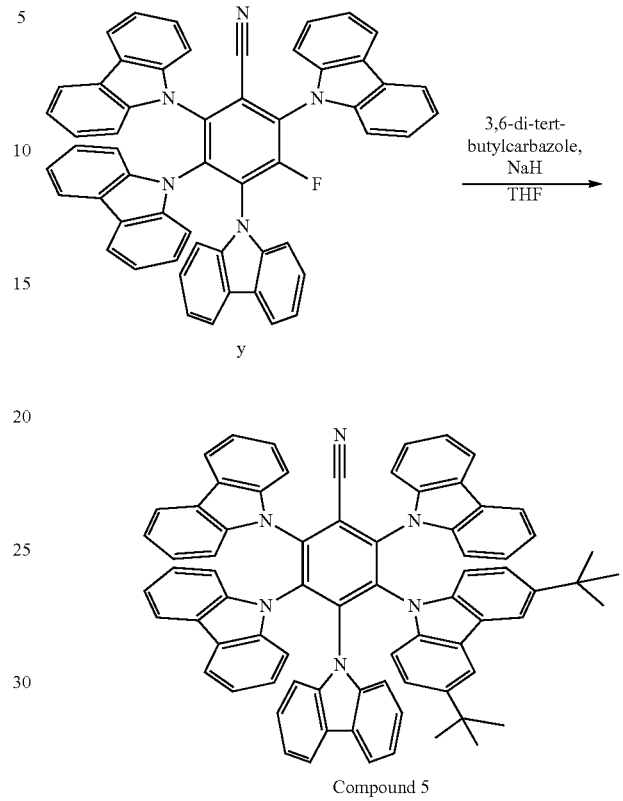

3,6-Di-tert-butylcarbazole (0.54 g, 1.92 mmol) was added to a tetrahydrofuran solution (20 mL) of sodium hydride (60% mineral oil dispersion, 0.08 g, 1.92 mmol) in a nitrogen stream atmosphere, and stirred at room temperature for 1 hour. The mixture was cooled to 0° C., the compound y (1.0 g, 1.28 mmol) was added thereto and stirred at 50° C. for 12 hours. The reaction mixture was quenched in water with ice, and filtered to give a crude product. The resultant crude product was purified through silica gel column chromatography (toluene/hexane=3/2) to give a compound 5 of a yellow solid (1.16 g, 1.11 mmol, yield 87%).

(Synthesis Example 6) Synthesis of Compound 6

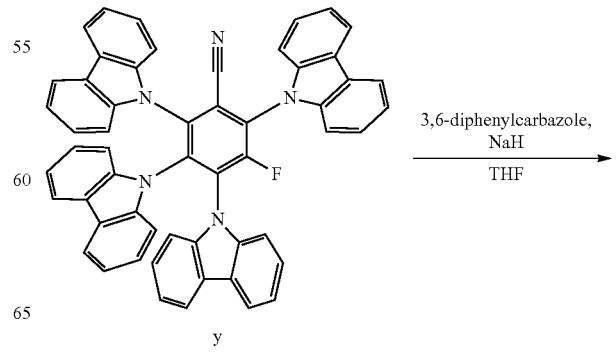

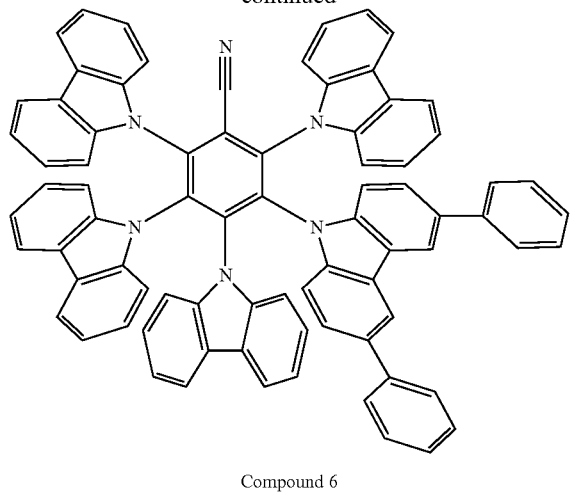

Compound 6

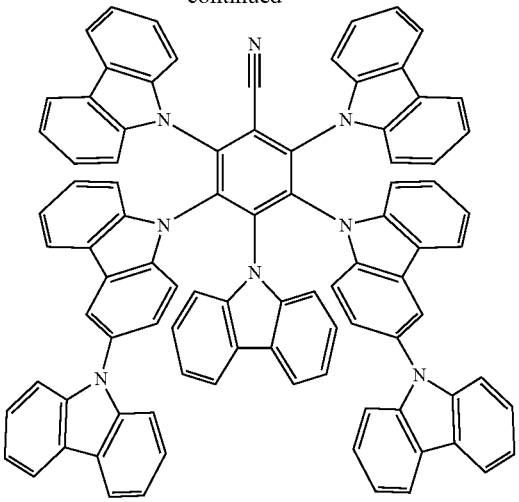

Compound 7

3,6-Diphenylcarbazole (0.61 g, 1.92 mmol) was added to a tetrahydrofuran solution (20 mL) of sodium hydride (60% mineral oil dispersion, 0.08 g, 1.92 mmol) in a nitrogen stream atmosphere, and stirred at room temperature for 1 hour. The mixture was cooled to 0° C., the compound y (1.0 g, 1.28 mmol) was added thereto and stirred at 50° C. for 12 hours. The reaction mixture was quenched in water with ice, and filtered to give a crude product. The resultant crude product was purified through silica gel column chromatography (toluene/hexane=3/2) to give a compound 6 of a yellow solid (1.18 g, 1.09 mmol, yield 85%).

$^1$H NMR: (500 MHz, acetone-d6): δ (ppm)=7.82 (m, 8H), 7.75 (m, 4H), 7.67 (t, J=7.8 Hz, 4H), 7.45 (m, 4H), 7.35 (m, 8H), 7.25 (t, J=8.0 Hz, 2H), 7.11 (m, 8H), 6.95 (d, J=8.6 Hz, 2H), 6.74 (m, 4H), 6.66 (t, J=7.8 Hz, 4H)

(Synthesis Example 7) Synthesis of Compound 7

3,9'-Bicarbazole (0.66 g, 1.98 mmol) was added to a tetrahydrofuran solution (15 mL) of sodium hydride (60% mineral oil dispersion, 0.08 g, 1.98 mmol) in a nitrogen stream atmosphere, and stirred at room temperature for 1 hour. The mixture was cooled to 0° C., the compound z (0.5 g, 0.79 mmol) was added thereto and stirred at 50° C. for 12 hours. The reaction mixture was quenched in water with ice, and filtered to give a crude product. The resultant crude product was purified through silica gel column chromatography (toluene/hexane=1/1) to give a compound 7 of a yellow solid (0.54 g, 0.43 mmol, yield 54%).

(Synthesis Example 8) Synthesis of Compound 35

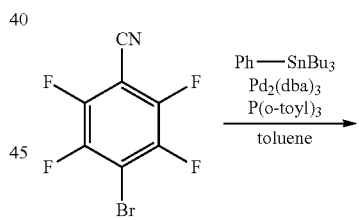

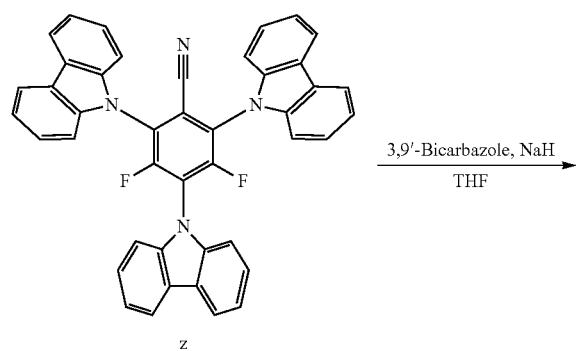

z

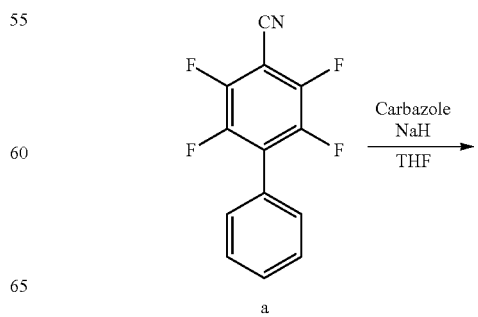

a

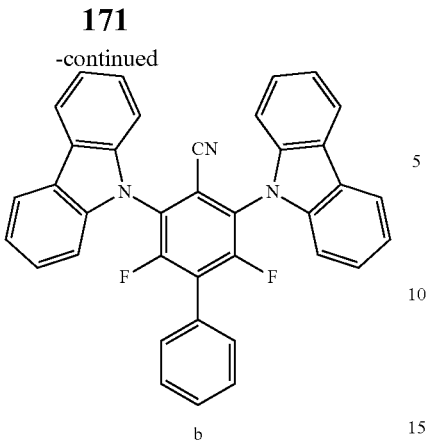

b

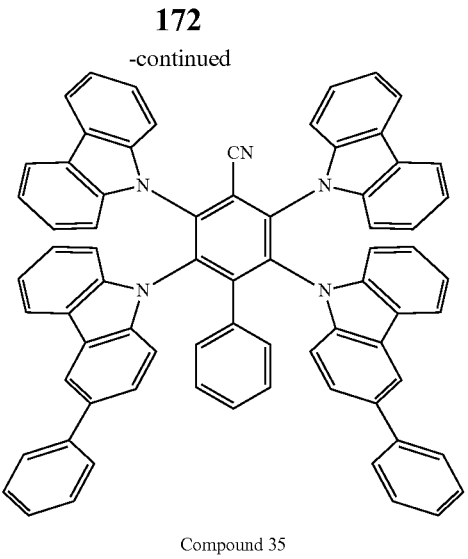

Compound 35

Tri(o-tolyl) phosphine (0.525 g, 1.72 mmol) and tris(dibenzylideneacetone)palladium(0) (1.57 g, 1.72 mmol) were added to a toluene solution (50 mL) of tributyltin chloride (5.06 g, 4.45 mL, 13.78 mmol) and 4-bromo-2,3,5,6-tetrafluorobenzonitrile (2.92 g, 11.50 mmol), heated up to 100° C., and stirred for 21 hours. The mixture was restored to room temperature, quenched in water, extracted with ethyl acetate, and filtered through Celite. Next, the organic layer was washed with saturated saline water, and dried with anhydrous magnesium sulfate. This was concentrated under reduced pressure, and the resultant mixture was purified through silica gel column chromatography (dichloromethane/hexane=1/2) to give a compound a of a white solid (2.42 g, 9.63 mmol, yield 83.7%). $^1$H-NMR (500 MHz, CDCl$_3$, δ): 7.56-7.51 (m, 3H), 7.48-7.45 (m, 2H)

ASAP mass spectrometry: theoretical 251.0, found 251.1.

9H-carbazole (0.397 g, 2.38 mmol) was added to a tetrahydrofuran solution (10 mL) of sodium hydride (60% mineral oil dispersion, 0.125 g, 3.14 mmol) in a nitrogen stream atmosphere, and stirred at room temperature for 1 hour. The mixture was cooled to −50° C., and the compound a (0.3 g, 1.19 mmol) was added thereto. The cooling bath was removed, and this was stirred for 22 hours while gradually restored to room temperature. The reaction mixture was quenched in water with ice, extracted with ethyl acetate, and the organic layer was washed with saturated saline water, and dried with anhydrous magnesium sulfate. This was concentrated under reduced pressure, and the resultant mixture was purified through silica gel column chromatography (chloroform/hexane=1/2) to give a compound b of a yellow solid (0.486 g, 0.89 mmol, yield 74.8%).

$^1$H-NMR (500 MHz, CDCl$_3$, δ): 8.16 (d, J=7.5 Hz, 4H), 7.62-7.59 (m, 2H), 7.54-7.49 (m, 7H), 7.38 (dt, J=7.5 Hz, 1.0 Hz, 4H), 7.30 (d, J=7.5 Hz, 4H),

ASAP mass spectrometry: theoretical 545.2, found 545.2.

3-Phenyl-9H-carbazole (0.575 g, 2.36 mmol), potassium carbonate (0.702 g, 3.94 mmol) and the compound b (0.5 g, 0.788 mmol) were put into a 100-mL three-neck flask, which was then purged with nitrogen. Dewatered 1-methyl-2-pyrrolidone (10 mL) was added to the mixture, and then heated with stirring at 100° C. for 12 hours in a nitrogen atmosphere. After stirring, the mixture was restored to room temperature, and water was added and filtered under suction. The resultant solid was dissolved in toluene, and purified through silica gel column chromatography. The resultant fraction was concentrated and recrystallized with a mixed solvent of chloroform and acetonitrile to give a compound 35 of a pale yellow solid (yield amount 0.60 g, yield percentage 77%).

$^1$H NMR (500 MHz, CDCl$_3$, δ): 7.77 (d, J=1.2, 2H), 7.55-7.69 (m, 4H), 7.60 (d, J=7.5 Hz, 2H), 7.51 (dd, J=8.5 Hz, 4H), 7.42 (td, J=8.0, J=2.0, 4H), 7.32-6.94 (m, 24H), 6.75 (d, J=7.5, 2H), 6.55 (td, J=7.51, J=1.2, 1H), 6.46 (t, J=7.5, 2H)

ASAP mass spectrometry: theoretical 991.37, found 992.39.

(Synthesis Example 9) Synthesis of Compound 38

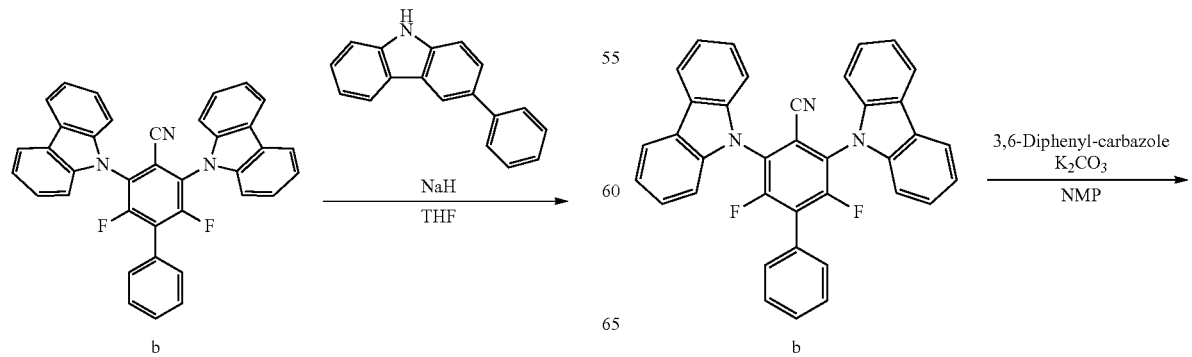

b

-continued

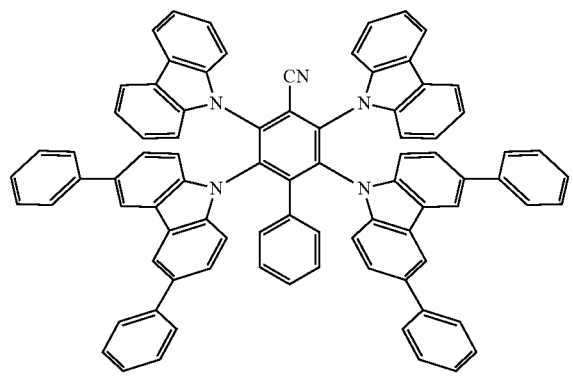

Compound 38

The compound b (0.45 g, 0.825 mmol) obtained in Synthesis Example 8 was added to a 1-methyl-2-pyrrolidone solution (10 mL) of 3,6-diphenylcarbazole (0.66 g, 2.06 mmol) and potassium carbonate (0.43 g, 3.11 mmol) in a nitrogen stream atmosphere, and stirred at 100° C. for 48 hours. The mixture was restored to room temperature, quenched in water, extracted with ethyl acetate, and the organic layer was washed with saturated saline water and dried with anhydrous magnesium sulfate. This was concentrated under reduced pressure, and the resultant mixture was purified through silica gel column chromatography (chloroform/hexane=1/1) to give a compound 38 of a yellow solid (0.575 g, 0.502 mmol, yield 60.9%).

$^1$H-NMR (500 MHz, CDCl$_3$, δ): 7.81 (d, J=1.5 Hz, 4H), 7.72-7.70 (m, 4H), 7.54-7.52 (m, 8H), 7.43 (t, J=7.5 Hz, 8H), 7.32 (t, J=7.5 Hz, 4H), 7.29-7.06 (m, 20H), 6.86-6.83 (m, 2H), 6.61-6.58 (m, 1H), 6.56-6.52 (m, 2H)

ASAP mass spectrometry: theoretical 1143.4, found 1143.4.

(Synthesis Example 10) Synthesis of Compound 48

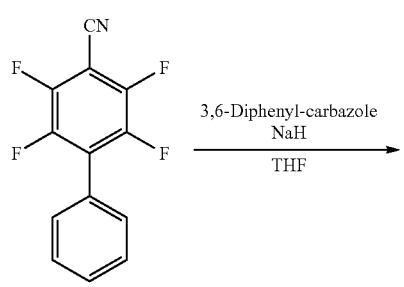

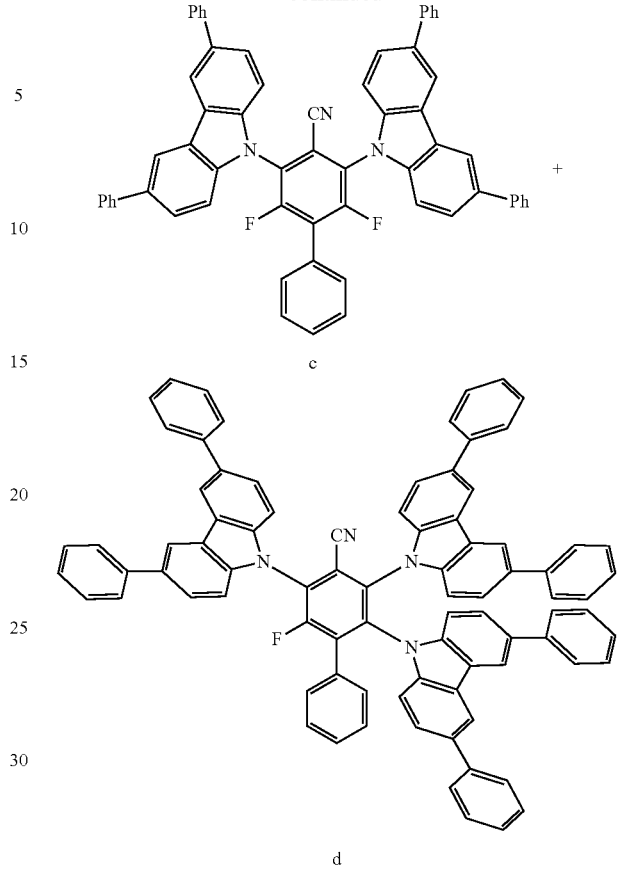

3,6-Diphenylcarbazole (0.95 g, 2.97 mmol) was added to a tetrahydrofuran solution (10 mL) of sodium hydride (60% mineral oil dispersion, 0.315 g, 7.88 mmol) in a nitrogen stream atmosphere, and stirred at room temperature for 1 hour. The mixture was cooled to −50° C., the compound a (0.3 g, 1.19 mmol) obtained in Synthesis Example 8 was added thereto. The cooling bath was removed, and this was stirred for 17 hours while gradually restored to room temperature. The reaction mixture was quenched in water with ice, extracted with ethyl acetate, and the organic layer was washed with saturated saline water, and dried with anhydrous magnesium sulfate. This was concentrated under reduced pressure, and the resultant mixture was purified through silica gel column chromatography (chloroform/hexane=1/2) to give a compound c of a yellow solid (0.308 g, 0.362 mmol, yield 30.4%) and a compound d of a yellow solid (0.70 g, 0.609 mol, yield 51.2%).

Compound c:

$^1$H-NMR (500 MHz, CDCl$_3$, δ): 8.42 (d, J=1.0 Hz, 4H), 7.80 (dd, J=7.0 Hz, 2.0 Hz, 4H), 7.74 (dd, J=8.0 Hz, 1.0 Hz, 8H), 7.68-7.65 (m, 2H), 7.58-7.48 (m, 11H), 7.42 (d, J=8.0 Hz, 4H), 7.40-7.36 (m, 4H)

ASAP mass spectrometry: theoretical 849.3, found 849.3.

Compound d:

$^1$H-NMR (500 MHz, CDCl$_3$, δ): 8.47 (d, J=1.5 Hz, 2H), 7.89 (dd, J=8.5 Hz, 2.0 Hz, 2H), 7.83 (d, J=1.5 Hz, 2H), 7.80-7.78 (m, 4H), 7.74 (d, J=1.5 Hz, 2H), 7.66 (d, J=8.0 Hz, 2H), 7.54-7.52 (m, 4H), 7.48-7.44 (m, 8H), 7.42-7.27 (m, 18H), 7.19-7.16 (m, 7H), 7.01 (d, J=8.0 Hz, 2H)

ASAP mass spectrometry: theoretical 1148.4, found 1148.4.

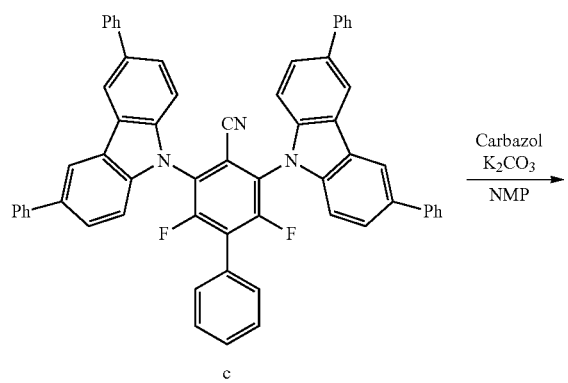

c

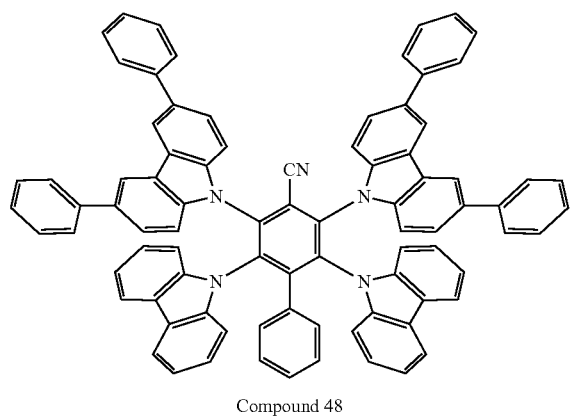

Compound 48

The compound c (0.30 g, 0.35 mmol) was added to a 1-methyl-2-pyrrolidone solution (10 ml) of 9H-carbazole (0.175 g, 1.05 mmol) and potassium carbonate (0.184 g, 1.33 mmol), and stirred at 100° C. for 20 hours. The mixture was restored to room temperature, quenched in water, extracted with ethyl acetate, and the organic layer was washed with saturated saline water and dried with anhydrous magnesium sulfate. This was concentrated under reduced pressure, and the resultant mixture was purified through silica gel column chromatography (chloroform/hexane=1/2) to give a compound 48 of a yellow solid (0.317 g, 0.277 mmol, yield 79.1%).

$^1$H-NMR (500 MHz, CDCl$_3$, δ): 7.96 (d, J=1.5 Hz, 4H), 7.59-7.55 (m, 12H), 7.45 (t, J=7.5 Hz, 8H), 7.35-7.31 (m, 12H), 7.07-7.01 (m, 4H), 7.00-6.94 (m, 8H), 6.76-6.74 (m, 2H), 6.58-6.54 (m, 1H), 6.45 (t, J=8.0 Hz, 2H)

ASAP mass spectrometry: theoretical 1143.4, found 1143.3.

(Synthesis Example 11) Synthesis of Compound 55

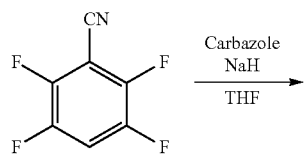

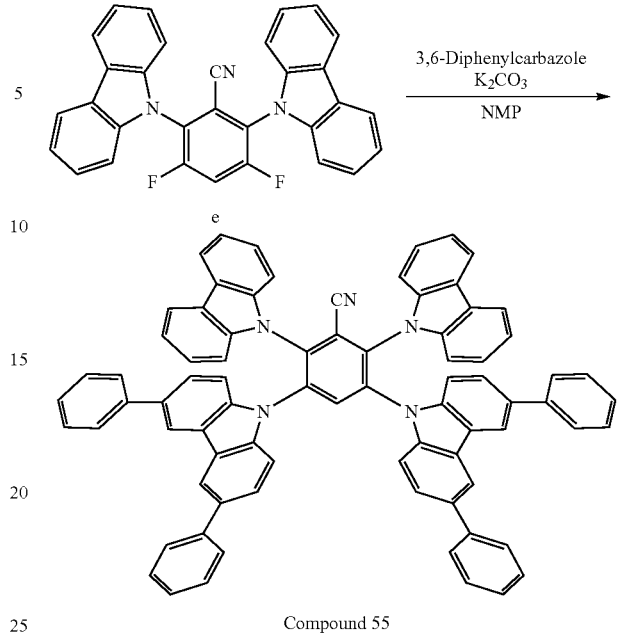

Compound 55

9H-carbazole (4.78 g, 28.59 mmol) was added to a tetrahydrofuran solution (120 mL) of sodium hydride (60% mineral oil dispersion, 0.90 g, 22.51 mmol) in a nitrogen stream atmosphere, and stirred at room temperature for 1 hour. The mixture was cooled to −50° C., and 2.3.5.6-tetrafluorobenzonitrile (2.50 g, 14.28 mmol) was added thereto. The cooling bath was removed, and this was stirred for 110 hours while gradually restored to room temperature. The reaction mixture was quenched in water with ice, extracted with ethyl acetate, and the organic layer was washed with saturated saline water, and dried with anhydrous magnesium sulfate. This was concentrated under reduced pressure, and the resultant mixture was purified through silica gel column chromatography (toluene/hexane=1/1) to give a compound e of a pale yellow solid (2.42 g, 5.15 mmol, yield 36.1%).

$^1$H-NMR (500 MHz, CDCl$_3$, δ): 8.16 (d, J=7.5 Hz, 4H), 7.68 (t, $J_{H-F}$ 9.0 Hz, 1H), 7.51 (dt, J=7.5 Hz, 1.0 Hz, 4H), 7.38 (dt, J=7.5 Hz, 1.0 Hz, 4H), 7.23 (d, J=7.5 Hz, 4H)

ASAP mass spectrometry: theoretical 469.1, found 469.1.

The compound e (0.34 g, 0.724 mmol) was added to a 1-methyl-2-pyrrolidone solution (9 mL) of 3,6-diphenylcarbazole (0.57 g, 1.81 mmol) and potassium carbonate (0.38 g, 2.75 mmol) in a nitrogen stream atmosphere, and stirred at 100° C. for 24 hours. The mixture was restored to room temperature, quenched in water, extracted with ethyl acetate, and the organic layer was washed with saturated saline water and dried with anhydrous magnesium sulfate. This was concentrated under reduced pressure, and the resultant mixture was purified through silica gel column chromatography (toluene/hexane=1/1) to give a compound 55 of a yellow solid (0.515 g, 0.482 mmol, yield 66.6%).

$^1$H-NMR (500 MHz, CDCl$_3$, δ): 8.54 (s, 1H), 8.04 (s, 4H), 7.81 (d, J=7.5 Hz, 4H), 7.61-7.59 (m, 8H), 7.47-7.39 (m, 20H), 7.36-7.33 (m, 4H), 7.25-7.22 (m, 4H), 7.18-7.15 (m, 4H)

ASAP mass spectrometry: theoretical 1067.4, found 1067.4.

(Synthesis Example 12) Synthesis of Compound 108

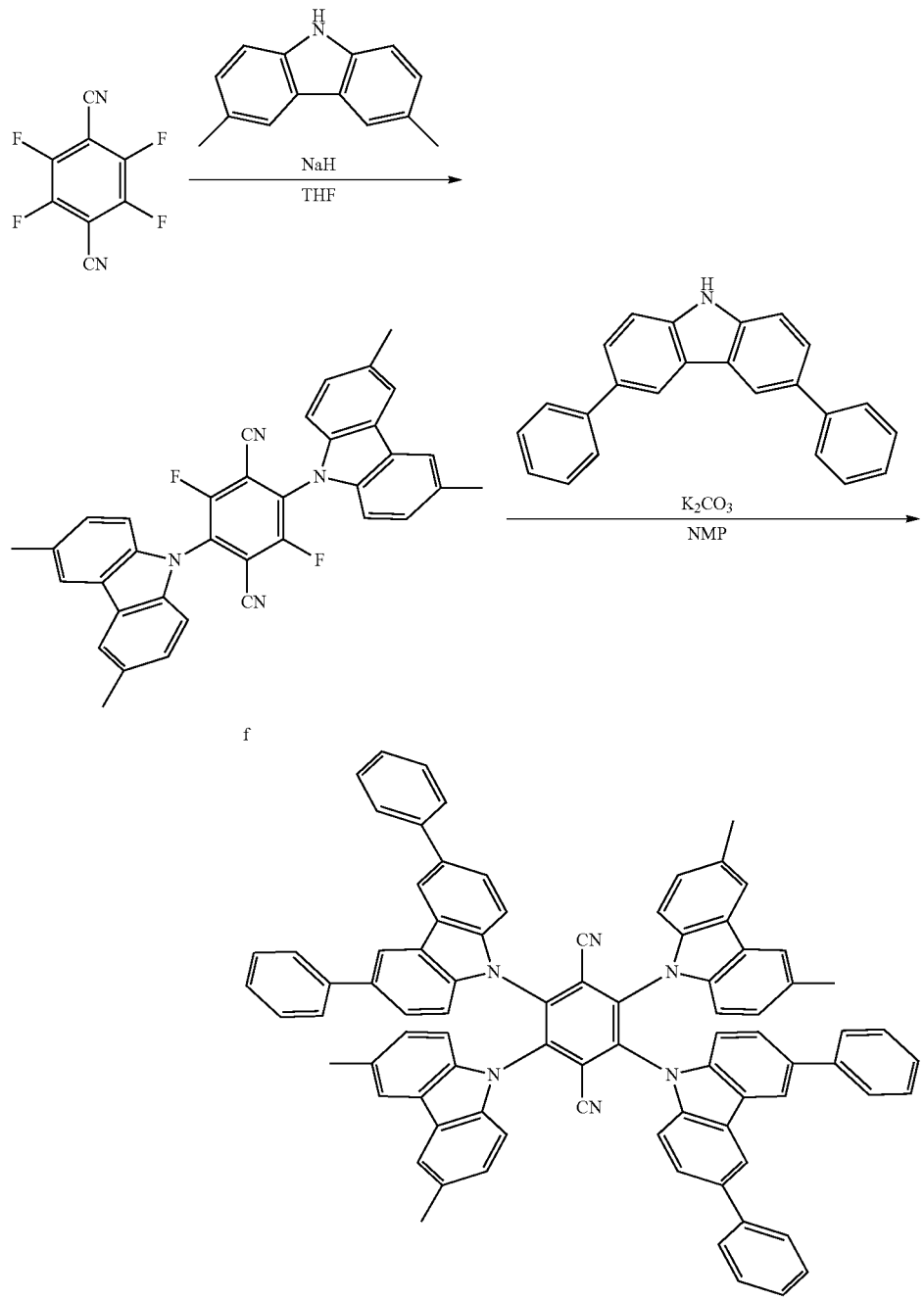

Compound 108

3,6-Dimethyl-9H-carbazole (1.56 g, 9.00 mmol) and sodium hydride (0.400 g, 60% mineral oil dispersion, 1.00 mmol) were put into a 100-mL three-neck flask, which was then purged with nitrogen. Dewatered tetrahydrofuran (80 mL) was added to the mixture, then stirred for 1 hour in a nitrogen atmosphere, and thereafter tetrafluoroterephthalonitrile (0.8 g, 4.00 mmol) was added thereto. The mixture was heated with stirring at 50° C. for 12 hours, then restored to room temperature, and water was added and filtered under suction to give a solid. The resultant solid was purified through sublimation to give a compound f of a red solid (yield amount 0.8 g, yield percentage 36%).

3,6-Dimethyl-9H-carbazole (0.696 g, 2.18 mmol), potassium carbonate (0.647 g, 3.63 mmol) and the compound f (0.4 g, 0.726 mmol) were put into a 100-mL three-neck flask, which was then purged with nitrogen. Dewatered 1-methyl-2-pyrrolidone (10 mL) was added to the mixture, then stirred at 100° C. for 12 hours in a nitrogen atmosphere.

After stirring, the mixture was restored to room temperature, water was added thereto and filtered under suction. The resultant solid was recrystallized with a mixed solvent of chloroform and acetonitrile to give a compound 108 of a red solid (yield amount 0.62 g, yield percentage 74%).

$^1$H NMR (500 MHz, CDCl$_3$, δ): 8.01 (d, J=1.5 Hz, 4H), 7.62 (dd, J=8.0 Hz, J=1.0 Hz, 8H), 7.50-7.43 (m, 12H), 7.41 (dd, J=7.5, J=1.5, 4H), 7.37 (t, J=7.5, 4H), 7.33 (d, J=8.5 Hz, 4H), 7.17 (d, J=8 Hz, 4H), 6.99 (dd, J=8 Hz, J=1.5 Hz, 4H), 2.41 (s, 12H)

ASAP mass spectrometry: theoretical 1148.46, found 1150.51.

(Synthesis Example 13) Synthesis of Compound 149

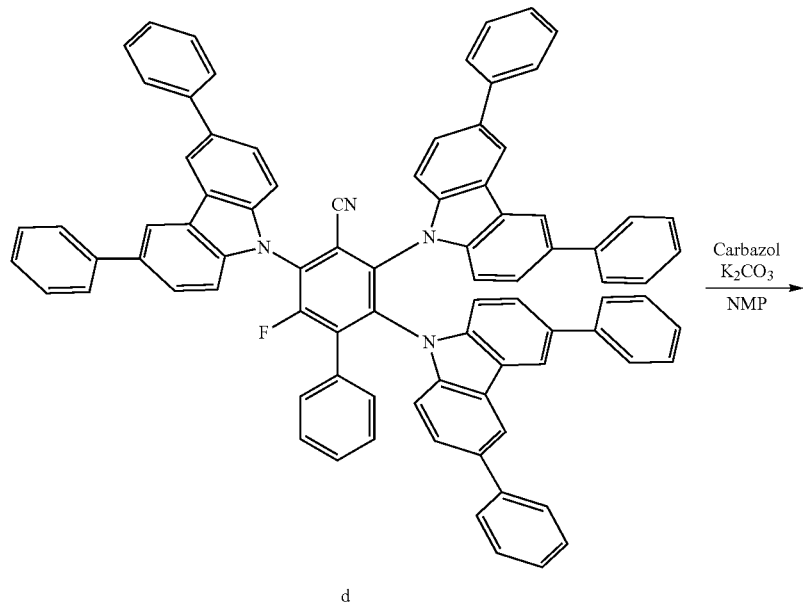

d

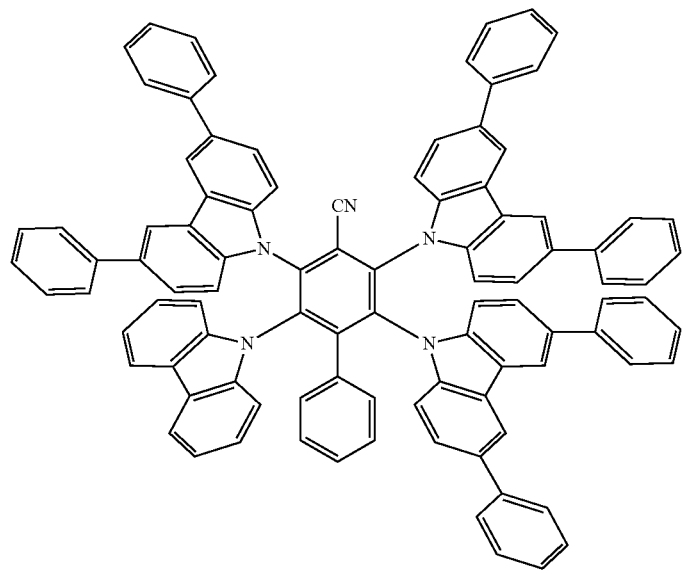

Compound 149

The compound d (0.65 g, 0.566 mmol) was added to a 1-methyl-2-pyrrolidone solution (10 mL) of 9H-carbazole (0.142 g, 0.849 mmol) and potassium carbonate (0.18 g, 1.30 mmol) in a nitrogen stream atmosphere, and stirred at 100° C. for 120 hours. The mixture was restored to room temperature, and quenched in water. The resultant precipitate was washed with methanol, and this was purified through silica gel column chromatography (toluene/hexane=3/2) to give a compound 149 of an orange solid (0.284 g, 0.219 mmol, yield 38.7%).

$^1$H-NMR (500 MHz, CDCl$_3$, δ): 7.98 (d, J=1.0 Hz, 2H), 7.85 (d, J=1.0 Hz, 2H), 7.73 (d, J=2.0 Hz, 2H), 7.60-7.58 (m, 6H), 7.49-7.44 (m, 12H), 7.39-7.24 (m, 20H), 7.19-7.16 (m, 4H), 7.12-7.09 (m, 2H), 7.05-6.97 (m, 6H), 6.93 (d, J=8.0 Hz, 2H), 6.64 (t, J=8.0 Hz, 1H), 6.58 (t, J=8.0 Hz, 2H)

ASAP mass spectrometry: theoretical 1295.5, found 1295.2.

(Synthesis Example 14) Synthesis of Compound 313

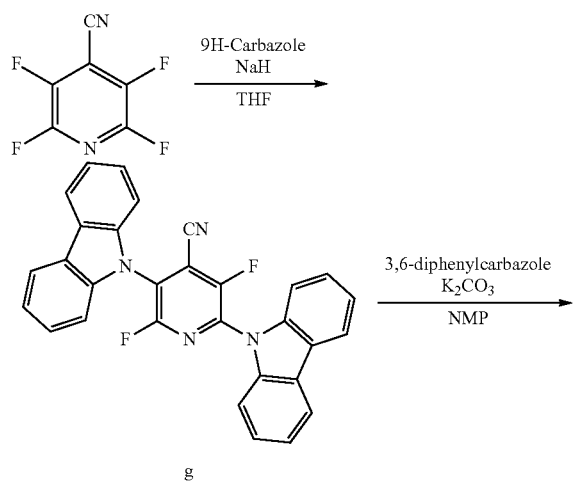

g

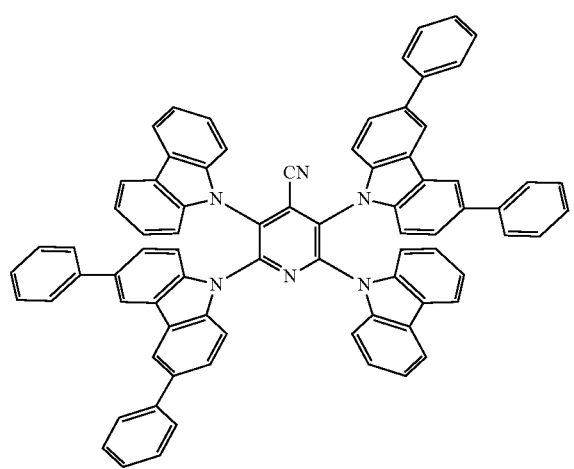

Compound 313

9H-carbazole (1.42 g, 8.49 mmol) was added to a tetrahydrofuran solution (45 mL) of sodium hydride (60% mineral oil dispersion, 0.265 g, 6.63 mmol) in a nitrogen stream atmosphere, and stirred at room temperature for 1 hour. The mixture was cooled to −50° C., and 2,3,5,6-tetrafluoro-4-pyridinecarbonitrile (0.749 g, 4.25 mmol) was added thereto. The cooling bath was removed, and this was stirred for 24 hours while gradually restored to room temperature. The reaction mixture was quenched in water with ice, extracted with ethyl acetate, and the organic layer was washed with saturated saline water, and dried with anhydrous magnesium sulfate. This was concentrated under reduced pressure, and the resultant mixture was reprecipitated in ethyl acetate/methanol to give a compound g of an orange solid (0.989 g, 2.10 mmol, yield 49.4%).

$^1$H-NMR (500 MHz, CDCl$_3$, δ): 8.19 (d, J=7.5 Hz, 2H), 8.15 (d, J=7.5 Hz, 2H), 7.69-7.67 (m, 2H), 7.54 (dt, J=7.5, 1.0 Hz, 4H), 7.44 (dt, J=7.5, 1.5 Hz, 4H), 7.30 (d, J=8.0 Hz, 2H)

$^{13}$C-NMR (125 MHz, CDCl$_3$, δ): 154.66, 154.64, 152.67, 152.65, 150.66, 150.62, 148.47, 148.43, 139.63, 138.59, 126.80, 126.76, 125.14, 124.55, 122.71, 122.14, 120.98, 120.54, 120.02, 119.75, 115.74, 115.69, 115.62, 115.57, 111.53, 111.50, 109.74, 108.76, 108.73

ASAP mass spectrometry: theoretical 470.1, found 470.1.

The compound g (0.50 g, 1.06 mmol) was added to a 1-methyl-2-pyrrolidone solution (13 mL) of 3,6-diphenylcarbazole (0.849 g, 2.66 mmol) and potassium carbonate (0.55 g, 3.99 mmol) in a nitrogen stream atmosphere, and stirred at 100° C. for 48 hours. The mixture was restored to room temperature, quenched in water, extracted with ethyl acetate, and the organic layer was washed with saturated saline water, and dried with anhydrous magnesium sulfate. This was concentrated under reduced pressure, and the resultant mixture was purified through silica gel column chromatography (toluene/hexane=1/1) to give a compound 313 of an orange solid (0.963 g, 0.901 mmol, yield 84.7%).

$^1$H-NMR (500 MHz, CDCl$_3$, δ): 8.07 (d, J=1.5 Hz, 2H), 8.00 (d, J=1.5 Hz, 2H), 7.84 (d, J=7.0 Hz, 2H), 7.76 (d, J=7.0 Hz, 2H), 7.63 (d, J=8.0 Hz, 4H) 7.58 (d, J=8.0 Hz, 4H), 7.54-7.43 (m, 14H), 7.38-7.32 (m, 8H), 7.30-7.07 (m, 10H)

ASAP mass spectrometry: theoretical 1068.4, found 1068.3.

(Synthesis Example 15) Synthesis of Compound 11

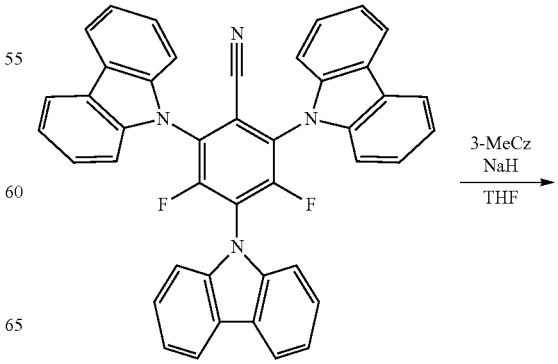

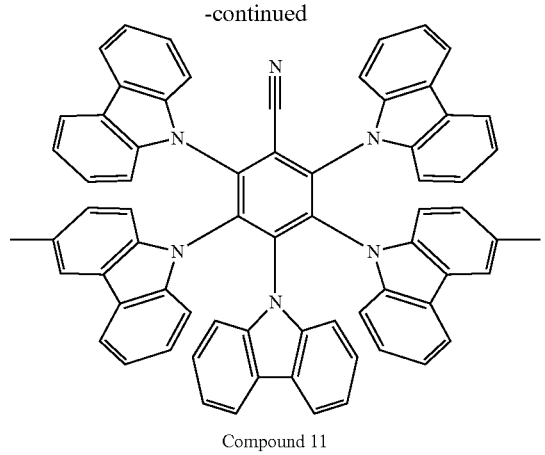

Compound 11

3-Methyl-9H-carbazole (0.51 g, 83 mmol) was added to a tetrahydrofuran solution (15 mL) of sodium hydride (60% mineral oil dispersion, 0.15 g, 3.78 mmol) in a nitrogen stream atmosphere, and stirred at room temperature for 1 hour. The mixture was cooled to −50° C., and the compound z (0.6 g, 0.95 mmol) was added, heated at 50° C. and stirred for 12 hours. Water was added to the reaction mixture to form a precipitate, and the precipitate was taken out through filtration. The resultant mixture was purified through silica gel column chromatography (toluene) to give a compound 11 (0.65 g, 0.68 mmol, yield 71.9%).

$^1$H-NMR (500 MHz, CDCl$_3$, δ): 7.76-7.72 (m, 4H), 7.30-7.12 (m, 10H), 7.10-7.02 (m, 10H), 6.98 (t, J=8.5 Hz, 2H), 6.91 (t, J=8.5 Hz, 2H), 6.76-6.71 (m, 4H), 6.61-6.53 (m, 4H), 6.41 (t, J=8.5 Hz, 2H), 2.17-2.16 (m, 6H)

ASAP mass spectrometry: theoretical 956.4, found 957.3.

(Synthesis Example 16) Synthesis of Compound 150

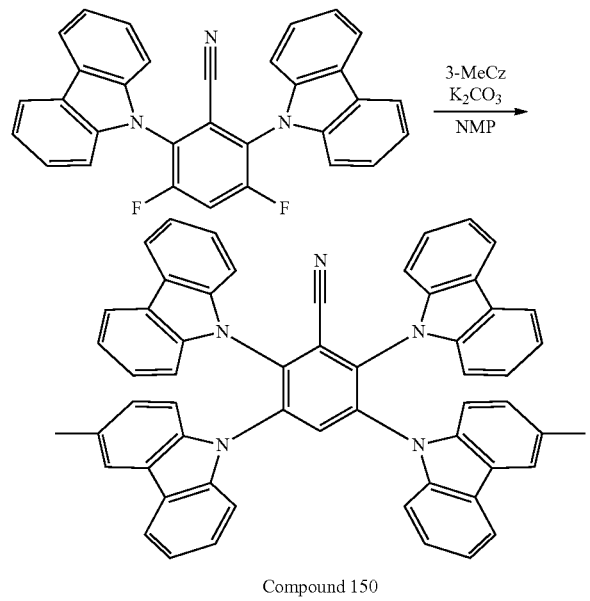

Compound 150

The compound e (0.50 g, 1.07 mmol) was added to a 1-methyl-2-pyrrolidone solution (10 mL) of 3-methyl-9H-carbazole (0.57 g, 3.20 mmol) and potassium carbonate (0.95 g, 5.33 mmol) in a nitrogen stream atmosphere, and stirred at 120° C. for 36 hours. The mixture was restored to room temperature, precipitated in water and the precipitate was taken out through filtration. The resultant mixture was purified through silica gel column chromatography (toluene) to give a compound 150 (0.40 g, 0.51 mmol, yield 47.4%).

$^1$H-NMR (500 MHz, CDCl$_3$, δ): 8.38 (s, 1H), 7.83-7.79 (m, 4H), 7.75-7.72 (m, 2H), 7.58 (d, J=4.0 Hz, 2H), 7.43-7.33 (m, 4H), 7.30-7.11 (m, 12H), 7.10-7.03 (m, 4H), 7.00-6.93 (m, 2H), 2.41 (s, 3H), 2.39 (s, 3H)

ASAP mass spectrometry: theoretical 791.3, found 792.4.

(Synthesis Example 17) Synthesis of Compound 151

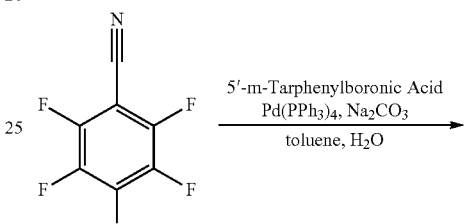

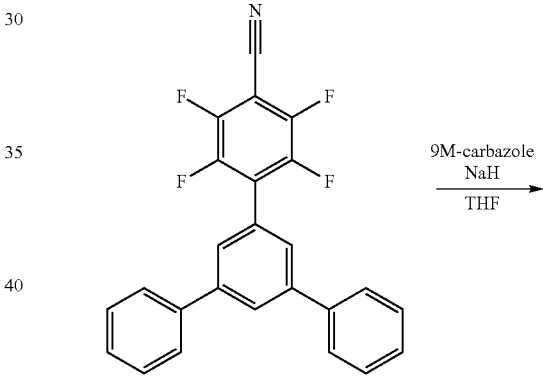

i

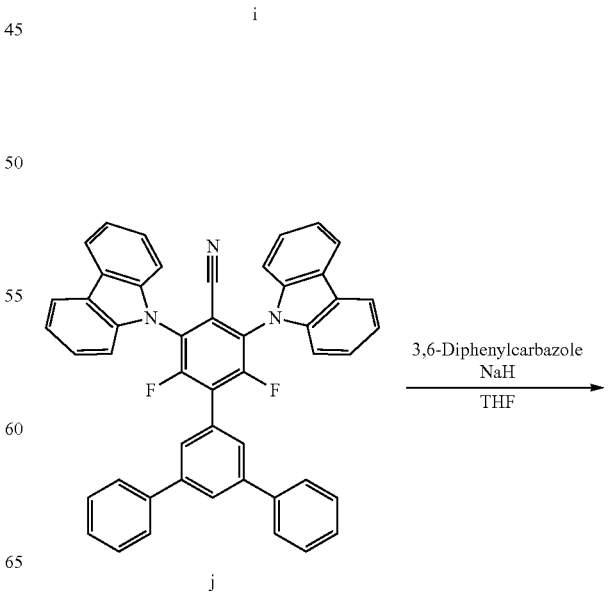

j

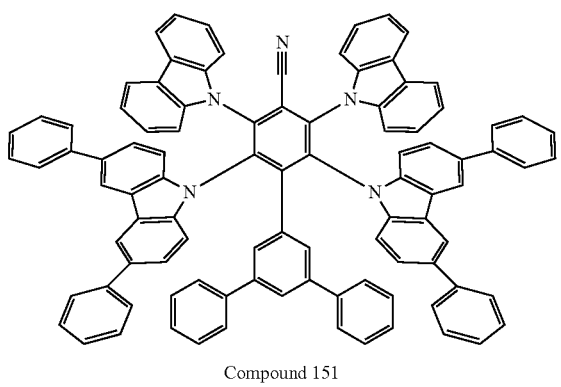

Compound 151

In an argon stream atmosphere, 4-bromo-2,3,5,6-tetrafluorobenzonitrile (3 g, 11.9 mmol) was dissolved in toluene (100 mL), and an aqueous 0.3 M sodium carbonate solution (67 ml) was added thereto. Pd(PPh$_3$)$_4$ (1.38 g, 1.19 mmol) and 5'-m-tetraphenylboronic acid (3.92 g, 14.3 mmol) were added and heated under reflux overnight. After cooled to room temperature, the organic layer was separated, and the aqueous layer was extracted with dichloromethane. The organic layers were combined, and dried with anhydrous sodium sulfate. The drying agent was filtered off and the filtrate was concentrated through distillation under reduced pressure to give a crude product. The resulting crude product was purified through silica gel column chromatography (hexane/chloroform=4/1) to give a compound i of a white powder (2.37 g, 5.88 mmol, 49.4%).

In an argon stream atmosphere, 9H-carbazole (0.83 g, 4.96 mmol) was added to a tetrahydrofuran solution (50 mL) of sodium hydride (60% mineral oil dispersion, 0.2 g, 4.96 mmol), and stirred at room temperature for 1 hour. The mixture was cooled to −50° C., and the compound i (1.0 g, 2.48 mmol) was added thereto. The cooling bath was removed, and this was stirred for 2 hours while gradually restored to room temperature. The reaction mixture was quenched in water with ice, extracted with dichloromethane, and the organic layer was washed with saturated saline water, and dried with anhydrous magnesium sulfate. This was concentrated under reduced pressure, and the resultant mixture was purified through silica gel column chromatography (hexane/toluene=3/2) to give a compound j of a white solid (0.96 g, 1.38 mmol, 55.6%).

In an argon stream atmosphere, 3,6-diphenylcarbazole (1.32 g, 4.14 mmol) was added to a tetrahydrofuran solution (30 mL) of sodium hydride (60% mineral oil dispersion, 0.17 g, 4.14 mmol), and stirred at room temperature for 1 hour. The compound 2 (0.96 g, 1.38 mmol) was added thereto and heated at 50° C. overnight. The reaction mixture was quenched in water with ice, and the solid was collected. The resultant solid was purified through silica gel column chromatography (toluene) to give a compound 151 of a yellow solid (1.10 g, 0.85 mmol, 61.5%).

(Synthesis Example 18) Synthesis of Compound 152

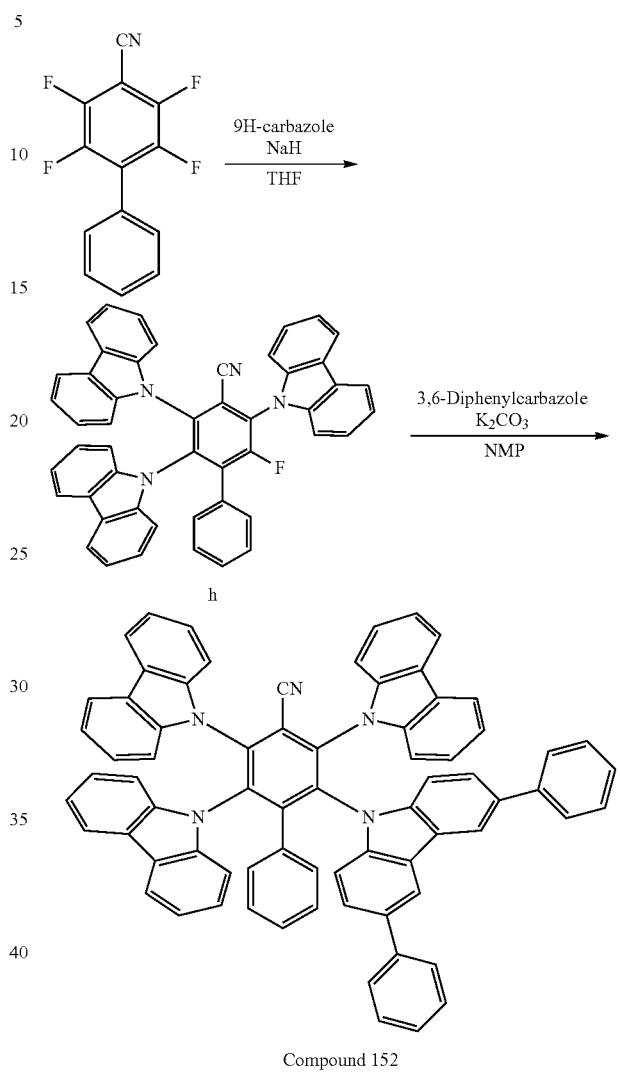

Compound 152

In a nitrogen stream atmosphere, 9H-carbazole (0.80 g, 4.78 mmol) was added to a tetrahydrofuran solution (15 mL) of sodium hydride (60% mineral oil dispersion, 0.17 g, 7.17 mmol), and stirred at room temperature for 1 hour. The mixture was cooled to −50° C., and the compound 1 (0.4 g, 1.59 mmol) was added thereto. The cooling bath was removed, and this was stirred for 24 hours while gradually restored to room temperature. The reaction mixture was quenched in water with ice, extracted with ethyl acetate, and the organic layer was washed with saturated saline water, and dried with anhydrous magnesium sulfate. This was concentrated under reduced pressure, and the resultant mixture was purified through silica gel column chromatography (hexane/toluene=2/1) to give a compound h of a yellow solid (0.69 g, 1.00 mmol, yield 62.9%).

$^1$H-NMR (500 MHz, CDCl$_3$, δ): 8.20 (d, J=8.5 Hz, 2H), 7.72-7.68 (m, 2H), 7.61-7.56 (m, 4H), 7.51 (d, J=8.5 Hz, 2H), 7.44 (t, J=8.5 Hz, 2H), 7.16-7.11 (m, 4H), 7.10-6.94 (m, 13H)

ASAP mass spectrometry: theoretical 692.2, found 692.1.

The compound h (0.50 g, 0.72 mmol) was added to a 1-methyl-2-pyrrolidone solution (10 mL) of 3,6-diphenylcarbazole (0.35 g, 1.08 mmol) and potassium carbonate (0.20 g, 1.44 mmol) in a nitrogen stream atmosphere, and stirred at 100° C. for 48 hours. The mixture was restored to room temperature, quenched in water, and the resultant precipitate was washed with methanol. This was reprecipitated in chloroform/methanol to give a compound 152 of a yellow solid (0.56 g, 0.564 mmol, yield 77.6%).

$^1$H-NMR (500 MHz, CDCl$_3$, δ): 7.80 (d, J=1.5 Hz, 2H), 7.73-7.68 (m, 4H), 7.59-7.57 (m, 2H), 7.52 (dd, J=8.0 Hz, J=1.5 Hz, 4H), 7.42 (t, J=8.0 Hz, 4H), 7.33-7.22 (m, 6H), 7.19 (dd, J=8.0 Hz, J=1.5 Hz, 2H), 7.14-6.92 (m, 16H), 6.74 (dd, J=8.0 Hz, J=1.5 Hz, 2H), 6.55 (t, J=8.0 Hz, 1H), 6.48 (t, J=8.0 Hz, 2H)

ASAP mass spectrometry: theoretical 991.4, found 991.8.

Production and Evaluation of Organic Photoluminescent Device (Example 1) Production of Organic Photoluminescent Device Using Compound 1

A toluene solution of the compound 1 (concentration $10^{-5}$ mol/L) was prepared. According to a vacuum evaporation method, a thin film of the compound 1 was formed on a quartz substrate in a thickness of 50 nm in a vacuum degree of $5\times10^{-4}$ Pa or less to be an organic photoluminescent device.

(Examples 2 to 6) Production of Organic Photoluminescent Devices Using any of Compounds 2 to 6

A toluene solution of any of the compounds 2 to 6 was prepared in the same manner as in Example 1 except that any of the compounds 2 to 6 was used in place of the compound 1, and a thin film of any of the compounds 2 to 6 was formed to be an organic photoluminescent device.

(Comparative Examples 1 to 3) Production of Organic Photoluminescent Devices Using any of Comparative Compounds 1 to 3

A toluene solution of any of comparative compounds 1 to 3 was prepared in the same manner as in Example 1 except that any of comparative compounds 1 to 3 was used in place of the compound 1, and a thin film of any of comparative compounds 1 to 3 was formed to be an organic photoluminescent device.

Comparative Compound 1

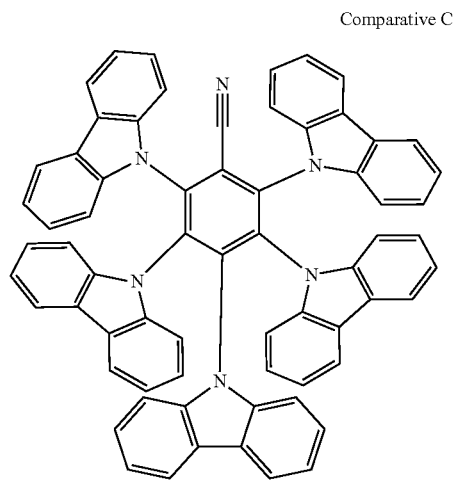

Comparative Compound 2

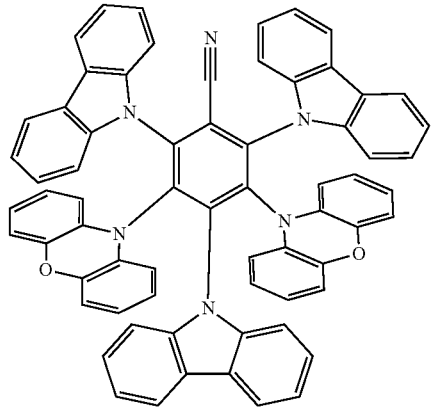

Comparative Compound 3

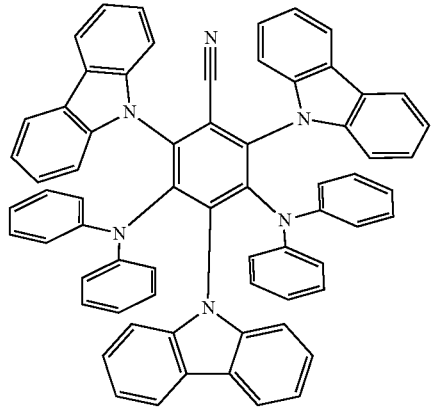

Figure 4:
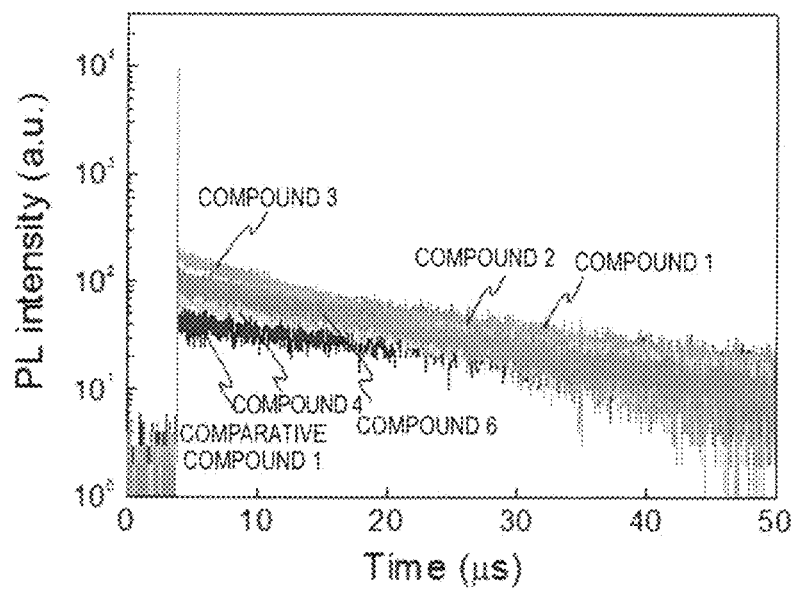
FIG. 4 This shows transient decay curves in light emission of organic photoluminescent devices using any of compounds 1 to 4 and 6.
Figure 5:
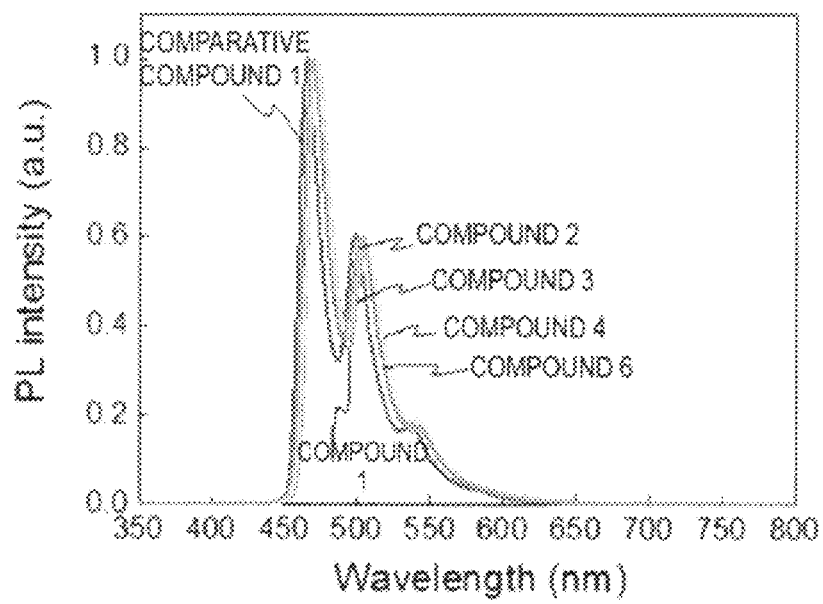
FIG. 5 This shows phosphorescence spectra of organic photoluminescent devices using any of compounds 1 to 4 and 6.

Absorption spectra of organic photoluminescent devices produced in Examples 1 to 3, 4 and 6 and Comparative Example 1 are shown in FIG. 2; fluorescence spectra with excitation light at 340 nm thereof are in FIG. 3; transient decay curves in light emission with excitation light at 340 nm thereof are in FIG. 4; and phosphorescence spectra with excitation light at 340 nm thereof are in FIG. 5. The compounds used in these Examples and the optical property values thereof are shown in Table 9. In Table 9, "–" means no measurement.

TABLE 9

| Example No. | Compound No. | PL Quantum Yield (%) in air | PL Quantum Yield (%) in argon | Fluorescence Lifetime $\tau_p$ (ns) | Delayed Fluorescence Lifetime $\tau_d$ (μs) | Radiative Rate $K_r$ (×10$^7$ s$^{-1}$) | Non-Radiative Rate Constant $K_{nr}^T$ (×10$^4$ s$^{-1}$) | Rate Constant in Intersystem Crossing $k_{ISC}$ (×10$^8$ s$_{-1}$) | Rate Constant in Reverse Intersystem Crossing $k_{RISC}$ (×10$^5$ s$_{-1}$) | $\Delta E_{st}$ (eV) |
|---|---|---|---|---|---|---|---|---|---|---|
| Example 1 | Compound 1 | 8 | 85 | 5.97 | 23.6 | 1.34 | 0.691 | 1.54 | 4.43 | 0.16 |
| Example 2 | Compound 2 | 9 | 83 | 6.19 | 19.5 | 1.45 | 0.958 | 1.47 | 4.63 | 0.17 |
| Example 3 | Compound 3 | 9 | 81 | 5.85 | 12.2 | 1.53 | 1.71 | 1.54 | 7.21 | 0.18 |
| Example 4 | Compound 4 | 11 | 81 | 8.49 | 23.0 | 1.30 | 0.928 | 1.05 | 3.11 | 0.15 |
| Example 5 | Compound 5 | 12 | 85 | 9.49 | 20.2 | 1.05 | 0.869 | 0.927 | 3.43 | — |
| Example 6 | Compound 6 | 11 | 85 | 7.04 | 19.4 | 1.56 | 0.869 | 1.26 | 3.90 | 0.16 |
| Comparative Example 1 | Comparative Compound 1 | 7 | 75 | 3.78 | 46.8 | 1.85 | 0.574 | 2.46 | 2.23 | 0.17 |
| Comparative Example 2 | Comparative Compound 2 | — | 1 | — | — | — | — | — | — | 0.1 |
| Comparative Example 3 | Comparative Compound 3 | — | 11 | — | — | — | — | — | — | 0.3 |

As shown in Table 9, the compounds 1 to 6 each had a far larger rate constant in reverse intersystem crossing $k_{RISC}$ as compared with the comparative compound 1, and had a higher PL quantum yield (photoluminescent quantum yield) as compared with the comparative compounds 1 to 3.

(Examples 7 to 13) Production and Evaluation of Organic Photoluminescent Devices Using any of Compound 11, 35, 38, 55, 150, 151 or 152 and Host Material The light-emitting material and the host material shown in Table 10 were co-deposited from different evaporation sources in a vacuum degree of 5×10$^{-4}$ Pa or less to form a thin film having a thickness of 50 nm on a quartz substrate to be an organic photoluminescent device. The maximum emission wavelength in the fluorescence spectra of each device, the PL quantum yield in a nitrogen atmosphere, the delayed fluorescence lifetime and $\Delta E_{ST}$ are shown in Table 10. All these devices had a high PL quantum yield.

TABLE 10

| Example No. | Light-Emitting Material | Host Material | Maximum Emission Wavelength λmax (nm) | PL Quantum Yield (%) | Delayed Fluorescence Lifetime $\tau_d$ (μs) | $\Delta E_{ST}$ (eV) |
|---|---|---|---|---|---|---|
| Example 7 | Compound 11 | mCBP | 495 nm | 80% | 5.0 | 0.11 eV |
| Example 8 | Compound 35 | DPEPO | 490 nm | 93% | 4.2 | 0.12 eV |
| Example 9 | Compound 38 | mCBP | 490 nm | 83% | 3.4 | 0.13 eV |
| Example 10 | Compound 55 | DPEPO | 481 nm | 80% | 4.3 | 0.17 eV |
| Example 11 | Compound 150 | mCBP | 466 nm | 94% | 10.0 | 0.15 eV |
| Example 12 | Compound 151 | mCBP | 488 nm | 97% | 3.6 | 0.11 eV |
| Example 13 | Compound 152 | PYD2Cz | 493 nm | 97% | 5.4 | 0.09 eV |

(Examples 14 and 15) Production and Evaluation of Organic Photoluminescent Devices Using any of Compound 108 or 313 and Host Material Organic photoluminescent devices were produced and evaluated in the same manner as in Examples 7 to 13 except that the compound 108 or 313 was used as the light-emitting material and mCBP was used as the host material.

The delayed fluorescence lifetime of the device using the compound 108 was 8.9 μs, and $\Delta E_{ST}$ thereof was 0.15 eV; and the delayed fluorescence lifetime of the device using the compound 313 was 4.0 μs, and $\Delta E_{ST}$ thereof was 0.11 eV.

Production and Evaluation of Organic Electroluminescent Device (Example 16) Production and Evaluation of Organic Electroluminescent Device Using Compound 3

On a glass substrate having, as formed thereon, an anode of indium tin oxide (ITO) having a thickness of 50 nm, each thin film was layered according to a vacuum evaporation method under a vacuum degree of 2×10$^{-5}$ Pa.

First, HATCN was vapor-deposited on ITO in a thickness of 60 nm to form a hole injection layer, and on this, Tris PCz was vapor-deposited in a thickness of 30 nm to form a hole transport layer. Subsequently, mCBP was vapor-deposited in a thickness of 5 nm to form an electron blocking layer. Next, the compound 3 and mCBP were co-deposited from different evaporation sources to form a light-emitting layer having a thickness of 30 nm. At this time, the concentration of the compound 3 was 20% by weight. On this, DTRZ was vapor-deposited in a thickness of 10 nm to form a hole blocking layer, and further on this, BpyTP2 and Liq (weight ratio 7/3) were co-deposited from different evaporation sources in a thickness of 30 nm to form an electron transport layer. Further, Liq was layered in a thickness of 2 nm, and then aluminum (Al) was layered in a thickness of 100 nm to form a cathode.

According to the above process, an organic electroluminescent device of Example 16 was produced.

(Example 17) Production and Evaluation of Organic Electroluminescent Device Using Compound 6

An organic electroluminescent device of Example 17 was produced in the same manner as in Example 16 except that the compound 6 was used in place of the compound 3.

(Comparative Example 4) Production and Evaluation of Organic Electroluminescent Device Using Comparative Compound 1

An organic electroluminescent device of Comparative Example 4 was produced in the same manner as in Example 16 except that the comparative compound 1 was used in place of the compound 3.

Figure 6:
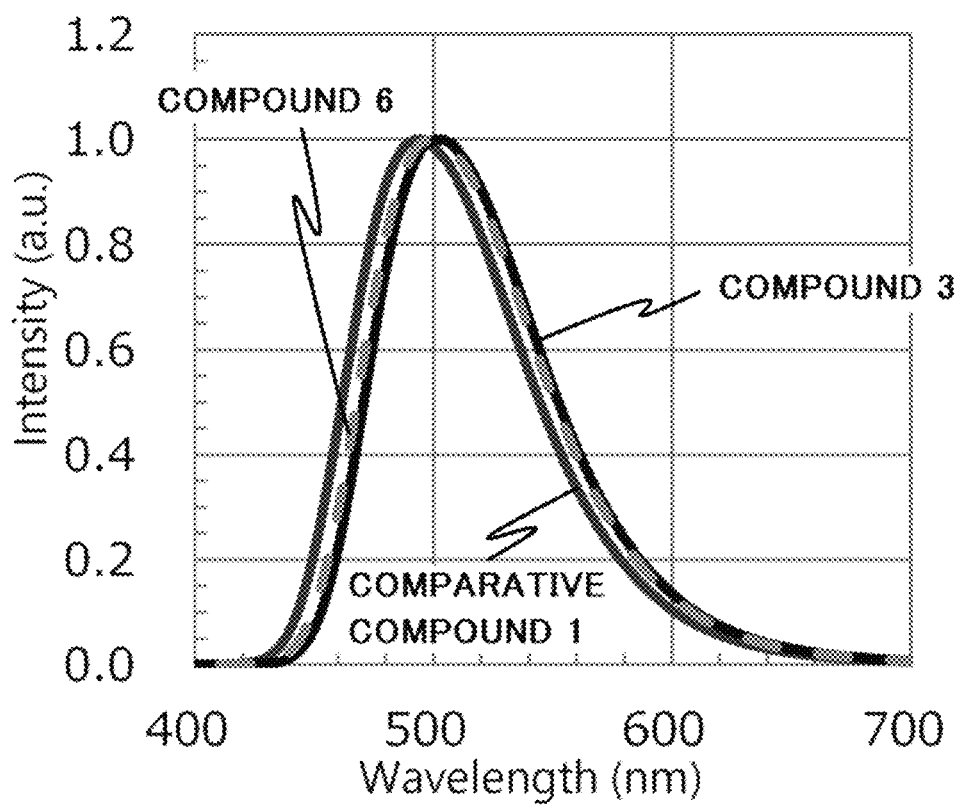
FIG. 6 This shows fluorescence spectra of organic electroluminescent devices using any of compounds 3 and 6 and a comparative compound 1.
Figure 7:
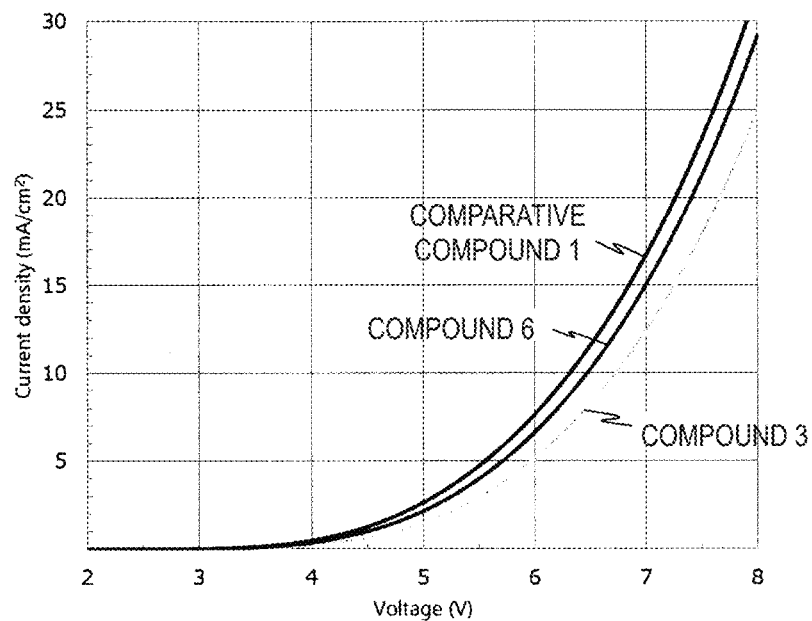
FIG. 7 This shows graphs of current density-voltage characteristic of organic electroluminescent devices using any of compounds 3 and 6 and a comparative compound 1.
Figure 8:
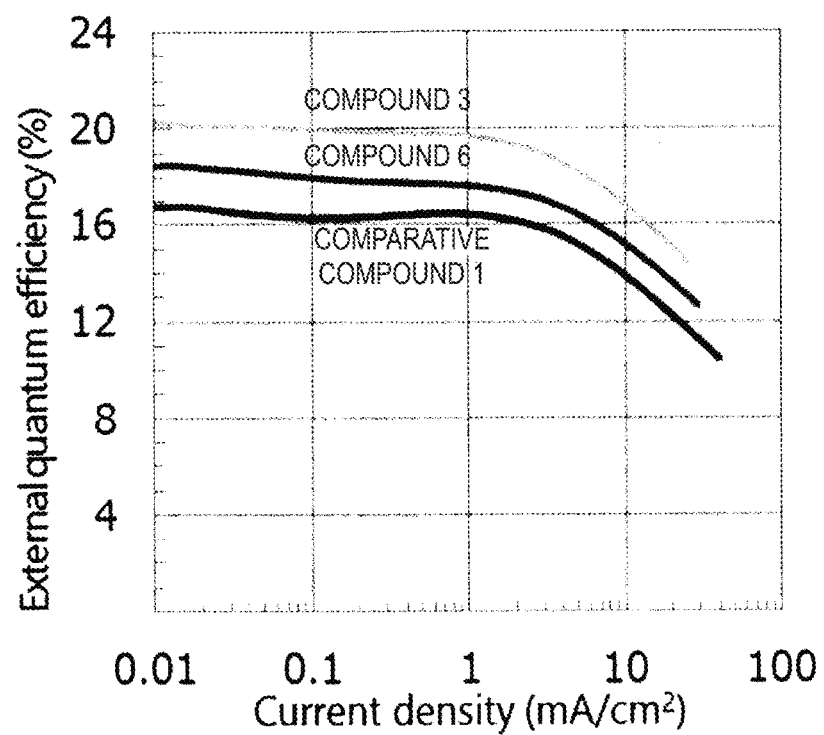
FIG. 8 This shows graphs of current density-external quantum efficiency characteristic of organic electroluminescent devices using any of compounds 3 and 6 and a comparative compound 1.

Fluorescence spectra of organic photoluminescent devices produced in Examples 16 and 17 and Comparative Example 4 are shown in FIG. 6; graphs of current density-voltage characteristic thereof are in FIG. 7; graphs of current density-external quantum efficiency characteristic thereof are in FIG. 8; and graphs of time-dependent luminance change thereof are in FIG. 9. As shown in FIG. 7, the organic electroluminescent devices of Example 16 and Example 17 attained a high external quantum efficiency of 19.4% and 17.3%, respectively. These data of external quantum efficiency were further higher than the external quantum efficiency (16.0%) of the organic electroluminescent device of Comparative Example 4 in which, in the light-emitting material used, the groups each having a negative Hammett's σp value were all the same. In addition, as shown in FIG. 9, the organic electroluminescent devices of Example 16 and Example 17 each had an obviously longer lifetime than the organic electroluminescent device of Comparative Example 4.

(Examples 18 to 25) Production and Evaluation of Organic Electroluminescent Devices Using any of Compound 11, 13, 38, 55, 150, 151, 152, or 313

On a glass substrate having, as formed thereon, an anode of indium tin oxide (ITO) having a thickness of 50 nm, each thin film was layered according to a vacuum evaporation method under a vacuum degree of $2 \times 10^{-5}$ Pa.

First, HATCN was vapor-deposited on ITO in a thickness of 60 nm to form a hole injection layer, and on this, Tris PCz was vapor-deposited in a thickness of 15 nm to form a hole transport layer. Subsequently, mCBP was vapor-deposited in a thickness of 5 nm to form an electron blocking layer. Next, the light-emitting material and the host material shown in Table 11 were co-deposited from different evaporation sources to form a light-emitting layer having a thickness of 30 nm. At this time, the concentration of the light-emitting material was 20% by weight. On this, SF3-TRZ was vapor-deposited in a thickness of 10 nm to form a hole blocking layer, and further on this, SF3-TRZ and Liq (weight ratio 7/3) were co-deposited from different evaporation sources in a thickness of 30 nm to form an electron transport layer. Further, Liq was layered in a thickness of 20 nm, and then aluminum (Al) was layered in a thickness of 100 nm to form a cathode. According to the process, 8 types of organic electroluminescent devices were produced as shown in Table 11.

Measurement results of the maximum emission wavelength of the fluorescence spectra of these organic electroluminescent devices and the external quantum efficiency at 1000 cd/m² thereof are shown in Table 11. The devices all had a high external quantum efficiency.

TABLE 11

| Example No. | Light-Emitting Material | Host Material | Maximum Emission Wavelength λmax (nm) | External Quantum Efficiency (%) |
| --- | --- | --- | --- | --- |
| Example 18 | Compound 11 | mCBP | 497 nm | 19.2% |
| Example 19 | Compound 35 | mCBP | 491 nm | 15.9% |
| Example 20 | Compound 38 | mCBP | 487 nm | 17.1% |
| Example 21 | Compound 55 | mCBP | 477 nm | 14.5% |
| Example 22 | Compound 150 | PYD2Cz | 477 nm | 9.8% |
| Example 23 | Compound 151 | mCBP | 489 nm | 19.3% |
| Example 24 | Compound 152 | PYD2Cz | 495 nm | 17.6% |
| Example 25 | Compound 313 | mCBP | 553 nm | 9.6% |

(Example 26) Production and Evaluation of Organic Electroluminescent Device Using Compound 108

An organic electroluminescent device was produced in the same manner as in Examples 18 to 25 except that the compound 108 was used as the light-emitting material and mCBP was used as the host material. The maximum emission wavelength of the device was 576 nm.

Structural formulae of the materials used in Examples are shown below.

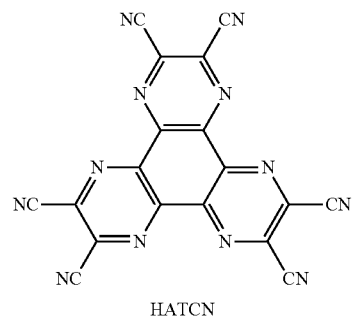

HATCN

-continued

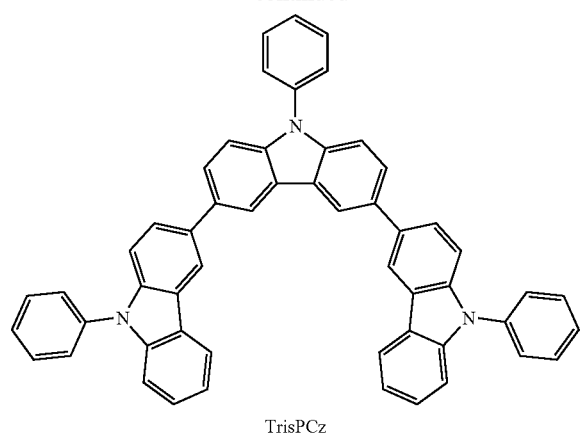
TrisPCz

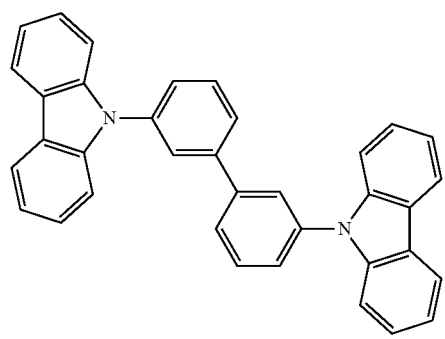
mCBP

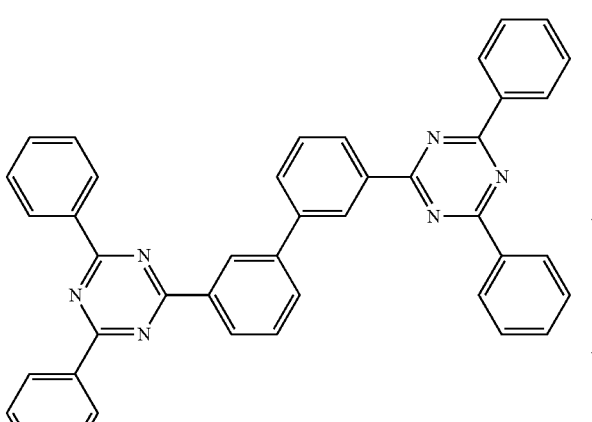
DTRZ

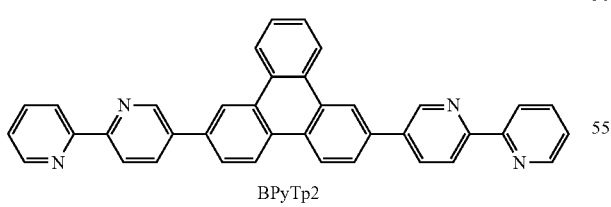
BPyTp2

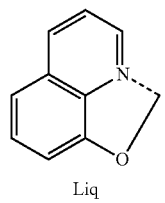
Liq

-continued

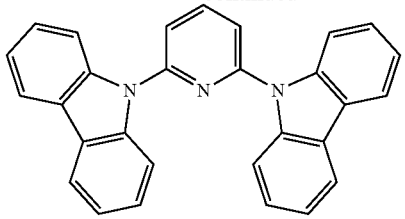
PYD2Cz

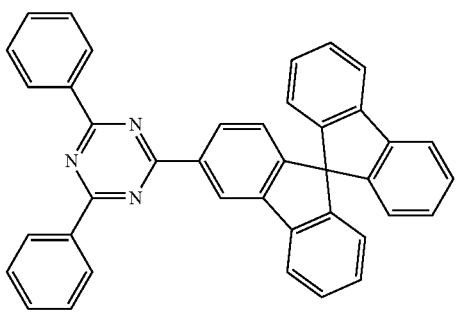
SF3-TRZ

INDUSTRIAL APPLICABILITY

The compound of the present invention has a high emission efficiency and is useful as a light-emitting material. Using the compound of the present invention, a light-emitting device having an extremely high emission efficiency can be provided. Accordingly, the industrial applicability of the present invention is high.

REFERENCE SIGNS LIST

1 Substrate
2 Anode
3 Hole Injection Layer
4 Hole Transport Layer
5 Light-Emitting Layer
6 Electron Transport Layer
7 Cathode

The invention claimed is:
1. A compound represented by the following general formula (10):

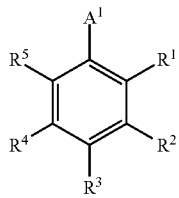

General Formula (10)

wherein $A^1$ represents a cyano group; $R^1$ to $R^5$ each independently represent a hydrogen atom or a group having a negative Hammett's σp value; at most one of $R^1$ to $R^5$ is a hydrogen atom; and for the $R^1$ to $R^5$ groups having a negative Hammett's σp value, two of the negative Hammett's σp-value groups have a different structure but have a common aromatic ring containing an atom bonding to the benzene ring of the general formula (10) in which the common aromatic ring of at least one of the two is substituted with a substituted or unsubstituted alkyl group having 1 to 20 carbon atoms or an substituted or unsubstituted aryl group having 6 to 40 carbon atoms, and a cyclic structure may be formed by the common aromatic ring in combination with the substituted or unsubstituted aryl group or the substituted or unsubstituted alkyl group.

2. The compound according to claim 1, wherein the two of the negative Hammett's σp value groups are a group containing carbazole structure in which the nitrogen atom bonds to the benzene ring in the general formula (10) via a single bond, and $R^1$ and $R^5$ each are a group having a negative Hammett's σp value.

3. The compound according to claim 1, wherein the two of the negative Hammett's σp value groups differ from each other in point of at least one condition of the number of the substituents on the aromatic ring, the substitution site of the aromatic ring substituted with the substituent, and the structure of the substituent on the aromatic ring.

4. The compound according to claim 3, wherein the two of the negative Hammett's σp value groups are the combination of $R^2$ and $R^5$.

5. The compound according to claim 3, wherein the two of the negative Hammett's σp value groups are the combination of $R^1$ and $R^4$.

6. A light-emitting material containing the compound of claim 1.

7. A light-emitting device containing the compound of claim 1.

8. The light-emitting device according to claim 7 wherein a light-emitting layer contains the compound and a host material.

9. The light-emitting device according to claim 7 configured to emit delayed fluorescence.

* * * * *